United States Patent
Zhang et al.

(10) Patent No.: US 12,070,460 B2
(45) Date of Patent: Aug. 27, 2024

(54) METHODS OF TREATING SKIN CANCER WITH CARBOXYPEPTIDASE VITELLOGENIC LIKE (CPVL) INHIBITORS

(71) Applicant: Regeneron Pharmaceuticals, Inc., Tarrytown, NY (US)

(72) Inventors: Xinyuan Zhang, Tarrytown, NY (US); Julie Horowitz, Tarrytown, NY (US); Stefan Semrau, Tarrytown, NY (US); Goncalo Abecasis, Tarrytown, NY (US); Gavin Thurston, Tarrytown, NY (US); Eric Jorgenson, Tarrytown, NY (US); Aris Baras, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 17/857,625

(22) Filed: Jul. 5, 2022

(65) Prior Publication Data
US 2023/0037524 A1 Feb. 9, 2023

Related U.S. Application Data

(60) Provisional application No. 63/219,464, filed on Jul. 8, 2021.

(51) Int. Cl.
*A61K 31/506* (2006.01)
*A61K 31/713* (2006.01)
*C07K 16/28* (2006.01)

(52) U.S. Cl.
CPC .......... *A61K 31/506* (2013.01); *A61K 31/713* (2013.01); *C07K 16/2896* (2013.01)

(58) Field of Classification Search
None
See application file for complete search history.

(56) References Cited

U.S. PATENT DOCUMENTS

2007/0154889 A1* 7/2007 Wang .................. C12Q 1/6886
435/6.14

FOREIGN PATENT DOCUMENTS

| CN | 109825587 | 5/2019 |
| CN | 109929844 | 2/2021 |
| JP | 6659250 | 3/2020 |
| JP | 6659250 B2 * | 3/2020 |
| WO | 2011127222 | 10/2011 |
| WO | 2013160894 | 10/2013 |

OTHER PUBLICATIONS

NCBI Reference Sequence (NM_031311) (Year: 2023).*
GeneAnnot Search (208146_S_at). (Year: 2023).*
Yost et al., "Clonal replacement of tumor-specific T cells following PD-1 blockade", Nat Med, 2019, 25, 1251-1259.

* cited by examiner

*Primary Examiner* — Laura B Goddard
*Assistant Examiner* — Sarah A Alsomairy
(74) *Attorney, Agent, or Firm* — Armstrong Teasdale LLP

(57) ABSTRACT

The present disclosure provides methods of treating a subject having skin cancer or preventing a subject from developing skin cancer, and methods of identifying subjects having an increased risk of developing skin cancer.

8 Claims, 2 Drawing Sheets
(2 of 2 Drawing Sheet(s) Filed in Color)
Specification includes a Sequence Listing.

METHODS OF TREATING SKIN CANCER WITH CARBOXYPEPTIDASE VITELLOGENIC LIKE (CPVL) INHIBITORS

REFERENCE TO SEQUENCE LISTING

This application includes a Sequence Listing filed electronically as an XML file named 381203481SEQ220609, created on Sep. 6, 2022, with a size of 393 kilobytes. The Sequence Listing is incorporated herein by reference.

FIELD

The present disclosure relates generally to the treatment of subjects having skin cancer with Carboxypeptidase Vitellogenic Like (CPVL) inhibitors, and methods of identifying subjects having an increased risk of developing skin cancer.

BACKGROUND

Skin cancer refers to all cancers that occur in the skin. These relatively common cancers are often mistaken by patients for non-malignant skin abnormalities, which can result in late detection that leads to difficulties in treating the disease and fatal outcomes. The most common of skin cancers is basal cell carcinoma (BCC), which accounts for about 80% of all skin cancers. Other types of skin cancers are squamous cell carcinoma (SCC), which accounts for approximately 16%, of all skin cancers, and melanoma, which accounts for about 4%. BCC and SCC are collectively referred to as non-melanoma skin cancer (NMSC). Melanoma occurs from melanocytes in the epidermis, many of which are metastatic cancers or carcinomas that lead to death. In 2000, 47,000 people were identified as having new melanomas, of which 7,700 were reported to have died (Greenlee et al., Cancer J. Clin., 2000, 50, 7-33. It is estimated that melanoma caused by ultraviolet rays is caused by intermittent exposure, such as intense tanning rather than chronic exposure to ultraviolet rays (Gilchrest et al., New Engl. J. Med., 1999, 340, 1341-1348). Another rare form of aggressive skin cancer is Merkel cell carcinoma (MCC), which is similar to melanoma.

Carboxypeptidase Vitellogenic Like (CPVL) is a carboxypeptidase and bears strong sequence similarity to serine carboxypeptidases. Carboxypeptidases are a large class of proteases that act to cleave a single amino acid from the carboxy termini of proteins or peptides. The exact function of this protein, however, has not been determined. CPVL may be involved in the digestion of phagocytosed particles in the lysosome, participation in an inflammatory protease cascade, and trimming of peptides for antigen presentation.

SUMMARY

The present disclosure provides methods of treating a subject having skin cancer or preventing a subject from developing skin cancer, the methods comprising administering a CPVL inhibitor to the subject.

The present disclosure also provides methods of treating a subject having non-melanoma skin cancer or preventing a subject from developing non-melanoma skin cancer, the methods comprising administering a CPVL inhibitor to the subject.

The present disclosure also provides methods of treating a subject having basal cell carcinoma or preventing a subject from developing basal cell carcinoma, the methods comprising administering a CPVL inhibitor to the subject.

The present disclosure also provides methods of treating a subject having squamous cell carcinoma or preventing a subject from developing squamous cell carcinoma, the methods comprising administering a CPVL to the subject.

The present disclosure also provides methods of treating a subject having melanoma or preventing a subject from developing melanoma, the methods comprising administering a CPVL inhibitor to the subject.

The present disclosure also provides methods of treating a subject having Merkel cell carcinoma or preventing a subject from developing Merkel cell carcinoma, the methods comprising administering a CPVL inhibitor to the subject.

The present disclosure also provides methods of treating a subject having dermatofibrosarcoma protuberans or preventing a subject from developing dermatofibrosarcoma protuberans, the methods comprising administering a CPVL inhibitor to the subject.

The present disclosure also provides methods of treating a subject having sebaceous carcinoma or preventing a subject from developing sebaceous carcinoma, the methods comprising administering a CPVL inhibitor to the subject.

The present disclosure also provides methods of treating a subject with a therapeutic agent that treats or inhibits skin cancer, wherein the subject has skin cancer, the methods comprising the steps of: determining whether the subject has a CPVL missense variant nucleic acid molecule encoding a CPVL predicted loss-of-function polypeptide by: obtaining or having obtained a biological sample from the subject; and performing or having performed a sequence analysis on the biological sample to determine if the subject has a genotype comprising the CPVL missense variant nucleic acid molecule encoding a CPVL predicted loss-of-function polypeptide; and: i) administering or continuing to administer the therapeutic agent that treats or inhibits skin cancer in a standard dosage amount to a subject that is CPVL reference, and/or administering a CPVL inhibitor to the subject; ii) administering or continuing to administer the therapeutic agent that treats or inhibits skin cancer in an amount that is the same as or less than a standard dosage amount to a subject that is heterozygous for the CPVL missense variant nucleic acid molecule, and/or administering a CPVL inhibitor to the subject; or iii) administering or continuing to administer the therapeutic agent that treats or inhibits skin cancer in an amount that is the same as or less than a standard dosage amount to a subject that is homozygous for the CPVL missense variant nucleic acid molecule; wherein the presence of a genotype having the CPVL missense variant nucleic acid molecule encoding the CPVL predicted loss-of-function polypeptide indicates the subject has a decreased risk of developing skin cancer.

The present disclosure also provides methods of treating a subject with a therapeutic agent that prevents skin cancer, the methods comprising the steps of: determining whether the subject has a CPVL missense variant nucleic acid molecule encoding a CPVL predicted loss-of-function polypeptide by: obtaining or having obtained a biological sample from the subject; and performing or having performed a sequence analysis on the biological sample to determine if the subject has a genotype comprising the CPVL missense variant nucleic acid molecule encoding a CPVL predicted loss-of-function polypeptide; and: i) administering or continuing to administer the therapeutic agent that prevents skin cancer in a standard dosage amount to a subject that is CPVL reference, and/or administering a CPVL inhibitor to the subject; ii) administering or continuing to administer the therapeutic agent that prevents skin cancer in an amount that is the same as or less than a standard dosage amount to a subject that is heterozygous for the CPVL missense variant nucleic acid molecule, and/or administering a CPVL inhibitor to the subject; or iii) administering or continuing to administer the therapeutic agent that prevents skin cancer in an amount that is the same as or less than a standard dosage amount to a subject that is homozygous for the CPVL missense variant nucleic acid molecule; wherein the presence of a genotype having the CPVL missense variant nucleic acid molecule encoding the CPVL predicted loss-of-function polypeptide indicates the subject has a decreased risk of developing skin cancer.

The present disclosure also provides methods of identifying a subject having an increased risk of developing skin cancer, the methods comprising: determining or having determined the presence or absence of a CPVL missense variant nucleic acid molecule encoding a CPVL predicted loss-of-function polypeptide in a biological sample obtained from the subject; when the subject is CPVL reference, then the subject has an increased risk of developing skin cancer; and when the subject is heterozygous or homozygous for the CPVL missense variant nucleic acid molecule encoding the CPVL predicted loss-of-function polypeptide, then the subject has a decreased risk of developing skin cancer.

The present disclosure also provides therapeutic agents that treat or inhibit or prevent skin cancer for use in the treatment or prevention of skin cancer in a subject that: a) is reference for a CPVL genomic nucleic acid molecule, a CPVL mRNA molecule, or a CPVL cDNA molecule; or b) is heterozygous for: i) a CPVL missense variant genomic nucleic acid molecule encoding a CPVL predicted loss-of-function polypeptide; ii) a CPVL missense variant mRNA molecule encoding a CPVL predicted loss-of-function polypeptide; or iii) a CPVL missense variant cDNA molecule encoding a CPVL predicted loss-of-function polypeptide.

The present disclosure also provides CPVL inhibitors for use in the treatment or prevention of skin cancer in a subject that: a) is reference for a CPVL genomic nucleic acid molecule, a CPVL mRNA molecule, or a CPVL cDNA molecule; or b) is heterozygous for: i) a CPVL missense variant genomic nucleic acid molecule encoding a CPVL predicted loss-of-function polypeptide; ii) a CPVL missense variant mRNA molecule encoding a CPVL predicted loss-of-function polypeptide; or iii) a CPVL missense variant cDNA molecule encoding a CPVL predicted loss-of-function polypeptide.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION

Figure 1:
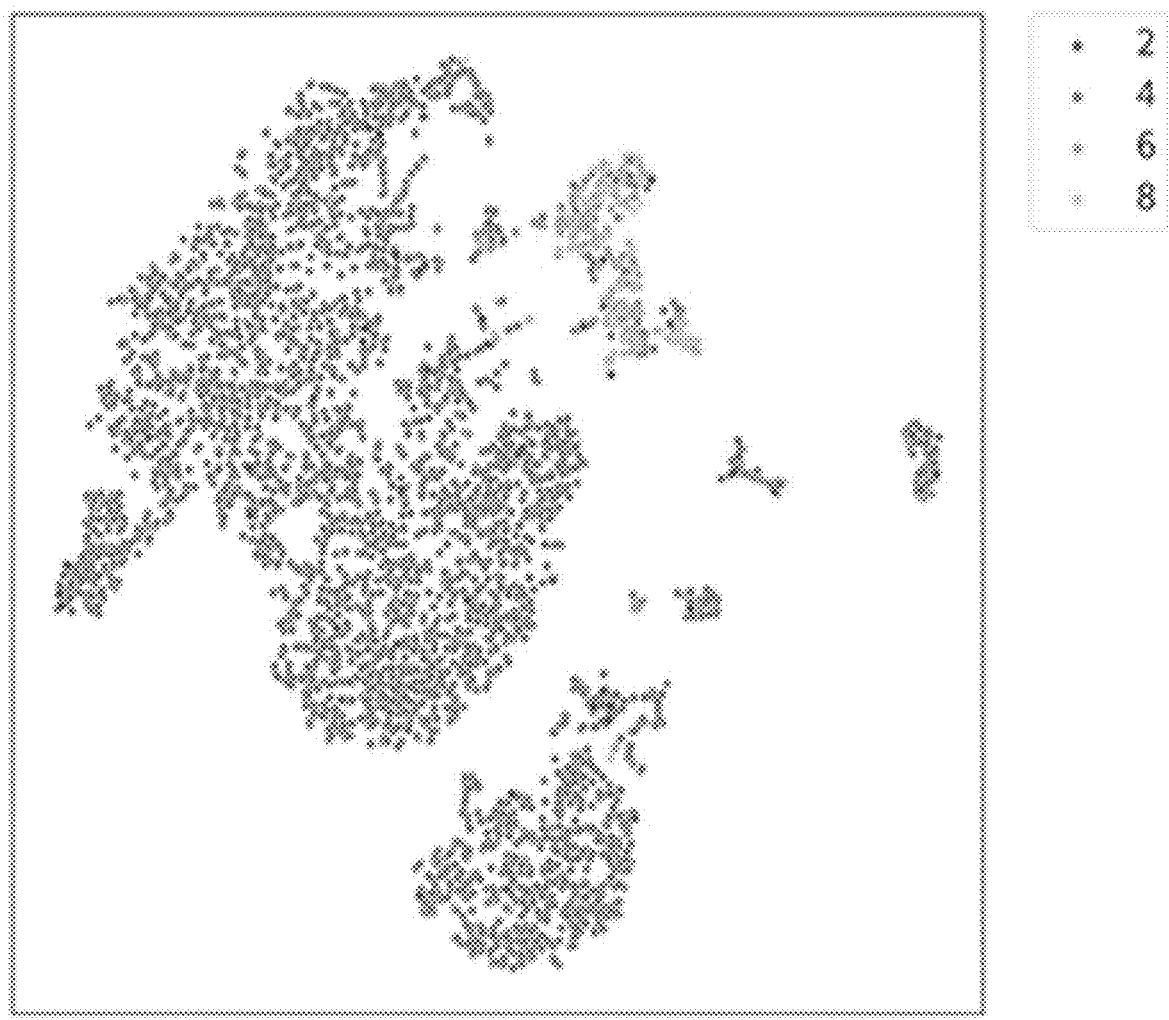
FIG. 1 shows CPVL expression (recovered molecules/cell) of melanoma tumor.

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or Alternately phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human. In some embodiments, the human is a patient under the care of a physician.

It has been observed in accordance with the present disclosure that CPVL missense variant nucleic acid molecules encoding a CPVL predicted loss-of-function polypeptide (whether these variations are homozygous or heterozygous in a particular subject) associate with a decreased risk of developing skin cancer. It is believed that CPVL missense variant nucleic acid molecules encoding a CPVL predicted loss-of-function polypeptide have not been associated with melanoma. Moreover, the identification by the present disclosure of the association between additional variants and gene burden masks indicates that CPVL itself (rather than linkage disequilibrium with variants in another gene) is responsible for a protective effect in non-melanoma skin cancer and melanoma.

Therefore, subjects that are CPVL reference or heterozygous for CPVL missense variant nucleic acid molecules encoding a CPVL predicted loss-of-function polypeptide may be treated with a CPVL inhibitor such that skin cancer is inhibited or prevented, the symptoms thereof are reduced or prevented, and/or development of symptoms is repressed or prevented. It is also believed that such subjects having skin cancer may further be treated with therapeutic agents that treat or inhibit skin cancer.

For purposes of the present disclosure, any particular subject, such as a human, can be categorized as having one of three CPVL genotypes: i) CPVL reference; ii) heterozygous for a CPVL missense variant nucleic acid molecule encoding a CPVL predicted loss-of-function polypeptide; or iii) homozygous for a CPVL missense variant nucleic acid molecules encoding a CPVL predicted loss-of-function polypeptide. A subject is CPVL reference when the subject does not have a copy of a CPVL missense variant nucleic acid molecules encoding a CPVL predicted loss-of-function polypeptide. A subject is heterozygous for a CPVL missense variant nucleic acid molecules encoding a CPVL predicted loss-of-function polypeptide when the subject has a single copy of a CPVL missense variant nucleic acid molecules encoding a CPVL predicted loss-of-function polypeptide. A CPVL missense variant nucleic acid molecules encoding a CPVL predicted loss-of-function polypeptide is any nucleic acid molecule (such as, a genomic nucleic acid molecule, an mRNA molecule, or a cDNA molecule) encoding a variant CPVL polypeptide having a partial loss-of-function, a complete loss-of-function, a predicted partial loss-of-function, or a predicted complete loss-of-function. A subject who has a CPVL polypeptide having a partial loss-of-function (or predicted partial loss-of-function) is hypomorphic for CPVL. A subject is homozygous for a CPVL missense variant nucleic acid molecules encoding a CPVL predicted loss-of-function polypeptide when the subject has two copies (same or different) of a CPVL missense variant nucleic acid molecules encoding a CPVL predicted loss-of-function polypeptide.

For subjects that are genotyped or determined to be CPVL reference, such subjects have an increased risk of developing skin cancer, such as non-melanoma skin cancer, basal cell carcinoma, squamous cell carcinoma, melanoma, Merkel cell carcinoma, dermatofibrosarcoma protuberans, and/or sebaceous carcinoma. For subjects that are genotyped or determined to be either CPVL reference or heterozygous for a CPVL missense variant nucleic acid molecules encoding a CPVL predicted loss-of-function polypeptide, such subjects or subjects can be treated with a CPVL inhibitor.

In any of the embodiments described herein, the subject in whom skin cancer is prevented by administering the CPVL inhibitor can be anyone at risk for developing skin cancer including, but not limited to, subjects with a familial or genetic risk, older subjects, subjects having European descent, and subjects having lighter skin pigmentation. In addition, in some embodiments, any subject can be at risk of developing skin cancer. In some embodiments, administering a CPVL inhibitor may be carried out to prevent development of an additional skin cancer(s) in a subject who has already had one or more skin cancers.

In any of the embodiments described herein, the CPVL missense variant nucleic acid molecules encoding a CPVL predicted loss-of-function polypeptide can be any nucleic acid molecule (such as, for example, genomic nucleic acid molecule, mRNA molecule, or cDNA molecule) encoding a CPVL variant polypeptide having a partial loss-of-function, a complete loss-of-function, a predicted partial loss-of-function, or a predicted complete loss-of-function. In some embodiments, the CPVL missense variant nucleic acid molecules encoding a CPVL predicted loss-of-function polypeptide is associated with a reduced in vitro response to CPVL ligands compared with reference CPVL. In some embodiments, the CPVL missense variant nucleic acid molecules encoding a CPVL predicted loss-of-function polypeptide is a CPVL variant that results or is predicted to result in a premature truncation of a CPVL polypeptide compared to the human reference genome sequence. In some embodiments, the CPVL missense variant nucleic acid molecules encoding a CPVL predicted loss-of-function polypeptide is a variant that is predicted to be damaging by in vitro prediction algorithms such as Polyphen, SIFT, or similar algorithms. In some embodiments, the CPVL missense variant nucleic acid molecules encoding a CPVL predicted loss-of-function polypeptide is a variant that causes or is predicted to cause a nonsynonymous amino-acid substitution in CPVL and whose allele frequency is less than $1/100$ alleles in the population from which the subject is selected. In some embodiments, the CPVL missense variant nucleic acid molecules encoding a CPVL predicted loss-of-function polypeptide is any rare missense variant (allele frequency <0.1%; or 1 in 1,000 alleles), or any splice-site, stop-gain, start-loss, stop-loss, frameshift, or in-frame indel, or other frameshift CPVL variant.

In any of the embodiments described herein, the CPVL predicted loss-of-function polypeptide can be any CPVL polypeptide having a partial loss-of-function, a complete loss-of-function, a predicted partial loss-of-function, or a predicted complete loss-of-function.

In any of the embodiments described herein, the CPVL missense variant nucleic acid molecules encoding a CPVL predicted loss-of-function polypeptide can include variations at positions of chromosome 7 using the nucleotide sequence of the CPVL reference genomic nucleic acid molecule (SEQ ID NO:1; ENSG00000106066.15 chr7:28,995,637-29,195,276 in the GRCh38/hg38 human genome assembly) as a reference sequence.

Numerous genetic variants in CPVL exist which cause subsequent changes in the CPVL polypeptide sequence including, but not limited to: rs117744081 (Tyr168His), rs147771477 (Arg464Gln), and rs138216401 (Ser61Asn).

Any one or more (i.e., any combination) of the CPVL missense variant nucleic acid molecules encoding a CPVL predicted loss-of-function polypeptide can be used within any of the methods described herein to determine whether a subject has an increased risk of developing skin cancer. The combinations of particular variants can form a mask used for statistical analysis of the particular correlation of CPVL and increased risk of developing skin cancer.

In any of the embodiments described herein, the skin cancer is non-melanoma skin cancer, basal cell carcinoma, squamous cell carcinoma (including cutaneous squamous cell carcinoma), melanoma, Merkel cell carcinoma, dermatofibrosarcoma protuberans, and/or sebaceous carcinoma. In some embodiments, the skin cancer is non-melanoma skin cancer. In some embodiments, the skin cancer is basal cell carcinoma. In some embodiments, the skin cancer is squamous cell carcinoma. In some embodiments, the skin cancer is melanoma. In some embodiments, the skin cancer is Merkel cell carcinoma. In some embodiments, the skin cancer is dermatofibrosarcoma protuberans. In some embodiments, the skin cancer is sebaceous carcinoma.

Symptoms of basal cell carcinoma include, but are not limited to, a raised, smooth, pearly bump on the sun-exposed skin of an individual's head, neck or shoulders. Often small blood vessels can be seen within the tumor. Crusting of the tumor, as well as bleeding can occur. Individuals sometimes mistake basal cell carcinoma as a sore that will not heal. Basal cell carcinoma is the least deadly form of skin cancer and often times with proper treatment can be completely eliminated.

Symptoms of squamous cell carcinoma include, but are not limited to a red, scaling, thickened patch on the sun exposed skin of an individual. Some forms of squamous cell carcinoma appear as firm hard nodules and as dome shapes. Breaks and bleeding of the nodules may occur. If left untreated, the squamous cell carcinoma could develop into a large mass. Squamous cell carcinoma is the second most common form of skin cancer.

Symptoms of melanoma include, but are not limited to, shades or brown to black lesions. There are also some melanomas which appear pink, red or flesh color, these are called amelanotic melanomas. The amelanotic melanomas are a more aggressive form of melanoma. Some of the warning signs of malignant melanoma could include changes in size, shape, color, elevation of a mole, the development of a new mole in the transitional period from puberty to adulthood, itching, ulceration or bleeding. Melanoma is the most deadly form of skin cancer.

Symptoms of Merkel cell carcinoma include, but are not limited to rapid growing, non-tender flesh colored to red/violet bumps that are usually not painful or itchy. These bumps appear on the highly sun exposed skin of the head, neck and arms. Individuals often mistake Merkel cell carcinoma for a cyst or other type of cancer.

Symptoms of dermatofibrosarcoma protuberans include, but are not limited to small, slightly-raised, red or purple patch of skin 1 to 5 centimeters wide that can become a raised nodule and in some cases may cause redness, open up or bleed.

Symptoms of sebaceous carcinoma include, but are not limited to slow-growing sometimes yellow painless lump at an eyelid. The bump may bleed or ooze and may also have a thickening or yellow or reddish crust, where the eyelid meets the lash The present disclosure provides methods of treating a subject having skin cancer, the methods comprising administering a CPVL inhibitor to the subject.

The present disclosure also provides methods of treating a subject having non-melanoma skin cancer, the methods comprising administering a CPVL inhibitor to the subject.

The present disclosure also provides methods of treating a subject having basal cell carcinoma, the methods comprising administering a CPVL inhibitor to the subject.

The present disclosure also provides methods of treating a subject having squamous cell carcinoma, the methods comprising administering a CPVL inhibitor to the subject.

The present disclosure also provides methods of treating a subject having melanoma, the methods comprising administering a CPVL inhibitor to the subject.

The present disclosure also provides methods of treating a subject Merkel cell carcinoma, the methods comprising administering a CPVL inhibitor to the subject.

The present disclosure also provides methods of treating a subject having dermatofibrosarcoma protuberans, the methods comprising administering a CPVL inhibitor to the subject.

The present disclosure also provides methods of treating a subject having sebaceous carcinoma, the methods comprising administering a CPVL inhibitor to the subject.

The present disclosure also provides methods of preventing a subject from developing skin cancer, the methods comprising administering a CPVL inhibitor to the subject.

The present disclosure also provides methods of preventing a subject from developing non-melanoma skin cancer, the methods comprising administering a CPVL inhibitor to the subject.

The present disclosure also provides methods of preventing a subject from developing basal cell carcinoma, the methods comprising administering a CPVL inhibitor to the subject.

The present disclosure also provides methods of preventing a subject from developing squamous cell carcinoma, the methods comprising administering a CPVL to the subject.

The present disclosure also provides methods of preventing a subject from developing melanoma, the methods comprising administering a CPVL inhibitor to the subject.

The present disclosure also provides methods of preventing a subject from developing Merkel cell carcinoma, the methods comprising administering a CPVL inhibitor to the subject.

The present disclosure also provides methods of preventing a subject from developing dermatofibrosarcoma protuberans, the methods comprising administering a CPVL inhibitor to the subject.

The present disclosure also provides methods of preventing a subject from developing sebaceous carcinoma, the methods comprising administering a CPVL inhibitor to the subject.

In some embodiments, the CPVL inhibitor comprises an inhibitory nucleic acid molecule. Examples of inhibitory nucleic acid molecules include, but are not limited to, antisense nucleic acid molecules, small interfering RNAs (siRNAs), and short hairpin RNAs (shRNAs). Such inhibitory nucleic acid molecules can be designed to target any region of a CPVL nucleic acid molecule. In some embodiments, the antisense RNA, siRNA, or shRNA hybridizes to a sequence within a CPVL genomic nucleic acid molecule or mRNA molecule and decreases expression of the CPVL polypeptide in a cell in the subject. In some embodiments, the CPVL inhibitor comprises an antisense molecule that hybridizes to a CPVL genomic nucleic acid molecule or mRNA molecule and decreases expression of the CPVL polypeptide in a cell in the subject. In some embodiments, the CPVL inhibitor comprises an siRNA that hybridizes to a CPVL genomic nucleic acid molecule or mRNA molecule and decreases expression of the CPVL polypeptide in a cell in the subject. In some embodiments, the CPVL inhibitor comprises an shRNA that hybridizes to a CPVL genomic nucleic acid molecule or mRNA molecule and decreases expression of the CPVL polypeptide in a cell in the subject.

The inhibitory nucleic acid molecules can comprise RNA, DNA, or both RNA and DNA. The inhibitory nucleic acid molecules can also be linked or fused to a heterologous nucleic acid sequence, such as in a vector, or a heterologous label. For example, the inhibitory nucleic acid molecules can be within a vector or as an exogenous donor sequence comprising the inhibitory nucleic acid molecule and a heterologous nucleic acid sequence. The inhibitory nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The inhibitory nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The inhibitory nucleic acid molecules can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as CH$_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

In some embodiments, the antisense nucleic acid molecules are gapmers, whereby the first one to seven nucleotides at the 5' and 3' ends each have 2'-methoxyethyl (2'-MOE) modifications. In some embodiments, the first five nucleotides at the 5' and 3' ends each have 2'-MOE modifications. In some embodiments, the first one to seven nucleotides at the 5' and 3' ends are RNA nucleotides. In some embodiments, the first five nucleotides at the 5' and 3' ends are RNA nucleotides. In some embodiments, each of the backbone linkages between the nucleotides is a phosphorothioate linkage.

In some embodiments, the siRNA molecules have termini modifications. In some embodiments, the 5' end of the antisense strand is phosphorylated. In some embodiments, 5'-phosphate analogs that cannot be hydrolyzed, such as 5'-(E)-vinyl-phosphonate are used.

In some embodiments, the siRNA molecules have backbone modifications. In some embodiments, the modified phosphodiester groups that link consecutive ribose nucleosides have been shown to enhance the stability and in vivo bioavailability of siRNAs The non-ester groups (—OH, =O) of the phosphodiester linkage can be replaced with sulfur, boron, or acetate to give phosphorothioate, boranophosphate, and phosphonoacetate linkages. In addition, substituting the phosphodiester group with a phosphotriester can facilitate cellular uptake of siRNAs and retention on serum components by eliminating their negative charge. In some embodiments, the siRNA molecules have sugar modifications. In some embodiments, the sugars are deprotonated (reaction catalyzed by exo- and endonucleases) whereby the 2'-hydroxyl can act as a nucleophile and attack the adjacent phosphorous in the phosphodiester bond. Such alternatives include 2'-O-methyl, 2'-O-methoxyethyl, and 2'-fluoro modifications.

In some embodiments, the siRNA molecules have base modifications. In some embodiments, the bases can be substituted with modified bases such as pseudouridine, 5'-methylcytidine, N6-methyladenosine, inosine, and N7-methylguanosine.

In some embodiments, the siRNA molecules are conjugated to lipids. Lipids can be conjugated to the 5' or 3' termini of siRNA to improve their in vivo bioavailability by allowing them to associate with serum lipoproteins. Representative lipids include, but are not limited to, cholesterol and vitamin E, and fatty acids, such as palmitate and tocopherol.

In some embodiments, a representative siRNA has the following formula:
Sense: mN*mN*/i2FN/mN/i2FN/mN/i2FN/mN/i2FN/mN/i2FN/mN/i2FN/mN/i2FN/mN/i2FN/*mN*/32FN/
Antisense: /52FN/*/i2FN/*mN/i2FN/mN/i2FN/mN/i2FN/mN/i2FN/mN/i2FN/mN/i2FN/mN/i2FN/mN/i2FN/mN*N*N
  wherein: "N" is the base; "2F" is a 2'-F modification; "m" is a 2'-O-methyl modification, "I" is an internal base; and "*" is a phosphorothioate backbone linkage.

The present disclosure also provides vectors comprising any one or more of the inhibitory nucleic acid molecules. In some embodiments, the vectors comprise any one or more of the inhibitory nucleic acid molecules and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

The present disclosure also provides compositions comprising any one or more of the inhibitory nucleic acid molecules. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

In some embodiments, the CPVL inhibitor comprises a nuclease agent that induces one or more nicks or double-strand breaks at a recognition sequence(s) or a DNA-binding protein that binds to a recognition sequence within a CPVL genomic nucleic acid molecule. The recognition sequence can be located within a coding region of the CPVL gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the CPVL gene. For example, the recognition sequence can be located about 10, about 20, about 30, about 40, about 50, about 100, about 200, about 300, about 400, about 500, or about 1,000 nucleotides from the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair, about 15-18 by for each ZFN, about 36 by fora TALE protein or TALEN, and about 20 by for a CRISPR/Cas guide RNA.

In some embodiments, CRISPR/Cas systems can be used to modify a CPVL genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of CPVL nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in a CPVL genomic nucleic acid molecule or it can be a nickase that creates a single-strand break in a CPVL genomic nucleic acid molecule. Additional examples of Cas proteins include, but are not limited to, Cas1, Cas1B, Cast, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of CPVL genomic nucleic acid molecules can be generated by contacting a cell with a Cas protein and one or more gRNAs that hybridize to one or more gRNA recognition sequences within a target genomic locus in the CPVL genomic nucleic acid molecule. For example, a gRNA recognition sequence can be located within a region of SEQ ID NO:1. The gRNA recognition sequence can include or be proximate to the start codon of a CPVL genomic nucleic acid molecule or the stop codon of a CPVL genomic nucleic acid molecule. For example, the gRNA recognition sequence can be located from about 10, from about 20, from about 30, from about 40, from about 50, from about 100, from about 200, from about 300, from about 400, from about 500, or from about 1,000 nucleotides of the start codon or the stop codon.

The gRNA recognition sequences within a target genomic locus in a CPVL genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within a CPVL genomic nucleic acid molecule. An exemplary gRNA is a gRNA effective to direct a Cas enzyme to bind to or cleave a CPVL genomic nucleic acid molecule, wherein the gRNA comprises a DNA-targeting segment that hybridizes to a gRNA recognition sequence within the CPVL genomic nucleic acid molecule. Exemplary gRNAs comprise a DNA-targeting segment that hybridizes to a gRNA recognition sequence present within a CPVL genomic nucleic acid molecule that includes or is proximate to the start codon or the stop codon. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the start codon or located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the human CPVL reference gene are set forth in Table 1 as SEQ ID NOs:57-76.

TABLE 1

Guide RNA Recognition Sequences Near CPVL Variation(s)

| Strand | gRNA Recognition Sequence | SEQ ID NO: |
|---|---|---|
| - | GTAAAGCATGGAGAGCGTTGTGG | 57 |
| - | CTCATTGACTGCATATCCGTGGG | 58 |
| - | CTGTAGCCAGAGAACTACTGGGG | 59 |
| + | CCACGGATATGCAGTCAATGAGG | 60 |
| + | TCAATGAGGACGATGTAGCACGG | 61 |
| + | TCACCCCTTACATTGAAGCTGGG | 62 |
| - | GCATAGCCCCCTATAATCTGAGG | 63 |
| + | AGTGTTTCCATGCCACCTAAGGG | 64 |
| - | CTTCCCAGCTTCAATGTAAGGGG | 65 |
| + | TTGGACTCTTTGTGGAACATGGG | 66 |
| + | ATGCCACCTAAGGGAGACTCAGG | 67 |
| + | GTCCTTCTCAGTCTTATGCAGGG | 68 |
| - | CCAACAAGCCAATTTGGTACAGG | 69 |
| + | GAGGTGAAGATCAACCTGAACGG | 70 |
| - | TTCCACAAAGAGTCCAAACATGG | 71 |
| - | TGTAAGTCTTATTCACGGTGAGG | 72 |
| - | TGTCCTGAGTCTCCCTTAGGTGG | 73 |
| + | CAATGAGGACGATGTAGCACGGG | 74 |
| + | ATACTGGATAAACTACTAGATGG | 75 |
| - | TGCATTCATGGCACTGCTTCTGG | 76 |

The Cas protein and the gRNA form a complex, and the Cas protein cleaves the target CPVL genomic nucleic acid molecule. The Cas protein can cleave the nucleic acid molecule at a site within or outside of the nucleic acid sequence present in the target CPVL genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the CPVL genomic nucleic acid molecule to which a DNA-targeting segment of a gRNA will bind.

Such methods can result, for example, in a CPVL genomic nucleic acid molecule in which a region of SEQ ID NO:1 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the CPVL genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the methods of treatment and/or prevention further comprise detecting the presence or absence of a CPVL missense variant nucleic acid molecule encoding a CPVL predicted loss-of-function polypeptide in a biological sample from the subject. As used throughout the present disclosure, a "CPVL missense variant nucleic acid molecule encoding a CPVL predicted loss-of-function polypeptide" is any CPVL nucleic acid molecule (such as, for example, genomic nucleic acid molecule, mRNA molecule, or cDNA molecule) encoding a CPVL polypeptide having a partial loss-of-function, a complete loss-of-function, a predicted partial loss-of-function, or a predicted complete loss-of-function.

The present disclosure also provides methods of treating a subject with a therapeutic agent that treats or inhibits skin cancer, wherein the subject has skin cancer. The present disclosure also provides methods of preventing a subject from developing skin cancer by administering a therapeutic agent that prevents skin cancer. In some embodiments, the methods comprise determining whether the subject has a CPVL missense variant nucleic acid molecule encoding a CPVL predicted loss-of-function polypeptide by obtaining or having obtained a biological sample from the subject, and performing or having performed a sequence analysis on the biological sample to determine if the subject has a genotype comprising the CPVL missense variant nucleic acid molecule encoding a CPVL predicted loss-of-function polypeptide. In some embodiments, the methods further comprise administering or continuing to administer the therapeutic agent that treats, prevents, or inhibits skin cancer in a standard dosage amount to a subject that is CPVL reference, and/or administering a CPVL inhibitor to the subject. In some embodiments, the methods further comprise administering or continuing to administer the therapeutic agent that treats, prevents, or inhibits skin cancer in an amount that is the same as or less than a standard dosage amount to a subject that is heterozygous for the CPVL missense variant nucleic acid molecule, and/or administering a CPVL inhibitor to the subject. In some embodiments, the methods further comprise administering or continuing to administer the therapeutic agent that treats, prevents, or inhibits skin cancer in an amount that is the same as or less than a standard dosage amount to a subject that is homozygous for the CPVL missense variant nucleic acid molecule. The presence of a genotype having the CPVL missense variant nucleic acid molecule encoding the CPVL predicted loss-of-function polypeptide indicates the subject has a decreased risk of developing skin cancer. In some embodiments, the subject is CPVL reference. In some embodiments, the subject is heterozygous for a CPVL missense variant nucleic acid molecule encoding a CPVL predicted loss-of-function polypeptide.

For subjects that are genotyped or determined to be either CPVL reference or heterozygous for a CPVL missense variant nucleic acid molecule encoding a CPVL predicted loss-of-function polypeptide, such subjects can be administered a CPVL inhibitor, as described herein.

Detecting the presence or absence of a CPVL missense variant nucleic acid molecule encoding a CPVL predicted loss-of-function polypeptide in a biological sample from a subject and/or determining whether a subject has a CPVL missense variant nucleic acid molecule encoding a CPVL predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when the subject is CPVL reference, the subject is administered a therapeutic agent that treats, prevents, or inhibits skin cancer in a standard dosage amount. In some embodiments, when the subject is heterozygous for a CPVL missense variant nucleic acid molecule encoding a CPVL predicted loss-of-function polypeptide, the subject is administered a therapeutic agent that treats, prevents, or inhibits skin cancer in a dosage amount that is the same as or less than a standard dosage amount.

In some embodiments, the treatment and/or prevention methods further comprise detecting the presence or absence of a CPVL predicted loss-of-function polypeptide in a biological sample from the subject. In some embodiments, when the subject does not have a CPVL predicted loss-of-function polypeptide, the subject is also administered a therapeutic agent that treats, prevents, or inhibits skin cancer in a standard dosage amount. In some embodiments, when the subject has a CPVL predicted loss-of-function polypeptide, the subject is also administered a therapeutic agent that treats, prevents, or inhibits skin cancer in a dosage amount that is the same as or less than a standard dosage amount.

The present disclosure also provides methods of treating a subject with a therapeutic agent that treats or inhibits skin cancer, wherein the subject has skin cancer. In some embodiments, the method comprises determining whether the subject has a CPVL predicted loss-of-function polypeptide by obtaining or having obtained a biological sample from the subject, and performing or having performed an assay on the biological sample to determine if the subject has a CPVL predicted loss-of-function polypeptide. When the subject does not have a CPVL predicted loss-of-function polypeptide, the therapeutic agent that treats or inhibits skin cancer is administered or continued to be administered to the subject in a standard dosage amount, and/or a CPVL inhibitor is administered to the subject. When the subject has a CPVL predicted loss-of-function polypeptide, the therapeutic agent that treats or inhibits skin cancer is administered or continued to be administered to the subject in an amount that is the same as or less than a standard dosage amount, and/or a CPVL inhibitor is administered to the subject. The presence of a CPVL predicted loss-of-function polypeptide indicates the subject has a decreased risk of developing skin cancer. In some embodiments, the subject has a CPVL predicted loss-of-function polypeptide. In some embodiments, the subject does not have a CPVL predicted loss-of-function polypeptide.

The present disclosure also provides methods of preventing a subject from developing skin cancer by administering a therapeutic agent that prevents skin cancer. In some embodiments, the method comprises determining whether the subject has a CPVL predicted loss-of-function polypeptide by obtaining or having obtained a biological sample from the subject, and performing or having performed an assay on the biological sample to determine if the subject has a CPVL predicted loss-of-function polypeptide. When the subject does not have a CPVL predicted loss-of-function polypeptide, the therapeutic agent that prevents skin cancer is administered or continued to be administered to the subject in a standard dosage amount, and/or a CPVL inhibitor is administered to the subject. When the subject has a CPVL predicted loss-of-function polypeptide, the therapeutic agent that prevents skin cancer is administered or continued to be administered to the subject in an amount that is the same as or less than a standard dosage amount, and/or a CPVL inhibitor is administered to the subject. The presence of a CPVL predicted loss-of-function polypeptide indicates the subject has a decreased risk of developing skin cancer. In some embodiments, the subject has a CPVL predicted loss-of-function polypeptide. In some embodiments, the subject does not have a CPVL predicted loss-of-function polypeptide.

Detecting the presence or absence of a CPVL predicted loss-of-function polypeptide in a biological sample from a subject and/or determining whether a subject has a CPVL predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

In some embodiments, the CPVL inhibitor is a small molecule. In some embodiments, the CPVL inhibitor is hydroxymethyl(N-methyliminodiacetic acid)boronate (hydroxymethyl(MIDA)boronate), azidomethyl(N-methyliminodiacetic acid)boronate (azidomethyl(MIDA)boronate), or an α-functionalized alkyl(MIDA)boronate compound (see, Table 1 of Adachi et al., Chem. Commun., 2015, 51, 3608-3611. Additional inhibitors include, but are not limited to, the following compounds:

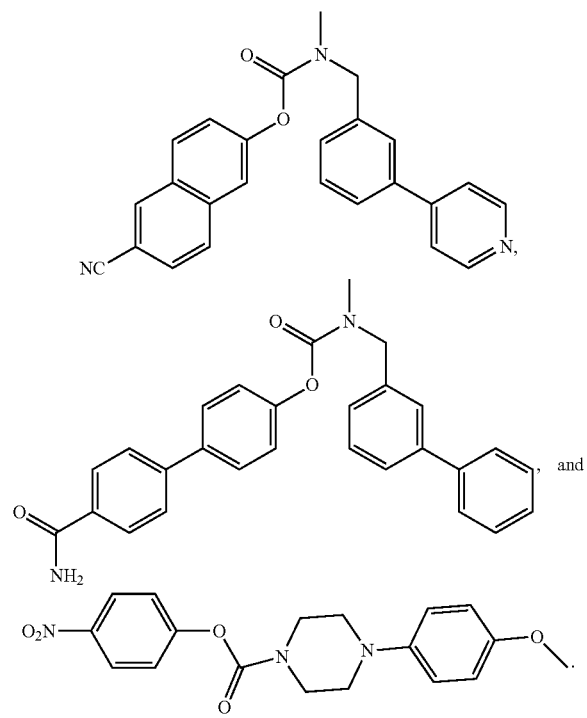

In some embodiments, the CPVL inhibitor is an immune-oncology agent or an immune checkpoint inhibitor. In some embodiments, the immune checkpoint inhibitor is an anti-PD-1 agent, an anti-PD-L1 agent, or an anti-CTLA-4 agent. In some embodiments, the immune checkpoint inhibitor is an anti-PD-1 agent, such as for example, KEYTRUDA® (pembrolizumab), OPDIVO® (nivolumab), and LIBTAYO® (cemiplimab). In some embodiments, the immune checkpoint inhibitor is KEYTRUDA® (pembrolizumab). In some embodiments, the immune checkpoint inhibitor is pembrolizumab. In some embodiments, the immune checkpoint inhibitor is OPDIVO® (nivolumab). In some embodiments, the immune checkpoint inhibitor is nivolumab. In some embodiments, the immune checkpoint inhibitor is LIBTAYO® (cemiplimab). In some embodiments, the immune checkpoint inhibitor is cemiplimab. In some embodiments, the immune checkpoint inhibitor is an anti-PD-L1 agent, such as for example, TECENTRIQ® (atezolizumab), BAVENCIO® (avelumab), and IMFINZI® (durvalumab). In some embodiments, the immune checkpoint inhibitor is TECENTRIQ® (atezolizumab). In some embodiments, the immune checkpoint inhibitor is atezolizumab. In some embodiments, the immune checkpoint inhibitor is BAVENCIO® (avelumab). In some embodiments, the immune checkpoint inhibitor is avelumab. In some embodiments, the immune checkpoint inhibitor is IMFINZI® (durvalumab). In some embodiments, the immune checkpoint inhibitor is durvalumab. In some embodiments, the immune checkpoint inhibitor is an anti-CTLA-4 agent, such as for example, YERVOY® (ipilimumab) and tremelimumab. In some embodiments, the immune checkpoint inhibitor is YERVOY® (ipilimumab) or tremelimumab. In some embodiments, the immune checkpoint inhibitor is YERVOY® (ipilimumab). In some embodiments, the immune checkpoint inhibitor is ipilimumab. In some embodiments, the immune checkpoint inhibitor is tremelimumab. In some embodiments, the CPVL inhibitor is a combination of any of the CPVL inhibitors described herein and any of the immune checkpoint inhibitors described herein. In some embodiments, the CPVL inhibitor is a combination of any of the CPVL inhibitors described herein and an anti-PD-1 agent and an anti-CTLA-4 agent.

Examples of therapeutic agents that treat or inhibit basal cell carcinoma include, but are not limited to, imiquimod, fluorouracil, cemiplimab-rwlc, sonidegib, and vismodegib, or any combination thereof. In some embodiments, the therapeutic agent is imiquimod. In some embodiments, the therapeutic agent is fluorouracil. In some embodiments, the therapeutic agent is cemiplimab-rwlc. In some embodiments, the therapeutic agent is sonidegib. In some embodiments, the therapeutic agent is vismodegib.

Examples of therapeutic agents that treat or inhibit squamous cell carcinoma include, but are not limited to, cemiplimab-rwlc and pembrolizumab, or a combination thereof. In some embodiments, the therapeutic agent is cemiplimab-rwlc. In some embodiments, the therapeutic agent is pembrolizumab.

Examples of therapeutic agents that treat or inhibit melanoma include, but are not limited to, aldesleukin, cobimetinib, dabrafenib, dacarbazine, recombinant interferon alfa-2b, ipilimumab, nivolumab, nivolumab, peginterferon alfa-2b, pembrolizumab, talimogene laherparepvec, trametinib dimethyl sulfoxide, and vemurafenib, or any combination thereof. In some embodiments, the therapeutic agent is aldesleukin. In some embodiments, the therapeutic agent is cobimetinib. In some embodiments, the therapeutic agent is dabrafenib. In some embodiments, the therapeutic agent is dacarbazine. In some embodiments, the therapeutic agent is recombinant interferon alfa-2b. In some embodiments, the therapeutic agent is ipilimumab. In some embodiments, the therapeutic agent is nivolumab. In some embodiments, the therapeutic agent is nivolumab. In some embodiments, the therapeutic agent is peginterferon alfa-2b. In some embodiments, the therapeutic agent is pembrolizumab. In some embodiments, the therapeutic agent is talimogene laherparepvec. In some embodiments, the therapeutic agent is trametinib dimethyl sulfoxide. In some embodiments, the therapeutic agent is vemurafenib.

Examples of therapeutic agents that treat or inhibit Merkel cell carcinoma include, but are not limited to, avelumab, pembrolizumab, etoposide (VP16), and carboplatin combination regimen, or any combination thereof. In some embodiments, the therapeutic agent is avelumab. In some embodiments, the therapeutic agent is pembrolizumab. In some embodiments, the therapeutic agent is etoposide (VP16). In some embodiments, the therapeutic agent is carboplatin combination regimen.

Examples of therapeutic agents that treat or inhibit dermatofibrosarcoma protuberans include, but are not limited to, imatinib.

In some embodiments, the dose of the therapeutic agents that treat, prevent, or inhibit skin cancer can be decreased by about 10%, by about 20%, by about 30%, by about 40%, by about 50%, by about 60%, by about 70%, by about 80%, or by about 90% for subjects that are heterozygous for a CPVL missense variant nucleic acid molecule encoding a CPVL predicted loss-of-function polypeptide (i.e., a less than the standard dosage amount) compared to subjects that are CPVL reference (who may receive a standard dosage amount). In some embodiments, the dose of the therapeutic agents that treat, prevent, or inhibit skin cancer can be decreased by about 10%, by about 20%, by about 30%, by about 40%, or by about 50%. In addition, the subjects that are heterozygous for a CPVL missense variant nucleic acid molecule encoding a CPVL predicted loss-of-function polypeptide can be administered less frequently compared to subjects that are CPVL reference.

In some embodiments, the dose of the therapeutic agents that treat, prevent, or inhibit skin cancer can be decreased by about 10%, by about 20%, by about 30%, by about 40%, by about 50%, for subjects that are homozygous for a CPVL missense variant nucleic acid molecule encoding a CPVL predicted loss-of-function polypeptide compared to subjects that are heterozygous for a CPVL missense variant nucleic acid molecule encoding a CPVL predicted loss-of-function polypeptide. In some embodiments, the dose of the therapeutic agents that treat, prevent, or inhibit skin cancer can be decreased by about 10%, by about 20%, by about 30%, by about 40%, or by about 50%. In addition, the dose of therapeutic agents that treat, prevent, or inhibit skin cancer in subjects that are homozygous for a CPVL missense variant nucleic acid molecule encoding a CPVL predicted loss-of-function polypeptide can be administered less frequently compared to subjects that are heterozygous for a CPVL missense variant nucleic acid molecule encoding a CPVL predicted loss-of-function polypeptide.

Administration of the therapeutic agents that treat, prevent, or inhibit skin cancer and/or CPVL inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat, prevent, or inhibit skin cancer and/or CPVL inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in skin cancer, a decrease/reduction in the severity of skin cancer (such as, for example, a reduction or inhibition of development of skin cancer), a decrease/reduction in symptoms and skin cancer-related effects, delaying the onset of symptoms and skin cancer-related effects, reducing the severity of symptoms of skin cancer-related effects, reducing the number of symptoms and skin cancer-related effects, reducing the latency of symptoms and skin cancer-related effects, an amelioration of symptoms and skin cancer-related effects, reducing secondary symptoms, reducing secondary infections, preventing relapse to skin cancer, decreasing the number or frequency of relapse episodes, increasing latency between symptomatic episodes, increasing time to sustained progression, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of skin cancer development/progression (such as, for example, a complete or partial avoidance/inhibition or a delay), and an increased survival time of the affected host animal, following administration of a therapeutic protocol. Treatment of skin cancer encompasses the treatment of a subject already diagnosed as having any form of skin cancer at any clinical stage or manifestation, the delay of the onset or evolution or aggravation or deterioration of the symptoms or signs of skin cancer, and/or preventing and/or reducing the severity of skin cancer.

The present disclosure also provides methods of identifying a subject having an increased risk of developing skin cancer. In some embodiments, the method comprises determining or having determined in a biological sample obtained from the subject the presence or absence of a CPVL missense variant nucleic acid molecule (such as a genomic nucleic acid molecule, mRNA molecule, and/or cDNA molecule) encoding a CPVL predicted loss-of-function polypeptide encoding a CPVL polypeptide. When the subject lacks a CPVL missense variant nucleic acid molecule encoding a CPVL predicted loss-of-function polypeptide (i.e., the subject is genotypically categorized as a CPVL reference), then the subject has an increased risk of developing skin cancer. When the subject has a CPVL missense variant nucleic acid molecule encoding a CPVL predicted loss-of-function polypeptide (i.e., the subject is heterozygous or homozygous for a CPVL missense variant nucleic acid molecule encoding a CPVL predicted loss-of-function polypeptide), then the subject has a decreased risk of developing skin cancer.

Having a single copy of a CPVL missense variant nucleic acid molecule encoding a CPVL predicted loss-of-function polypeptide is more protective of a subject from developing skin cancer than having no copies of a CPVL missense variant nucleic acid molecule encoding a CPVL predicted loss-of-function polypeptide. Without intending to be limited to any particular theory or mechanism of action, it is believed that a single copy of a CPVL missense variant nucleic acid molecule encoding a CPVL predicted loss-of-function polypeptide (i.e., heterozygous for a CPVL missense variant nucleic acid molecule encoding a CPVL predicted loss-of-function polypeptide) is protective of a subject from developing skin cancer, and it is also believed that having two copies of a CPVL missense variant nucleic acid molecule encoding a CPVL predicted loss-of-function polypeptide (i.e., homozygous for a CPVL missense variant nucleic acid molecule encoding a CPVL predicted loss-of-function polypeptide) may be more protective of a subject from developing skin cancer, relative to a subject with a single copy. Thus, in some embodiments, a single copy of a CPVL missense variant nucleic acid molecule encoding a CPVL predicted loss-of-function polypeptide may not be completely protective, but instead, may be partially or incompletely protective of a subject from developing skin cancer. While not desiring to be bound by any particular theory, there may be additional factors or molecules involved in the development of skin cancer that are still present in a subject having a single copy of a CPVL missense variant nucleic acid molecule encoding a CPVL predicted loss-of-function polypeptide, thus resulting in less than complete protection from the development of skin cancer.

Determining whether a subject has a CPVL missense variant nucleic acid molecule encoding a CPVL predicted loss-of-function polypeptide in a biological sample from a subject and/or determining whether a subject has a CPVL missense variant nucleic acid molecule encoding a CPVL predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when a subject is identified as having an increased risk of developing skin cancer, the subject is administered a therapeutic agent that treats, prevents, or inhibits skin cancer, and/or a CPVL inhibitor, as described herein. For example, when the subject is CPVL reference, and therefore has an increased risk of developing skin cancer, the subject is administered a CPVL inhibitor. In some embodiments, such a subject is also administered a therapeutic agent that treats, prevents, or inhibits skin cancer. In some embodiments, when the subject is heterozygous for a CPVL missense variant nucleic acid molecule encoding a CPVL predicted loss-of-function polypeptide, the subject is administered the therapeutic agent that treats, prevents, or inhibits skin cancer in a dosage amount that is the same as or less than a standard dosage amount, and/or is administered a CPVL inhibitor. In some embodiments, such a subject is also administered a therapeutic agent that treats, prevents, or inhibits skin cancer. In some embodiments, when the subject is homozygous for a CPVL missense variant nucleic acid molecule encoding a CPVL predicted loss-of-function polypeptide, the subject is administered the therapeutic agent that treats, prevents, or inhibits skin cancer in a dosage amount that is the same as or less than a standard dosage amount. In some embodiments, the subject is CPVL reference. In some embodiments, the subject is heterozygous for a CPVL missense variant nucleic acid molecule encoding a CPVL predicted loss-of-function polypeptide. In some embodiments, the subject is homozygous for a CPVL missense variant nucleic acid molecule encoding a CPVL predicted loss-of-function polypeptide.

In some embodiments, any of the methods described herein can further comprise determining the subject's aggregate burden of having a CPVL missense variant nucleic acid molecule encoding a CPVL predicted loss-of-function polypeptide, and/or a CPVL predicted loss-of-function variant polypeptide associated with a decreased risk of developing skin cancer. The aggregate burden is the sum of all variants in the CPVL gene, which can be carried out in an association analysis with skin cancer. In some embodiments, the subject is homozygous for one or more CPVL missense variant nucleic acid molecules encoding a CPVL predicted loss-of-function polypeptide associated with a decreased risk of developing skin cancer. In some embodiments, the subject is heterozygous for one or more CPVL missense variant nucleic acid molecules encoding a CPVL predicted loss-of-function polypeptide associated with a decreased risk of developing skin cancer. The result of the association analysis suggests that CPVL missense variant nucleic acid molecules encoding a CPVL predicted loss-of-function polypeptide are associated with decreased risk of developing skin cancer. When the subject has a lower aggregate burden, the subject is at a higher risk of developing skin cancer and the subject is administered or continued to be administered the therapeutic agent that treats, prevents, or inhibits skin cancer in a standard dosage amount. When the subject has a greater aggregate burden, the subject is at a lower risk of developing skin cancer and the subject is administered or continued to be administered the therapeutic agent that treats, prevents, or inhibits skin cancer in an amount that is the same as or less than the standard dosage amount. The greater the aggregate burden, the lower the risk of developing skin cancer. CPVL variants that can be used in the aggregate burden analysis include any one or more, or any combination, of the following in Table 2:

TABLE 2

| Variant | rsID |
|---|---|
| 7:29096102:C:T | |
| 7:28995873:G:A | |
| 7:29030645:C:CT | |
| 7:29096125:A:T | |
| 7:29066109:GT:G | |
| 7:29064221:T:TG | |
| 7:29120891:A:C | |
| 7:29071905:C:CT | |
| 7:29071905:C:G | |
| 7:29064060:C:T | |
| 7:29064167:AC:A | rs777604046 |
| 7:29086513:T:A | rs764980288 |
| 7:29064132:C:CA | rs748209844 |
| 7:29066026:G:T | |
| 7:28995813:G:A | |
| 7:29092703:C:T | rs201027082 |
| 7:29195076:C:T | |

TABLE 2-continued

| Variant | rsID |
|---|---|
| 7:29120892:C:A | |
| 7:29066070:G:A | |
| 7:29064236:T:C | |
| 7:29095143:C:T | |
| 7:29095143:CT:C | |
| 7:29071879:AG:A | |
| 7:29064077:AT:A | |
| 7:29064100:TG:T | |
| 7:29030600:GGA:G | |
| 7:29066069:TG:T | |
| 7:29064120:G:A | |
| 7:28995858:TA:T | |
| 7:29096218:C:T | |
| 7:29120903:CT:C | |
| 7:29112720:C:T | |
| 7:29195076:C:A | |
| 7:29030581:TGGAA:T | |
| 7:29096219:T:C | |
| 7:29096142:CAA:C | |
| 7:29071905:C:T | |
| 7:29121003:CAG:C | |
| 7:29096102:C:G | |
| 7:29064120:G:GC | rs774891146 |
| 7:29071772:C:A | rs201079331 |
| 7:29120995:GC:G | |
| 7:29066060:G:GT | |
| 7:29030645:CT:C | |
| 7:29064060:C:A | |
| 7:29066032:CA:C | |
| 7:29112740:G:T | |
| 7:29120989:G:GA | |
| 7:29112702:A:G | rs745744964 |
| 7:29030604:GT:G | |
| 7:29064150:TAA:T | |
| 7:29064087:A:AG | |
| 7:29064093:GC:G | |
| 7:29112740:G:C | |
| 7:29064060:CCTTAT:C | rs749642830 |
| 7:28995830:GCT:G | |
| 7:29064221:TG:T | |
| 7:29086483:C:T | |
| 7:29030760:C:CTGAAA | |
| 7:29096207:T:TCTGG | |
| 7:29066114:TC:T | |
| 7:29072425:T:A | |
| 7:29112817:C:A | rs770230527 |
| 7:29064115:TTC:T | |
| 7:29086488:C:T | |
| 7:29095087:A:T | |
| 7:28995863:C:T | |
| 7:29092645:C:A | |
| 7:29096130:G:A | |
| 7:29112766:C:T | rs368319631 |
| 7:29112757:T:C | rs776115114 |
| 7:29096177:C:T | |
| 7:28995863:C:A | |
| 7:29066115:C:A | |
| 7:29030726:C:T | rs776719397 |
| 7:29030584:A:T | |
| 7:29072407:T:C | rs200576601 |
| 7:29064135:C:G | |
| 7:29030749:T:C | rs375729583 |
| 7:29095089:T:G | |
| 7:29030710:G:C | |
| 7:28995876:T:A | |
| 7:29066063:A:T | rs770831396 |
| 7:29064068:T:A | |
| 7:29112774:C:T | |
| 7:29071894:C:T | |
| 7:29096198:G:A | |
| 7:29112810:C:T | rs138216401 |
| 7:29120923:G:C | |
| 7:29086539:T:C | |
| 7:29072410:T:C | |
| 7:29120922:G:C | rs774751381 |
| 7:28995851:G:C | |
| 7:29030642:A:T | |
| 7:29096199:G:C | |

TABLE 2-continued

| Variant | rsID |
|---|---|
| 7:29096169:C:T | |
| 7:29030738:G:C | |
| 7:29064134:A:G | |
| 7:29064173:A:G | |
| 7:28995809:A:C | rs757457600 |
| 7:29096199:G:A | rs188939784 |
| 7:29096150:C:A | |
| 7:29030599:C:T | rs760718602 |
| 7:29072321:C:T | rs778818106 |
| 7:29030737:A:C | |
| 7:29030578:T:C | |
| 7:29096172:G:A | rs752979580 |
| 7:29092663:A:G | rs117744081 |
| 7:29030682:C:A | |
| 7:29095097:T:C | |
| 7:29086497:T:G | |
| 7:29092632:T:A | |
| 7:29030611:G:A | |
| 7:28995872:C:T | rs771602383 |
| 7:28995816:T:G | |
| 7:29092666:C:T | rs751543732 |
| 7:29066097:C:T | |
| 7:28995859:A:T | |
| 7:29086486:C:G | rs376816938 |
| 7:29086549:C:T | |
| 7:29072416:G:A | |
| 7:29096136:G:C | |
| 7:29095103:A:G | |
| 7:29092638:G:A | |
| 7:29092660:C:T | |
| 7:29066058:C:G | |
| 7:29072329:A:G | |
| 7:29030727:G:C | |
| 7:29095088:T:A | |
| 7:29064125:T:C | |
| 7:29086515:T:C | |
| 7:29064122:A:G | |
| 7:29064090:A:G | |
| 7:29096171:G:A | |
| 7:29086548:G:T | |
| 7:28995873:G:C | |
| 7:29066117:A:G | |
| 7:29064101:G:A | |
| 7:29030740:T:C | rs763825813 |
| 7:29095089:T:C | |
| 7:29064164:C:T | |
| 7:29071803:G:C | |
| 7:29064168:C:T | rs761706669 |
| 7:28995864:C:T | |
| 7:29096144:A:G | |
| 7:29096172:G:T | |
| 7:29071780:G:C | |
| 7:29112725:G:T | |
| 7:29092680:G:A | |
| 7:29066071:G:C | |
| 7:29096184:G:C | |
| 7:29096112:T:A | |
| 7:29072423:A:G | |
| 7:29030722:G:A | |
| 7:29064098:A:C | |
| 7:28995852:G:C | |
| 7:28995846:C:T | |
| 7:29030609:C:A | |
| 7:29112754:C:T | rs200681795 |
| 7:29092683:G:C | |
| 7:29112732:T:C | rs769831040 |
| 7:29096139:C:T | |
| 7:29096136:G:A | |
| 7:29112719:C:A | |
| 7:29072347:T:G | |
| 7:29086548:G:A | rs756688128 |
| 7:29064092:G:T | |
| 7:29112750:T:C | rs771212555 |
| 7:29112735:C:G | |
| 7:29096121:C:A | |
| 7:28995814:A:T | |
| 7:29066108:A:G | |
| 7:29092693:C:T | |

TABLE 2-continued

| Variant | rsID |
|---|---|
| 7:29096169:C:G | |
| 7:29095101:G:A | |
| 7:29064212:T:C | rs778672021 |
| 7:29120929:G:A | rs771997351 |
| 7:29030705:G:A | rs773880380 |
| 7:29095086:G:T | rs540749696 |
| 7:28995812:C:T | rs147771477 |
| 7:29096143:A:C | rs147286046 |
| 7:29030577:C:G | rs768929266 |
| 7:28995822:T:C | |
| 7:29096174:C:G | |
| 7:29072380:T:C | |
| 7:29066105:A:G | |
| 7:29064213:A:T | |
| 7:29096138:T:C | |
| 7:29064174:T:C | |
| 7:29086498:A:G | rs147774594 |
| 7:29064152:A:G | rs775477781 |
| 7:29096159:G:A | |
| 7:29096160:A:G | |
| 7:29030750:A:G | |
| 7:29071781:C:T | |
| 7:29072339:C:T | rs775870649 |
| 7:29030600:G:A | |
| 7:29096120:A:G | |

In some embodiments, the subject's aggregate burden of having any one or more CPVL missense variant nucleic acid molecules encoding a CPVL predicted loss-of-function polypeptide represents a weighted sum of a plurality of any of the CPVL missense variant nucleic acid molecules encoding a CPVL predicted loss-of-function polypeptide. In some embodiments, the aggregate burden is calculated using at least about 2, at least about 3, at least about 4, at least about 5, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, at least about 1,000, at least about 10,000, at least about 100,000, or at least about or more than 1,000,000 genetic variants present in or around (up to 10 Mb) the CPVL gene where the genetic burden is the number of alleles multiplied by the association estimate with skin cancer or related outcome for each allele (e.g., a weighted polygenic burden score). This can include any genetic variants, regardless of their genomic annotation, in proximity to the CPVL gene (up to 10 Mb around the gene) that show a non-zero association with skin cancer-related traits in a genetic association analysis. In some embodiments, when the subject has an aggregate burden above a desired threshold score, the subject has a decreased risk of developing skin cancer. In some embodiments, when the subject has an aggregate burden below a desired threshold score, the subject has an increased risk of developing skin cancer.

In some embodiments, the aggregate burden may be divided into quintiles, e.g., top quintile, intermediate quintile, and bottom quintile, wherein the top quintile of aggregate burden corresponds to the lowest risk group and the bottom quintile of aggregate burden corresponds to the highest risk group. In some embodiments, a subject having a greater aggregate burden comprises the highest weighted aggregate burdens, including, but not limited to the top 10%, top 20%, top 30%, top 40%, or top 50% of aggregate burdens from a subject population. In some embodiments, the genetic variants comprise the genetic variants having association with skin cancer in the top 10%, top 20%, top 30%, top 40%, or top 50% of p-value range for the association. In some embodiments, each of the identified genetic variants comprise the genetic variants having association with skin cancer with p-value of no more than about $10^{-2}$, about $10^{-3}$, about $10^{-4}$, about $10^{-5}$, about $10^{-6}$, about $10^{-7}$, about $10^{-8}$, about $10^{-9}$, about $10^{-10}$, about $10^{-11}$, about $10^{-12}$, about $10^{-13}$, about $10^{-14}$, about or $10^{-15}$. In some embodiments, the identified genetic variants comprise the genetic variants having association with skin cancer with p-value of less than $5\times10^{-8}$. In some embodiments, the identified genetic variants comprise genetic variants having association with skin cancer in high-risk subjects as compared to the rest of the reference population with odds ratio (OR) about 1.5 or greater, about 1.75 or greater, about 2.0 or greater, or about 2.25 or greater for the top 20% of the distribution; or about 1.5 or greater, about 1.75 or greater, about 2.0 or greater, about 2.25 or greater, about 2.5 or greater, or about 2.75 or greater. In some embodiments, the odds ratio (OR) may range from about 1.0 to about 1.5, from about 1.5 to about 2.0, from about 2.0 to about 2.5, from about 2.5 to about 3.0, from about 3.0 to about 3.5, from about 3.5 to about 4.0, from about 4.0 to about 4.5, from about 4.5 to about 5.0, from about 5.0 to about 5.5, from about 5.5 to about 6.0, from about 6.0 to about 6.5, from about 6.5 to about 7.0, or greater than 7.0. In some embodiments, high-risk subjects comprise subjects having aggregate burdens in the bottom decile, quintile, or tertile in a reference population. The threshold of the aggregate burden is determined on the basis of the nature of the intended practical application and the risk difference that would be considered meaningful for that practical application.

In some embodiments, when a subject is identified as having an increased risk of developing skin cancer, the subject is further administered a therapeutic agent that treats, prevents, or inhibits skin cancer, and/or a CPVL inhibitor, as described herein. For example, when the subject is CPVL reference, and therefore has an increased risk of developing skin cancer, the subject is administered a CPVL inhibitor. In some embodiments, such a subject is also administered a therapeutic agent that treats, prevents, or inhibits skin cancer. In some embodiments, when the subject is heterozygous for a CPVL missense variant nucleic acid molecule encoding a CPVL predicted loss-of-function polypeptide, the subject is administered the therapeutic agent that treats, prevents, or inhibits skin cancer in a dosage amount that is the same as or less than a standard dosage amount, and/or is administered a CPVL inhibitor. In some embodiments, the subject is CPVL reference. In some embodiments, the subject is heterozygous for a CPVL missense variant nucleic acid molecule encoding a CPVL predicted loss-of-function polypeptide. Furthermore, when the subject has a lower aggregate burden for having a CPVL missense variant nucleic acid molecule encoding a CPVL predicted loss-of-function polypeptide, and therefore has an increased risk of developing skin cancer, the subject is administered a therapeutic agent that treats, prevents, or inhibits skin cancer. In some embodiments, when the subject has a lower aggregate burden for having a CPVL missense variant nucleic acid molecule encoding a CPVL predicted loss-of-function polypeptide, the subject is administered the therapeutic agent that treats, prevents, or inhibits skin cancer in a dosage amount that is the same as or greater than the standard dosage amount administered to a subject who has a greater aggregate burden for having a CPVL missense variant nucleic acid molecule encoding a CPVL predicted loss-of-function polypeptide.

The present disclosure also provides methods of detecting the presence or absence of a CPVL missense variant nucleic acid molecule (i.e., a genomic nucleic acid molecule, an mRNA molecule, or a cDNA molecule produced from an mRNA molecule) encoding a CPVL predicted loss-of-function polypeptide in a biological sample from a subject. It is understood that gene sequences within a population and mRNA molecules encoded by such genes can vary due to polymorphisms such as single-nucleotide polymorphisms. The sequences provided herein for the CPVL variant genomic nucleic acid molecule, CPVL variant mRNA molecule, and CPVL variant cDNA molecule are only exemplary sequences. Other sequences for the CPVL variant genomic nucleic acid molecule, variant mRNA molecule, and variant cDNA molecule are also possible.

The biological sample can be derived from any cell, tissue, or biological fluid from the subject. The biological sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any CPVL missense variant nucleic acid molecule encoding a CPVL predicted loss-of-function polypeptide, preliminary processing designed to isolate or enrich the biological sample for the genomic DNA can be employed. A variety of techniques may be used for this purpose. When detecting the level of any CPVL variant mRNA molecule, different techniques can be used enrich the biological sample with mRNA molecules. Various methods to detect the presence or level of an mRNA molecule or the presence of a particular variant genomic DNA locus can be used.

In some embodiments, detecting a CPVL missense variant nucleic acid molecule encoding a CPVL predicted loss-of-function polypeptide in a subject comprises performing a sequence analysis on a biological sample obtained from the subject to determine whether a CPVL genomic nucleic acid molecule in the biological sample, and/or a CPVL mRNA molecule in the biological sample, and/or a CPVL cDNA molecule produced from an mRNA molecule in the biological sample, comprises one or more variations that cause a loss-of-function (partial or complete) or are predicted to cause a loss-of-function (partial or complete).

In some embodiments, the methods of detecting the presence or absence of a CPVL missense variant nucleic acid molecule encoding a CPVL predicted loss-of-function polypeptide (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence.

In some embodiments, the biological sample comprises a cell or cell lysate. Such methods can further comprise, for example, obtaining a biological sample from the subject comprising a CPVL genomic nucleic acid molecule or mRNA molecule, and if mRNA, optionally reverse transcribing the mRNA into cDNA. Such assays can comprise, for example determining the identity of these positions of the particular CPVL nucleic acid molecule. In some embodiments, the method is an in vitro method.

In some embodiments, the determining step, detecting step, or sequence analysis comprises sequencing at least a portion of the nucleotide sequence of the CPVL genomic nucleic acid molecule, the CPVL mRNA molecule, or the CPVL cDNA molecule in the biological sample, wherein the sequenced portion comprises one or more variations that cause a loss-of-function (partial or complete) or are predicted to cause a loss-of-function (partial or complete).

In some embodiments, the assay comprises sequencing the entire nucleic acid molecule. In some embodiments, only a CPVL genomic nucleic acid molecule is analyzed. In some embodiments, only a CPVL mRNA is analyzed. In some embodiments, only a CPVL cDNA obtained from CPVL mRNA is analyzed.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay comprises contacting the biological sample with a primer or probe, such as an alteration-specific primer or alteration-specific probe, that specifically hybridizes to a CPVL variant genomic sequence, variant mRNA sequence, or variant cDNA sequence and not the corresponding CPVL reference sequence under stringent conditions, and determining whether hybridization has occurred.

In some embodiments, the determining step, detecting step, or sequence analysis comprises: a) amplifying at least a portion of the nucleic acid molecule that encodes the CPVL polypeptide; b) labeling the amplified nucleic acid molecule with a detectable label; c) contacting the labeled nucleic acid molecule with a support comprising an alteration-specific probe; and d) detecting the detectable label.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a CPVL variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to CPVL missense variant nucleic acid molecules (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to CPVL missense variant genomic nucleic acid molecules, CPVL missense variant mRNA molecules, and/or CPVL missense variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the CPVL variant missense genomic nucleic acid molecules, CPVL missense variant mRNA molecules, and/or CPVL missense variant cDNA molecules disclosed herein. The primers described herein can be used to amplify CPVL missense variant genomic nucleic acid molecules, CPVL missense variant mRNA molecules, or CPVL missense variant cDNA molecules, or a fragment thereof.

In the context of the disclosure "specifically hybridizes" means that the probe or primer (such as, for example, the alteration-specific probe or alteration-specific primer) does not hybridize to a nucleic acid sequence encoding a CPVL reference genomic nucleic acid molecule, a CPVL reference mRNA molecule, and/or a CPVL reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The nucleotide sequence of a CPVL reference genomic nucleic acid molecule is set forth in SEQ ID NO:1 (ENSG00000106066.15 encompassing chr7:28,995,637-29,195,276 in the GRCh38/hg38 human genome assembly).

The nucleotide sequence of a CPVL reference mRNA molecule is set forth in SEQ ID NO:2. The nucleotide sequence of another CPVL reference mRNA molecule is set forth in SEQ ID NO:3. The nucleotide sequence of another CPVL reference mRNA molecule is set forth in SEQ ID NO:4. The nucleotide sequence of another CPVL reference mRNA molecule is set forth in SEQ ID NO:5. The nucleotide sequence of another CPVL reference mRNA molecule is set forth in SEQ ID NO:6. The nucleotide sequence of another CPVL reference mRNA molecule is set forth in SEQ ID NO:7. The nucleotide sequence of another CPVL reference mRNA molecule is set forth in SEQ ID NO:8. The nucleotide sequence of another CPVL reference mRNA molecule is set forth in SEQ ID NO:9. The nucleotide sequence of another CPVL reference mRNA molecule is set forth in SEQ ID NO:10. The nucleotide sequence of another CPVL reference mRNA molecule is set forth in SEQ ID NO:11. The nucleotide sequence of another CPVL reference mRNA molecule is set forth in SEQ ID NO:12. The nucleotide sequence of another CPVL reference mRNA molecule is set forth in SEQ ID NO:13. The nucleotide sequence of another CPVL reference mRNA molecule is set forth in SEQ ID NO:14. The nucleotide sequence of another CPVL reference mRNA molecule is set forth in SEQ ID NO:15. The nucleotide sequence of another CPVL reference mRNA molecule is set forth in SEQ ID NO:16. The nucleotide sequence of another CPVL reference mRNA molecule is set forth in SEQ ID NO:17. The nucleotide sequence of another CPVL reference mRNA molecule is set forth in SEQ ID NO:18. The nucleotide sequence of another CPVL reference mRNA molecule is set forth in SEQ ID NO:19. The nucleotide sequence of another CPVL reference mRNA molecule is set forth in SEQ ID NO:20. The nucleotide sequence of another CPVL reference mRNA molecule is set forth in SEQ ID NO:21. The nucleotide sequence of another CPVL reference mRNA molecule is set forth in SEQ ID NO:22. The nucleotide sequence of another CPVL reference mRNA molecule is set forth in SEQ ID NO:23. The nucleotide sequence of another CPVL reference mRNA molecule is set forth in SEQ ID NO:24. The nucleotide sequence of another CPVL reference mRNA molecule is set forth in SEQ ID NO:25. The nucleotide sequence of another CPVL reference mRNA molecule is set forth in SEQ ID NO:26.

The nucleotide sequence of a CPVL reference cDNA molecule is set forth in SEQ ID NO:27. The nucleotide sequence of another CPVL reference cDNA molecule is set forth in SEQ ID NO:28. The nucleotide sequence of another CPVL reference cDNA molecule is set forth in SEQ ID NO:29. The nucleotide sequence of another CPVL reference cDNA molecule is set forth in SEQ ID NO:30. The nucleotide sequence of another CPVL reference cDNA molecule is set forth in SEQ ID NO:31. The nucleotide sequence of another CPVL reference cDNA molecule is set forth in SEQ ID NO:32. The nucleotide sequence of another CPVL reference cDNA molecule is set forth in SEQ ID NO:33. The nucleotide sequence of another CPVL reference cDNA molecule is set forth in SEQ ID NO:34. The nucleotide sequence of another CPVL reference cDNA molecule is set forth in SEQ ID NO:35. The nucleotide sequence of another CPVL reference cDNA molecule is set forth in SEQ ID NO:36. The nucleotide sequence of another CPVL reference cDNA molecule is set forth in SEQ ID NO:37. The nucleotide sequence of another CPVL reference cDNA molecule is set forth in SEQ ID NO:38. The nucleotide sequence of another CPVL reference cDNA molecule is set forth in SEQ ID NO:39. The nucleotide sequence of another CPVL reference cDNA molecule is set forth in SEQ ID NO:40. The nucleotide sequence of another CPVL reference cDNA molecule is set forth in SEQ ID NO:41. The nucleotide sequence of another CPVL reference cDNA molecule is set forth in SEQ ID NO:42. The nucleotide sequence of another CPVL reference cDNA molecule is set forth in SEQ ID NO:43. The nucleotide sequence of another CPVL reference cDNA molecule is set forth in SEQ ID NO:44. The nucleotide sequence of another CPVL reference cDNA molecule is set forth in SEQ ID NO:45. The nucleotide sequence of another CPVL reference cDNA molecule is set forth in SEQ ID NO:46. The nucleotide sequence of another CPVL reference cDNA molecule is set forth in SEQ ID NO:47. The nucleotide sequence of another CPVL reference cDNA molecule is set forth in SEQ ID NO:48. The nucleotide sequence of another CPVL reference cDNA molecule is set forth in SEQ ID NO:49. The nucleotide sequence of another CPVL reference cDNA molecule is set forth in SEQ ID NO:50. The nucleotide sequence of another CPVL reference cDNA molecule is set forth in SEQ ID NO:51.

The amino acid sequence of a CPVL reference polypeptide is set forth in SEQ ID NO:52, and is 476 amino acids in length. The amino acid sequence of another CPVL reference polypeptide is set forth in SEQ ID NO:53, and is 406 amino acids in length. The amino acid sequence of another CPVL reference polypeptide is set forth in SEQ ID NO:54, and is 490 amino acids in length. The amino acid sequence of another CPVL reference polypeptide is set forth in SEQ ID NO:55, and is 298 amino acids in length. The amino acid sequence of another CPVL reference polypeptide is set forth in SEQ ID NO:56, and is 233 amino acids in length.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×his or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat, prevent, or inhibit skin cancer for use in the treatment and/or prevention of skin cancer in a subject that: a) is reference for a Carboxypeptidase Vitellogenic Like (CPVL) genomic nucleic acid molecule, a CPVL mRNA molecule, or a CPVL cDNA molecule; or b) is heterozygous for: i) a CPVL missense variant genomic nucleic acid molecule encoding a CPVL predicted loss-of-function polypeptide; ii) a CPVL missense variant mRNA molecule encoding a CPVL predicted loss-of-function polypeptide; or iii) a CPVL missense variant cDNA molecule encoding a CPVL predicted loss-of-function polypeptide. Any of the therapeutic agents that treat, prevent, or inhibit skin cancer described herein can be used in these methods.

The present disclosure also provides uses of therapeutic agents that treat, prevent, or inhibit skin cancer for use in the preparation of a medicament for treating and/or preventing skin cancer in a subject that: a) is reference for a Carboxypeptidase Vitellogenic Like (CPVL) genomic nucleic acid molecule, a CPVL mRNA molecule, or a CPVL cDNA molecule; or b) is heterozygous for: i) a CPVL missense variant genomic nucleic acid molecule encoding a CPVL predicted loss-of-function polypeptide; ii) a CPVL missense variant mRNA molecule encoding a CPVL predicted loss-of-function polypeptide; or iii) a CPVL missense variant cDNA molecule encoding a CPVL predicted loss-of-function polypeptide. Any of the therapeutic agents that treat, prevent, or inhibit skin cancer described herein can be used in these methods.

The present disclosure also provides CPVL inhibitors for use in the treatment and/or prevention of skin cancer in a subject that: a) is reference for a Carboxypeptidase Vitellogenic Like (CPVL) genomic nucleic acid molecule, a CPVL mRNA molecule, or a CPVL cDNA molecule; or b) is heterozygous for: i) a CPVL missense variant genomic nucleic acid molecule encoding a CPVL predicted loss-of-function polypeptide; ii) a CPVL missense variant mRNA molecule encoding a CPVL predicted loss-of-function polypeptide; or iii) a CPVL missense variant cDNA molecule encoding a CPVL predicted loss-of-function polypeptide. Any of the CPVL inhibitors described herein can be used in these methods.

The present disclosure also provides uses of CPVL inhibitors in the preparation of a medicament for treating and/or preventing skin cancer in a subject that: a) is reference for a Carboxypeptidase Vitellogenic Like (CPVL) genomic nucleic acid molecule, a CPVL mRNA molecule, or a CPVL cDNA molecule; or b) is heterozygous for: i) a CPVL missense variant genomic nucleic acid molecule encoding a CPVL predicted loss-of-function polypeptide; ii) a CPVL missense variant mRNA molecule encoding a CPVL predicted loss-of-function polypeptide; or iii) a CPVL missense variant cDNA molecule encoding a CPVL predicted loss-of-function polypeptide. Any of the CPVL inhibitors described herein can be used in these methods.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: Meta-Analysis of GWAS Show Protective Gene Burden Association of CPVL Regeneron has performed the largest exome-wide cancer association analysis to date, which has led to the identification of CPVL. A meta-analysis of genome-wide association study (GWAS) carried out on UKB and GHS cohorts demonstrated that CPVL pLOF mutations were associated with a decreased risk of non-melanoma skin cancer (Table 3; phenotype=NMSC; chromosome 7, position 28995771 in CPVL). In addition, most of the loci associated with vitiligo in previous GWAS are protective for non-melanoma skin cancer (data not shown).

TABLE 3

Meta-analysis of GWAS in UKB and GHS

| Mask or SNP | Cases (RR\|RA\|AA) | Controls (RR\|RA\|AA) | AAF | Effect (LCI, UCI) | P-value |
|---|---|---|---|---|---|
| M3.5 | 30662\|2138\|22 | 470832\|40070\|563 | 0.0398 | 0.81 (0.77, 0.85) | 2.31e−21 |
| M3.1 | 32406\|416\|0 | 503306\|8139\|20 | 0.0079 | 0.79 (0.72, 0.87) | 3.19e−6 |
| M1.1 | 32765\|57\|0 | 510235\|1229\|1 | 0.0012 | 0.77 (0.60, 0.98) | 0.03 |

Mask definitions: M3.5 variant rs117744081 encodes missense p.Tyr168 in CPVL peptidase domain; M3.1 association driven by p.Arg464Gln missense in same functional domain; and p.Ser61Asn falls outside peptidase domain and contributes to M3.1 mask.

Moreover, GWAS carried out on UKB and GHS cohorts showed CPVL pLOF mutations are associated with a decreased risk of melanoma (Table 4; phenotype=melanoma; chromosome 7, position 28995771 in CPVL).

TABLE 4

| Mask or SNP | Cases (RR\|RA\|AA) | Controls (RR\|RA\|AA) | AAF | Effect (LCI, UCI) | P-value |
|---|---|---|---|---|---|
| M3.5 | 4922\|340\|5 | 497544\|41972\|584 | 0.0399 | 0.82 (0.74, 0.91) | 3e-4 |

Example 2: CPVL Expression in Macrophages

Publicly available single-cell RNA expression studies were analyzed to quantify the cell type specificity of CPVL expression (see, Table 5, Jerby-Arnon et al., Cell, 2018, 175, 984-987; Table 6, Yost et al., Nat. Med., 2019, 25, 1251-1259; and Table 7, Hughes et al., Immunity, 2020, 53, 878-894).

TABLE 5

| Cell Type | CPVL Fraction |
|---|---|
| Macrophage | 0.83 |
| CAF | 0.16 |
| Endothelial Cell | .011 |
| B Cell | 0.02 |
| NK | 0.02 |
| T Cell | 0.02 |
| T Cell, CD4 | 0.01 |
| T Cell, CD8 | 0.01 |

TABLE 6

| Cluster | CPVL Fraction |
|---|---|
| Macrophages | 0.6 |
| pDCs | 0.08 |
| DCs | 0.08 |
| Melanocytes | 0.07 |
| Endothelial | 0.06 |
| Tumor | 0.02 |
| CAFs | 0.01 |
| NK Cells | 0.01 |
| Plasma Cells | 0.01 |
| Myofibroblasts | 0.01 |

TABLE 7

| Disease | Cell Type | CPVL Fraction |
|---|---|---|
| Normal | Langerhans Cell | 0.86 |
| Acne (disease) | Langerhans Cell | 0.85 |

TABLE 7-continued

| Disease | Cell Type | CPVL Fraction |
|---|---|---|
| Granuloma annulare | Langerhans Cell | 0.68 |
| Psoriasis | Myeloid Cell | 0.66 |
| Leprosy | Langerhans Cell | 0.64 |
| Alopecia | Langerhans Cell | 0.64 |
| Alopecia | Myeloid Cell | 0.58 |
| Normal | Myeloid Cell | 0.53 |
| Psoriasis | Langerhans Cell | 0.46 |
| Acne (disease) | Myeloid Cell | 0.45 |
| Granuloma annulare | Myeloid Cell | 0.38 |
| Leprosy | Myeloid Cell | 0.34 |
| Alopecia | Endothelial Cell of Venule | 0.21 |
| Normal | Endothelial Cell of Venule | 0.17 |
| Leprosy | Endothelial Cell of Venule | 0.14 |
| Leprosy | Plasma Cell | 0.12 |
| Granuloma annulare | Endothelial Cell of Venule | 0.11 |
| Alopecia | Plasma Cell | 0.09 |
| Psoriasis | Endothelial Cell of Venule | 0.09 |
| Acne (disease) | Endothelial Cell of Venule | 0.08 |
| Granuloma annulare | Fibroblast | 0.06 |

Figure 2:
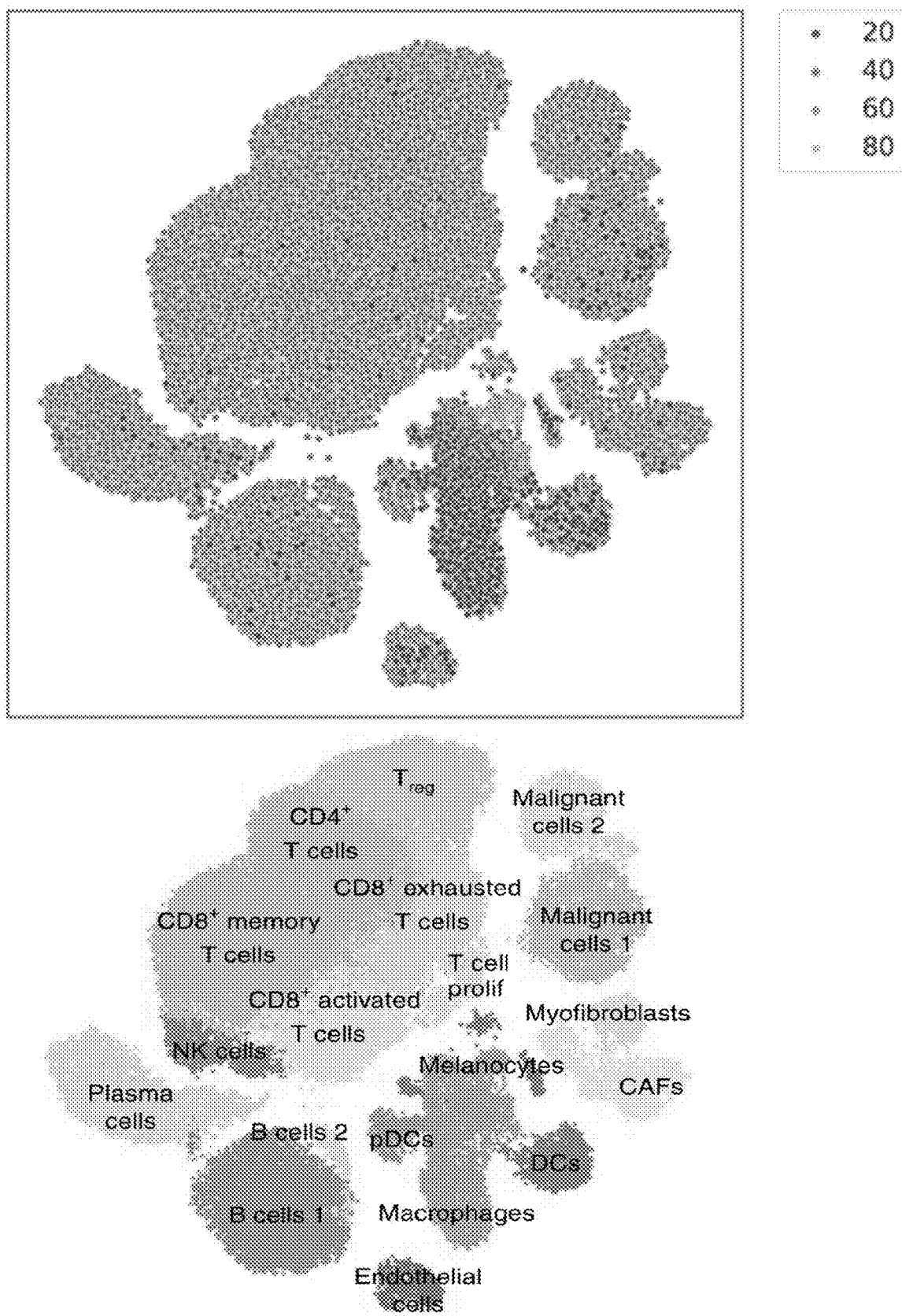
FIG. 2 shows CPVL expression (recovered molecules/cell) of basal cell carcinoma.

In the tumor microenvironment of melanoma tumors, CPVL was found to be expressed almost exclusively by macrophages. A subpopulation of cancer associated fibroblasts (CAFs) and endothelial cells also seemed to express the gene (see, FIG. 1). In addition, in a basal cell carcinoma (BCC) dataset, CPVL was found to be highly expressed in macrophages and modestly expressed in melanocytes (see, FIG. 2; bottom panel is from Yost et al., Nat. Med., 2019, 25, 1251-1259 for context).

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of treating a subject having skin cancer, wherein the subject is heterozygous for a Carboxypeptidase Vitellogenic Like (CPVL) variant genomic nucleic acid molecule, the method comprising administering a Carboxypeptidase Vitellogenic Like (CPVL) inhibitor to the subject; wherein the CPVL variant genomic nucleic acid molecule comprises 7:29096102:C:T, 7:28995873:G:A, 7:29030645:C:CT, 7:29096125:A:T, 7:29066109: GT:G, 7:29064221:T:TG, 7:29120891:A:C, 7:29071905:C:CT, 7:29071905:C:G, 7:29064060:C:T, 7:29064167:AC: A, 7:29086513: T: A, 7:29064132:C: CA, 7:29066026:G:T, 7:28995813:G:A, 7:29092703: C:T, 7:29195076:C:T, 7:29120892:C:A, 7:29066070: G:A, 7:29064236:T:C, 7:29095143:C:T, 7:29095143: CT:C, 7:29071879: AG:A, 7:29064077: AT: A, 7:29064100:TG:T, 7:29030600:GGA:G, 7:29066069: TG:T, 7:29064120:G:A, 7:28995858:TA:T, 7:29096218:C:T, 7:29120903: CT:C, 7:29112720:C:T, 7:29195076:C:A, 7:29030581: TGGAA:T, 7:29096219:T:C, 7:29096142:CAA:C, 7:29071905:C: T, 7:29121003: CAG:C, 7:29096102:C:G, 7:29064120: G:GC, 7:29071772:C:A, 7:29120995:GC: G, 7:29066060:G:GT, 7:29030645:CT:C, 7:29064060:C:

A, 7:29066032:CA:C, 7:29112740:G:T, 7:29120989: G:GA, 7:29112702:A:G, 7:29030604:GT:G, 7:29064150:TAA:T, 7:29064087: A:AG, 7:29064093: GC:G, 7:29112740:G:C, 7:29064060:CCTTAT:C, 7:28995830; GCT:G, 7:29064221: TG:T, 7:29086483: C:T, 7:29030760:C:CTGAAA, 7:29096207:T: TCTGG, 7:29066114:TC:T, 7:29072425:T:A, 7:29112817:C:A, 7:29064115:TTC:T, 7:29086488:C: T, 7:29095087:A:T, 7:28995863:C:T, 7:29092645:C:A, 7:29096130:G:A, 7:29112766:C:T, 7:29112757:T:C, 7:29096177:C:T, 7:28995863:C:A, 7:29066115:C:A, 7:29030726:C:T, 7:29030584: A:T, 7:29072407:T:C, 7:29064135:C:G, 7:29030749:T:C, 7:29095089: T:G, 7:29030710:G:C, 7:28995876:T: A, 7:29066063: A:T, 7:29064068: T:A, 7:29112774:C:T, 7:29071894:C:T, 7:29096198:G:A, 7:29112810:C:T, 7:29120923:G:C, 7:29086539:T:C, 7:29072410:T:C 7:29120922:G:C, 7:28995851:G:C, 7:29030642:A:T, 7:29096199:G:C, 7:29096169:C:T, 7:29030738:G:C, 7:29064134: A:G, 7:29064173: A:G, 7:28995809: A:C, 7:29096199:G:A, 7:29096150:C:A, 7:29030599:C:T, 7:29072321:C:T, 7:29030737: A:C, 7:29030578:T:C, 7:29096172:G:A, 7:29092663: A:G, 7:29030682:C:A, 7:29095097:T:C, 7:29086497:T:G, 7:29092632:T:A, 7:29030611:G:A, 7:28995872:C:T, 7:28995816:T:G, 7:29092666:C:T, 7:29066097:C:T, 7:28995859: A:T, 7:29086486:C:G, 7:29086549:C:T, 7:29072416:G:A, 7:29096136:G:C, 7:29095103: A:G, 7:29092638:G:A, 7:29092660:C:T, 7:29066058:C:G, 7:29072329:A:G, 7:29030727:G:C, 7:29095088:T:A, 7:29064125:T:C, 7:29086515:T:C, 7:29064122: A:G, 7:29064090: A:G, 7:29096171:G:A, 7:29086548:G:T, 7:28995873:G:C, 7:29066117:A:G, 7:29064101:G:A, 7:29030740:T:C, 7:29095089: T:C, 7:29064164:C:T, 7:29071803:G:C, 7:29064168:C:T, 7:28995864:C:T, 7:29096144: A:G, 7:29096172:G:T, 7:29071780:G:C, 7:29112725:G:T, 7:29092680:G:A, 7:29066071:G:C, 7:29096184:G:C 7:29096112:T: A, 7:29072423: A:G, 7:29030722:G:A, 7:29064098: A:C, 7:28995852:G:A, 7:28995846:C:T, 7:29030609:C:A, 7:29112754:C:T, 7:29092683: A:C, 7:29112732:T:C, 7:29096139:C:T, 7:29096136:G:A, 7:29112719:C:A, 7:29072347:T:G, 7:29086548:G:A, 7:29064092:G:T, 7:29112750:T:C, 7:29112735:C:G, 7:29096121:C:A, 7:28995814: A:T, 7:29066108: A:G, 7:29092693:C:T, 7:29096169:C:G, 7:29095101:G:A, 7:29064212:T:C, 7:29120929:G: A, 7:29030705:G: A, 7:29095086:G:T, 7:28995812:C:T, 7:29096143: A:C, 7:29030577:C:G, 7:28995822:T:C, 7:29096174:C:G, 7:29072380: T:C, 7:29066105: A:G, 7:29064213: A:T, 7:29096138:T:C, 7:29064174:T:C, 7:29086498: A:G, 7:29064152: A:G, 7:29096159:G: A, 7:29096160: A:G, 7:29030750: A:G, 7:29071781:C:T, 7:29072339:C:T, 7:29030600:G:A, and/or 7:29096120:A:G; and wherein the CPVL inhibitor comprises:
i) an inhibitory nucleic acid molecule that hybridizes to a CPVL nucleic acid molecule;
ii) hydroxymethyl(N-methyliminodiacetic acid)boronate (hydroxymethyl(MIDA)boronate), azidomethyl (N-methyliminodiacetic acid)boronate (azidomethyl (MIDA)boronate), or an α-functionalized alkyl (MIDA)boronate compound;

iii) a compound selected from the group consisting of

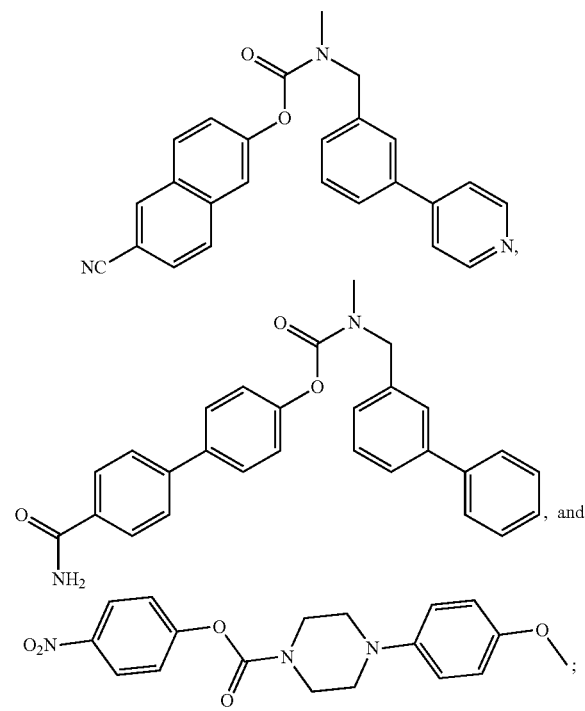

or
iv) an immune checkpoint inhibitor.

2. The method according to claim 1, wherein the skin cancer comprises non-melanoma skin cancer, basal cell carcinoma, squamous cell carcinoma, melanoma, Merkel cell carcinoma, dermatofibrosarcoma protuberans, or sebaceous carcinoma.

3. The method according to claim 1, wherein the inhibitory nucleic acid molecule comprises an antisense nucleic acid molecule, a small interfering RNA (siRNA), or a short hairpin RNA (shRNA).

4. The method according to claim 1, further comprising detecting the presence or absence of a CPVL missense variant nucleic acid molecule encoding a CPVL predicted loss-of-function polypeptide in a biological sample from the subject.

5. The method according to claim 4, further comprising administering a therapeutic agent that treats, or inhibits skin cancer in a standard dosage amount to a subject wherein the CPVL missense variant nucleic acid molecule is absent from the biological sample.

6. The method according to claim 4, further comprising administering a therapeutic agent that treats, or inhibits skin cancer in a dosage amount that is the same as or less than a standard dosage amount to a subject that is heterozygous for the CPVL missense variant nucleic acid molecule.

7. The method according to claim 4, wherein the CPVL missense variant nucleic acid molecule is a splice-site variant, a stop-gain variant, a start-loss variant, a stop-loss variant, a frameshift variant, or an in-frame indel variant, or a variant that encodes a truncated CPVL predicted loss-of-function polypeptide.

8. The method according to claim 7, wherein the CPVL missense variant nucleic acid molecule encodes a truncated CPVL predicted loss-of-function polypeptide.

* * * * *

SEQUENCE LISTING

```
Sequence total quantity: 76
SEQ ID NO: 1          moltype = DNA  length = 199640
FEATURE               Location/Qualifiers
source                1..199640
                      mol_type = genomic DNA
                      organism = Homo sapiens
SEQUENCE: 1
gctcctttcg cttttcgctc gctgcactcc aagcccgga acacccgcgt ccgcacacta   60
agggcaccac cgctctccca cctctgcgct gtcagatgtc aggcgcggag gtgtctctggg  120
caccgaggtg ctggcgaacc aaacaagtat caccccggac gcctgccccc attccgagag  180
agcgggcggg atgccacag gtaggctctg tccatcccag gctgcggggc gagggcagtg   240
gggcgagacc cggcgcggca gcagcgcccg acgggctgaa actcaccgga ggacaccgac   300
gagccggaca ggctggagtt gctggacgct gccatctccg cgcgcccctc gcgtcgctgc   360
tcgctcagcc ccggtgcgga cgccgccgcc gctgccctcg cccggccgct cgcagcctcc   420
```

```
gcggccccca gcccatggca aagtcctggg gacgcgcaga aagcaccagc ctccggactc    480
tgcctgcact tcctgctcca ccagatgacg cgctgccgcc gccgctattt atttgtggtt    540
tccgtcccgc tccgcgcctt tgcacgcttt tctatggtg tcaggggta ggtgggagca     600
gagggaggcc gaggggcagc cgggacgggc ggatctcggc tcccgccgag cccctctgcc    660
gtccacgctc ccctgtgcgc ggctgggacc agggcgtcc ggcagctccg agccgccccg     720
ccagctcccg caccctctcc tgggctcccg cctctcccgc cgcacttcga gtagaccggg    780
cagaggcggc gggagacgga cagacagagc gacctccccc ttctccctcc gccccaactc    840
cgctcgcgca cacacaaagg aagaagagga gacgcggtcg ctcggggggt ggttcggctg    900
ctgcgggctt gacagctccc gccactgggg ctggagggg aggctgcgga ctgctggaca    960
ggggaggggg ggacggggga ccgggtcccc gggtgctgg ggaggccggg gccgggcggg   1020
gggcgagcgc ggctgctgcg cgcagcgctg ctcctaggat ttgaagggga tggggaggga   1080
gggtgtgggg gaaggtggtg gggctcaccg cgccccgccg ggctctcgag cagcgagaca   1140
gtgggggtgg gggatccaga gggcgaaggc gggatcacta gggccacggt gctaggcaga   1200
agggaacctg ggatgacaga gccactatgg agcgctcctt ccactcctct ccaaattgtc   1260
ctttgttgct ctggagctga cggtccctgc cctgcaagaa ggtgcgtttc ctaaacacc    1320
cgggaagcca acccagctac acttaagtaa cccagccacg gacagtgccc gacgcgtccg   1380
tgggcctctg aggttggcct tcaaagaaat agagccgtcc aaacgtgtca tcaggcccac   1440
acaaagctgg tgtcaaagag aaagaggttc tccgtgcctt gcaaaaaaag attctcacaa   1500
aagacttaag acttggcagc aggtccgact gtgcccttc aggataggaa ctgctcaggt    1560
gtgtgagaga aagagactcg agcacaaggt gtgtcccttc cccctgtatt taaacctaaa   1620
ttaatttcac tgggaggaaa taccatgcag attttttta agtctgttc acgctcccag     1680
cgggctaatc ggttctttca atcctaaagc aacagaaaac tgtgaaattt gaagagaaat   1740
tgttagatca aaggaaaaag caaacattaa aggaatgaaa gtactctcat tatatagcaa   1800
aaatggaaag tgttcacatt ggggtagttc aactttttaa aacatggtta aaagaacata   1860
gtcaatttaa aaattatcag gagtgacaca gaacagcagc taggccctgg ggatccacat   1920
caaccaagga cctaacatac agtgaataat gaatgttaaa taatcacagt acgcacccac   1980
gtcacatttt ctagttgatt agaacttaaa aaaaaaaatc cctccaggat actatcccag   2040
tgtgtcttct cattaaggtc cattttttaa aaatacacct tgctaaactg ttaaaggagt   2100
gtgagcactc ttcagtcacg tgggactgcg tcttcctacc cctcaactgt atggaccttg   2160
aaacagccct ggctggtcta aggagaccca agcgcccgca ttttcccagc ccctaccact   2220
atccttcatt ttgtgactg cacgaaatga tgcagttcct aatctggagc cttcagggac    2280
acgtgaccca tcacacactt ggctgttga tcagatcaga aggaacttac tgtttcccca    2340
gagttcttct gatagaaaac agcacttact tgtttgacta gtaatctatg tagccccca    2400
gatcttaga tggtggacta tctgctcgcc cggtagaatt ttaccatctg               2460
ggcttcgaag acaactgggt tcaaactctg gttctgtcac ttagctgcga acttgagcaa    2520
attacttaga cctactgagc ctcagtttct cacctgccca caaaaatctg ataacacagg   2580
atgctgtgaa gattaaataa gatgctatgt ggaaagctac agtgtacctg gcatgaagtt   2640
tgtgttccaa agtgattgta agttgctcac tttaaggaag aatgtatag tttgaaaat     2700
ttttgctttc ttcattgcat ctggagataa ctaatcaact gtgacctgtt ctactagggg   2760
gaaatgtctt atcttcaatc tatggcttat atttcttgtc ccaaattgtg caataggta    2820
acaggtttca ttattcatct ctgaaatttc acaaaaggac aacagattat gtttctgcag   2880
ttcggatact catatttccc ttcatagtgt tttaactgga gaaagtaaag catggctctg   2940
tgaggcagat tattttttatt gtcctaaatt gacagatgaa gggacggggg tatttgctgt   3000
gaaggcacca cctgaaggcc ctgtgctgta cagaagtaga aaaagctga gactcatgtt    3060
ttcctgatc ctggggccag aagaggaata caaggcaaac aaaacacgctt gctgaacaga    3120
gaagtgctga tgggggaggc ccagtctgtc ggtgtgtatat gagctataac tttgacaccc   3180
attattttga ataccaaaca gaaagctcca ggttcagaac taaaatctga aagttgattg   3240
atcatctgga ttgataaagc cataaccaat gcagaaaact caacatgaat aatcattcac   3300
tatcatcctt cttagattca ggagcctgaa ggctggctgc tccttgcaaa aatgtttagt   3360
atcagtaagt tatcaggaca tgctggaaat aaaaatgctaa catccctctt tggtaggctc   3420
agggacctgt ttgtggacct tctaaagtat ttctccaaga gaaacaatga aaaagtatc    3480
atctattta ttcatttatg tgttgcctta attctaggta ataccctattt gccagtggaa    3540
agaatattgg tgctacagaa atcttaattg ttttggaaagt agaatttaa aagacatttc    3600
tgccttttt cttcaaatat taaaagactt atgggataaa cggagtcttg tggataatgt    3660
gggcttctta agaataaaaa ttatcattt gttttaactt agcttttcacc tggcattcaa    3720
agccttccaa acttaccttt ccaatctaat ctctgttccc cccttttcaca aaggcaaccc   3780
tctttcatgg tggcctatgc ccttgggct agcagcactg gattctgcca ttccttcctg    3840
cttcccatcc tacataccaa aagggttcaa ccagaatgca ccttctctgg aaagttttcc   3900
ctgattccca aggcagaaaa taactcttct tctgttggat ttctctagtc catctactgt   3960
acctctcaat gggcagatct catgctctgt cttattttaa tggtactttt ggtatatatt   4020
tcattacctt agtccattaa tagcgggctt ggcctggtgg ctcatgccta taatcccagt   4080
gactcagtaa gttgaggtgg gaggatccct tgaggcaagg agtttgagac catcctgagc   4140
aacatgaggc ctcatctcta aaaacataaa aaataaatta gccaggcgtt gtagttaacc   4200
tgtagtccta gctacttggg aggctgaggg gggaaattg cttgagtcca gaagttcaag    4260
gatgcagtga gctctgttga tgccactgca ccccagcctg ggagacagag tgaggccctg   4320
tctcagggaa aaaaaaaaa gcatggtggg gcaggatcc ttgtttgccc agcccctgta     4380
ttgtctacca tactttgcat acaataggtg tcagtggat gttgttcaat tgtttactca    4440
ttgagtaaat gagcaaatta aggacatctg taaatggttc tcttgtatgc cagttcctt    4500
ccacgttagt agctgtgacc actgagctac aagacaatga gtaacaacac atctgcagca   4560
aaagaaagaa cttgacgtc atgtaaggat actacctttg ctgtgatcaa aaaagactga   4620
aacggtgaaa cataagaata aatcttgat ggagtaaata tttgcaatcc caccccacc     4680
ctccttcacc ggctgttaca attcacatga tttattgttt gcagggtagc tcttatggtg   4740
gtgtaatttg tttatttgt ttcaccattc tttgaagtt taaagcaga caagaaagca     4800
ctgcagggtg aacgtggctg tcatagcagg agctgtgctc cctcactgca ggcattctgg   4860
agtgtttttt agtgaaggtc attccctttc cctgtgctaa acacagaatg aaatactgta   4920
ttccttactt tcaagattaa tccagtggt ggcattcaca ggagaatagc agggctattc    4980
gtcaactagc tttaaatatt ttatggcaag tactctaccg tacccctgaaa gtggtccttt   5040
tgccatcaat ttctcaacat caaatgctc ttttgctgta gtgagaaata tttcgctctg    5100
tagtttaagc cttatttcaa atacaaagac acctagtcct gagaaagaga acgcattggc   5160
```

```
tcttctgagg caggcgtcac taggggcagg agctgagaaa cccgctgttt cctcaggagg   5220
tgcacagacg gcccaggatg ggttaatgag caggcagctc agacgccgca ggtagcggcc   5280
ctgcctctga acaaagagga gtccacacct ggggtgcaga caaagggagg ccgcctctgc   5340
tacccaattc ccagttcaca tcgcctgctg ctggggaccc ctagtggcgg cacacgacgg   5400
aggcacaggt attcctgcat cgtctttctc actgagctgg gggggcgctt gggggtattg   5460
cctggagtat cctatttggc cacttagctt gggcggatca gatcggcaca tgcaggcact   5520
taaggcatgc catccgctgc agtctctttg actggaaaga cagagaggga gaaggggagt   5580
gtaggggtg gggggccgag agagagagag ttttctttc tgtttgaaga gaaaaacagg    5640
atagcattca gaaactcatt gaatatgttt tcttctgcat gttgcacctt ctggctttgt   5700
tccctgacac ttcaggttac aaacatcttt tctgtcttca atgtcctaag agaaatctag   5760
gataaactaa agtgaagcca gctgtaagcc tgctctgggc aaaagcaggg agtgagtttg   5820
ttttttcgtgt cttctgcggg ggttcctatg gctttatgct cttttctat gaaaatttgc    5880
tttcataacg atatccaata tattcattct ctactacctg ttcatttatt caagcattca   5940
ttaattcact cagtcatgtt gactaaacac tcattatgtg tcagggagta tacgaggcct   6000
ggggaataaa gatatgaggg aaactggctg ggcgcggtgg ctcacacctg taatcccagc   6060
cctttgggag gctgaggttg ggcagatcat ttgaggtcag gagttcgaga ccagcctggc   6120
caacatggtg aaaccccgtc tctactaaaa atataaaaat tagccaggcg tgatggtgtg   6180
cgcctgtaat gtcagctact cgggaggctg agacaggaga attgcttgaa cccaggaggc   6240
agaggttgca gtgagctgag attgtgccac tgtactccag cttgggcgac agagcaagag   6300
attctgtctc aaaaaaaaaa aaaaaaaagg tatgaggaaa actatatcct tgctgtgggg   6360
gatcctacaa aacaaccttg actccttcct gtgacattta catttcaact gggacaaatt   6420
tttaaaatag ctatagaaat gatttctgtt tgggaattaa agctattatc catgccggtg   6480
acgactttct tttcagcagt tttgttgttg ttgttgtttt taacaaaacg tccaaaatca   6540
agcctcaaag actatttcta gacagctggc attttcttat ccacagtttt agcttgtcag   6600
cccagggaac cgagcagatc ctgtactctg aatgtcctct gccttcactc cccaagaaaa   6660
tctgaatcaa tattttcatt tctttccctg tagcagctat acgttcaata acaaaacaga   6720
aatcctcttt ttttttaaaaa aaaaataaaa aaaggagagt aaatgggcat tgaaggaaag   6780
ctaacagaca caatatctga gccaatcttc tgatacagaa aacatatttt ggccttttac   6840
aaatattcca gattgtctgt aaaacaaagc atgaaaaat gattctagga aagtttaata    6900
tgtatttatg gagtcaaaaa gacctggct tcactcctag cttgtcattt attagctgtg    6960
tgaccctgag caaattattt aatcttatat tcttggtctc taaaatgggt taataatccc   7020
tatttacaga ctttgtgatg atggaatgaa gtgatagatg taatatagtg tctaaagcat   7080
aaaagtccga ttaggaactc taggtggcct ctgttcctta gagcaaagta tagcgtgctc   7140
acatctgctt ttctggagta atctgtgaga attaaagtct gatgcaaaag taatttcat   7200
ctctccctac caccccctg ttacatcacc tctatgcgag tatattaaga cataggagcc    7260
aggcctgggc tttgaagata aatctgagtt caaatcctaa tttagctaca gatactttgg   7320
tgatcttgga caaataacct ttcacattca cagtctcctc atcaggtaaa atggagataa   7380
taatatacct catatttatg taaatgaatg tatgcccaac aataatgtta ttagcactca   7440
attatattct gcacggcagg tagttttaa ctgtgtatta attcctgggg agagagtgga    7500
tgttgacaat acatcaggat cttttttttat tttttatttt tattttttga gagggagtct   7560
tgctcttgtt gcccaggctg gagtgcaatg gtgcaatctc ggctcattgc aacctctgcc   7620
tccctggttc aagcgattct cctgcctcag cctcccgagt agctgggatt acaggtggga   7680
ttacaccaca acaccccagct aattttttgta ttttttagtag agacgggggtt tctccatgtt   7740
ggctaggctg gtctcaaact cctgacctca ggtgatccgc ccacctcggc ctcccaaagt   7800
gctgggatta caggcgtgag ccaccgtgcc tggccataca tcagaatctt taggaagtgg   7860
catgtataat ataacagagt acactcaagt gctctctgtc tctctctttg tcacacacac   7920
acacacacac agacacacaa acacacacac cactagatga taatgtctta catctggaca   7980
tttccccacc cagtcccatt gggtgagaaa cctggtggaa tttcaaagta gatttcaata   8040
aaagtataga cagattactt aagctctctg ccaaatttgg cccctataag ataaaggagt   8100
ggaaaccaac atttgatgac cactactact gctccaggta ttatgaccac tctccaccatg   8160
ctttctgcca ttagtgatat agaaaagtca ctctccttaa gtaatcattt cctatgtgct   8220
aggatcatgc taaacacttt gtatacattg tcatataccc ataacaatcc tgaagtgaga   8280
attgttatcc tcattttcca tttggggaaa ctgaggctag aaaacttata taatatctta   8340
attaaaatgc tcaacaactc cagctgtaga tattatcatc cctgctcttt ttggttaaga   8400
aaacaaaaaa ttagggtaag taatttatca aggttacagg cattaatttg aacccacctt   8460
tggctgattc attccaatac acactaaaaa aaaaattacc ctttagtttt tacttgaaat   8520
ttcagcctgc tgttatggta agtattttcc tgtttgagac tttagtcagt tgagaagtct   8580
ttaaaataca tgttctttgc ttgaatactc atgtttttat ttttattttt ccttccttct   8640
ctccctctcc ctccctccct tcctgcctct cttccttcct tcctccctct ctttcttttcc   8700
tttcctttcc tttcatctct gtcacgcagg ctgcaataca gtgacacgat cacagctcac   8760
tgctacagcc tctacctcct gggcttaatc catcctccct cctcagcctc caagcagct   8820
gggactacag gcacgtggct gcttttttaaa attttagtg gagacagggt tttgcaatgt   8880
tgtccaggct tgtctcagac tcctgggccc aggtaatcta tccaccctgg cctcccaaag   8940
tgctggtaca ggcgtgagcc aacacgcatg gcctacttat gttttttcaat ttgaacctat  9000
gatgatactg tcattttttt tttgcctaaa acataaactt tggggcaggc caggctctgg   9060
ggaactcata ggacttgtac tcctgacccc aagggccctg gcaaggacag gcacagtata   9120
ggaagactaa gaagtcattt gcctgagtgc aggaatttca agggatcaaa attattccct   9180
aatcaaaaac tccatcctgt tcaacttcca gttgctcaga gttccatagt tagaacttt   9240
acttcttaaa cttactcaaa caatacagtg agcatctgcc ataatttgat cacctctgtg   9300
gaactgaagg aattaaataa cgattttcac atgggcgagt ttccctatcc ctaaaagcta   9360
aatttaattg caaggaggga ccaacacata ggacagggct gtgcaacctt taatatatct   9420
acatattggt cttgctaaaa tgcagattca catccagggg caggccctg aatttccaac    9480
aagcttggag gtgatgtgaa taattttgaa taataaaggt cctagggcga tggtttgcaa   9540
tcggggtat atatgagaat cactcagaag gcttttagaa gcttccatgc cgagatcacg   9600
ctccagaata aacaaatcag aatctgaggg tggcagaagg tagaaaccaa atatcagcct   9660
ttttttttttt aattcccagg tgattttgat atgctgctaa ggtttgataa agaaaatgag   9720
attcagagaa cagattatat tgttgaagag cttgactgga aatggtaaga gctaatgttg   9780
ctccatgttt ttgccgggat tgtctctggt catgaaggaa agagagggaa tcaaattctt   9840
atcaagagcg tgtaaccaca gacatcatga tatgagaaaa tagaataaaa tctaacatta   9900
```

-continued

```
gcatgacatt ttctcagtca atgtggggca attcttcttc aaattttggt ccatgttatg   9960
atctttaaaa gacacttctc aatgaataag cataaacaat aggcacttag ggtcactccc  10020
acaagaacag ccagctgtca gtgaggcaga tgttttccag caaatctact ctatcatttc  10080
tcaatcataa agaagattag aaatgggatt ttcagttcag atggggttga aaggtgatgt  10140
ttatgcctga gaaatacttc acaccacagc tagaaaaatt ggtttggaga aaaaatatct  10200
cacaacttct taggtgttct gaatatatga aaataaaacc ctcagcttgg acagaaagag  10260
ggggtatcac agacaaatgc acttagagac atctactctc aatggtggca gcaacagaga  10320
ggcgaaagta ttttagctga ctctttatgc ccaaagattt ttgtccttat ccacataaac  10380
tcccattcct cagggctggc attgaaaggg tgaataatta agtcaaccac aatgtttaca  10440
gtggttaact caggtgtgat gcttaatttt atgcgtcaac ttgattgggc tgtggggtgc  10500
ccaggtatgt ggtcaaacat tatttctggg tgtttctgtg tgtctttgaa tgaagttaaa  10560
tttaaatcag aacactgagt aacacagatt ttcccccagt atgtagatgg gccccatcac  10620
atcagttgaa ggcctggaga aaacagaaag gctgacccct ccttgagagt aagagaaaac  10680
tcttgtgatg gccttttggac tgatcatcag ctgttttcct gccttcagat ccaaacggaa  10740
acattggctc ttcctggggt tccagcctgc tgtcttgaca ggaactatac catcagctct  10800
cctgggtctc ttacatgcca agtcatcctg cagatctggg actcactccg taatcagtga  10860
gccaattgca tatactaaat ctctcttatc tgtatatctc atacagtcat atattttctc  10920
ataaaatat atatatgaga tacatagatg tatgagatat gagatatacc atatataaa   10980
ttcctaaaata tatatatcat atatatccac tatatatctt atatatagat tgtatatgta  11040
tatctcctat atatatttct tctataaata tctcttttat ctatctatct atctatctat  11100
ctatctatct atctatctat ctatcatcta tctgtatctt ctgtacagtt agtagtcctt  11160
tggtatccat gggagattgg atccagaacc cccactcaga tatcaaaatc tgcatatgcc  11220
caagtgtctt atataaaata gtgtagtatt tgcagataac ctatgcatag cctcctgtat  11280
acttgaatc atgtctagat tacttacaat acctatacta tgtaaatgct atgtaactcg   11340
ttgttatgcc ccattgtttt ttatttgtat cattttttaat tgttgtttgt aattttttat  11400
gttttttcta acatttttgg ttggttgaat gcatgggtgt ggaatctaca aatatagaga  11460
gctgactgca tatgtatctc ctattaatct atatctaatc tacatatatc atatatccta  11520
tacatatatc ttcctatatat ctctcttatt ggttctcttt ctctagagaa tgccaccaat  11580
tcagcactta aaaaattctg ggccaggtgt ggtggctcac acctgtaatc ctagtacttt  11640
gggaggccaa gaccggcaga ccacttgagg ccagaagttt gagaccagcc tggccaacat  11700
ggtgaaaccc tgtctctact aaaaatacaa aagttagcca ggtgtggtgg cacacacttg  11760
taaacccagc tacttgggag gctgaggcaa gagaattgtt tgaacccaag agacaaaagt  11820
tgcagtgagc cgagatcatg ccacctcact ccagcctggg caacagagca agaccctgtc  11880
tcaaaaaaaa aaaggctagg cacggtggct cacacctata atcccagcac tttgggaggc  11940
caaggcaggc agatcacctg agatcgggag ttcgagacca gcctgaccaa catggagaaa  12000
ccctgtctct actgaaaata caaaattagc cagtcatgtt ggcatatgcc tgtaacccca  12060
gctactcagg aggctgaggc aggagaatcg cttgaacctg ggaggcggag gttacaatga  12120
gccaagattg cgccgttgca ctccagccta ggcaacaaga gcgaaactcc gtttcaaaaa  12180
aaaaaaaaaa aaaaagtctg ccatgttttc cagttgcctt cgtacctgtc tcatataatg  12240
ggaagattct ggagggcagc aatggtgctc tgctgttttc atatatccct tctttaaccc  12300
aagaatcttt cctgtaatag aatttcaaaa atgtagaatc cagctgagtg tttatctttg  12360
ttctggattc tcaagccatt taaggcagc aggctgtcat gattttccac acaaaagggc   12420
aaaaacggga ttaacacaat aggatgctgt ctctactctc atctaccctg tccaaggaat  12480
ttaatttcct ataagcctac ctccaattcc ccttgggaca gttatattta agaaccttaa  12540
tgcttcagac cctctttttga cattaaatct ttgtctgctg aatgctaaca atcttgaggg  12600
acattgggtt tactcaattt gtattttttag acatgagtgt acgtaattgt gtagacaaag  12660
tatttgaacg ttgaattgat atttttaaagt tttgatccaa atgtgtgata ttggataaaa  12720
atactctagg aggcttaacg tgggtaatac agactaaact tgtcaagtag ttaaatagga  12780
tgatctggca ggacttatga aaatgtctga agaatattac aactttctac gttttctttt  12840
tgatctgggt ccccatagcc ctattctgct acactctatg tgtcatatca caatgaggag  12900
cttttgcttt ttactgctgc ttatgatctt atttcattat tggtaggtgg aacactatca  12960
gattaataca actctcttta ggcattgaat agaaagattc caccactgct aaccttcctc  13020
tgcgctccta tttttcaaac tctatcatta ccttctcttc tgtagagcat cctgtcacca  13080
tcttataata gaagttcagt tcatttgcat atgcatttgc aggttttcat taagaggaag  13140
acagcaggagt gattaatgag tgttagttct catttttgcaa aaggaatatt gtctttttaa  13200
aaaatattcc atctttcaga gcactgaaag aaatagttat aatttaagta agaaaaagtc  13260
atttacagca tttatgttat ttaagatgtt ttgcttataa agtaatccat gcttactgta  13320
gatatgttaa aggcaaaaaa gagataagta aaacaaaaaa agaaatcatc catattccct  13380
ccaccatgaa taaatactta ggtacttttc cccccccttag gaattagcag tttagcagcc  13440
tgattttgc agtttacatt acatagcaat atgaacattc atgtggaaaa aaagtttgtt   13500
aggacctata taaaaagtg tctatttggg aatgttaaga tcattagtgt ctactttatt   13560
tagttttct agattgtgta attttaaaa tgaatacatt ttacttttct agttggaggc    13620
cataataaag ctactttcct tttggaatga acttgtacaa ttattccta tgtcttatag   13680
attcctaatg tgacttttaa tggcaatata aaattccttt ctattaatct acaataattc  13740
atgttgttat tcctccattg attgaaattt aggttgtttc acagttttttg gcttttctg   13800
aattactctt ggacaaactt ccttacacat aaatctatat gtgcctttct gtttatttc   13860
ttaggcttga ttgctgtaag ttgaaacacgt cagtggcatg gcaccagct gcacaaccct   13920
aggagccacc aaacacagta tattctatat aaatgttgct gccaggagcc ccagttcaaa  13980
ctacaatgtg agtaacgcct gctggagtag agcaatagct gaagccttgg tcaaaggcta  14040
tgaaaatgtt taaagcacta gataaaaatt gccaagctgc cttctggaaa aattgtctga  14100
atttatattc attccagaac tcaccacata tatcatgact gagaattaga atatatttta  14160
aaacacaaat tccctaggaa aaaatggcct cccattgctg tattcatttg tatctaactg  14220
attactaggg agattaactt tttgcttatg tctactagtc atttgtatt cttcttttgc    14280
aaactgccta ttcatctctt ttggcaaaat aatagtaagt gctgggtacc agtgattggt  14340
accaagagtt gtttatgtat gatcttacgt actcttttca attacactgc aagcagtcat  14400
gcttattatc tccatattac aaattagaac tccaagaggt atacggatga tacgagtctt  14460
gtccaacatc acacagaatg tgacagggcc tggatttgaa cccagctcta actccagagc  14520
ctgagctctt aatcactgga ctctagtgcc ccttaattag tgtgttagtg ttcttcttat  14580
tagttttgtaa taactcttta catagtaatt ataataactt ttaattggtc aaatttgtgc  14640
```

```
caaaggtatt tttattggct catcatttgc cttaatttga tttatacaga tttaagtcat   14700
ttttatatca atttagatga cttttttttt tttgagatgg agtcttgctc tgttgctctg   14760
tcgctctgtc gctctgtcgc ccagtgcagt ggcgcgatct cggctcactg caacctccgc   14820
ctccaggttc aagtgattc tcctgcctca gcctcctgag tagctgggac tacaggcatg   14880
tgccaccacg cctggctaat tttttgtatt tttagtagag atagggtttc accgtgttag   14940
tcaggacggt ctcaatctgt cctgaccttg tgatctgccc gcctcagctt cccaaagtgc   15000
tgggattaca ggcgtgagcc accacacccg gcctagatgt cactattggt acgttatcac   15060
atttaaaaa tattctaaat ttgattcaca atattattaa aatgtttgat gtgaaatatt   15120
ttcctttcta ataaaaaaac tattgggaa cagattgact tcggaatatt aagaatgaaa   15180
cacatgtaag cataatatgt gaatatttgg aaatgaaata acctacatca ttgatgaaag   15240
gacatcttat ttctcattga tatttccact gtctgcaggg aaatataatc atttgaaaat   15300
acaagacaaa tagcaaaaga tcaatagaat gcttagcaat gtaagttatc ttaatgcttt   15360
caaaataaca gtgaccagat ttttttgttg taatacttaa gttgatttgc ttgcaataat   15420
aaataatcc tcacatgcac taactcagtt ttgcaaagca taagaaaaca aatgaacctc   15480
ataaatgcta tatagcccct ccacaaatgt ccagttctta cccgtgtttt gcattgatat   15540
aaaatagaat agctattaag tattttgtaa tttgagaaat aaaaaacctg gtaattattg   15600
atggtttctc tacttagaaa aaggagaata tttatttaca tatatcagag taattctatt   15660
tggcaaagga tatatagcaa aataatcatt tgtgttacta acatctgcct tgttcttgct   15720
tatgaagaag acttaggaca agtatcagaa tcttttccttc tcactcctga agaatttgtg   15780
ttgagtctgg gttcctggat tttctagcat ctgagagtgg tcaaaaaatt ctcagactgc   15840
aaaacttcag cctgagtttc tgtgcagagc attctgagt cttttcttca acaaggctga   15900
ctgaagaagg ctgacactgt gtgggaagga aggcagaact gatctagcaa agagtgaagg   15960
gagcactctt cctcatgact tggcgtggga tgggtggtt cttaaggatg gcatcccatg   16020
cccactctca tgcagtgctg tgtgagggga tgagccttc tgaagggttc tccaagatg   16080
gcagcatggc ctaacacaaa taagcctat gcccaagctt ggcaaaaaga aaatggaggg   16140
gctgttttca aagggtccat gaggactgta agtgtgtcag catgatattg gaggatcacc   16200
tcctgttttc tgacaccaag agagatgctg gtcccctat aatcctaagg aggcaggaga   16260
cctcaaaacc ataactgagg aggtgcaaat gctggttagc tctggtaggt ggggtcctgc   16320
ctggactata atgtccctta aatggtgtgt tagtgttctt tttattagtt tgtaataact   16380
ctttacatag tagttaacct ttgattggtc aaatttgtgg caaacccatt tttattggct   16440
gattatttgc cttaatttga tatatcatag ggatttaagt cattttttcat atgaatgcag   16500
atggctaatt ccactccaag ttgtgaaatt aattaattaa tgccaaacag tcattcaaca   16560
aacaataact gagcccctac tatgatccag gcataggtat agaccctgag aatataacaa   16620
taaacaaagt ccctgccctt aagaggcaca gacaatgaac tgcttttttt aaaagataa   16680
cttcaaatgc tgaaaaatgt gttcagatga acataaaaca gcatgtcagg caactctctct   16740
cggaggatgt gacatttcag cagagacttg atcttgcagg tctggaggag ggaacagcag   16800
atttaaaggg ctgagtcaga cacgagctgg gcatgttaga ggaacaggaa aggcggccag   16860
tggagctggc gtcaaaggaa tgaaaccgca cgcagaggaa gaccaggtca gaggctgagt   16920
agatgtcaga tcctagcagc cacgtgggtc atagtggaga cttctgttt atttctagac   16980
acaatgggaa gccacagaag cttttaggaa ggggataaca tgttctgatt cactctgaaa   17040
agatcacttt ggcagctatg gaaaaggata gtaagaagag cagggtgcac ggtggctatg   17100
tgactattcc agtggttca aagaaaggct gatggtgtgg acagaggata gtagcagtgg   17160
agatgcaag acaccatcag acttaggta gaatctgaca acacttctg atgatggaat   17220
gtgaggcatg agataaacaa tcatcaaggt gactcctagg tttttagctg agcagttaaa   17280
tggctggtgg tgccacttgc tgtgatggt agggcttggg gagggggaac tttgtgtggg   17340
gatggaaccg agggttgtgt ttcggacatg tgaagtttga ggcacctatg aaatgtctaa   17400
ggagatgtca agtagcaagg tttggagaga ggtctggtt ggaaaaaag attttggtta   17460
taaagtgaat gaatgaaaga acagatagat aggtgggagc ataatgagat gggtaggtgt   17520
ttagaagtaa agagggttgg ggtatagctg gtaaagtgga tggatggatg gatgactgca   17580
cagatggatg gatggacaga tagataaata ggtagatatt aatagatgga cagatagata   17640
aacagatgga agaaggaaaa gagagagaga aaaaatggag ggacagagga aaagccagta   17700
aattaaaaaa aaaaaagtga gggggccagg cacggtgggt catgcctgta atcccagcac   17760
tgtgggaggc caaggcaggc agatgacttg aggtcaggag tttgagacca ggctggccaa   17820
catggtgaaa ccccatctct actaaaaata caaaattag cccagcattg tggtgtgcac   17880
ctgtaatccc agctactcag gagattgcgg caggagaatt gcttgaaccc gggaggcaga   17940
ggttgcagtg agcagagata gcaccactgc actccagcct ggatgacaga gtgagactc   18000
gtctcaaaac aaaacaaaac aaaacaaaac aaaacaaaat aaaacaaaaa aagaagaaa   18060
aaagaaaaag atctcctata taggtataaa ttactttaag caatctgaag attagaaagg   18120
aataagtttc ccagtgagta aatttttttag tgtctctgtg ctagaagaca atgttcacta   18180
aactaaaaat attttatctt aaggagataa ctatttatat tttgcctctt ccatctatat   18240
ttttttcccct ctctttcttg ctttctttg tattaaatga tttttttca ttcccatttt   18300
ctctgtattt atttggaagt tataaacact gtttctattc atttagaagt taacctaggc   18360
attttaacat ataagctaac gaagcctaat gtttatccat attcttacca ttctgaccaa   18420
tgataaaga gcaagaggtt gcttcccctt tccttcctgg cttcctattt atatgctctt   18480
ccttctagta tttcagctca atctcgtttt ttaaacacca gaagttagcc attatttgtt   18540
gtttatact gtcaacgtta atttaggttt aaacagaagt ttcccatttt cttggctcaa   18600
aattcttct tgtatattag atcttccttc tgtattcttt tttcttccta aaaaatacc   18660
ttttaaagct tcttttgtaag ggtgtcttag tagtaatccc tttcaatttt tgtctataaa   18720
tgtctttact ttgtcttcc tttggaatca aagtagatt tgtataggat tcaagctgac   18780
agttaatttc cttcagcaat ttgaagagac atactgctaa tgaagacata cccattgtgt   18840
tctgacatgt tttcctgcca ataagaagtc cactattaat ctagttatta tttcttttg   18900
gcattttttt ttcttttttcc tctctgtttg ggggaatctg aagctttcct acagtgtatc   18960
taaatgtgac tttattttta tttatcctgc tcaggaccta ttggccttct tgacttctct   19020
tctggatctt tgtagtcaga ataataaat agtcatgctt tttttttct tttatctgtt   19080
ttttttttct tgagacgag tcttgctctg tcgcctaggc tggagtgcag tggcgcgatc   19140
ttggctcact gtaagctccg cctcccaggt tcacaccatt ctcctgcctc agcctcccga   19200
gtagctggga ctacaggcgc ccaccaccac gcctggctaa tttttttgtat ttttagtaga   19260
gacgggtttt caccgtgtta gtcaggatgg tcttgatctc ctgaccttgt gatcttcccg   19320
cctcggcctc ccaaagtgct gggattacag gcatgagcca ccgcgcccgt ctggtctttt   19380
```

```
tttcaattat ggaaaatagt catgatctct ttgaatattg cctaatctgt cctaaaatgt   19440
cagtgaatta gacatgttag actttctcac tcaatacttc ctaacccttc tttcatattt   19500
ttcactgttt ttttgttttg tttttttccc tgtgctccgc ttgggtaact tatcttctac   19560
tactctcctt cccgttggct atcaatcaat ttatctgtgt tagtctgttc tcatgctgct   19620
aataaggca tactcaagat tggtaatcta caaagataag aggaaaaatt gactcagttc   19680
catacggctg gggaggcctc acaatcatgg tggaagagca aggaatgtct tacatggcgg   19740
caggcaagag agtatgagag ccaagtgaaa ggggaaatgc cttataaaat catcagctct   19800
cagccaggca tggtggctca tacctgtaat cccagcactt tggggaggcc aggcgggcag   19860
aaaacccgaa gtctggagtt tgagacccagc cttgccaata tggtgaaacc ccctctctca   19920
tgaaaataca aaaaattagt caggcgtggt ggcatgcgcc tgtaatccca gctactgagg   19980
gggctgaggc aggagaatca cttgaaccca ggagtcagag actgcagtga gcagagatcg   20040
tgccactaca ctccagcctg ggtgacagag agaggccccg tctcaaaaaa aaaaaaagga   20100
aaaagaaaaa gaaatcatca catctcatga gacttattca ctgccatgag aacagtatgg   20160
gggaagcact ccaaagattg aatcatctcc cactgggtcc ctgccacaac atatgggaat   20220
tatgggagct acaattcaag atgagatttg ggtgtggaca cagccaaacc atatcattat   20280
ctaatctgct gctatcaac tgagatgaat acaatttta tattttcat ttatagaatt   20340
ttgtttattt tgtgtctctc tctcttctag cttcttgttc ctgtatctct ctaaaaattc   20400
ttttttttt ttttttagat ggagttttgc tcttttttgc ccaggctgga gtgcgatggc   20460
acaatcttgg ctcactgcaa cctccacctc ttgggttcaa gcaatgcttc tgcctcagcc   20520
tcccaagtag ctgggattac aggtgtgtgc caccgtgccc agctaatttt gtatctttag   20580
catagatggg gtttcaccat gttggccagg ctgatctcga actcctgacc tcaggtgatc   20640
cgcccaagtc ggcctcccaa agtgctggat tacaggcgtg agtcactgca cctggactct   20700
caaaattgtt taatcattgt gttgggtatt ttctttctgc cccttccaaa tccactctac   20760
catgttccat cctgctttgt gcccccatgg ctaatcagct gagcaacctg tcccttgtct   20820
ggacaggttc ctgtccctct tggggagaa gcagaccttg gctatgtact ggtgtagcct   20880
ccaggcctcg aaaagcttta ctgtctctcc tcagggactg atgactttg cttctgtcct   20940
ttccccagaa gcagatatgt gcctgcatac caaaatatgg aaagacggga ttgctggccc   21000
ccctccagag gcagagggct ttgcttctca agggcttgct gcttcttcct gacagcttaa   21060
ttaaggcttt tgctcccatg agaggagcat caaggtgtgg gggcagccac ctcctcctgc   21120
atcctgtgcc accaaacggg gggtctctc cagcctttg ccctgcccta gtcttcctca   21180
agagcacccc ctcttcccca tggagactat gaagagaagc ttgggagtgt gtgtgaactc   21240
cgcttgtgtc tgggcctctc aattattcta aattaatatg agatatgagt gcatactcag   21300
tctttagaaa ttctttttt tttttttgag tcagtctccc tctgtcaccc aggctggagt   21360
gcagtggtgt gatctcagct cactgcagcc tccacctccc aggtccaagt aattctagtg   21420
cctcagcccc ccaagtaaga tggaattaca tgggattaca ggcatgaacc accacactcg   21480
actaattttt ttttttttt ttggtagaga cagggtttca ccatgttgga caggccgggc   21540
acctgacctc aagtgatctg cccgcctcag cctgccaaag taaggaattc attatttta   21600
aaaaaatatt tcttcttact cactccatgg caacaacccc ctccttcctc ccatactctg   21660
ccaaaggtgc aacaatttca tatcctgcct ctcattagag atgcttttta tcctttgaag   21720
tttacttttcc tggttgcctt gtgacctcaa gtctctgatg agtttaagga agaaagtta   21780
taatattgta cactgttcct cattttcttg ttgttaggat ggggggtgaca ttctctcgta   21840
gctttctata ttccaagcag gagcagaaat cctcatgtat tattaatagc accacctttc   21900
acttcataat actgtgggc tggaggataa attatatggc tgcagaaagt taggccccca   21960
ctcgaggcta ccagcacctg gcagatgcat tcagggcaat gccagctaca gggcttttt   22020
tcctctgggt tcctgcttag ctttctggcc ttagaagatt tccttgactt tcctataagc   22080
ttaggtgtgc attttaaaa atgttttttt aaaaactatc tcatccagct tttttttttt   22140
tttttgata cagagtcttg ctctgtcacc caggctggag tacattgggg caatctcagc   22200
tcactgcaac ctctgcctcc tgggttcaag cgattctcct tccccaggcc cctgagtggc   22260
tgggattaca ggcacccacc accatgccca gctaattttt gtattttag tagaaacagg   22320
ttttgccat actggccacg ctggtctcaa actcctaacc tcaggtgatc cacccacctc   22380
ggcctcccaa aacgctggtg agctaccaca ctcggcctta tccagcattt ttaagtgca   22440
gaaaagcttc tccagatatc tagtgagtca tacagctgga aacagaagtt gaaaaaaaa   22500
gttttataat attaaaatgt taaggtttta cttctttccc aattaacatt aatgattctt   22560
gaaatcgttg gtcagatgac tgtatgtcaa aaagcaatgg ttaatatgaa attaatattt   22620
aaaaaaagga atctgttaat gtcaaagatg gactttacta agcttttctt aaatattcta   22680
aaaattcaat ttatctggag ggtgttaaca tgaataattt aaaattcatt tcccaactgc   22740
aagggaaatc aaattgattc caatggtttt cctgaatctg aaggcttggt tattttaat   22800
aattttttt ggatgataaa tgggtggcaa tatgatgata gatgagacag agattattgt   22860
tacagcatat taagaaaact ttagacactg atgctatcat aaccaagggt gagcctaggt   22920
gtagaagtca caatgttcct gaagcagaat gttggtcaac tggatgagac cagtcaacta   22980
acagaaatca gctgtgatgc ccacagcaac catgctttca agaactcagt gggccggatg   23040
ctggagagta ggtggtgctg ttttaatgat ttacagtaag atgccccatt aaaggactga   23100
atcattgcag gaatccccc atatatggaa acctaggtac tccctgggtt ccttctaggt   23160
ggcaatgtaa tccaagccta taaacgtgat actgctgacc ctacatctga tttggcccat   23220
ctggctgact aggggggctgt ctccaccatt ccatgagttt tttctcctgt gtaccaccca   23280
ctgcaccctg cattgtgcac tctgttgagg aggacaatta cttcagatac agctggattg   23340
ttctttaaag tcaaacatat gggaattggg ggcttccctc caaatcagtt cgtaagtcca   23400
tttgtaagaa ctatatgtga cggcatgctt gaaagcttca gctacaacaa cttcatttct   23460
taaaagtga tggattcaat aatgttagat ggatttgata ggcatgtatt atattatgga   23520
aaaatgaaaa tgcattctct ggagacacac tggtagattt ctaaattatg tcatatgctt   23580
ggatttagcc tgcaacaact gctatactct gaattgttca tctccggaca agtatttagt   23640
ttgtggaatt tgatttaata gtgcccctta aggtattaga gtttgtcttt ccggtccacg   23700
ttaaaagtct ctgaccttaa actctgtaca aagaagccc ttcaaagaaa gctcgggct   23760
gaattgagga ggatttcttg ggg tagaatcctc tccgtggagg atcccaccc tattagttta   23820
cttgaggtgt ggcgctcctt ctaacaagtt cagcttgaag actctgaact ggctaatgcc   23880
gttgtttatt ccattacata tgtattatgt tggtttgtat ccccacagaa tcaccaagcc   23940
cagtttacag gttgttcttc tttatagacc tgtgaaatcc cctgggtgtt ccaaagagct   24000
ttgggggttc tgggaatgtg gcagaaagaa tacagtagga cgcgtattag gtgatgtctg   24060
cgctgttcct tcatgtgaaa gagcagtgcg tatgtaagca atgttagggc tctgcaggca   24120
```

```
agagtcagaa ctgggggaa accggcagtt cattatgtcc agcaccttcc atctcaattg   24180
acacatctca taaagtcgtt ttttaataaa tcagctgagt catagagaag tgtaagtgat   24240
atggtttggc tgtgtcccca cactaatctc atcttgaatt ccgacatgtt gtgggaggga   24300
ccccgtggga ggtaattgaa gcatgggggc aggtctttcc catgttttc ttgtgatagt    24360
gagtaagtct cacgagatct gatagttgct ataaggggaa gttttcctgc acaagctctc   24420
tctttacctg cagccatcca cataagatgt gacttgctcc tcctcgcctt ccgccatgat   24480
tgtgaggccc ccccaccagc catatggaac tataagtcca attaaacctc tttcttttgt   24540
aaattgccca gtcgcgagta cgtctttatc agcagtgtga aaacagacta atacagtaag   24600
tcatttttgc ctgagattag atattacaga aagtcacaca gaagtgttcc atgaagttta   24660
gaaataaaaa ttctagaaga catacatttg tcatgtaatg gttgatttt cttcaaaata    24720
ttcagtgaat gtacaaaacc cattttaaac taaggacatg tacaaattac ttaaattcgt   24780
ccccagatga acaattggag aaaatatgaa taatgggga aatctaaca tgtgcagtat     24840
tcaaaattaa ttaaagaaag ggcaaatctt tggcatcaaa tggaacaatg ttttactaga   24900
ggtatgcata aaaggaacac tgacatgaag gaaagcatat taaaatcttg tgtttgaaga   24960
ttcactgttc cctagagttg ctctagtaat taagattagc aagaaatttg tcagatatta   25020
aaacaaaaga agagtttcat cagtatcacc agcaatctat tgttaaacat aaagtagcca   25080
aggaagcacc ttaggaccat gtttaagagc tcagggaatc cccctccacc ccataggatt   25140
cctgtcagtt tacctccaga gaatgggctt ctgctagaaa tctgggagca ctggattagt   25200
caagaaggcc aaatacaagg atcaaaagga caccacagct gggcatggta ctcacacctg   25260
taactccagt gctttaggag gcagaggcag gaggatcact tgagcccagg ggttcaaggc   25320
tgcaatgagc tatgatggcg ccactgcacc ccagcctgag caacagagca gcaacctgta   25380
tacacatata tatatacaca cacacacaca cacgtata tatcttata tatatgtgtg      25440
tatatatata tatacatctt atccctgcca ggtagccatg gaataaggat gtgaaggtct   25500
ataggcacac cagctctgac tgagcaaaca gtggtcagaa gggaggaaga agcttttctg   25560
gatcaaatgt gtcaagcagg ccctgagaag aaaagacaga gcagcacatg atggcagcca   25620
tacataggac atgaaaaggc agaagccaaa gaagaataga tagaaaaagc caatggtcct   25680
gttttggtct tttcagttac tcttcagtac accgtcagct acttaatctc ccttcctct    25740
tgtttaagtg aaagataata taacaataac aaaacagttg tattattt taacataaca     25800
ttattgtata taaacattta tataaaaaca aaataggaca aatcactaat ggtaagttt    25860
taaaaataat taaaatggtg tgtttagagg ggtatgaaaa tggaattgtt aaactctaaa   25920
agagcacact gtacatgaat gccttagaag aagcaactca ataggatgat atattttaag   25980
ggattgaata atagaatgtt cttcccagaa tcttctacaa tggtaatatc agcatagtgc   26040
atttattcgt agtacaacca tgtatttga gtaacatgcc tttcaaaaac agtactgaat     26100
atacaatgca tagaccacct agaataggta tgaaagaaaa aaaactgaaa tgaataaaat   26160
ggggaaaatt ccatgtttta ttctatggga gataaatttc ttatatatcc attagaattg   26220
cctatgaaaa tcaaaccaca atttgagtcc attttcctca tgatattcta ataaccagga   26280
cttccatttt catcaaatag aatttattat acatttactt tgaatcaca ttgggctggg    26340
tattacttaa aacatggcga atagaaatag ttcatacctc ttagaagctt atagattaaa   26400
tggatagtgg taaacacgca tatgtaaaaa tcatgcacac ataatacata cttagtagta   26460
catgtctaaa caacatgaat acatgctaaa ctaaattact tctagtgctt ttagcataat   26520
ataatggaaa aatagttttt aagtgtgttt agccatctga ttagctgaga cacaaactct   26580
ccctggaagc ctacagctga ggtttgaggg ggaagaggga aagctttcag cctatacagg   26640
ttgggggatt ggaacagaga ccctcacata acactggacc tccaaattgc aaagagttct   26700
taccttaga gatacacaga tgaaactata ggatgtctgg catttcttc aaaataatcc     26760
aggggtggga ggaatgggta gagattacag atgcaaaaaa gattgactat gagtccataa   26820
ttatagaagc tgggtatggc tacatggagg cttattagaa tattctattt tgtatgcttg   26880
aaatttctta agataaaaag ttttatttaa gaaccattaa aagaaaaacc aaaaattgtg   26940
taatggaatt gaaacaaagc tgacacaaga tgagaatcca aaatgtctaa agaacttcta   27000
gaaatcaata agagaaagac aaagaaaccc attgaaagat ggtttaaaca aacaaataaa   27060
ccgacatttt atgaaataaa aaatgccca gaccaaacgt cagaagatgt gcagtctcat     27120
tagtaagcag gaaaaagcaa attaaaacca caatgagata ttctgtatgt tatgatatgc   27180
taggtaatat tgttgccacc aacacccaag aatcatacca acaaaatttt acttctcact   27240
cacacaaatg tccagtttag gtcatctggg aactgtggtc agtcatctgt tcattatgat   27300
cactcatgtt cccagggtca cacaacagtt acctccgatg ttgtaggcct ccttgtcaga   27360
gggaaggaaa gcatgggggt tttgcatca gtaagtaatt gctccagcca ggagctggca    27420
gacattcctt cacaattcat tacaagtcaa actcactcat aacaaggatt taggaagtgc   27480
aattccttct actatgtgct tggaagcaga gaaaactgga aatgtttagg gaaaacaaat   27540
gactttcaca gatgccagtt ttttctatc agattggcaa aactatatag tctgacaaaa    27600
ccaaatattg gtgaagatgt agagcaataa aaacacttac acacttttga ctgaagagta   27660
aattggtacc actactttaa aaaacaattt agtgttattt agcaaagttg aaaattcata   27720
tagtcttcga ctcagcaata ccactctaag atacatactt tagaaatagt tttgcatatg   27780
tgcaccaaag acatattcaa atatggtcat agaagcactg tttgtaccag cgaatcaaac   27840
aagcaaaaag aaaaactgga aatagctctc atgtccgcag atagtggata atttttgaa    27900
tattcattta atgaaatacc atttaggata gaatatgaat gaacagatac atgttcatct   27960
ggttgaattt cagaaacata ttgaatgaaa aaagtaagcc tagaattatt gtatttgaca   28020
aaggtctaaa aaagttaaaa ttaatatatt attttaggat tacatactta agcaaaata    28080
aataattaaa agttagttta acacaaaatt caagatattg taccttgag tacactttga    28140
gtgtatcaag gtagggatgt taccagggac agatttaagg tattgataat attctttcg    28200
tcaagttgtt tggagttgta aacattgttc actttgttat tattctttaa cttgtacata   28260
tacagtatat gtactctatg catgcaaaaa agcatagaaa tatatcttat attgtggaga   28320
aaaatcagtc aatggaaaca gaacaaaaat gacacagata gtagaactag tagtcaagga   28380
cattaaaaga actattataa atatgtttca aatgttcaag aaggtacagg aaatagaaaa   28440
acaaaaaata gagaatatca ttggaataaa aaactggttt tttgagatca gtgagtgata   28500
aagtttttagc tggattcatc aagaaaaaaa tagaaatgat acaaattatt aattatagaa   28560
atgagagaga ggataccaat acagttgtag atactaaaag tataagaaaa tattacaacc   28620
atctttttg ccataatatt tgcaaactta gataaaatgg acaaattctt tgaaagaaac     28680
cacctgccag agatcactca agaagacata gattacctgg atagctcaat agctattaaa   28740
gttattaaag gcttctaact ataaagctat tatagttaga aacctcccca taaaacaaac   28800
aaacgaacaa acaaacaaaa acccagaaaa cacatcaagc caagatggct tctctggtta   28860
```

```
attctaccag acacttaaat cagaaagaat atcaattcta cacaaaactt caagaaaatc  28920
aaagaggata aaacactttg ctatccatgt tgggcgcagt ggctcatgcc tctaatccca  28980
gcattctgag aggttgagat gggaggattg aggccaggag tttgagacta gcctggtcaa  29040
catagtgaga ccccacctct acaaaaacaa aaacaaaaaa aaactggatg tggtggcaca  29100
cacccgtggt cctagctact tgggagggtg aggcaggagg gtcacttgag cccaggaaat  29160
caaggctaca gtgagctgat attgcaccac tgcactccag cctaggcata gagtgagacc  29220
ctgtctaaaa acaaacagac aaacaaaaac ccactttgca actcaatcta tgaagccagc  29280
attaccttga taccaaaacc aaagatatta caagaaaaga aaatctacaa atcatgtccc  29340
ctgtgaacat agtgacaaac actgtttata aattttacca aataaaaggt ttatctcaag  29400
aatgcaaggt tggtttaaca tttgaaaatc aacccatgta attcaccata ttaatacact  29460
taaaaagaaa caccatatgg tcacctcaat atatgcagaa aagcatatga caaaaattca  29520
acatctattc atgatgaaaa aatttaaaaa agaaagaag aaaattcaac cacataaagg  29580
gcagctatga aaagcctaca gttaacacct cacctaatgg tgaaagactg aatgctttc  29640
atttaagaac agtgcaagta tatccattct atcacttcta cttgtcattg taacaaagat  29700
tatggcaaat gtattaatga aagaaaaaga aataacaaag gcatacaggt taaaaagaaa  29760
ggcataaagc agtctctatt aacagacaac atgactgtgg aaaattcttt gaaccagtat  29820
aggtgattta aaaaaaatct aagaaaccta cacacacaaa aatattggaa ctattcagtg  29880
agtttagcaa ggttaaagga taaagagtaa tatataaaaa tcaattttgt ttctatacag  29940
tagtaaagat caatccaaaa ttgcaataaa aataccattt aaaatagcag aaaatatgaa  30000
cttaagtatt ggtttgaaga aaacttatgc aagacccttta tatcaaaaac cataaaacat  30060
tgttgagata attgaaaaga tgagatatac atgcccataa atcaaaaact atattattta  30120
gatatctatt ctccccacat tgatctttag attaaatgca atgccaataa aaaaatcagc  30180
aggcttgttt tttagaaatt gacaaactga ttctaaaatt tatatggaag ttcaaaagat  30240
gtagaatagt caaaaacatc tgaaaagaaa taaagttgta gaactcacac tatacacttg  30300
agtttatatt tagggtttat catggagcta tggtaatcaa gacagtgtgg tattatcata  30360
atgatagata tacaaagatc aatgaacac tctagaaagt ttagaaacag acccacacat  30420
atatatcagt tgacctcttt caaagggaaa ctgggtgaag aaataataat ctttgttttt  30480
ttttttttttt ttttttgag acaggtcttg ctctgtcacc caggctggag tgcagtggtg  30540
agatctcggc tcactgcaac ctccgcctcc caggttcaag tgattctcct gcctcagcca  30600
ccagggatgc tgggattaca ggcatatgcc accacgcgtg gctaattttt tgtattttag  30660
tagagatggg gttttgccat gttgctcagg ctggtctctt ctgagttcaa atgatctgcc  30720
cgcctcagcc ccccgaagtg ctggaattat aggtgttagc cactgtgcct ggccaaaatt  30780
gaacactttt gctcttcaaa aaatgaaat gaaatgaaaa agaggaaatg aaaaggcaag  30840
ccaaaatctg ggcaaaatta tctgcaaaat atatatttta tgaagggtt gcatttttata  30900
taaaataaac ccttacaact taataagaag agaaacaacc taattaaaat actgtgcaaa  30960
aatcaaaatag acatttttaca aaaaagaaac tgtacaaaca ggaaataagc acataaaaag  31020
atgctggaca tcattagtca ttaggaaaat tcaagtttaa atcacggtga gttgacacct  31080
agcatgatgg caataatcaa aaagacacaa taagtgttgg gaaggatatg gagcaactaa  31140
aactctcatg cactgctggt gggaatggaa aatggcacaa cacttttgag aacaatttta  31200
tagcttgaaa agttaaacat tctctactat atgtgtcaac ctaggtatt acccaagaga  31260
aacgaaagca tatgtccaca taaggacttg tccacgaatg ttaacagcag cttttatttgt  31320
aatagtcaaa agctgggaac aacccagatg tccttgaaca agtaaatgga caaatatatt  31380
tcagtccaat tcagcaatga attcagcaat gaaaaggagt gaactattga tatgcataac  31440
atagatgaat cttaaagtaa ctacacaaag tgaaagatac caattaatat aattgtatttt  31500
atttaaaaat tttaaaaatg caagctaatc tatagtaatg gaaagctgat cagcaattgc  31560
ctggtgacag agatggcagg agggaggaaa cttttggggg caatgagaat gttgttatc  31620
ttgtgatgat gggttcatg ggttcataca tagctgaaac tgatcaaatt gtatacttta  31680
tatttagctt attgtatgcc agttatacct taataagatt gtaaaaaaaa atggatattg  31740
tctcttaggt aataattgct catatgcata tgcccattaa catatgtgtc aattttcagg  31800
gtaccatatt ctttgcttag agcaggaaat agaaatataa tatgaatcac atatgtaatt  31860
ttaaattatc taaaagacac attttaaac attttaaagg ttgaaaataa ttttaataat  31920
atattttact taattcaata tagagtattt taatcaatat aaaaactata agcgaagtat  31980
tttacaatgt ttttcatact aagtcttcaa atccagtat atactttaca cttgtagcac  32040
gtcttagatt taataacatt tacaatggag aaacagattc atatatcaaa catgcttaaa  32100
aattttccca taatagaatt gagtatcttt ttttaatttt taattttaaa ataattacag  32160
actcataagg agtaaaagta gtataaacag atcccatgaa tccatcaacc catggtaacg  32220
ttttacataa ctatagttca ttatcaaaac aaggatattg attggtacaa ttaactacac  32280
ctcatgcata tttcactgtt atttatatgt attcaaatgt tttatctgtc tctgtgtata  32340
tttctataac gttttatcac atgtacagaa ttgtttaagc acaatcacaa ccaacataca  32400
ggactgttcc atcacacaaa tgatctccta gtgctgctct gttatagtta ggctctccct  32460
cctcttccct aacctttggc agccatttca tttatctgtt ttctctgcaa ctttgtcatt  32520
ttaagaatgt tgtgtaaatg agatcataca atgtgtaatc cttcgagact ggcttttgtc  32580
acttgtcata atgttctttt tttttttttt ttttgagat ggagtttcac tcttgttgcc  32640
caggctggag tgcaatggca cgatctcggc tcactgcaac ttccgcctc cgggttcaag  32700
tgattctcct gcctcagcct cccaagtagt tgggattaca ggcatgcgcc accatgccca  32760
gctaattttg tatttttagt agagatgggg tttctccatg ttggtcagac tggtcttgaa  32820
ctcccgacct caggtgatct gcccgctttg gcctcccaaa gtgctggat tacaggtgtg  32880
agccaccacg cctggccatc ataatgttct taagatccac cctagctgtt tcatgtatca  32940
gtagtttgtt tcttttttat tgctgaatag tattctacta tatgcgtgtg tgttcaacta  33000
ttcaccttt gaaagagcatt tgggtcattt ccgttttttg gctattacac atacatttgt  33060
gaacagtttt tgtgtgaata taagatttta cctgcctagg ataaatgccc agaggtactg  33120
ttgttcagtt gtatagtaaa tgtgtgttta acttttaag aaactgccag atgcccagag  33180
tggctgtact gtttaacatt gccaccagcg atgtctgaga gatccagttt ccctgcatcc  33240
atgtcgtt ttggtattat tagtatttt attctaatag gtttataagt  33300
gatctgtctt ggtgatttta acttacattc ccctgatcac tagtgatgct gagtatcttt  33360
catgtgctta tttgccaact gtctatcttc tttagtgaaa tgtctgttca actctttggc  33420
ccatttaaaa atcagattgt tttctcactg ttgactttag agaactcttt atatattcta  33480
tagataaatc ttttacatat gatttgcaaa tattttcttc cagttggtgg ctcatcgttt  33540
tcatcttctt aacagggtct ttcacaaagc aaaagttttt aattttttaag tatctatttt  33600
```

```
taaattcaaa tggatttaaa ttaaaaattc agtgaaaagg ccagtctacc catcgtggtt   33660
acctactgaa tagcagaggc ttagagaata catggaattt ggttagggat cattccaggt   33720
ccgggaccac aataaccagg accaggagca tgaatgggta tgaaaagtta aagtgaatag   33780
acagacccaa ctggcaaaaa tgtggggttc gagataagta gaggggtcc agctggaaag    33840
ggaagttggg tgtagattgt gaaagttgct gcatgctaag aaaactgttg aaatcttatc   33900
tggcaggctc agtgaaatcc ttaggttttc ctgaccagga gaaagatgtg ctataggag    33960
tgttttagga agattcactt ggtaacgggg ttcaaagggg actggaaaaa gagtaaccat   34020
gctgtccttc ctttgcttca gtttccctgc acaaaccctc atgtgctaag acatgagcct   34080
ggtcaaggct aatgttgaaa acatttcagt ttttccccta accttgagca ccttcctcta   34140
tcttgctcat catagataag gtagaacgaa gggttttaag ataatatctg gtaagaagtc   34200
aggtagcttc taggtattat acagaaaata agttgataga gttgaaaaga agggtgagaa   34260
attaaagttt aaaaaagcag gaaaaactca atcagaggaa agactcaaga aaatgacact   34320
tgttcttaat attatctcag gggtgacaga tattttacag attaatctgt agcttttcac   34380
gttaatcaaa aaatagaaaa gactatcaac ctagtgtcaa tgattaatag atattatcat   34440
ttgaatgtga taaataagtc aagaggtaga ctggtctcag ggtgggtttg ttagatcaac   34500
gtcattaaga gcccaggctc ttttagccct cctctctgc ctcagtgcat atgtggtttt    34560
tcctcatggt cacaagatgg ctaccacagc accaggcatc atcacgtttt cacaacacac   34620
cacccaaatt aggagtcaag gtgctggggt tagggctaag gattgtggta cttcccctac   34680
cttctgacag ggagaaaaat cttttcccaag ccctccatta gaattctcat tatattccac  34740
tgaccaggac tggattacac acccacttgt agaccactca gtggcaaagg gaaaaggggt   34800
agccatgact gactagggtc aaacatgact caactcctgg gtacattatt gcccaaacta   34860
aaaggagata ccaaacagga aggggaatga catggataag ccagtaacgt tgtcagccac   34920
atacaggaac aggaaaattg atgggagaac atcaggaat cagataagtt ttatgaaaca    34980
ttagtctaat aggttccaga atgtactgct catgtctgtc accgtgaaca tctggcacca   35040
acttcacaca ctgtgggtgg ccagtacata ttttagatca actgactcta gaaagtagca   35100
aactgagtaa gatttaaaca tgtagaaata ttatgagggc caggaaacca tgttgatctt   35160
aggaaagtga gctttctta tcagagagc agaaggacac aatgtttaac ttttagtgag      35220
gcaagataat aatgaagatt ggctctccac aacactgtgt gctgatggac agggcacatc   35280
tagtcagaag atgaccacca accagaaaat gacgtgcacc catgggcaca caaggatgc    35340
catttgggga caattaatta cgtccttcca caaatactta agcattattt tatgtcaggc   35400
actgttctag gcacttgcat tacactagtt gagacaaatc acaataattt cctgttttca   35460
tggcttattt tctagcataa gaatgagtga attacatagt aagtcagcag gtgataggtg   35520
ctttgaagaa gagacaggac agagtaaaag ggatcagtaa tcccaggatg tgtgctgtga   35580
ggtaggttaa ataggggggt cagggtagat ctccatgaga aggtgacatt tgagcaaaat   35640
gtcctctgca cgaagcgggg aaggaggagg cataagactt gtgtgggaag aggttttctc   35700
gaattagcca ccccatttca tcactctaca taggagaact acaatgataa cacatacatg   35760
ttacatgata aaacacattt gaagtgcttt actttttaaa aataataggt tttcattcat   35820
ctgaagcaac tttcaaggca gatagttttc caatactgcc atccaaaaca ttattctggt   35880
atagaataat tcatcccacc tttaagacca tgaaggctct gtgatgccag gatgctgcag   35940
gcatttgggt ttcaaccctt attctgcttc taaccagctg tggatagtgg aaaaccacgt   36000
gacctcttct gtgctcagtt tcctcttctg caagtggaag aagctgaata attttcaagg   36060
tccatctcag gtctaaactt ctgtgactcc cagataaaga aatctgcttg caggagtctg   36120
cacaatgctt tctccactgg c tctgggaggg ctccttgtgc tgtgtagccc attaggaaaa  36180
cactgaagag ccacctaatg acttaatggg ctttaaaatg ggtggctagg ttttaatttt   36240
ctctgatagc agattccctg agggaaagtg tactttacag tggataataa ctacatagga   36300
tatttcgatt gccgcagggt atcttatttg gaaatcagtt ttcagttaca ttcctctagc   36360
aattttttact atcagaacaa aatgaaagcc cccaaaggaa tgttttataca gagctgaaat  36420
gtgttggaat gtcagaagta tctctctaag agttaagcat ctgtaaatat ttaaaatagg   36480
gtgaaatcac aaaatactgct actactaatc tctttcacat ttgattacag tccaaaagaa   36540
acaagcaaaa tctccaggaa cacttttata ttaaactgtt aactctacgg ccatgtctaa   36600
tgactcaaat tataaaagaa agttgggtga aatgcataat tcacctattc aggcatacag   36660
tcagctctac acatgtgaaa acagatctcg tagaggatgt tgaaggaaat attttcctct   36720
ctggtaaact taagtatcaa tattatcaca taaagactag gctacacaat aaaatcaagt   36780
gagccattct gcctgaattt tcaggattca gctatcccca ctcttaccca cacacatcat   36840
agcttacac attcctctag ttttcttttgg ttatgatca gacatcatgt tacatgtttt   36900
agtcacatca tctgatttaa tctgctctac agcaataaaa agtagcaatt atttgctcta   36960
ttataggatg tggaaactg aggtcctaag aaaaatgtg tgtgctataa actgcttttc     37020
cttcaaatgg caaagaacac tgaaggaaga tagtccttga ttgtagacat tcattcattc   37080
cggaactcat gctcttctta atatactcaa ctctaaggaa accttcctac caatacagcc   37140
cactcccctc ttcttaacca gtgttcagtg gagatgggaa tttggaggag tgatgagctc   37200
attgtgtctt ttttctcctt tatttgatta cctccctgcc atcttgcctt ttctgggcta   37260
aatgataaca cttccttccg tttctctttg gaaccatttt caaaaaacat ctctttagga   37320
gtggaatcac aaatgagaaa cagtattttc ataaggaaga gtaaaatgaa aggactgccg   37380
gagcattttt acattagcac atgacatttc taataatcta catgaaggta ttttttttttt  37440
agcatcctcc taagtgcctc tttgaaacct ctgtgacata tgagatagct actgactaat   37500
ttgttctggc agaaaaatga gtttagtgtt attgaaaata tgtttttctat caccagatct   37560
tgttcaggtc attgagtggc ttttcactgg tgaaggggag taggatttat ctccaatgaa   37620
acattatgga gcggagaaa ataacatttg acctatccca acattagcaa aatgcaaatc     37680
atagtcaatt ttccataggg tgatattttc atactttgga ttttttagt tgtgcatcag    37740
tctgaacatt ttaaagcaag gtgaatgaag ggtccatgaa agagactgtg aataagccac   37800
tgtgcgaagc taactttaaa gttccagcct tagtgactga gataacgcca tttctctaga   37860
gaagttctaa atatagagga ataatggata gcagttact gcaagctatg tagtgcccta    37920
aaccagcagg ggctgggcat tgagtggaga aggattcaa ttttgaggtt gattaaagat     37980
gcagtactga caggttccaa tgggtgtagc agggtggggg aggggtcgca tctcattctt   38040
ttttttcctcc ccactcagag gtgtgggtag ctgcagtgta aactgctgat gtgggtgatt  38100
aggatgttaa gtgggagaaa agacagctct tcattattct tttggaaata aagagggata   38160
aaattcagca atcatcaagc cttttcattt ccctacaatt tgtcggtgca gctaggaggc   38220
tggcttcctt tccacagacg agattacttc ctgctgacat caagtggggg tagggtggac  38280
caatgtgtga aaaagaaaat tgagctcgaa gggtagcttt tgttttgatg tttgttagat   38340
```

```
gtcttttctt gtgttaaaat tagatgtatc acctactggc agccacagga ttttcatgtt    38400
gagaatgcaa ggcagatttt gctagataga tctccaggtg cataatccac tgtcagtttt    38460
gataaagaat tatgacttct tggactttt  ctttagctat gcagaagcta aaaatctgat    38520
aatttagcat aatgcttgtg taagctgtgc tggagagtaa tacatagtcg ctttcatact    38580
aacataaagc tccttggtca aaattacacc aataatgcat atttaattag cgtttataga    38640
tatctaaaga ggaaaaaaaa cccacaaagt ttccctcaca gatgaccttt atcgggatg     38700
ccttagctga gttccttcag atgcctcagg gcaaaatttc agcccaata  aaaggagatg    38760
acatatggct ggtatttca  caagatcgcc atctttagat tgaatttaac ttttttttcc    38820
tcagagctag agctttatgg agttttcggg ttttggaggt agcttgatgg tacagtgcct    38880
cagatttata atttctaatt aaaatgtgtc cttcatatca attttagaga agtaccaagc    38940
ttaattttgg catttaatca tcgaaatttg ttttgacatt tttgaaacac agatcccaat    39000
actaagatgt aattactttg caacagattt gcaaggaagg cgacaggcca cagaagaact    39060
tctaaacaca ggcaaaacca gacgagtcca gtggggaat  ggaagataga cctgaatgtc    39120
aaaaaactca aaagtaaata tatggttttc cagttttctc tgtctgaggg ctcaccttgc    39180
acacattaac tcttccctct ctcaccatgc ttcgccggtt tatccctcag cactcttttg    39240
atttaaggga agaaaaccaa tattaaatgt aaaagtaagt tttctcacta acagcccaag    39300
gggcacagct ggctaggctg tgcaagagca cgtggccgtc tctagatcta tcggctcagg    39360
gcctatttcc cagctcacag accctgacag gacgctccga tgtggtctga aggacagagg    39420
gcatttagaa atgtcctcgc ctttccaggt gtcctgaggc ctagaaaaaa aaaatccatc    39480
acaaggatga gatttgtcaa caggacccct ccagccagcc taccctctg  gctcccgatg    39540
agggaggact gtccacggtt gaccttgcta aaggacagga tttaaaaaca cggaagcagg    39600
acgatgattg gaagaatcca aagcttgtat tccaagcttc agattggagt ggaggcagct    39660
agacaaagag gtgagaaaaa tggcagtttt ggtgtcagag agacctatgc ttgaattcca    39720
gttctgacac tcagtagctc tttgatcttg gacacatgtt tgaacatctc tattcttctg    39780
ttacatccat tagaaaatgg agaatataat atctacctt  tcgggttaca gtaagggctg    39840
aatgacctca tgtgtgatac acttagcatg actttggctg gtagtaagga tttaatacct    39900
tttaatttct ttcttttctc tcagccttgt ctttcctctt agcattggaa agagttctat    39960
ttatttattt ttgataatgg cttttaact  tatgttgtta aaatgtagtt gttttccctg    40020
aaatggtgca acccaagttt agataataat aatacttctt tatttcatt tatttatttt    40080
tttgagatgg agtgatatgg tttggctgtg tccccaccca aatctcatct tgaattccca    40140
cgtgttgtgg gagggacctg gtgggaggta attgaatcat gggggcaggt cctgtgctgt    40200
tctcctgaca gtgaataagt ctcacgagat ctgatggttt taaagagggg agtttccctg    40260
cacaagcacc cttctcttg  cctgccacca tccatgtaag atgtgacttg ctcctccttg    40320
tcttccacca tgattgtgag gcttcccag  ccacatggaa ctgtaagtac aattaaacat    40380
ctttcattg  taaattgccc agtctcgagt atgtcttat  cagcagtgtg aaaatggact    40440
aatacacgga gtctcactct gtcgcccagg ctggagtgca gtggcgtaat cttggttcac    40500
tgcaacctct gccttccggg ttctagagat tctcctgcct cagcctccca gtagctggg     40560
accacaggta cgtgccacca cacctggcta attttttta  tttttagtag agatgaagtt    40620
tcaccatgtt ggccaggctg gtctcaaact cctgacctca agaaatctgc ctgcctcggc    40680
ctcccaaagt gctgggatta caggcatgag tcaccgtgcc cagcctaata ataatacttc    40740
tttaaatatc gatcaggtgt gaactgtttc atgacatcta gagtataaga agtgtcatct    40800
cttttatgt  ttttgaaaaa gaatccagtt tgagctcaca cctgctgagt ttggcaggaa    40860
catccaaaat ctacaggtga agggaggcaa agagaaggga tgggaagcc  ccacccattt    40920
agctcataca gacatgctag aggctgattc actgcatacg aatggagagg ggcctgatct    40980
ccagcattta cactgctgtt gccttattg  ttccttcact tactcagagc tgctggctgg    41040
ggcccctcct ctgtctgctg gcatcctgtt ccacagattc tgcaatgaga gcccaccac     41100
cctcctcccc aggggcaact gtcagaataa atggaggtgc gatgtggtga caaacaggtc    41160
ctagatatta gttcagttga ctctcgagaa atgcagaggt tagggctgtc aacccctgt     41220
gcagtcaaaa atgcacatat aacttttgac ttctccaaaa cttaactact aatagcctac    41280
tgttgaccag aagccttatt ataacataac aattaatata ttttgtattt tatacatatt    41340
atatactata ttattacaag aaagtaagct agagaaaaga aaatgttact aagaaaatca    41400
taagggaggc caggtgcggt ggctcatgcc tgtaatccca gcacttagag aggccgagc     41460
aggtagatca cttgaggcca agagttcgag accagcctgg ccaacatggt gaaaccctgt    41520
ctctactaaa aatacaaaaa ttatctgggt gtggtggcac acacctgtaa tcccagccac    41580
tcagggaggct gaggcatgag aattccttga acctgggagg cggaggttgc agtgagccaa    41640
gatcatacca ctgcacttca gcctgggcaa aagtgagtga gactctgtct aaaagaaag     41700
aaaattataa gggagagaaa atgtatttac tgttcattaa gtggaattgg atcaccataa    41760
aggtcttcat cctcattgtc ttcacattga ataggctgaa gaggagaaga aggaagaga    41820
ggggttggtc ctgatgtctc aggggtggca aaaccagaaa aggtagagag gtgggagaa    41880
aggtggacac actcagtgtc acttttctag aaaaaaatcc gtgtataagt ggacttgtgt    41940
agttgaaaca catgcgttca agggtcaact gtagtttaaa tcaacagatg tttatttatt    42000
tccaagcctg cctctttctt tggaggcttg ggcaagagt  acacacagag gcccacatac    42060
catatgtcta gatatgtaac acttataaac cagggaacaa actgttaaat gaaatatacc    42120
ctcttacctt gaaagatata ccttgatagc aacctagata tcaatttga  gtttataatt    42180
ctgagacttc ctgaagttct gtgctacaac atggtggtgt agagtgctac ctttacacct    42240
gtccttctcc tggacatcct tccctgtgca tcccagctct gtaagcatgg cctttggcca    42300
cccctcagat agaggatgac tccaaggaag agtggcatgc aggctctgga agcaagcttg    42360
tggacatttg ggcaaagaat tctgaggtcc ttgttattca gaccatggag gagaatttgc    42420
aaatatggaa tccacgaata acaaggatcg agtgtatttt gttttgcttg cctgtttctt    42480
gtcaaaattt actgagagaa acttaacaat ggggtgcacc gaaagagaca aaatggcgtt    42540
aactcttcca accgtctcag agcaaaagag cccagaattt aacagctctg tgtcaggtca    42600
cttttctact gagaagaagg gataattcct ttttttcttt tgctgataga tctctgggtg    42660
gggtggatgg gaacaaacta agcccaggca atttatatca cattagtgat catggtgtca    42720
catgtggcat aagacaggca ctgtatcatt tagctagtgc attcagactc cttggctcag    42780
taaaggtgga tagagtgggt aagttgttat gacttccatt ttcaaatgag gaaagcaaga    42840
aagatttagc caggaactga gaatagaaa  caaagagacc tggggactgg cttttctggca   42900
ccttttctct ttctcactgc ttggtgctcc taggtgtagc tgtctcagaa tcaagggga     42960
atcctttaaa tccatagcag ttaacccagc aagaagttcc gagcagtcta gcctgagctg    43020
ccacgcataa aaagcaacat aaggttttat gcaattgctt gagcattcct accaagaaat    43080
```

```
accttttgcc cattttactt gtattcctttt atttggtgat gtgacctagt tcttgaagtt   43140
ctggaaaacc cttcagaggc tatagagtca cttttctaga taacccactt tggatcatgc   43200
aactcttcat aggcacaata tgagtaagca gagcacctgc actaaccact atttccattc   43260
gaagaaaata aaataaaacc taaacaagag aaaagagga gactccaaat actacttcac   43320
ctaagggagt ttgtttacta tctgtttgtc ctttgcaaat gtctttcctt caaccagtga   43380
atgacctgct tgctatgggc cagacattgt gttgatggct atacataaca tttcgtcaaa   43440
tcctcagatc agccttgtag gattggtggt gttctcttcc catacatgag aaggctaagg   43500
cttagagagg ttaattaaca cagcaaaggt cacacagcta atgagtggct gagctgggat   43560
tcagatgcca tcggtctact cctaaggcca tgccettaat cagatactat cctgagcaca   43620
ctggcaggtt catcataata tcaatatata cctcgcaggg ctgatgtgaa aattaaaaga   43680
gatgatatat ataaaaagtg ttgggcaaac cataaaatcc ttacaaagtt tcactatgat   43740
tatttctctt ggttttacac agggcttgct cagctgtcct tagtggccat gtctatatta   43800
atcccataat ttatccttaa atcaccgaag tcttatttgc ctggcttttt ccatagccga   43860
agggaaactg aaaatatgcc ttttgtaaga aagccttaac acctgctgct aaagggcgct   43920
aaaccatctg gatcgtcaaa ggagtatagg ctcacttaca aaagacgtag attaatttgg   43980
acattgtttc cctacataaa ccaggcataa ggaggcaagc aacccaggga aggataatca   44040
tgctaagagt ggaagcactt attagaaata attaccatgt aattatccac aacttccctg   44100
gagtcgtgag cctgtggcta gtcttaggag gtgcccttc cttaccaagt acaaggagac   44160
tgaagcactt caataagttg atcagggcat gtgtctgtgt cttagagctt ggttaccgcc   44220
acctgggcct acttctcact taatgaagcc ttcaatgctt atagctgagg tgcagaacag   44280
ctgtagactt tcttcagctg gatctaccac ccaccccctcc cttttttaat agcacagtgt   44340
tgttttgcaa gtgtgtgggt gtgacacatc tggcttcgtt ccttaagaaa agtgtttatt   44400
gaacaattaa ttgtggtgca tgggggctgt gacatttctc ttttcgctgt gcctctgagc   44460
tgtgtttcca ggctacccgg tggcccatt gaagatcagt aacaaactg aaaaggaaca   44520
atggctatag aagccttgac aagtgcaggg agagacctag acacttccaa gaggggcatg   44580
attgcctaca aggttaatca attcccccttg tttcattgcc cacat ttatcttgct   44640
ggcagcagct gcaaatgtaa aatcagacct acaaacttag acaattggaa ttgtatttac   44700
ctgatcaaga tgtgtaaatg atctattctc tgtgtcttct taactggaat ttaaggagtt   44760
cagcaaagct ccggctatag gtcagtgaga agcatgtttt tgtgtggtgt ccagatacaa   44820
tttagttgtc ttggatagac agttggaaag aactgcagtc acagcctaga atcttgattg   44880
tcatgatcac cattattatt gttacagctg ccatttttg agcctttata tatgacaagc   44940
acttatatg tactactatc ttatttcttc ctcttgataa taccgcaaga tagctaatag   45000
tattttatc atgtacagat gagaaaactg agattaagta acttgcttat ggtcattagg   45060
tgcaaggttc tagattcaaa ctgagtctga cccatgctct gaaccactag ggctaacaa   45120
acccaaacct cactagaata tgcaggtgca gagaacacaa gggcttgtga tcgacctgac   45180
agttttaaat cttgttttca ggaaagccaa tcaagaagg cttaacgaat ctctttgcaa   45240
accgattgt tggccaacct ttgaatattc tcaatacaag agaagggcta aaatatctca   45300
ttgcagcagt gaagtggcct tattttgaaa atgagtcttc atagaagtaa tcaagctaaa   45360
atgaggtcat tagagtggac cctaatccaa tgtcattggt gcctcataa ataggtgaaa   45420
ttgggacaca gagacagaca catggagggg agacactgtg aaaagacaca gagagaaagc   45480
cctgaaggc tgaagcagag attgggttga tgctgccaca agccaaggaa cacctggggc   45540
taccagaacc tagaagcagc gaggaaggat ccttcccctc caggtttcag agggaacctg   45600
gccctgctgg cactttaatt tcagacttgt agcctccaga actatgagac aataaatttc   45660
tactgttaat agctgctcag ttacaacctc cctggaaagc acatactcct gtcctatggt   45720
tctattctgt tctgtactat tttgttctat tttattctct ttcattaaga aaatgatttt   45780
ccaggctggg cacggtggct tacacctgta atcccagcac tttgggaggc caaggcaggt   45840
ggataacttg cggtcaggag ttcgagacca gcctggccaa ccccgtgtct   45900
actacaaaata caaaaaatta gctggctgtg gtggcgggtg cttgtagtcc cagcttactc   45960
ggggggctga agcagggaat cgcttgaacc cgggaggtgg aggttgcagt gagctgagat   46020
tgcgacattg cagtccagcc tgggcggcac agtaagactc tgtctcaaaa aaaaaaaaaa   46080
aaaaaaaggg aaacagactt cccaatctac taattttgaa caacatcagt ctctagagct   46140
cagcattctt gccctttcca agctggctcc agtctaatt tctaacctca gtattagtta   46200
accccgacc cacccctgaac acgcctggtg tcgcacagtc catctgtcca agagcacagc   46260
atcaacctga gtgcaggtgg cctgctcatt gcctgtgctg ccacctttcc cctcagtggc   46320
tattcatttt ttaatgtcta gcttcaagtc acctcctctg acaggattcc cctggctctt   46380
cgggcagagt catttggtcc ctgtcctctg ttccccacca cacacacttt atcagcccca   46440
attacagctc ttatattgta tgatgggatc aatctgtgtg tccccttcat cccttcccca   46500
caactaaact tcaagttccc taagaagac tatctttttt cttgttttt cttttttaatc   46560
aagtgtctag cacagaacct gacacacgac aaatccgaat acagggtacc ccaaaaaggt   46620
cagtcagtt ttaagcttta ataacttctt aagtcgaaat gctacaaaact tacaaaactc   46680
atttgaacgt ttacttcttt tgactctgtt ttaattattt taataaatgt aattttctct   46740
tctggttaat gtatgccata tttcactcag gggaactgaa acaaaaatta aagttaaaac   46800
gtgttattca acattcacag agataaatag tgttaaatta actttcaaat ggtgttctta   46860
taagttgcag catttatagc cttgaggtta ctaaaactgc aggaagactt ttgggacacc   46920
ctgttttga ataaatatgc ttacagcatg gctcctcctg tgtttactgt aaaattcagt   46980
ttagttttta agtggttcca cgtgggcaca ggtattcttt ggccagtagt tgtccttata   47040
cttagaccca aggagccctt gtccagggcc cacactttag aaggcaaatt ccaaattccc   47100
tccccaaatg gcactgagcc tgcttcaagg gtctgcacgc cagcagcagt gttatctgct   47160
aatgtctgta ctcccatggg cgaacattgc tgactcggt gttcatactc ttgtgcccaa   47220
gaggtggctg ggggacagct gcttctggga agcttgaccg agcttccacc aatgggctag   47280
agccctgtgg gaagagagga ggtggctgca aaccaggaac tggaaatcgc ctctccctgc   47340
accatcatat ttaagtgcag atcatccaaa gtttcaatct ggccttcat gtcaattccc   47400
aagtatatt tgtctaggta ggaaggtaga acttattgta cttaatcatt tgttaacttt   47460
gtttataact tttaaatatt taggtatctg gcctacagat ctctgttttgt acttttgccc   47520
tgggtcctgc atatattaaa ggtgggctga ttttggcctt aaaagaatta ttttcccaca   47580
aacagatttt tctccttaaa gagctaggtg ggtaggaagt acttccatat ggaaggtatg   47640
atagcaaaga atgactgcag tcactgagca catactttgt gctgggtgat ttacacatag   47700
tttttcagtg agtcctcaca acaacccaat aaagtaggta cttaggagaa aacagatatt   47760
cagtgacatt agtttgttcc agctcgtaaa actagtgctt tagttagcct tagttgcata   47820
```

```
acaaactacg cgaaactgaa agtggcttaa aacaattttt cccctgact gtcgggttgg    47880
ctggctgct ctactgcggg tttccctggg ctcactcctg cagctagctg tgaggagatg    47940
gaggttggcc cgggacagtg cagaagattc cccgtggcct ctcccacctg tctggcagtt    48000
gacgctgctg ttgctgataa tgatgaccct cctttatttt gtgttatcta cttgccattg    48060
caacctcctt gccttttta gttcttgctc ccgtactgtc tggctcgatg cccagcacct    48120
ggtggtggct aataatatac actcaggtca cttacaagca atgtgaccct ggatgggtta    48180
cttaacctca cttagtttgt gtccccaat tgcaaaatgg gtataatggt acagaacaca    48240
tcaggtggct ctgagactcc agcgcagtga ttcaggagag tgcttggcag acagtggca    48300
cttggtgcga gcttactgct agtgcagctg gaatgtagac catcagcgaa cgtgtgttgc    48360
ctttttaaac agtgggaatc aaacaccact cgctttccaa atgtaaatcc tgggcttgca    48420
agtaagtcct agagtgcaga aataaattca aaatacaggg ttgaaatttt aagatagcag    48480
cttttaaaaa ctgggagaca aaatcaaaat aaaacaaagg gacaaaccaa cctgaatggc    48540
accccgccga tgctcttcat taattttaa gattccaccc tggggctgct tgcttcttcc    48600
agcatgggaa gcgctgactt gatgcggcca ggtttctggg accaggaggt tgggacacga    48660
cgacgcactt tttgccctgt gggtctgggt catgtgagcc tagaggagcg cttaaaggct    48720
cgagttctgc agggtcctcg tgactgggtg gggctgcctc acttctgcct gatttgggaa    48780
gcgctgcaag acaaccggc tggggtcctt gcgcgccgcg gctcagggag gagcaccgac    48840
tgcgccgcgt aagtgccgcc tgccctgcgt gggtcgtgcc agctcagcgg gacaggtcct    48900
cgcctcggtc cctcggactt agggagcgcg gggcaggtag tctcaaaagc cctcagcacc    48960
aacaggggag aaagcaccgt agagtgagac tggagtgggg tggtcgtggc cgagtcaaag    49020
ttcaaattgg agcattgggg atgtactgcg tgcgcccagc cgagggaata ctcttgaagt    49080
ttcctggcac aactgtcgca cccggggttc ttccaggcta gaagccgtct cctactccag    49140
gagctcctcc ggggaagtac gaagctgtgg ggtcctctgc cgctcttagc gcgggagggt    49200
ggcgggtgca ggacactttc ccttactccc tcaacgcgtg ttttggggat gtgttgattt    49260
cgtgggtgct cagaagcaag agaagcgaa aatacccttct atttttgaacg tgcccaaagc    49320
agggaaactt ggcttctgcc taggaacgca taggaagact tttattcttg gaatgtagga    49380
ttagcagaaa ccaagggcac aggagacagg tggaagcagc tccctgtgaa gtgatacaga    49440
aacaaaagga ctttggaata tttgtggatt taaatcccag ttctggcctt ggctagtgag    49500
tgacctcggg caaattattt aagcctacta aacctcagtc tttccatctg aaagatggag    49560
ataataagtt tttctttta aagaattgtt ttattggaaa tagaaataac atacagaaaa    49620
tgcctcccta gcacgggact tggcttttca gctaagtgta attttcctta tcagttatga    49680
ttgatgatga agtctatggt gaagacagaa caaaataatg tttaaaactc tggccatata    49740
atgactgtgg ctatgcatga cccgtgtgca gtcacctctg agcccccac cttcactgca    49800
accccagtgg gtcccaagca aggtgcttgg gttttggagc tggacaattc tgtgcaattc    49860
ctggttccgg tatccactac ttggatgaca tcagggacgt aacttatctt ccacagcctc    49920
agttttggca tcagtaaatg aaaaaggagc ccctcagtac ttgcctttcc cttcccggc    49980
taaatgtaca actcatttt tttccattct ttgctttggg atgagtaaga acaaagatgt    50040
aagcagagta aaaagtccat tgagaataca tttattagc ttggtaaata acgttttaaga    50100
aagttgtcca aaaggagaat tggagcactt ttggaaaagt acactgcacc ggctttgttg    50160
gcatatgaaa gtctgcatgg tcgtcaagac cgtttggcta actgggcatt ctagatgtgt    50220
acctcatgct agtctaagta caggggcaac cctttataat gtagtgtcag tgttcttaac    50280
cagatgttgt tttattaatc tttatagga gatgattgtt tgggagggc aattgatccc    50340
ccaatttata taaatccagt ttataaatca cttttatagtg ggattctact agcctgagaa    50400
ataggtgggt tttgactgac agtttgaatg acttagaaga gtgttaagaa agtccactgg    50460
gtttaccagt tcactcccca caaaaataa aacaagaag caaataatat aacagaattc    50520
taaaaatgag tttgttttg ttttgggaag catctagttt gtcagaggaa acactgagtg    50580
ttgaatacta ccctgggatg cacagaacta aggcaatgag aggggaggaa ctcagttctt    50640
gccccaggta tcatcagata tctgtttatt agcaccccaaa tactcaaggt aaatagtaat    50700
gacccattct ttctttttt gagacaagag tctcactttg tcacccaagc tggagtggca    50760
ccatctctgc tcactgcaac ctccatctcc cgggttcaag ggattcttgt gcctcagcct    50820
cctgagtgac tggaattaca ggtgtacacc accatgcccg gctaatttt gtatctttag    50880
tagatgtggg gttttgccat gttgcccagg ctggtctcga actcctgacc tcaagtgatc    50940
ctcccacctc ggccttccaa agtgctggga ttacaggcat gagccactgt gcctggccag    51000
tgaccccttc ttaataggaa gtatggttca ctaaagagca aacatgattg ttttagttta    51060
ccatttccga tggcttata atgtgagatt ttcattgact gaactaagaa catttaaaag    51120
aagtaggcaa gcttctcaga attagaaaga tacctctaga acaatgactc attaacgtct    51180
atattgactt gtgagagagg taagctgggc aaaaagctaa gaactgtact ttcctggtaa    51240
aaacagtagt ggagtttgaa cttttatact atatttgcaa gctcaaagat gtaagcctta    51300
atagacagtt cacaagacag ctgttacagc gtatctgaaa tgaaaccagg gtattgagat    51360
tgctctcct taagagatat tagaggtata accttgaaca tgaaatcaca tgctttcatt    51420
gctttaactc agaccctggg gtgcaggaca gggtggtggt agtgaaagag ggggaaggac    51480
tgtgtcctta gatcttggag cctgaaaag caaattctta gcagcttatc tttccaaatat    51540
agttggaact tacctcctac ctttttctct ctagtctgat tctagttatt ggttgtcttt    51600
aaattgctta gaattgttta caggccaaaa tatttacttt gaaccctaaa ggtaactttt    51660
tcctcctttc ctttttggga ctctgtatcc cattacccct cttcaaaaa gatagtgcca    51720
catatctttt tgtactgtat gattcttggg agagaatgta acccaggtcc caagcgattc    51780
attttctcat ttatttattc atttaactaa tttttttccca gtgtttgatt atgaaaaggt    51840
ttaaactttc agaaaagtca aaagaattt gcaatactaga atctacctag attctattat    51900
tgattagaag ccagggtatt gatttcaatt gattaatcaa ctggcattga ttagttccta    51960
ctgtttgcct ggaggtttgc tcagcaaagc tgtaaaaaca taaaaggcag ggtagggtta    52020
gggaacaagg agagtttgga tttggcggag cataggctaa gagtttgtga aggaatcatg    52080
taactttggt ttgaaaagtt atgttgaagt tgtatcatgg aggacattaa atttcatcgt    52140
agaaagttta tactttttcc tggttgcagg tgggagccat tgaaggcatg ggaggaatgg    52200
agtgccttgt gttttagaaa gctcactgaa gcatcagtgt taggctaaat tgagggaaa    52260
aggaccggaa gtctgagaga tgtgttagga agctttgtaa atgtctcggg gcaagtaagg    52320
gttgaactgt ggatagaatg gagaaaaag gaagtagaan agcacttggt gacagatttg    52380
acttgaggac ttctggtttt agaactcagg catctgcaat tataagggag catcattaag    52440
aatctggaag tcgctgggca tggtggctca tgcttgtaat cccagcactt tgggaggctg    52500
aggcgggcag atcacctgag gtcaggagtt tgagaccagc ctggccaaca tggtgaaacc    52560
```

```
ctgtgtctac taaaaataca aaaattaacc aggcgtggtg gtgcatgcct gtaatcccaa   52620
ctactcagga ggctgaggcg ggagaatcgc tgcaacccgg cagcagaggc tccagtgaac   52680
cgagattgca ccactacact ccagcctggg caacagagca agactgtgtc tcaaaaaaaa   52740
aaaaaaaagt atctggaagt catagaagga ggaagtttga ggagaatgat gacgtcctgt   52800
tatagagtca gtgggtttga ggggcgatt ggttatcctt ttggaggtga cagctgacag   52860
tggtgatact gtcctgaaat gcccaatagc aatgtcagga ctgaacaaac atttggacta   52920
gtgattaata ctcaaggggt ggttgaatgg gaatgtacgg aaagagaaaa aaggataaga   52980
tcttgaagaa aatctgaata tatggagtcc ttggagcaaa aaataaatac aggtgttcaa   53040
tgatctgtta gtattttaat gcctgtttat ctacagtgtt actatagctg cagttctcat   53100
taataattga ccacagttcc taactaaaag accatatctg cactagtaaa gtgaagtaag   53160
tctttccttt tcccattctg ggaagttcag ggggtaaggt gaggcagagg aaagaagaag   53220
agaaagttaa ataaatttt ttatctagga cttttagagc atacaacgct ttttccaggt   53280
aacccacttg cagatcagaa gccaggtaat ttaatgaact tgtctatctt ttcacaaggc   53340
aacagctact ttttttttt ttgagatggt gtctcactct gttgcctagg ctggagtgcg   53400
gtggcacaat ctcagctcac tgcaacctct gcctcctggg ttcaagtgat tctcctgcct   53460
cagcctcctg agtagctggg actacaggcg tgtaccccca cgcctggcta attttttatat   53520
gtttagtaga gacagggttt taccacgttg gccaggatgg tctccatctc ctgacctcat   53580
gatccgccctg ccttagcttc ccaaagtgct gggattacag gcgtgagcca caacgcccgg   53640
ccaaggtaca gagttttttaa gtggcagaag ccacatttga agctgtgaag gcatactttg   53700
tttttttatt ttttatttt atttttttgaa atggagtttc accctgtcgc ccaggctgga   53760
gtgcagtggg gcgatcttgg ctcactgcaa cctccgcctc ctgggtaaaa gcgattctct   53820
tgcctcacct tcccaagtag ctgggactac aggcatgtgc caccatgccc agctaagttt   53880
tgtatttta gtagacacgg ggttttcacta tgttggccag gctggtctcc aactcctgac   53940
ctcatgatcc gcccacctca gcctcccaaa ttgttgggat tacaggcatc agccaccgtg   54000
cccggtctga gggcatactt taaatctttc atgctattcc caccggactg cattgccttc   54060
ctatatgcta ctgactgtat gctaggtact gtgttaggcg tttgcacatg taggctccttt   54120
actgtggccc ctctgttttg agaaggtgat cagcaggtga gctcaaagca cattgcacaa   54180
ttggttgttg cacaattggc aggatgtctg ccctctgatt gtgccttgtt ttcacccaac   54240
ttcttgaact ctacaggaag ggccagcctc tctcagaaat gccagcccct aaagctggta   54300
caaaggtcat gcaaccttcc tacttccctg agttcaacaa tcacttcatt cattctcctt   54360
aagatcatac ctaaaatcct ggcttattta agggtgaagt ggagaaaagc tctatttca   54420
cttatgcatt tgtttaccc catcaatctt ctgccttccc tcattgtccc acagttgtgc   54480
ctgtctaagg tcactttttg cttttttctt atttccttc cctggggagt ctttggagag   54540
agggtgcgat agaatgtgta gcctggagca agattacccc cagttgacta tggaagcgct   54600
gagaattatg ctgcttcctc aatgcttttt tcccaaagtt agaagtagca agttgtatag   54660
tgagtaatag gatttgcatt gtgaatgggg tcttcctcca gtgaggactt tactaagtgc   54720
agtgtttatt tgtagtgggg cacagaactg cattcctcat gctttatgac agtatttagg   54780
gtttactggt tttcatgcat gtctctcttt gctagaatga gggctccttg aaggtggata   54840
ctgtccccctt ttcatcttta actactccac aagttttagc aaagtgtctc acccttttact   54900
gtatggcttag aaaatctctg aagagttgag ttctgttaaa ggagagaaaa ctatttgtat   54960
agaagagtgt gggtagaagc ctgtttgttt gtttgtttga tgtgagacag ggtcttgcca   55020
cattgcgtag gctggtcttg aactcctagg ctcaaataat cctcctgcct cggcctccta   55080
aagtgccggg attacaagtg tgagccactg tgtccagccg aggcctgcat gtttgaatgg   55140
atcaagaaat gtgattgttt agtgctgagg gagggtaggg aggttgcagg gaaaggcctg   55200
gctagggaaa agctcatatg ctcctaagtc aagcaacaag aaatgtagaa cgtgaaataa   55260
agatgaagcc attctgagtc atgtgcagac cgtgggaaat atctccctgt atttgacaaa   55320
aggggaaatg gcagccatag ctaattctga agatgaaaag tgttcctgcc tgggttactt   55380
gatgaagaat attattagca atcagcaagt caagtggaaa taatttgttt tgttttgttt   55440
tctcccttc taactattgg catgttgta gaattaactt ggctggcagg agaatgaacc   55500
gcctgtgccg ttgggacaca ggagatttct gagctggcag actgcacact ccatgtaaaa   55560
ccatgactct ttccaccatt cttgtgtaca cgtgtgccta aacattggtg tctgcaaaat   55620
ccgagacgtc tgtttcagag aaaaattgct ggaagccact gatttagaat tttaatagga   55680
ttttttaaaaa atctgtgctt aaaaaacatg taatttaatc agtgttgtag ccccctgcc   55740
cccccaagaa tagcctttct taggtttctt aggttgtctt acgaacactg acagaaatgt   55800
gtaggttcag ggcacctaga gcagatgtgg aagttctttc attaaggtag cctgcgtgaa   55860
tcatccctgt gactcaaagc ctgaagcagt tttagcctga tctccttggc tgcatttta   55920
gaatcttaga cattccaagc tgaaagggat tttgggaatt atatagtcca tctaatctcc   55980
agaatttaca aatgaaggaa ctgaagtcca aggggagaag tgaattggct tgcccaagga   56040
tatacctgtt ggcaaagtga aggctggaac ttttgacctt gtacattcag gaattgtgcc   56100
agagcctttc ctgctcgtct tagaatgtaa tgtactatag ggagcccgca gccatcctct   56160
acggtctggc tttattgtct cttttctccc tattttttag tctccttcta cctttttctca   56220
gcacaccttt caagtgggat ggaagttgaa acccactcag cagagaatat gagaaataca   56280
tgtgtaatga cacaaagtta ggtgtgttag cattatgtcc agcaaaggag gacacatacc   56340
caaaggttgg gagaagtggg aagaggcctc tgaaaatatt ggccttgtgc tgaatgagtc   56400
gaaggaggga tcagggaaga ggtacccgct ggattagctg ctgccaagtg cccgtggcag   56460
ctcaggaact tagactctca gcagtctctg ttcaggagat ggggagggaca aagcgctatc   56520
attggtaaga atacagcagt tgctcagaaa aaaggactgt ccatcatact gcagctgcag   56580
agtggccttg ggtatataga aacattgtta atgttctgtt gggagcatct tagactgatt   56640
agcagcagag ctgattttca ctcccaggga tctgggtaca tctctttctc ggttaatgcc   56700
accactgtcc acccacccag ccatctaagt cacatctggg atcatcctag attctttgtt   56760
ctatttcaac tctaatatat aatcacaagt ttcttccagt tttacttttct tcttcttctt   56820
cttattatta ttatttggag acgtagtctc gctcttttgc ccaggctgga gtgcagcagc   56880
gtggtcttgg atcactgcaa cctctgcctc cggtgttcaa gtgatcctcc cacctgcagcc   56940
tcctgaatag ctgggattac aggcacatac caccaagcct gctaatttt tgtatttttt   57000
tgtagagaca gggttttgtc atgttggcca ggctggtctg gaactcctga cctctgtgta   57060
tcttacccac cttggcctcc caaagtgctg ggattacagg cgtgagccac tgctcccagt   57120
caaccttcta attattttta gtctgccct ctccacgcta ttattactag tttccagccc   57180
tagttcaaac tcctgtcatc tttattctag attattgtga aacatattaa ctggccttcc   57240
tgcctgctgt ctttctggct taagtccatc cttacattga tgttcatagt actcttttca   57300
```

-continued

```
aattatcaag cccttcagta gttcctagtc actagaggat aaagattctt agcatatcta 57360
gaaaactctc cctgatcagc tctctactga cttctctaga ttccatccta tttctccact 57420
tcctacttat gcttttctcc tgcctctgta ttggttatct attgctgcat aacaaatttt 57480
taaatgctat aaattctatg acctcccaaa atagtgatat aggcgttaag aagaaattat 57540
ttgggcagat agtgagagta caggagtcct cggtaaggtt ttcctttaa tgaaaagcag 57600
accccaaatc attttctttt ctaacaaaga gcagcctgcc tataaaattg agctacacac 57660
atagacaagt aagctggaag cttgcacagg tgaatgccgg cagttgtgcc aataggaaaa 57720
ggctacctgg gctaggcatg ttcaaaatgg cagctccgtc ttcccttttc ctttccaacc 57780
atgtgtacag tagggaacag acagtaatgc tggccaagtg gaaagcccat ttgcttaata 57840
aggttagggt gaggtggcca gcttcctgc atgctatgta aatgtcacac ctggtccagc 57900
caatctgtgg gccaatcttt gtctatataa atcagacacc acctcctcaa gcctgtctat 57960
aaaatctggt gcactccacg gagggccaga tttcccattc agatgcccct ctcttgcaag 58020
agagagaagt gttctccttt ctcttctt tgcctactaa acctctgctc ctaaactcac 58080
tccttgtgcg tgtccatgtc cttaatcttg gcatgagatg gcgaacccca ggtatttacc 58140
ccagacagtg atgccacctc aataggagag acagcagcac atgagggaag tatagaggga 58200
ttcatttaat taggagttaa agtcaaggtt ggaaactagt ttggaggttt gcagtagtcc 58260
aggcaagtca caataaagaa ctggattagg ccatgagagt agatttagag aggtgaaggt 58320
gaatttgaag aacatctagg agattcagtt ggtgattgat tgctgtggg aatgcagggc 58380
cagagaaaaa tggataaata aagaatacat cctggatttc tggctttagt acttgagttg 58440
atgggagtat ttccaaccaa gatgaaaaat agggaagtaa ggacaagttt agggaaggag 58500
ataataagtt tagttttttga gttcttctta actacttttg attttttgtca atataataaa 58560
agtaatgtta taattctcat gataaaaaat tttagtcttc ttctccccac ctcccccatcc 58620
ttctctctatc tctgagacct cctctcatac ttttacctgc ctgttctagc ctttaattcc 58680
aaatttccaa gtaatctgcc taatctgttt cttgatttat tggttttagg gttacacctt 58740
ttatttgagg tattttctat tgacttattc aacaaggtga aaattcacca cttttacata 58800
ccttacctcc tgactttcct accctccaac ctgtcataa ggtgatataa ttttctcttt 58860
tgccaaatca atatctaata tttaccttat tatgtaaata tgctcactgc tgagccaagt 58920
agtatactat aattgcaatc catgtcttgt acagttttat tttctcatc aacttaaaaa 58980
tttcctcttt ggattgttct attttctcta tcactcttat aacttctgtc caaacttgct 59040
gacagaactg taatatccctt attgatgta ttttttacaa aaactcatgc ggtagtcagt 59100
tatagatata tttcttcctt gaggacatct catgtggatc ccctctatc ttactgctcc 59160
aatatgcagt ggttgctctt taaatataac tgttattctg tgatttcact tcccctcttc 59220
agtcctagtt cccctgttag tgggctccca tgtcttcctc tttcttggtt tacatcattg 59280
ctttggtgga ccacatttgc cagtagcttt ctgagaagtg gtatatgaga aacaaacaaa 59340
caaaaaaaac tggctggttc ccaagctgta tatgaggtga aaaaattaa attaaaaata 59400
aaaatcaaaa tctagctggg tgtggtagct cacatctgta atagcagcac tctgggaggc 59460
taaggtggga tgattgcttg agcctgcaag ctagaagctg aagtgagctg taattgcagc 59520
attgtactgc cactgcagcc tgggtgacag agtgagaccc tatctgtaaa aataataaat 59580
aaataaaaat aaataaataa ctcttatgta tttctgaata tttatttatt ctcatgattg 59640
atataggctg ggcgtggtgg cttcaccctc taatccaagc actttgggag gctgaggtgg 59700
gtggatcacg aggtcaggag ttcgagacca gcctgatcaa catggtgaaa ccccgtctct 59760
actaaaata caaaaaaatt agttaggcat ggtggcgtgc acctgtaatc ccagctactc 59820
aggaggctga ggcaggagaa tagctttaac ctgggaggtg gaggttgcag tgagccaaga 59880
tcgcgccact gcactccagc ctgggcgaca gagcaagact ccgtctcaaa aaaaaaaaa 59940
atctaataca atttttggctt ttgattcttt ttatgtgata ccattctctt tctgtcttct 60000
tctctggaaa gtttctaata gtcacttctg aaatgtgttc ttcatctttt catttcttga 60060
tctgggaact tgatggttcc tttaaatctg aaaaatcata tctatacctc tgcagatatt 60120
ttcgcagtat ttctttgata atttcttacc ctgatttttt ttttttttt tttgaggcaa 60180
ggtctctctc tgtcatctag gctggagtgc agtggtgcga tcatggctca ctggagcctt 60240
gacctcctgg ggcccaagtg atcctcccac ttcagctccc taagtagctg ggatcacagg 60300
tgtgtgccac catgtctggc taattttta aaccttttt gtagaaatga aatttcatta 60360
tgttgcccag gctggtctcg aactcctggg ctggagctat ccttctgcct tggtctccca 60420
aggttctggg attacaggta tgagccacct gatctcccct gaattttatc tgccatcttt 60480
ttctggaact cccattagtc agatattggt cttctggaac caatcttcta atttccttat 60540
cttttttctt cctattttt aaagttctat tatctttcaa ttatattttc tgtgagattt 60600
ctataacttta attgcactgt ccttttatca aattcttaag atttcttaag attatgtttt 60660
taatttcag aagcatgttc ttgtatttta ttctgttgtt taatggatgc aatatcttct 60720
cttatctcct taaagacatt ttggttttg gagagttatt ctgcttcata cattgctatt 60780
tcttgtgat tttattttt gtgcagtttc tttggattt tctaccaagt tggaggcttt 60840
gctcaaatac ccaatggttc cttgaagtct atttacatat taagtgtgag aaactaaatt 60900
gctggttgga cactgtgttg aagggatttg tcagcagttc actggctccc tgcagttgat 60960
tggtggattc aacatgcttc attagaggat cctacatgtc attatgtgta ggttcttttct 61020
ctaagagaat gcagttgttg caaagaagaa ttcttcagtc cctgcagag gctgaagaat 61080
gaaggtatag agtccttact gcctacattc tttctgctga gtgttcaagg ggctggggtc 61140
tgtcagtgtg tagaatttct gagttttcag taggggtatc cttccccaac tttcactgtt 61200
tcttatattc ccaagtctag agtgtctcta ctgaaaatgt ccaaataatg aatttgctgc 61260
agaataaggc tttcacctct cttttagact ggggagggac ttgaggatct aaatgctgtt 61320
atagactctt gccaattcct ccattttcag ccccatactt tacttttgcc ttctgcagta 61380
accagtactt accatttttg acccttctg tagttgtatg gtttgaatta gcttgttttct 61440
tatttatatt ctgccttcat tctctgcaaa ctatctgttc actttccatc taacaacaaa 61500
aatttgatct gccccattta ctgttatctc ttctattttc tgggtattg ggattttataa 61560
ctttaaaaaaa tgtctttact ctcatttag agaggtttca tgaggggaca gaaataaaca 61620
aatgtttctg attcaccacg tttcagcagg attaaatgcc attttgacat gttgagtttc 61680
atatacccat ggggcatcag gtaaaaatgt taggcaggaa gtttgatgga tgaggcagaa 61740
gcttttgaga ggcactctca tttttgagtgg tgtccacaga aagtgctggt taaagtgatg 61800
agaccactct ttagtgtgtg gaagtgtgat aagctgtggg ccaaggatag acttctagaa 61860
gaattttaga agatctatga aaacacaaat tacagaaggc aaggcatcga taaatttgcc 61920
aaagggggcac tgtcagcatg tcagaaaagt caataaagat aaagacagat ttttcttttg 61980
aattagaaa tatggagatt attaatgatt ttggcaagat gatatgcaca gaagtcagaa 62040
```

```
tacattaaga aagaaaacag cgttttttgt tttttttttt tttgccttca gaaactgctg   62100
acagaagcaa taatagaggg tattcagtgg cttatgaagc agatgaacca gcctgtgggc   62160
tttttctgtt gtctgcacct tggatactat acgtagtgga ttttcaaata cctaatgagg   62220
gaatgcatgc agtgactttg ttgcccttgc attagctgtg tgaagacatt ttggctggtt   62280
tgatctgaga tgtcatttct catcctccac ttttctcttt cagggttggt gtgagcaagc   62340
cagactgtat ggggctttaa attctgggta tgactgatga agctgatact attaaccatg   62400
tctttcttca attgtatata tgatgaaatt ttgcaggata atagacag tggagtatag     62460
gggttacact agaataagac ctaaattcca ttttttgaggc ctctgaggga gctcaaaaca  62520
cagcactttg tcttttcttttc atgagttctg aaaaaattga gaataagaa agaagagcaa  62580
ggcaggagga cagtgaaaca tcagcttgat taacgaggga ggctgggctg gaatggcact   62640
tttcctttg ggcaaatggg tttcctatga ctgatgcctg actgagcaga cttgcccagc    62700
aatcctcaga ttcacacagg gtttagagag aaaagcaccg tttcatgtgg ggatggggag   62760
tgaggtgagc ccaacatgac cagtttatcc aaatgtaccc ataaggtgaa cctttctgcc   62820
tgcacaccta cccctacgga gggaagaagg cagcagcaag gggccagcag tgttacactg   62880
ttggacttcc tggacactga tagagatatc cagagctggg aagaagcagt gccctaaaat   62940
acaggttagc tttcaatacc cagcacgagc ctgtacctga tccccctccg aaccactccg   63000
accatcgctc acctggcccc caccatgggc ttccatctgc attgtttcct gttaatggcc   63060
tttgtagtca ctgttctcct gccaggaact ctcttcttcc tagacactgt ctcatgccct   63120
cagatctgct cagatgtcac ctactccagg gggccttccc tgaccaccta tctcaaaatag  63180
tgccactgct tgaccccttt cctctctatt ccgtttatcc tgctttgatt ttcttaaaag   63240
ctctcgccta tctctcttcc tcagttcatg aaggcagatg ctgtctgttt tattcattgt   63300
atgagctaag gatatattta ttcagtgaat gagtggatgg tccagtcaac ttgagtctg   63360
ttccaggtca gctgctgcct ggagtattat cacttgcaaa gtgcccagt cagcatgggc    63420
ctctattgaa gtgctacact aactcctttc aagagtggag gtgggccaag gcgcagtggc   63480
tcatgcctgt aattccagca ctttgggagg ccaaggcagg tgaatcgctt gagcccagga   63540
gctcgagacc agcctggcca acatgcaaa attccatttc tacaaaaagt acaaaatta    63600
gctgggcgtg gtggcatgca ccggtggtcc cagctactct ggaggatgag gtggaggat   63660
catttatgcc tcaggaggcg gaagttgctg tgagccaaga ttgtgggtga cagagtgaga   63720
ccgtgtctca aaaaaacaaa acaaaacaaa aaaacacaaa gagtggaggt gaagcttgaa   63780
tgagacaaca tatggaaaag agctgagaaa tgtactagaa tcatgaagc gagtcctata   63840
gagtggttac tgctacaaat agtagtcact cttttagaat cagggagaag tttcttgtca   63900
cttcagggag tggtacgttaa actgatgaca ttgccacatt tactaggatt atcctcatat   63960
aaaatgttct cattcattgt tcccaatctt agcctgtatt tgccacccgg tgtatcctaa   64020
tgttcttatt tgaaaatgct aattatagta ggcaataga aggaggcaat tcttttttt    64080
tttattttg tttattttta tttttttgaga cggagtctca ctctgttgcc caggctggag   64140
tgcagtgatg cgatctcggc tcactgcaag ctccgcctcc tgggttcaca ccattcaaaa   64200
ggaggcaatt ctaaagaaga acagagctac actgacttga gcaaaactaa caaaaatttc   64260
ttagtggaag acactgactt tgccatgaga ttttaatgtc ctaaagagta gagagcttca   64320
cttaccccaa aaagtaattt ctgaaactga aagaagtaca ctagaaatcc attatgaagc   64380
aatctgtgga cctgtgattt tcacttcttt acagataaat atgcctttca gtcatttgca   64440
atttcagtac ctataaattc tgcaaatgga caaaacaatc cagtttattc agaattccgt   64500
ttttatcaac agttgcattg aggcagattt cgttatattc tgtcgtttat atagtggtat   64560
atggaaaata cgtggacttt gacatcaccct agatatggct tcagattcca gctttgcaac   64620
tcaatagctg aggggggcatg agaaaattat ttaacctggg actgagttta ctcatatgga   64680
tatgtctcat ataaagctct ggccttaggg cttgtctaag aatagtgtca cagtcaagaa   64740
aaggtgtgct gtctgttagt gaacggctat gagatgttct gtaacaaggg agcccattta   64800
attgtattta acccagactt tcccaaatgt ttttccttat aaaatctgt aatatagaca    64860
gataaaatct gtctatatta taaaatctgt taatataata cagaattggt attccataaa   64920
ggaccctgtg ggaaatcctg gcttgcataa tgccagacat atttgatgta agaaatcagt    64980
tttgcttccc ttttccagct tagtgttggc cagtcagaat tttcactgga cgcctaccag   65040
gcaacttaaa gtagaactct tgggttttg tgccttcaca ccctccatcc caactcctc    65100
catagtcttc ctgatctcca atcatgcccc cactattcat gtattagttt cctagggatg   65160
ctgtaacaaa acaccaccat ctgggtaact taacagaaat ttattgtctc acagttctga   65220
atggtagagt ccaaaattaa tgtgtcagca ggaccatgct cctcctgaaa cctgtaggct   65280
acgatcttcc ctgcctcttc tagctgttga tgtttaccag caatcctggg cttcttggct   65340
tgtagataca tcacttagtg tctgcctctt cgtcacatgg cattctcctc taaagttccc   65400
tcctctcttatt ataaggacac gagttatatt ggatgaaagc cctgccctaa tccaactcca   65460
gcataatctc attgtagcta attattaggt tggtgtaaag ttacttttaa ttaaaagtag   65520
tgtggctcac acctgtaatc ccagcacttt gggaagccga ggtgggcagt tcacaaggtc   65580
aggagatcga gaccatcctg gccaacatgg tgaaaccca cctctactaa aatgcaaaaa    65640
attagccagg agtggtagca cacacctgta gccccagcta cttgggaggc tgaggcaggg   65700
gaattgcttg aatctgggag gcagaggttg catgagctgc gatcgtgcca ctgcactcca   65760
ccctggcgac cgagcgagac tcgtctcaaa aaaaaaaaa gtaatggcaa aaaccacaat    65820
tacttttgca tcaacctta tacgtctgca aagaccctat ctgcatattc                65880
tgaggtacta ggagatagaa cttcaaaata tcttcagctc agcacataac aattcatgca   65940
gttactctgg gcagaaaaca ggtgccatcc ttgtacttct tttctttccc ttagccatta   66000
tgtctggtct atgagcaaat attcatggat ctgccttcac aatgtagctg accatttctc   66060
attacctccc ctgctactcc ttgaccccag cctttgtcat atctcttggg ttataacagt   66120
ggcctcttat gaggtatcat ggttccatcc tgattctcat taagcctact tgttagatag   66180
caaccagagc aatcatgtca cagtgtaaat cagatgatat tcctcccttg ctctaaactc   66240
tccagtggtc tcccattatc attagaataa aatgctaaca cagatgaagg aagataagac   66300
tctaggagct ctgctttatc tgtctctcca gcctcattgt gtaccactcc ctcccctatt   66360
gactgtgccc gccaacccac agtaagcacc tgtttgcac tgcagggctt ttgtactgtt     66420
ggagggc tggctcccctc tcagtctcag atcatctacc agagatgtg tttcccactc       66480
attgttagct gaaacacttg caccccatct ggcagagagc agagaaagtt ttttttcttt   66540
ttttaatttt tttttttttt ttgagacaga tctactct gttgcccagg ctggagtgca    66600
gtggtgcaat ctcagctcat gcaacctcca cctcctgggt tcaagcgatt cccctgcctc   66660
aacctcatga gtagctggga ttacaggcgt gtgccaccat gcctggctaa ttttttgtatt   66720
tttaatagag acagggtttc accgtgttgg ccaggctgat cttaaactct tgacctcaag   66780
```

```
tgatctgcct gccttggcct cccaaagtgc tgggattaca ggcataagcc atcatgccgg   66840
gcccagagag agttttgtca ccactcatga agcgaagcac tcaggaaaca aaaggagaga   66900
aacaggaatg agatagctgt ccctgggagg gaaaggatca ataactaatg ggtatcccca   66960
aatcagattt acatgagtca caatccaaac aaatgatttt cttctgctaa tctgaatttg   67020
gaaaggaaat ccctacctag gagcagagat ccaagagac tgatcttggt ttaaaaaaaa   67080
aaaaaaaaaa aaaaaaaaaa actcttaact ttttgttgtt tttttattgg ttgtcccagg   67140
atctcatctg caggttctgg aactagtggg gtgtcacagc cacccatgt tggctgccag   67200
aaactgtaag gggagaaaaa gaatatcttt tcctcatcca tcacaaggtt catggctgag   67260
cccctataac aaataaaaag aaaaaaaaaa aagattaaat gggaaaagta taaaagttat   67320
atttaatgta agttttcagt gacacagaaa ccttcagaaa acgaagcccc aaggacccag   67380
ggaaaaccat gtgtgtttag ggacagttgt gcagaagtgt aattggagga caaaagagtg   67440
tgatctaata gtaataatct ggggaactca gcgaggccta tttgttcaga ttcctttcag   67500
cctcggtgtg acattccttc cctctgggta tagggcagga cccctctgga atggggtct   67560
tatgacctac tttcagggga agtaggtcag agaattcttt catggccagc tctcaggaga   67620
aaaaggtggg aaaaggtcag agagcagcct tcctgcttct gctgttttt caatttcctg   67680
ctgtttaaaa tactcactgt gccaaggtgc cattatttg ggttatcatg ttgtgagccc   67740
cgacacctca gttccttgct ttaccactta ctaactgtga acctgagcaa atcacttaga   67800
ttctctgagg atcggtatct cgtctataaa atgagatgac aaggtaaggt tgtttgtaac   67860
ccttaccttc ctggttagaa ataaaaaata taaagcaatc agtacagttt tttgtacata   67920
gtaagcattc agtaattggt agctattaac tggtatcatt atcatgatgg tgcctttagt   67980
cacaggcatg gcccttctat ttcaaaactg ttgaagaaca tgttgggata atgtttacat   68040
tttactttcc accacatgcc cacttaaatt tcccttctgg ttggagtggg atttcaagga   68100
aaagctctag actgtggtgt cagattatat tattttctcc tcttcctgat ttttctcatt   68160
ctctccctgc cacacacctc tagtttcctt ttcctgcaca tccaaggata tggtggcaga   68220
gacagggatg actaattcgt tagagagatt agacatcact gtctgatgcc agagaggaac   68280
ctgtgaaaag gagataggcg tgtctcagtg ccacttcagc aaaaggttgc cctttacctt   68340
gcatgccatg actgtgtcct ccctgggaaa agagtacttc aagagtgttg tccagggtgt   68400
caacatagtg agactctgtc ccttaaataa ataaataaat aaactcctgg gctcaaggga   68460
tcctcccgcc ttggcctccc aaagtgccag gattacaggc atgagccaat gtgccgggca   68520
ataactatt taattgcagc tacaatggtt attatatgaa agatatgtat cctttgattg   68580
gagtaatcga tagtgtaaag tggggaagtg gaaacgagtg aagggagaa tataaggctg   68640
gtttaaaatac ctgctctttg tttgtttgtc ctcatcctgc aggttttgtt tttgattctt   68700
tttctcttgg caaacacac acctccagtg gcattttcag gtttcttttc ttgaggtctt   68760
gcaaatctga ttatgctact ggttgatcag gtagggggaga actggccagg attttccctt   68820
tttgtctctt ctgatggtca ggtcgattgg aattggagtg tgagctaatg gaaatagca   68880
tctagctcat tttaccaata atgaagatga gcccagtatg tgcaggtaaa tgtttaacaa   68940
ttggcagtct gaaaaaaga aggcctgatt tctggtgttt gctggttact gtggtataaa   69000
tactcctacc atagttgatt tcaagctacc aacaagatta ctgaacacat agttggaaaa   69060
agatgcccag aagcaaatca tcatatgtgt aatctgtcta cccacagat acaaaaaaca   69120
taactctaga tcacagataa tagtaaaatg tagtaaaatc attaggaaat gataagtttt   69180
gagtactttg aacatatgtt ttaaaatgta acttcttcaa taacagttta attgttaacg   69240
gtggctctgt tgaacaactg actctcaata tttctgaaaa tttaaccatc agctctcttg   69300
cgctgctga agcacatcag gtgggaccca gagaagttac tgtcttacca aggtcctcga   69360
atgagtcatg gcaggacctg ggttattaca gagttgtttc taaaaaccag actactctag   69420
acagatttac ttatcaacgt ttcttttttat tcatttgttt atttatttac tccatccttt   69480
aacaatccat aaaagggatt taagactatt acaggctgtt attatctatt gagacagtaa   69540
gagtcagaat atttgaatat atctggaata aaggtaggcc gggggcggtggc   69600
tcacgcctgt aatcccagca ctttgggagg ccgaggcggg tggatcacct gagatcagga   69660
acctgaggtc agcctggcca acgtggtgaa accccgcctc tactaaaaat acaaaaatta   69720
gctaggtgta gtggtgggtg cctgtaatcc cagctacatg gggggctgag gcaagagaat   69780
cgcttgaacc gaggaggcgg aggttgtagt gagctgagat cgcaccactg cactccagcc   69840
tgggtgacag agcgagactc tgtctcaaaa aaaaaaaaaa aaaaaaaaga cgggagagtg   69900
gaaagcagat gagatttaga gccataagta aattctggct ttgagtcttg gccttgtcat   69960
cttgatcaag tcagttactc cttggtaaaa gttttctaat ctgaagatga aggaactgga   70020
ccacatgaac atttaatatc ttgtaggtct aaaatatggt tccttattta gattcatcaa   70080
ttcaataata tttgcttagt accaactata tgcactctca ttatgaactg tactccagcc   70140
agaatgaaat tcagatatga taataaatat tattataata gcatctcaca tttatgcaga   70200
gccttctgat ttgccgaaga gaaaatttac tttgagtctc tgggattctg tggctttagg   70260
agatcaggac atatcttaac agaatgttag agaaagaaga agctattcta gaagtacaaa   70320
tagaacctta ttcctaggaa acagaagagg tcatacccag gtagtaataa ggaataagca   70380
cttttttctgc catgtctagc agttgcttca cttttgtttt ttaaaaaagc aacaaaatta   70440
cctttttttct gagtataaaa ttttgtaga aatttagaa attattaaga agtattaat   70500
aaggaaaaaa accatatatc caatcctaata tcctgctttt ctttacctaa taatatttta   70560
tcatattttt caaaacattc ttagtagaat cattttaatt gctgtatgta taataatttt   70620
atctttttgg tatatagtaa cttatctgat gtcttactgt tggaaatttt atttattgac   70680
aattttatt attctaaaga acactgtgga taaatagctt tgttccatat caaaaatcat   70740
acattggaca catgattttc aactttaata tttaaggttt agtaagacaa ttttagcaaa   70800
ttatatactt ttgaccttta gagtctttga ttctgttgat attgtttttgt atttaccag   70860
atttttattct gtttctaaac atttattaag aagaacattt tgtttgaatt cttcaatatg   70920
atatgtttga actggaaata gcaccactgt tttcatatta tttcaagtag gtatgataaa   70980
gtgtagggtt aacaatttc ttttttcaact ttctgtggga gatatcctct gtctagtata   71040
aggtttgttg gttttagaaat tgctcaataa atgttcaata aataaaagga ctcatgctaa   71100
tttaggataa gcaaaacat atgagagggt gtttaaaaaaa cccacttctc catttatgat   71160
aatagcttca attctcataa ggagagatga cagctaagca cagttcagga attctgactg   71220
ttgaatgaga actgtaaaat gaagtatgtc ggtgctttaa ttcacctgaa tgggaaacca   71280
tgactcagat agttatttga ttaaatgtta atgagatcta ctaaattgac ccaattcttat   71340
cttttatgta ttagatttat atcaattaaa acaggaccag ttttacctgt tttccttttt   71400
taacatcttt gagtcaacat ctgcttacaa gggaagtgct gtaactaccc tggttattta   71460
aatattaatg gcttccatta aagggagcta gggattggca gcaggaagat tgagaaatta   71520
```

```
gatggcatga ttggtttctt gtttctgtcc ccaggggaaa aaaaaaaaac aaaaacctct    71580
tactggaaga gcttcttcca ttattttttt ttaatattgc atatatatat atatatatat    71640
atatatattt tttttttttt tttttttttt ttttttttc tgaaccagtt agagagtaag    71700
attgttgatt tcaggcatcc cttgaaagta gctgtgctat aaaagcatca gtgtaaacaa    71760
gttcaagtaa tttaaaaaaa tgttttcaca gtgccataga ggtcattacc ctgggcttc    71820
ttgggaacct aatttcagtt cctaaattca ttttgttctt tattatagtc agtaataggc    71880
aaaagcattt tttagctcca tcctggattt ggttggcctt atttacatta agtgtgggga    71940
attctagtaa gttaaccctg agagacatga caagggttat atattcaatc acattataat    72000
tataaccctt tatcttactg gggaaatgtg cctgaaaagc ttttaaaatt tgctataacc    72060
aatattttca tgttatgcca aattgggttg taataagcat gtcgttaaaa gattttttaca   72120
cgttttgtat ttttaagatg ttctaatggc ttggcatttt aaagcactga acaaaagcag    72180
gcattatatt tgcataattg tgtatctctt tttgcatcca gaaatgtgaa tgtgtggagt    72240
acccttcat ttcatgtatt tgatttagaa tttacagcta agaacataga tcatgcttaa    72300
atagcaggag tgcagagtca tgtaacggcc ctggtgtgct tgtcataatt ccctacttag    72360
caaggtcagg attagggtga gacaagagag gcactacctc aggtgtaaaa cttaagaaag    72420
tgtcaaaaaa aattcaagac tagtaatatg ttaatgtaat agttaaaaaa ctgtataatg    72480
cagagaaaaa ttaatgataa taaaaatggt caacatttta gatcaagatg agatctgacc    72540
ctgcatctgt acctccctcg cttctcccta gtcctggcct tctctacttt catgtccttg    72600
catgagacac tcttttgatt caagtttttcc ttacctgaat ttggtgacaa tagtcctcac    72660
tttcctggtg acaaggattt ttttccttgg ccaaatttta gtcaggcttc tgaatctcct    72720
gctaggcctg tttgtgcacg tccttgtaaa atccagtttt agcaaaggac actagctaag    72780
tcgttttacc aagaaccagc aacatcaaca tccgatcgcc tcaatgtctg accaggtttc    72840
tcatcctgca ccatccccca ggtgatgtct gatcaccctg gcctgtcttc agtgagaatc    72900
ctgttaggtt tagccagatc caccttaccc caacgcttcc tttgagtaat tttccatcca    72960
ctgacccca cactgctcct tggctataaa ttcccactgg cccgtgctgc atttggagtt    73020
gagcccaatc tctcttcctt gctgcaagac tgttgactgc aaggtccctg tgcctgtcat    73080
tatcctgaca aagtctttgt ctccatgctt taacaaatac cattcagtcg tttttctgta    73140
acactggtgg aattaggaga ttcaaatcat ctacaaatac atgggaaagc ccactataaa    73200
tataatttac atattgatgt tcaagtaaat aattatacag ttttatgcca ttattattat    73260
aatctcagat gaatattcta agcaaacatc agatctgaag atctttggaa agctttgtgc    73320
taatggtttg gggcctaatg tctttaattt acttatcagc tagcaataag gggaggaacc    73380
taagggtagt tgtaggaccc tcccccccttt cttcttcct tcctgttttt gtttttgttg    73440
ttgttgttct tgatacaaa ctggggcttt ataagagata gagaacataa ccagaaatcc    73500
attgcttctt tgaaatttcc ctgaaaggtg tgcatggatg cctgaggtct caccttttgt    73560
taagctgttt ccacccaccc atgatgcctt tcccatttct cccaccctgtc tgagaaccat    73620
tcaccttttta tccatatcca acttggataa ggcctttctg tgatcttccg gcctgaaatg    73680
tgctttcaat cctctgccct tctgtggtgg cataatggtt tctaccaccc atttatggtc    73740
agttacagag ttcttgttgt tctgagtctt tatctaatcc tccattgaat ttactttcca    73800
aactgcattt taaaaaatgt cagtggttca ctcctataat cccagcactt tgggaggctg    73860
aggtgggagg attgcttgag ctcaggaggt caaggcaaca gtgagacgtg actgtgctac    73920
tgtactctag cttgagcaac agagcaagac tctgttttaaa aaaaaaaaat cagtaattga    73980
aaaattactg acactgtaaa tcccttgaag agtctcccat tagcctttga atttaagagt    74040
aagcagggat tgggtgtgct tatttatggt gctatccaag gtccttgcag agggccttta    74100
cacacaatat ttttttttaag tgaataaatg aatttcttgc atgtaaaagg gccaggtaaa    74160
tatttactct tatgattcat ttttggaatg ctgtttttat cctagaccct gagagatggt    74220
tggtgccatg tggaaggtga ttgtttcgct ggtcctgttg atgcctggcc cctgtgatgg    74280
gctgtttcgc tccctataca gaagtgtttc catgccaact aagggagact caggacagcc    74340
attatttctc acccccttaca ttgaagctgg gaagatccaa aaaggtaagt aagtttaatt    74400
aaatcagaaa accactggca tgagttcaac agtttctctt tttttttttt ttttttttga    74460
gacgaagtct cgcctgtcac taggctggag gtcagtggcg cgatctcagc tcactgcaac    74520
ctccgcctcc cgggttcaag caattctcct gcctcagcct cccaagtagc tgggattaa    74580
ggcacaagcc accatgccca gataattttt gtatttttag tagagagggg tttcaccatg    74640
ttggccagga tggtctcgat ctcttgacct cgagattcac ccacctcggc ctcccaaagt    74700
gctgggatta cagctgtgag ccactgcacc tggccaataa ttttttctttaa aacaagtaac    74760
ccataggatg caaaatatat ttcagtattt ttactcagtt gttttattc aaatatatat    74820
atatatattt tgtttgtttg tttgtttgtt tgtttgagac agagtcttgc tctgttgccc    74880
aggctggagt gcggtggcgc aatctctgct tactgcaacc tctgcctcct gggctcaagt    74940
gattctcctg cctcagcctc ctgagtagct gggattacag gtgccacca ccatgcctag    75000
ctaatttttg tattttagt agagatgggg tttcaccatg ttggccagge tagtttgaa    75060
ctcctaacct ttggtgatcc accctccctca gccttcaaaa gtggctgggat tataggcatg    75120
agccaccgca cccagcctat gtcaaatatt aatgacttga tgtcatatgt tgtctgagtt    75180
tttagctaaa atgagaatta gccggggttg aattacctgc atggttgagt tgcagcattt    75240
tatttataag actagtagag tgcctgtccc ccagtggtca cttaatgcta atactatcct    75300
taaaacttac tatgagtcaa tcactggttc caagctttct gcatgaactt atttaaacat    75360
ctcaacatcc cggggaggtg gacccatttt acacatgtga aaccaaggca gaaagagatt    75420
gagctactag ccagagttca tgcagatatc agctggtgtg taggcttcat actcagcctc    75480
actgcagcct ccctgctgtg ccccgttatc cagcaagtct gggccttagt tttctcatta    75540
agataagatg gagcttaac aacttaccca acttacagag atgttatgaa aatccaatga    75600
gataaggcac gtgaaaatct tttgtactct ataagttgtt ctccaaatat gagtgtttgt    75660
aattggcttt atttagagat tgtgggtttt tctattgtta ttaccaatag gaaaaaaggt    75720
atcacttagt gttatcagag gctaaaattt atgacctgca tctgctcttt ttttttttt    75780
tttttttttt tgagacagaa tcttgctctg ttgccaggct ggagtgcagt ggtgcagcct    75840
cggctcactg cgctctgcac ctcctgcgtt caagcgattc tcctgcctca gcctcctgag    75900
tagctggaac tacaggcatg tgctaccacg cccggctaat ttttattttt ttagtagaga    75960
tgggattttg ccttgttggc caagcttgtc tcaaactcct gacctcaagt catctgcctg    76020
ccttggcctc ccaaagtgct gggattatag gcgtgagcca ctgccccggg ccctgtatct    76080
gctcttaatg cttctttgcg cttaatcact gtgcgagtaa atgatttcaa ctttctggac    76140
ttcagtaggt tcctaagcta taaaacagta gacaggtagc tattctgagg agctgtttgc    76200
aaagagcagc agaaaaatgg ggtagtggct ggagggagca ctgggtgtcca ggaagggtct    76260
```

```
ttaacagaat aggagagaat gtttgtttgc tgatgaaat gatgagtggg gaattggttt   76320
ggtttgggga accattgttg gagactgtgt ttaagaaggt gagagacagg gatctggcac   76380
acaggggccc caaggttgtc ccttgtcaca ggtgggaagg cagagatggt gcctgtgaag   76440
ctggcaggtt ggcagatgtg atgggaatga agaagaacac cggaaatttt agacaaatgg   76500
tcattttaaa gatcaaaagc aaatctaaat actctataaa gaagtttaaa ataaagcaag   76560
ttttattcgt tcaaagtgtt ctcacagcca ataggatgtc attgttttt ggttttcgtt    76620
ttacacgaag acattcttgt attttaaggg tatgtgtaag tgctgttcat atgtcttttt   76680
ctgaaataca cattggcttc aagtttcacc atctcttttc taaggaaaga tgaaaaactt   76740
tgataatgta tttagtgtat tttaaaaagg actgatttt acctcacaag agaagtcttg    76800
ggaagatggc tgccccacca tatgggctga taccattaag atgcttgtga agaggcaaag   76860
tgtcgttaaa ccctccaaat tggattacat gcacgtattt cagcttcctt aacaagtgga   76920
ttctgatggc ttagatttct gttcattaac agtaaatcaa agcaaccat ttaatgtagg    76980
gatgaaaagg agttaagtaa ttgttataac caaattctac caatccacat atgaggaaat   77040
tgagactgaa atactttatc cgagttgccc aacgggatgt gtgcagtaga gttgggtagc   77100
agagatgggt ttaggaccca aatccttctga cttctgctct gtgatttgcc tactataatt   77160
tagttctgtt tgtttcagaa gcttctaaag tgttcttcta aagtgaccag atgcatacac   77220
acaaaacaat taaggaatta ggcagtgcat actaaagtac taaagtatta catttaaagt   77280
aagtgcactg gagattcgga ggaggaacct atccctgtcg gttggcataa tcgagggaga   77340
aaatactaga gctgtcgtag ttgtaaaaat aataagtagc taacatttag tcattatatc   77400
cctagtacct agcatagtac ctatacataa taggtatgta taaatatgta tggaatttaa   77460
atttgggtac caaccatgtg ccaggcattg tgctttacat ccattagctc atgtagttct   77520
cagagcaacc ctaatgaaga atccataagc atttgttccca ttttacaaat gagaacactg   77580
aggcccggag aaatcaaata tcttgcctag ggccataaaa ctagtaagtg gcagagcttg   77640
aattaaaacc tatactggcc aaccccaggg cccatggtat gaaccactat gctatatgag   77700
cagctctgaa ttaaacccta tactggccaa ccccagagcc catgatatga accactatgc   77760
tgtatgacca gctctggact tcagagtgtc gggtaagatt tacgtaaata gcgaaaggtc   77820
tgtgcgtacc aaatgagaga aacagcttaa acaaaggcat taagtgaaag tgaccatggt   77880
gtttctgtat catacatctg gtggaaccaa gtaaaaagaa tacagagaaa tccatctgag   77940
agactactga catctctcct gttcttgtct tccttgccta tgagcatttc tcagttatgg   78000
gtattagcag cagccaagaa agattccaag ggaggtagtt ttatcttcca ccctcccaag   78060
tcaagattgg tagatcttca tctgatgatt gacaacattt aaaatattaa atctgtgtat   78120
aatatcactt cctgaagtta tgttacacag tcaaattctt tgaacagaat tttaagtggc   78180
tgattcaaaa tctggtacat ctgggtattc aaatgtagcc ctgacaacat aattaaggat   78240
aattttattc atccgctttg ctgaaagttc aggaagctct ggacagatgg tcagctcact   78300
cccctaaatc cctttgttt atcgagtctg tcaaaaccct aggaacgtga gtcttattat   78360
tgcaatggaa catttcgag ataaacagta gctcgcaaaa aaacaaggga aatttttaat    78420
ttttaaatcc tcatttagct ggcttagttt tatgtaattg taattgcatg tttactttct   78480
ctgaagctag aataaatctt tactccctga aacaaaatga agtaggaggc acattttagc   78540
ttgtttataa acactgcatt ttcacacttt aaagactatt ttactggtag gtcctaattt   78600
attgttactt atgatctgat aatgtctgtc cacactggtg ataacttgag tgtttgtgaa   78660
tctggcatgc atgctgatta gctggttcaa gcccttttgtt ggtcacattc caatgttttt   78720
gaaagtgtta atatcacaaa cattggttgc agcagtaaaa aacaaggagg aagtaaaatc   78780
acttcaaaga aaacctttc cttttttaaaa ctgttctaaa cattttgtatt gtgagtcatg   78840
gtgctggaaa gatagaaact cctccatctt gggagtttgt tttccacatt ccattaataag   78900
aaggatgcac aggacatttg aaaatataaa aagtcatttt agttgatgac atttttaaatt   78960
attttactgg gatttagtta gtggaaattt aaaatttgaa acagggcaaa acttttttta   79020
tgggctagag aaaagttcta aaatttcttaa gatcttttag caaggtctgc cttaggaggt   79080
ttttgtagaa ataagccaat cttggtgcct tgtcagtagg gcttgttta gttcattcat    79140
ttattgactt gttcatccat tcatttgtta acattcattc attaaaaagt atttattgaa   79200
tgtcttaggt gtgtaagtca gcatgccgag tcccaaggta tgcaaagtta aataacacaa   79260
attcccact ttccaacctc ctgacctagg agggaaggtc tgaaacatac tcaagtaaa    79320
ggtagtagag aagctacttt ggcatcctca ggaagggagg gatgagtgaa catctgaatc   79380
atttgagagc agtctgtgga ccctgtgtgg tgctggtctt gggagagata gattgattga   79440
atcatccttt cctctgttcc attccctcca gctcctttct attatatatt ttctcttttt   79500
ctcattatac tttgaccttt tcattttttg tgttgtcttt ctcaaatcct cttcttccca   79560
tttacctctc tgtggtccac atctcactca tttccaatcc acagttttta cttctctact   79620
ctccttttt tttttgggag gcaggggtg gtatctgttt gattttgaga agattaaatag   79680
ttttgctaaa aatatttcaa aagcatttta aaggctgccc agccctgggg ggtgatcttt   79740
ctctgggcta attaagaagg gaagtgaaga aagggagaag aaaaacgaca gatgcggga   79800
agagtgggag gggaggagtg gcaaaaacca cttttcccaa acacctcccct ttctttctc   79860
ataagatcct cacctctctc tcttttctc tggcttttt tctgatggag gagggataga   79920
cctcattggg aacagaatgt gaagaccaac agaggttgca ttaagcaatc ttccctggga   79980
gaaccaggct gagccagaaa aaggaaattc ttctagactt cacttggagt ggcaaaggc   80040
taatgataac tttccctttcc aattgactga acccatattt tatgtgcagt gctagggctaa  80100
gggttcatat gcatttttgt tgtttgatcc tcacagaaag cccaggatag cggaatcagt   80160
atttatattt tgcataaaag gaaagaggct cagagatgc gagcaacttg ctggggagtc    80220
ctaatcagt taggattcca aacccaggtc tgtcaggcta ggaaacccat gctcttctat   80280
tgtgctagcc taacaggacc ctcaaggacc acctgttgag acctttcttt tgtccccatg   80340
acctcctctg ctcagaggtg ctccctgttc ctagtcagga ggtgcattc acagacagca   80400
acagtagttc tgctccctac ctgccagctt ctttatatag attttacatg tgggggctct   80460
tttaatccag gtgccccaca ggcagtacat cttccataga ggagaaactg aagaacaggg   80520
aggttaaaatg cctgtatggt gggtcaccag ctggtctata ggagcactag gatcagcaaa   80580
ggaactgtgt ggtctagatg agaggttttc cttttgagag gcatgcctat atatatgttt   80640
ttttttgag acagggtctc gctgtgttat ccaggctgga gtgcagtggc atgatcatgg   80700
ctcactgcag ccttgacctc ctgggctcaa gtgatcctcc cacctcagcc tcccgagttg   80760
ctgggactac aagcactgcc accatgctca gctaagaggc atgccactac ttcccttccc   80820
actccttgcc acctgcacct tctgactcac tctagttgaa agccctgggg gaaggaacaa   80880
actctgcagc ctgactgctg tgtttaatcc cagctctcct ctactagctg gcaagtcact   80940
taacctctct gtgcttcagc tttcttatct gtaaagtggg aatgagaact atacttccca   81000
```

```
catcatgtaa agccctggta ttctggcctt gtaaaatagg aactagtggt cccaaaacag   81060
cagtgtgctg gtaaaagttt agcaaccagc ccttgcagtc aggacccctga cttgtagcat  81120
ctattccctt gagtgttaat attgtcacct tggcttattt tatcctgtca atgtctctga   81180
atgctgagct gggaaaagat gctaacaatt agccttccag agcctaaggg ctccacctac   81240
cgtcaaaggc atctttagtc gatggcatgt gaggagtcaa gcttcctgac ctactagcca   81300
gtctccaact taatatggct cagacttaca tcgcttttct tgagtgactg gttcctactg   81360
gggacacatt ctttgtcacc actaaaggat tcttcttcac ccaaactttc ccttttactt   81420
cgccaccaca ttctgctgtt ttctgttcct ttgccactcc cttcctgacc actacttccc   81480
ttcccactcc ttgccacctg caccttctga ctcactctag ttgaaagccc tgggggaagg   81540
aacaaactct gcagcctgac tgctgtgttt aatcccagct ctcctctact agctggcaag   81600
tcacttaacc tctctgtgct tcagctttct tatctgtaaa gtgggaatga gaattatact   81660
tcccacatca tgtaaagccc tggtattctg gccttgtaaa tgtcagctcc tagtagcatt   81720
ctttactcct gggcatcctt ggctgtctaa gcatccccaa ttactccttc cctgtgcctg   81780
tcccaatggt gccataagaa cgccaggacc cctgccccc acaactgcca cattgtccta   81840
tttggctccc cctgagtagc catgaggtca ctcccagtct ccccactgtc caccactgtc   81900
caccttttccc caatgtccac agccaccac actcccatat gcctcagccc actcctctta   81960
gtagatgtga caggctttt gccttcatga aaacaagagc gtgaaggaca caggccttct   82020
cggggcgagg ccgagagctg cttcaccaca ttgttactct tgcaccccac tgtttcaggt   82080
caggttactt tatcctgctc ctttccatgt ggcccaaggt gatcaccttg gtttatgcaa   82140
ggtgtaatga taggagattt tctttttcttc tttttaaaag aacttaaaaa aaaacttatt   82200
acagcttata aatatatttt gggcacccct ccccaaaggc ttaaaacttt cacatatcct   82260
tggctaaatt gtgaacgtgg actatgtggg atttggccagg ggcaggctgg aatttgctga   82320
aggaactacc tgtcatacca gttcccttt agcttatcta atcactccat ttcatccaga   82380
ctgagataga tggctcacat ttttgttgtt attgttttct gtaatcctcg ggtaaatttt   82440
ttttccccca ctaggaagag aattgagttt ggtcggccct ttcccaggac tgaacatgaa   82500
gagttatgcc ggcttcctca ccgtgaataa gacttacaac agcaacctct tcttctggtt   82560
cttcccagct caggtaggtg cccaacagaa agaacaccag tgttcaagac ctggcttgcc   82620
gtttgagggt agaaatgtta gcctaccgag ctacaggtct ttaaaaaaaa atctcataga   82680
tttttttctaa aaataagatt tttgtttttc taaaaataag caaacctgca tggtgttcct   82740
atttatggggc aggaaacaaa tgttttctgc gggagtggga agtgtccaac ttctaaattt   82800
cttgcagcct tatttggagt gttaatacta ccaccttctt cctgccacag tcttcttcct   82860
atcattttgt tgtattttgt ttctaaaaat acttagggca gggatgggtc aggggagccc   82920
aaggaggata ggaagtaagg agattcctga agtgaacagg taatgcgtgg ctaagtatgt   82980
ttatatctag tcagccatgg ccttgtatag ctgcgctgtc tgtggactcc ttcatgcact   83040
cagtacccca ttattgagca tattctgttc tgtgggggcc acagaggaga cagaactgaa   83100
ctcagactct atggatcttt agaagattgg gaggattgcc gatctaggaa ggcttctggc   83160
aggaaaggcc atcactttcc caaatctcta tagacagagg tgggtatgtt tttctacttc   83220
accaatccta tgtagttcac ctcagatta tgccattctt ctgtatgaac aagacattt   83280
tagcttagag gtgctgttgc gggtattgct ggaagcgctg agaagcaaat cttattccac   83340
tgcagagtaa ttttctgttt tcatcctcca aattggattt gttttacagg ctagagaaag   83400
caaagaaaaa gctatcccta tggagggtgt tatttatatt ttcatgtgat ttgcatatag   83460
ctgggttgca tctgtagtaa ctgagtaaat tgcttggtcc agggtggttt tcaagttacg   83520
ttgttctcc tggtactatt gagttatatt ttcttgactt tctttcctg ctctctcaa    83580
tacatggcct ctgacatagt tcaccccaaa gcagcctgtg gtgggatgtg gtcaggttgg   83640
ggcatgtaag aaatggtgaa aaattccaga tcctttgtcg ttgggctcac agtagccgtc   83700
agcctgtcgt ctttttctgga aggctttctt ggccctaga gagggcttct tatttcttcg   83760
tcagtgttgt gttgagtgag gcaagtgaga tgcctagagc ttgcaatgca aggagacact   83820
caccctgagg gtcatacaag tgcaaggtca gcactgagc ctgagcaccc tccagtgtct   83880
tgcttggtgc ctcccatagg tagagcccaa ctgggagcca ggtggaatcg ggtggtctag   83940
cccataggg tctgcctaac agggcacaga gcggatggga ggagagtgat aataggcctt   84000
cccagtctct taaactttat gccttcaga aatattctgt atgtgtgcat tttttatatc   84060
atatctattg atgtcattga atgcagtcat ttatctgcag taacttcttt atattagttt   84120
tctcttgctg ctataacaaa ttgccacaaa cttaatgtct taaaacaacg cacattttat   84180
ttcacaattc tgcagattag aagtctgaca caggtctccc tgggctgaaa tcaaggacca   84240
gtagggttgt ggtacttctg gaggctctaa gggagaatct cttttcttgc ctcttgcagt   84300
gtctagaggc tgctcgcatt ccttggctta tggtcccttc ctccagcttc aaagcctgca   84360
aaggcagcct gagtccttct cacagcacat aatctccatg gtcatgtttc cttctctgac   84420
tcttgtcttc tacctctgtc ttctaaaagg actcttatga tgcatttggg gccacctgga   84480
taatccagga taatctccct attttaaggc cagttgatta gcaactttaa ttccatctga   84540
aacctgaatt ctcttttgcc ctctaaccta acatattcta ggaattaaga cactaacatc   84600
tttagggagt tattattctg tacaaaatgg atacttgaac atttgcctag attattgagt   84660
ctcgatatgt tttctctcag ggattctcac atgttattgc atacaagaat tctctgactt   84720
cccccagaga ttctgacttg taaattggca gaagccagca ggttgcagaa ttaccaagtg   84780
aaccttctc tgtgaaacca ctccagccta tgggccatca ccctctgcct gaagctcctg   84840
gctgaaaagt gaccaacacg ccttttacca gaaagaaatg cctacagcag ccaaacccaa   84900
acagaggtga tgtgtttccc atgttgaggg ttgaaatgag gggagtgaag agacctgtgc   84960
agcctgtgga ggttggcttc cctaatccag cttgcggatt ctctaagaac tgttaggact   85020
gcttccccat cttctttcca cttctagtcct cctccccccac tctagctgga gaactccaat   85080
tccttacttt cccttctgct ttgttactttg ttttgacac cagtcagtcc cttgttaccc   85140
tctgaatgtt gagtcttctt tggtaatgat ccagatttgt aaaaacagga actaagggtg   85200
agagaagaga tcagatggaa acaaagcaaa aacccagttt ttttcttct caggttgcct    85260
ctgggcaggt gaacagctat gtctagaatg taggtggtgc tttggcaccg taaacctgtt   85320
catggaaagg aatttagttt gcatgctcta ctggttgcca gactgaagtc tgaaaacccc   85380
cttcattaaa caatgactgg actgttggtt tttgcttttt ccccttaatt aaatgaaaac  85440
ctagctgtgc atcccctgac caggttatgt tcttttgagt ccagtactgt agccataaac   85500
acaacctaag atgatcccag gagacacaac gggaaagaat gtcttaagt gtacatggtg   85560
ttctggtgag agtgatagat gaagcttcgg gagaagaggg gcagagatga aaaaacggta   85620
cccacagatg ggtaccacca tgtggcagcc aagatagatt gttccaagaa cctcttacca   85680
ggaagcccac atgcagagcc agatatctga ggcttctggc tataaattat ggagtcacac   85740
```

-continued

```
cagtttgggt gaaggagata aagcaggtgt gacaagaaga agcagtggtc actgagacac 85800
atttggcaga gatattagtt cattgtctgt cataggaaag cagctgatat tgtcaccagg 85860
ggagaaatga cccctttaaa aaactgaagg tagagaaaat aagagatcca ggaaggatgg 85920
cacacttgtc atatcctctg agtattttt ggggggatgc tgtttcttaa attagttttg 85980
ttttcctgtt attgctgtga gactgccctg ttattgtata caaatcagtg cagaataaat 86040
tccagaactt gaaattggtg tgcagtggga atacaacctg caagagaaag gagtaggcat 86100
tttgcatggg ataaaaagta taaggaaact agcagaaatg tagcagttat agctgctggt 86160
aattgaacac tgactatgtg ctaggcactg tgcattttct tatctaatcc ttacctgaac 86220
cccatgagga aggaattgtt atcctcattt tatagatgga gagattaaat aatcagcccc 86280
aagttactca actagaaatt ggcagaactg gaatataaaa ttaggcctcc gatgtggaaa 86340
tccttgagct tggccgtcat gtgttagatc cagagaaaac gagtcatgga aggcacttga 86400
gtatagtggc caagactaca gtctcttcgg taagtcaggc ttggatagaa atcttggctt 86460
cgctgcttaa gctaaaggtg accttgggga atttcttagt gtctctgagc actggtttcc 86520
tcattttaaa atgggaacca aaataacctac ttggcaatgg tttttgagaca gaagagataa 86580
taagggaaag cattagagtg gcacctaaaa catagtaact atagttgcta ttgtcattat 86640
ttcattatga ttacgattat tatgttatt attactttta aaattattaa cacaaataat 86700
gtcaagaact aaaccagtca caatttgaga ggttacagat gacagcaaat agagggaaat 86760
tgtaaattag aaggacctga accccagcca tcaaggtgga ttaattgcta ccaggtcagg 86820
aaattactaa gtgaaattgg gatttttttg cactgaagaa gataaaaaag acatagagat 86880
tattactctt taaagtcagc atccttctca ttggaaaaaa aatagctagt attggacttt 86940
gccttataga tgtaggaaca tagataattc attggacaca tttagccaaa acctgcagat 87000
cagttacctc aaatgccatg gagccaaaac ctggggcatt tagagtcagg cctaggcccc 87060
ttcacggagg acccccacctt gatcctcagg ccaagaggaa aggcccagat tcctggattt 87120
gagaatctag tgtctatgaa agatcaggat tacactgctg aggcccgtga ggtgctgggg 87180
caacctacag gaagggctcc ctctcaggat cctgcaggct gggccctgct gaatcagata 87240
ctaggatgat cagatagcac aatcagcagt caattggaga gaaaatgaac cgctctaatg 87300
ctcctggtcc aaaacaaaag gcgttctctc tggcagtaga agagcatgtc ccagaggtgc 87360
ctggaagcca acagaacagc ccttcctggg ggtgaaggcg tggaatcagg ccccaccata 87420
cttcagcatg gtgccatgta cactccctca tctgcacatc tgaacttctc cagtaacaca 87480
gttaatgtga aagaggacag gaattcccaa atgtgctact gctcaccaga aatacctgga 87540
gagctttgga aatatgacag atctcccagc tcattgtcta gctgcaccca gcagagattc 87600
tgattctgca gatctggaga gggcccaggg atcagtgttt gtaatgtgct ccacagtggt 87660
cccagtgcag ccagtcaatg ggctggaatt tgggaaaaga gatctagagg tttggataca 87720
gggattctaa ttccaagtct gcgattcccg gctgtataac ttgggagatg gcattcgtat 87780
tctctgggcc tcagttctct catttagaaa taaagatgtt aaacctagtg gattgctaag 87840
gctccatccc agcattacat tctgtggttc tatagttaag tataaaaata tccagtaact 87900
ccaaatcagg atgtggattg aatgaaggag cccttgaacg tgtggcctgt gtggtagcca 87960
gccttcaggc tagttcccag tgctcttcat tcatcccttg gtgtatgtgc ccttgggcag 88020
tcccctccca tactgaatca aggctggctt tgtgaccaac atgctagcag aaatgatgat 88080
gtttgacttc cacggctacc ttataaaggg caatattact tgtgccttgg tctcttgaat 88140
cttttcagtct gaggaaagga tgccatgttg ggagggcact caaacagccc catgctgag 88200
cctctgtgga gaggaagtga ggcctccacc ctccagtggg taccaacctt ggaagaggtt 88260
catctagtac cagtcaatcc ttctgatgac tgcagctctg ctgattcct taccacagt 88320
ttatgggaga ccctgtgcca gaactgccca gccagacacc ctcaaatttc tgacccacag 88380
gaatcccgag agatcaaaaa ttattattgt tgtcttaagc cattaagttt tggagagatg 88440
ttgtgcggca ttagataact aacatagctt cttgtcttgt acttctaggc tgtggctgtg 88500
agatcttgtg acaactagca tatactccct gcctggggga aggatgagga cataaggagt 88560
ggggattact atgcgagcta ctttttaattt ttgtttttttt ttgcctctca gctccaattc 88620
taccctcttc cctgttctgc catagtagag ctctcagcat ttctcctttg cagcaagcac 88680
aatattaagc tttgtcagta gagggtgctg gagagacatt gcaggaggaa tttgtcttct 88740
cttcctgtgc ctatgtcctg ccttggcttt tttcttggcc ccactgccta gtctgtcagg 88800
agtgtgttga ggtgggggt ggggacatcc agtgacactc tgccttagct atgcacccag 88860
accaccaaga ctcttagcaa gatgatatcc ctggctctgt ccaggtgatc acctggctgt 88920
ggccctccca gtatgaacac aatataccct aggccttgcc ggtgagcagg ctccctacag 88980
cctgctctc tctgcagccc tctcactagc ctttggccatt tgcaccccag agggtcgttc 89040
ccttgtccct cccagtgtgg acaccgtgtg ctccaggctg tgtgcaacct ttcaggcaag 89100
caggctccca gcctcctgag tctctctgtg tccacctgcc agtcacagcc cacctgttcc 89160
tatttaccca aggatggttg accagctttg gaccagggta ctcagtgaac ttctcagcta 89220
ctcagaaggc tgcaaccata cctctccac cgaggtctgg acagcagcct tgggaagggt 89280
ccccctccta acttatgggc ttgtccatct gtgagcactc tccctagccc agggcattct 89340
ttggaattct ctttgtatat gtatgtttag ttctctgtaa taatgaatac ttctaggtat 89400
taacatttcc ttgttcctta gtggacatag gaagcctacc cagcattctg gtctttggcc 89460
aacactgagg atgtggctgt gggagaacag gcccctctgg tgtttcatct tcactttttgc 89520
ccaagggtgt ctgtgatacc catggctggc tggggccaga gtaaacactg gaacttgtaa 89580
cagaattaaa ggtgaatgtt tccaagtaaa aaaataaatt aaataaaaaa ttaaatgac 89640
tctgtggttt ttgacttctg attgggcctt aactgatgca ggtaccattc taaatctttc 89700
tccagccctg agacaccaag ggctggacat gtggtctggc ctaaggaacg agtaataaga 89760
aagcctcggg aggaaaggca gtcagttctt ctgtctcagc cctattctgt ctgagaccac 89820
aggattccct catctgtgct tcattcttct cccttgacag atcaacatgc tttgcttctc 89880
caggcactcg gccaagtatg gccaaccttt catttccaag tttacctgtc cttgcatcat 89940
gtagccagca gagattaact agcacccatg gctgccacag tctggatcac gtcttcttcc 90000
ttggtccagt cagctgagac tgaaggtgct gggtattagc catgatataa acatggctag 90060
caggctagcc atggatgaat ggagactcat ttcttagaga aggggacatg gactggacag 90120
atttattaaa atatatctca aaatgtatct aacacaggtg gatacaaatc caccagcgct 90180
gcaacaaaga tttggagatc acagataatt gtcttcttca aactgactct atttatcttc 90240
tctttgctac gtacttaatg gcatcagaga tatagaagaa tagagggtgt cagagacaaa 90300
ataaaaagaa agtagcttaa ggtgatgtta tagatcacca cccataggta taggtatatt 90360
tgaacactct gcagaaactt ttgcatgcct gatttccttt gtgaaatgaa ataacatag 90420
agagaaagta actaactttt gcatcaagaa gggaaagtaa ggtgtcttct ccacacctcc 90480
```

```
ctgcatccgc ccacttccct attccttata aagtataact ttctggcagg aggcacaaag   90540
agaatagcca taactatctc atgaaggaat gagccaggta gaaaggttag gaaggagaaa   90600
gttaggattc taatggggtg taagctggta caaatcaatg agacaagcca aaacttgatg   90660
agagtcagga gcttcggaat gatgcaagaa ggcctcaaaa caaaaaaaga ttttgaggct   90720
gggtgcagtg gctcatgcct ataatcccag tacgttgggg ggccaaagca ggtggatcac   90780
ttgaggtcag aagttcgaga ccagcctggc caacatggtg caaccccgtc tctaataaaa   90840
atacaaaaat tagccagggg ctgtggcagg tacctgtaat cccagccact ccagaggctg   90900
aggcaggaga atcgcttgca ctgggaaggt ggaggttgca gtgagccaag tcgtgccatt   90960
gcactccagc ctgggtaaca agagtgagac tccatctcaa aaacaaaaaa caaaaaagat   91020
tttgaaaaaa ttaattttct gtatgatggt gccatggcag cagtcatagt aaaggaagat   91080
ttggtgagta gtcaacacca accacttgaa ataaaatttc tttgaaaaac atgaatgtct   91140
ttagcaactt gtgtgtatgt gttgagtgtg tgtgtgtaga attaaaatgt tatgtaccta   91200
tttaacaatt ctagtcacaa aattaattgc tttaaataaa aagctctgcc ttgattaata   91260
ccattagtgt agcagctaaa gtattagctg aactgggatc tgtatggcaa aatgggagtc   91320
catttaaaca tacttgtggg aatttaaaga catttacttg gggtactaat gacttcaatt   91380
aagtagaaac acattactta aaccaagcaa atgatcagcc tctgcatata gaagtgtgaa   91440
gagggcctta attaatttac taattgcact tctcatctta agcagtgcca ttgatttgga   91500
tctgttagtg gtttagttgc tgttttctct aaccaagcgt ggcattcctt attggagata   91560
ggaagaaagg ggtgctaggg atatgtaacc agtcctgaag attggcagat gcctgtctac   91620
tttaagtgac tttccggtcc aaaatgttgc cctaacactt gttgagattc ctaaaatttc   91680
caagggtcac tccaataaag tcctcttata aaacacaatc atgaggctgg gtgtggtggc   91740
tcatgcctgt aatcccagca ctttgggagg ccgaggcagg cagatcatga ggttaagagt   91800
tcgagaccag cctcaccaac atggtgaaac cccatctcta ctaaaaatac aaaaaaaaaa   91860
aaaaatagct gagcatggtg gtgcacacct ctaatcccag ctactcagga ggctgaggca   91920
ggataatcac ttgaacctgg gaggtggagg ttgcagtgaa ctgagatcac gctattgcac   91980
tccagcatgg gcgacagagc aagcctccat ctcaaaaaaa aaaaaaaaca aacaacaat   92040
tatgtttctt aaaagtactg aaattggcaa gtttttagca cccccccccc ccccccagta   92100
tattaactta ctgtttcagt gataggcata tggtctgagc agaaggttat ctctattctc   92160
tctttctctc tgatgcaaag gagggcctgg gggataaggg ctgatggaag atgagggtgg   92220
aaaggaagac tcagggcaaa ggtgatgctg tccagggagg gtatatcaat ctggggaaca   92280
atagggcaga caggatttag tactagtttt gtttcaatga gtttcacttt ctttgaatga   92340
cattccatta agacatggag tagatttttc atcatcattg tgaataagca atggaatttg   92400
ctaatgtgag aaattgtgaa attccttttt gtagagattc tggcagaata gataacttct   92460
ctcttttctgg gccgttcctt ctggaagaaa ccctgaggaa agagtgtcca agttcatggg   92520
ttggtcacca ggggtcgcca gaagaatcga aagggcttct gaggcaaagc catagttgct   92580
tcttgtgctc caataaaggg cccaggtttg tgggacccgc gggccgaccc tcttctgttg   92640
ctagggagac ttctcactta agtatttagg attcctttgt tctttcttta atatttagaa   92700
cttttttgtc cgttcccttt taatcatcag ttcttgctgc aggactttga ccttttaagtc   92760
attagtagag gttttatttt cttcttaaat atgtagtatg agggaattac tcatattta    92820
gatctcagct caaatgttac cctaccacca gaggccttct ttaagtactt aatctagtgt   92880
ctctccattc ctctttcata tcactcattt atttagtttgc ttgtttactg tcttcccaca   92940
ccagcagaaa aatcatcaga gctgacactt aaatagatgt gccaggcact gttctcagtg   93000
ctgtgcatat atcgactcta aaactgcatg aaaaccttag gagacagaca ttaatagtat   93060
ccatattttc aatcagagga cgctgaaaca cagaggagtt aagtaacttg cccaaggtca   93120
cagagctaca aaatagcata gctggaattc aaaccttggc attctggctc cagaatccat   93180
gctcgtaact ataaagtatt ctgcctgctc atgggtagga gttggtctgc atccacagcc   93240
ttagcaaatc cctgtgagta gttggcgttg tatgttaaat gaattaatac attgtggtaa   93300
attcgtagag tgcatactgt tgagcaaaat aatgatatgt attgatataa agagatcttc   93360
acaacatatt gttaagtgaa taagcatata tagagtatag cctggttcta ttttttggaaa   93420
aaaaacgtgt gtatgtatat tgcatatata atagctatag gatatgtcta tatgtgtatg   93480
tgtagaggag gaccatagag aaaaatctgg aagggtaaac ataagcatct ccatgatgat   93540
ctctaggaag tagaatttgt cggggaagag gggctgttaa aaataccttc actgaagaaa   93600
aaaaaaaacc tttagttaag aataagtact gttttttataa tagaaaaagt tttaagaaaa   93660
atttttaaagc tttttttgtt ttgagacgga gtctcgctct gtcgcccagg ctggagtgca   93720
gtggcgctat tttggctcac tgcaagctcc gcctcccggg ttcacgccat tcttctgcct   93780
cagcctccca agtaactggg actacaggcg cccgccacca cgcccagcta atttttttgta   93840
tttagagacg gggtttcacc gtgttagcaa ggatggtttc gatctcctga cctcgtgatc   93900
cacccgcctc agcctcccaa agtgctggga ttataggcat gagccaccgc gcccagccac   93960
attttaaagc ttttgaaaaa aataaatgca ttaattgtct tgcttcatac actcttgaat   94020
tacaacttca atatggtaaa tgttttttaaa ttcctgaatt ttgtaatgct gtaaatgaac   94080
taaagtggtc atttcttcat tcggtcttaa gtattgcaat gtggttttgt tcaggaagtc   94140
ttttattctt tccaaagttg agagttggct aaaggctgca ttctcacaat tgacagctga   94200
atatatcacc ctaaggattg tcacataata acctcatgcc attactgtgg acataattaa   94260
tattatactg catatcatga catttgatgc catattatat tacaaaagtc tgcatgctga   94320
gacacaactg actcttgggg ttttggcatt gaacacatat acttttattt tccagatctg   94380
acttttatgt tttattacag ataagggtga cattagttca caggttggtt ggcccatcaa   94440
agtagaaaga tgtatgtgtg ggcttttctt taaaaacagg cttcttccag ggttattgag   94500
cctcattcac ctcctccagg aaagtaaatc aggagcaagg tcagctgagg ctgaggtgt    94560
gtacacagat cttgttattt aagcattcca agaatgcagt gtcctgtgct tcaaagttgc   94620
ataataaaga tatttggcac tgaggtgttt gacttgactt tgtagtgtgg gctctcaggg   94680
tcaggctatt tttctgagtc cagaggtccg gttcattgtg ccaggtcaca ggaagggaca   94740
tggaaggcca aggaggata gggtggagga taggggagga caggctggag accagaggcc    94800
tgagatattt agagggcaaa ctctccatcc accttcgac ccttggcgcc gcctgcacat    94860
tagaacccacc tgggagcttt tgagaaagac tgatgagtcc tcctccccac agaccaattgg  94920
aattggaatc tctgggattt gggcctaggc agtagtataa aaatactact ctccaaaaga   94980
gaaaagctct ccaaaatgtt ttaatgagca cattgcagct tctgggagtt cacatgtagt   95040
ttaggaagga agtgggggctg gatatccgct ggaatcagtt ggactcgcag catctcacac   95100
tccctgggag gctgggaaga gcaggggcta ccttccaccc gatcccatt gttttttctac   95160
ctctcatatg tgtaatttgc tcctactgct gagtgaatac aagtggaagg cagtactggt   95220
```

-continued

```
gagtggatct gagaggagat aaaaatcact tatttaaaca aaacacagct ccacaggcag   95280
gttggggcag agctggttat ttttattcag cacattggag tttacagcat catttcatgt   95340
acatttgctc ctcagagcct tcaggcaatc ctgtgaggca ggcattatgg tcatttgaca   95400
gacgaggaaa ctgagggcca ggatggcaca gctgttatgt ggccaactgg aaccacagcc   95460
tgtctggctc ccaattccac ggctcactct gcttccaagc agcagcttaa aaaggctgtc   95520
attgattttc attttttctg ctttgactta ttattattat tatttgagac agaatccttgt   95580
tctgttgccc aggctgaagt gtagtggcat gatctcggct cactgcaacc tctgcctccc   95640
aggttcaggt gattctcctg cctcagcctc taaagtagct aggattacag gcatctgcca   95700
ccatgcccag ctaattttg tattttagt agagatgcgg tttcaccata ttggccaggc   95760
tggtctcgaa ctcctgacct caggtgatct tgctgcctcg gcctcccaaa gtgctgggat   95820
cataggcatg cgccaccata cccagcctct gctttgactt ataaaacaaa accctcattc   95880
tgttgacttg ttcatagaca tttgaacact tgaggcaggg ggaataacta gtaaaactga   95940
tcaggaagt tgtgggctac aggagcgaga ataaaaccac cacacagccc actttcctat   96000
tctgtcattt acagatagat tgtgttcaag ccatctacaa attcctcgtg attatctatt   96060
atagcaatag ctaatatttg gagaacacat actatacagc tgaggtttat gaaaaggaat   96120
tcatttaatc ctcccagcaa gcatacagtg tagctactat tattgatctt ttttcaattt   96180
ttatttatt tattattatt attatttttt tgagacggag tttcactctt gttgcccagg   96240
ctggagtgca atggcgcaat cttggctcac cgcaatgacc gcctcctggg ttcaagcgat   96300
tctcctgcct tagcctccca agtagctggt attacagaca cgtgccacta ggcccagcta   96360
attttttgt attttttagta gagatggggt ttctccatgt tggtcaggct ggtctcgaac   96420
tcttgacctc tggtgatccg cccgcctcga cctcccaaag tgctgggatt acaggcacga   96480
gccaccgtgc ctggcctatt gatcccattt ttataggtgg ggaaactgag atccagagag   96540
cttaggcaac ttgccaaaag ttacacactg gtgggtagta aagcctagat ttgaattcaa   96600
acagtttggg gcaagagctt ccatgcttat ttgttatata ataccgcgct gaccctgga   96660
gcttcaggct gctcatcaga ggcctcagtc ggactcttgg cttctaccat ttctacctgt   96720
ttccttagtc ataataatca tttatattta ttgtgctttt tcatacatt aggcattgtt   96780
cgaagggctt taattatgtt gcttaatttg ttaacactca agaatgagcc cgagaggtgg   96840
cgcctcatag gagggtgtg ccccagctca tggccattct tcccagcacc tatcttgtag   96900
caggtccccc tgggccccctt tccaaagccg tgaaggactc tatcaggctc ttggtgactg   96960
ggaaagttcc tctgtgccct ctgtggccat ggttagaact ctgctcagct cttcctgcag   97020
gtcttggccg tggcatccca gtcacctttc cttgagtcag tcttgccttc tgcctcagcc   97080
ttctcccgcc atccaggtca atggaacgca tccactcaga ccttccaaca acaccttgat   97140
ttgtctgtat agccaggcca agtcagaggt ggtgggattt tattctgggc tgaagccagg   97200
ggatccttgc tgactaacca tccaacgagc catgccatca tgcaagggcc cactgttagg   97260
tcctgctaga agccaagcag gggagccaag tagagctttt tcaggtggtt ctgggggatt   97320
cgcctggcga ctgtgccttc ctccctttct aagtctgttc tggtgagagg gtttcccttg   97380
tcatttccct tgtgcacagc tctgctgtct ggctctgctc ctggctggat ccttctcagc   97440
tttcagggct cagggcagcg ctcagacctc attgaagcct tcgctaatca ccttctcctt   97500
ttcagcctcc aatgactctt aaatcaccca tatttccttt tcacactctc caatcattgt   97560
cttaattat ttatttattt gagacagagt ttcactcttg ttgcccaggc ttgagtacag   97620
tggtgctatc tcagctcact gcaacctctg cctcccggt tcaagggatt cttctgcctc   97680
agcctcccaa gtagctggga ttacaggtac ccgccatcac gcccagctaa ttttttgtat   97740
ttttagtgga gatgggggttt tgccatgttg gtcaggctag tcttgaactc ccgaactaag   97800
gtgatccacc cgccttggcc tcccaaagtg ctgggattac aggcatgagt caccgctccc   97860
agccttgtct ttatttctta cttactgcct atattgccca tgcaattcta agttccaaga   97920
ggacatgcgt tttcttcttc actcagtgtt ctgtgtactt agctcccggc gctatgcctg   97980
gcccataatg ggtgctcaat aaatacacat tgaatgaaat agttgaaaag gtctctgtca   98040
ttgaaggtga tggtattgac actacggcca gtagctcatt ttcaaacatca ccgcccctgcc   98100
aatacccttt tctagtttat gtctcccaca tctcctaaat aaatctgtac cttgttcagg   98160
gttttgtcgt tgttatttgc gttggctaaa ggccctggg gctgtctgct cctcctcatt   98220
tttccaccat gttgaatgaa gttgtcctgg tccctatgga cacattcttt ttttttttt   98280
ttttttttt ttgagacaga gtctcgctct gtcacccagg ctggagtgca gtggtgcaat   98340
cttggctcac tgcaacctcc gtccaggg tttgagcgag tctcctgtct ctgcctccca   98400
agtagctcgg attacaggca tgtgccacca cgcctggcta acttttttgta tttttagtag   98460
agacaggg t tcactatgtt ggccaggctg gtcttgaact cctgaccca ggtgatctga   98520
ctgcctcggc ctcccaaagt gctgggatta caggcgtgag ccaccgcgac cagctgtgaa   98580
cacgttctta gtgagtaaaa tcagaaaggc gtttgggctc tcagtgcaga agggaaggtg   98640
tcactgagaa tggattcttt gttgtgcctc tgtttgggaat atgtgtgtta aatgaagag   98700
tcccaaattt tagtttaaac agctaaaaat atataaccat gcccccaggca gtatgctaga   98760
tgtctggcag catgcacaag ccaagcatct acatttaagg agctttctgt ctcttgttgg   98820
gaaaagactt gactgcatga taagaagaca ccagcatatg aggcacagcc tcattcaaag   98880
aaccaaagat gatcagtact ttgctcatag tggagagtgg ttactgaggt ctggggaggt   98940
tttgtaggat ttagtcacag ccctgtaaca cagagaggat ttgggtaagt ttgcttgtgt   99000
gtgttctgta gccttaagtg agtgttctgt gtggtcactg gttttactgt ttcctctaga   99060
tacagccaga agatgcccca gtagttctct ggctacaggg tgggccggga ggttcatcca   99120
tgtttggact ctttgtggaa catgggcctt atgttgtcac aagtaacatg acctgtcaagt   99180
atcccttgca ctgtatttcc tatagaatct ttcatctgag cctcatacct gctccaaaac   99240
taatttagag taaacactga accactatga atagcttaac cgttccagat tatcaaaaca   99300
caactttctg gcaatatcca tccgagaagg aggagcctcg gggtgagtgt cctgactggg   99360
ctgcttttctc ccttgaaatt tgggtgaaaa gttctaatcc gctttcttgc agtctgctgc   99420
tgactcaagc attctgggtt tgcaaaacag ttggtattta ttactatttg gacagctct   99480
ttgcagtgga ctaatgggtg gaattatatt cttaattact cacatgaact aaacactta   99540
tggttcagtc acactcatta tctgataact tggaagcaag acgctattcc cggtggggc   99600
tgaggcggag gaaggataaa gaaagagcaa catctggctg tcactaagtt taccttcatc   99660
tcattttgtt tttttttttt ttaattttg tttacttccc ctgggtcaga atttggagtg   99720
tgagccagtt tgtgactcag tataaagggct tatgtgccag ttttgttgaa gtagttctgt   99780
tcaagagatg gagcattaag gatgattgat ttaattggac atatggatat tattgcagag   99840
gtggttggtg ggtgtttttt catgaaccag ctttgttcca agcttttgct gggttttgtt   99900
tccaagcttt atctcaggtg tagaaacact ctgggctggg ggaaagtaaa ggagaggagt   99960
```

```
ggggagggta aaggtgcagg tgcctgttcc ccaccatgag agtgtgcagc actgttagag    100020
ggtacgccaa cagctcatga ggaccgtggg gtgtgttggg cttctgacca ccatgaggcc    100080
tcggtggaat gcttgtccac gactctatct caccctctt ctttgttttc acagtgcgtg     100140
acagagactt cccctggacc acaacgctct ccatgcttta cattgacaat ccagtaagtc    100200
cgggatgacc ctgtgagctg tcagtgctgg cgtctcctgt cttttatttt ttcctttta    100260
ttaagtacat ttaaaaaata gatttcgttt ttccttttga aaatagaatt taatctgtaa    100320
aattaaaacc attttgagat ttagttttt tgttaacatg tataatcata tcggagtttg     100380
gcaattttcc ttgctgcctt ctctcatttc ctcatttttt tttttctat tgagatggag     100440
tctcgctctg tcgcccaggc tggcagctca ctgcaacctc cgcctcccg gttcaactcg     100500
gttctcctgc ctcagcctcc caagtagctg ggattacagg cgtgtgccac cacacctggc    100560
tgattttgt attttagta gagatgggag cgtggggtgg gggtgttca ccatgttagc       100620
cagtctggtc tcaaactcct gaccttaggt gatccacctg ccttggcctc ccaaaatgat    100680
aggattacag gtgtgagcca ccacgcctgg cccatttcct tattttaat cctatgagat     100740
gtcctgttca ctgaattagg taacccagga ggaggaattc atttcttttc actaacagtt   100800
tgggttcctt atatcacagg ttattatata gtgtcagaac ttgtaatctt tcacaatcgt    100860
ctaatctttc acatagagtt atagatataa aaagtcaaaa tgggtctcca ctttttttt     100920
ttaattttta tttttttgag atgaatctca ctctgtcacc cagactggag tgcagttgca    100980
ccatctcagc tcactgcaac ctcccacttcc caggttgaaa caattcctcc gcctcagcct   101040
cctgaatagc tgggattaca gacttgcgcc accatgcctg gctaacttt gtattttag      101100
tagagatggg atttcaccat gttggccagg ctggtcttga actcctgacc tcaagtgatc    101160
cgcccacctc agcctcccaa agtgctggga ttataggcat gagctactgc tcttggcctc   101220
cttcacttgt taagacaagc aaacatgcttc atctctggac aaaaagtgat actctccttg   101280
gggaggtctt ctgatattgg ttctattaag gtgcaaaata ggagagaaac ttagggtcag    101340
cttctacaga tttggagtat cttgtgccctc ttaactaaaa tctttaactt ctctcacttt   101400
tcagatggtc caaagaaca caaataaaag cggaaaaaaa tgtcaacatg ctcttcccc      101460
caccttgttt tgtcagcctt ccattttcct catccataac tgtgtattta agtaaaagat    101520
gaattaaaca tccttgggtg tttgaaaac aaaaacacaa aaatctttat accagatagg     101580
gagtgcattc cttatgcaaa ttgttgacat aaaaatagta gcttcttctt ttgaatttgc   101640
agttcagttt cttttgaatt tgcagttcag ttgtctgtga acttctaggt tctaataaga    101700
aaatattagt ttaaaattag tcttaattat gttaaaactc cttacctact gaagatgaaa   101760
tggcttaatg gccatatttc ttgcaaataa agacaagaag gggaggagg aggaggaaga    101820
agaagaagag gaagacaatg tacaactacc ttttttctcc gcctaaagag tttctttctt    101880
tttttttttt ttttttttg gagacggagt ctcgcttggt cacccaggct ggaatgcagt    101940
ggcatgatct cagctcactg caatctccgc ctcctgggct caggtgattc ttatgcctca    102000
gcctcctgag tagctgggat tacaggtgcc cgccatcatg ccgcctctaat tttcgtattt    102060
ttagtagaaa cggggtttcg ccaggctggt ctcaaactcc tgacctcagg tgttccgccc    102120
gcctcagcct cccaaagtgc tgggattaca gaagtgagcc actgcgccaa ccaagagttt    102180
cttcttggca ggacagagcc atgcactctc caggtttcag agaggagaca actttggatc    102240
ttttgatact gtagcagggg atgaaaaaga tgaatccttc ttccttaaat caacatctga    102300
cagggtctcc actgaggcac aggacagctc agccactgac cccagggcaa agctctgtgt    102360
tgctgtttta tttgggcttt aggggtgga gagataggt ggcacctagc atcctcctgg      102420
gaggagggct aaaggcatag gggggcaacg gcaaaaatct gaagtctgag cttggccttt   102480
ggaacaaggt caccttccag tgtgggacct ctctgcaggt ccctaaggca tgtgtttctc    102540
tgtgtttata cctgcgtgtt tatttctcct gcaggtgggc acaggcttca gttttactga   102600
tgatacccac ggatatgcag tcaatgagga cgatgtagca cgggatttat acaggtaaaa    102660
tgctcctgct ttctcttggc tttcctaaga ccaaacattt ttctatctca ataggaaaat    102720
tattctagtg ttgaaatttt tattgactga gcctatagt ccaattcctg aagataattt    102780
aaggatattt tcacatccac acacacagag cagaattttt caattaaaga ttatttttta   102840
aacctttcaa ccagacatct gaaaggtttc tacttgttttt ccaaatttgt atttaactttt   102900
gcatttgcag ggagacaaca tcttttcaga tatttgtttg tttctcagga ttcttctttt    102960
cgtggcttttt ggatgcaatt ttttacttttt tgcttctatt tcatgactttt tccaggctga   103020
aaacttagct tgttagtctc tagtattctc tcttcttctt atgaaagttt tgtttttgctt   103080
aaaaaaaaaa aaaaaggaa aaatgtaaag ttgtaagtct ggccaaacag tgtccatata    103140
atttctccct tttttcactc atattaatca ttgctatttt tagcattttt aaaaaaaagc    103200
aagtgacctt tcttatttgg tcagatttt ccagtctaca aattattact agagaccaag     103260
tcctagattc tttctggtca ctagggcacc gctttatgta ttataataat ttactaaaag    103320
aaccctagtg gccagaagga gttaactagc tccctacccc acacctccac caagcactct    103380
gttaattact accaatcctc aaagcgaaag tgcatctaat aggagtcaga gtttgctgat    103440
ctctgacaaa agcttttcgt tttactttc ttttctctcg aggcagatag gtggccgggg    103500
ggagagaaga aagaactact tccaagcccc tttcccaaag atctctccct ctgcccaccc    103560
agaaaagaat atggcgttg tcttctccac ttttgtttgt ttttcacatg ttccatgatt     103620
cgatcacttc tattcagttt ctaggggat gccccagggcc ccacttct gcttccacat     103680
acagtggggt cctagggaca tatttgccaa gatgctgacg gggtgttccc cccagccct     103740
cctcccctc cctccacaga cgtaacggac ggcagtcctc ctcacaggct tcttcagagc     103800
cagggccagg gctctcttgg cactgtgtgc tctctttcctt cagattagaa acctactccc   103860
cgcccccacc tcccatccct ctttggttta aatccaaaca agctcagtgg ttaactagca    103920
aacaccctga gggcagaggt tctgtattga agagatgcat cgggcccct ctaagacaga     103980
gcatcactgc caagccgttt ctgtcttcc ttccctcc ccaaagacag ttacagctcc         104040
cagttgccc tccatatggg gatgtcgact gctgacatgt ggtccatctc ctcttcctg     104100
acatgtaaag ggaacctatt tcaaagcatc tattgtttat agctgttgta gttcttttg     104160
cttcgggctc ttagaactgg aaaatagcta atcaagggtg gtgcagaaaa ctgatttcag   104220
ctgtttcctt tatagtttac actattcatt tcccttgtg accacattct tctctccagc    104280
tctccagatg ggtgtttgga ataagagggt cgcttcaaaa cctgcaaatg ggctactaca    104340
aagaataaga gttgagcttt cattttctcc ctttgaaaa ggtttcagaaa                104400
atctcattct ttttgactat taatagtgca tggctgtaag gagacattta ccgttcacag    104460
ttttgctgct tttgtgtttg gaaataaaac ttttcacga acaagatgtt aaaatactct     104520
cccacttttc ttatttggaa tatgctattt agtcacaatg cctctctggt ttaaaacaaa    104580
ttatgaaatg tattaacttt gatttggagt acactagctg gtgccaatct ccttctgcca   104640
ttgtttacca attgcctatt atgtgccagc tgctgttctt ggtgctggtg agacagtagt    104700
```

```
aagcagtcct caaaccccct gccctcctgg tgctcagtct agtggtggac ctatagttat   104760
tttcttagca gccaaatgga agtgctgcta tagttttctc ctacatgttg gtttgcaatg   104820
ggaaatgata tgtagtgttg ctaaacaaag cttcatagca atgcagctag aagcaggct    104880
tcctatatta aatgagaaaa ctctgtgtcc tgtgccaggt ggagaggatc atggctcagc   104940
cttgctagat gtagagtgaa tgcagaagag gctccctca cgggttccaa cagagcagca    105000
ctgccaggat tcctgttgct gagcttgtat cggtccagtg caaggcagat gagcccaaa    105060
gtggggctta gcctgtgagg ggttttggat ttgcccagga aagaattcaa gggtggccag   105120
gtgtggtggc tcacacctgt aatcccagca ctttgggagg ccgaggcagg cagatcacct   105180
gaggtcagga gttccagacc agcctgacca acatggagaa accccatctc tactaaaat    105240
agaaaaatta gctgggcttg gtggtgcatg cctgtaatcc cagctacttg ggaggctgag   105300
gcaggagaat cacttgaacc tgggaggcag aggttgtggt gagccgagat cacaccactg   105360
cactgcagcc tgggcaacaa gagcgaaact ccatctcaat aaaaaaaaa aaaaagaat    105420
tcaatggtga gatggaggta aagaaaata gctttattga aggggcagtg ttacaactcc    105480
gtgtctgctc ctgcagggct actgcctagt ccgagtagca gcttagggca attttgcagt   105540
tgtatttaaa cccactttta attacatgca gattaagggt tggttcatgc agaattttct   105600
agggaatgga tggtagcttt tgagtctttg ggtcattgcc atggaaaggg gtggtaacgc   105660
ctgggtgttg ccatcacaat ggtaaactga catggcccac tgataggcat gtcttatgga   105720
aagctgcttc cgcccaggcc ctgtcttagc tagtcctcaa tttgatccag tgtccaagcc   105780
ctacctttgt agttgagtcc cacctcttac ctcaagtcca ctgccagtga ctgtaggtac   105840
actttgcttg gctttttttgg catggaactt ttgcttagat tatctgaaac tcgattatcc   105900
tgaatgttgc ttgtgtttat gattatgctt ctgactctat tagaactgac cagattccag   105960
tgctgtcttt gggtctacaa tgcatgatca tgtccactca ccttttctgc cctgcatcca   106020
cccaatctct gttaaaaaac ttatctgagg aataattttc tcctagtcat tcttccttgc   106080
aatctgtttc tcttttttggt cctttaaggt acctttctgc gagcagagag cccttaacta   106140
aaaattctgtt tatgagacaa gtccttagca caatgccagc aaggtggcca aatggaatca   106200
ccaagaagaa gcatgcttct tgtgccatgt agctcttgta cctgaataaa tgcatggagt   106260
gtgcacttgt gaacacacat gcttatgtat tattattatt attgagacgg agtctcacta   106320
tgtcgccagg ctggagtgca gtggcgtgat ctcggctcac tgccacctct gcctcccagg   106380
ttcaagcaat tctcctgcct cagcctcctg agtagctggg actacaggcg cccaccacca   106440
cacccagata attttgtat ttttagtaga aacggggttt caccacgttg gccagaatgg    106500
tctcaatctc ttgacctcgt gatctgcccc cctcggcctc ccacaggtgt gagccaccgc   106560
gcccggccac ttatgtatta tatatatgtt tagcagatct gcttctaaaa tttgtaattt   106620
catgtgggct tgattctaga ttctattttc tagaaaatgc tcaccatgta ataagaagag   106680
ttcttgacta aaatacagtt aaatgagcaa atggcatagt ttactaaatt               106740
tactttttc attcttcact ctcttttaag aaacaggagt gctaccacgc tactaagtgc    106800
ttgcttaaaa aaaaatagcc agttttttgg ctgtgaaata aaaactgaaa ttgaaactcg   106860
atgataactt cctcaagtgg aacttgagct ggagaatcct gccattttcg agatagaagt   106920
aacctgggag attatctctg accaagatta tcagataaaa cacaaaatac ccagttaaat   106980
ttgaatttca ggtaaacaac aaataaaatt ttaatgtaag tatattccat gcaatatttg   107040
ggacatactt atactaagcc attatttgtt atctgaaatt caaaattaag ccatgtctta   107100
tgttttcatt tgctaaatcc agcaacccta atgactctcc agcaaatact acaaggaaat   107160
aagctttaag ctaaagccaa aggcttaatt gagatttact atgctaaatt atctcctgcc   107220
attccaacaa gcaggaagag agaaaaggaa gtagattta gcctgaaggt tggagagga    107280
agggtggaga atgaatgcct atttttatct gcactctaaa gccagcttat tgccagcaca   107340
aacatagaag ctataaaatg cagcttctca gatttagttg ctacaaaggc cactataaat   107400
aatgaataca gaaatacacc gaaactctac agtagtgttt catggtgaat ttttatgcag   107460
cctttgaaaa ttaaatatag ctaggatcat ggtgattgta atgacccaat ttggcctctt   107520
tgtaacccctt gaacttcgcc atcctcctgg gttttcagag cctccttgcc tttcatcttc   107580
ctggatggtt catggctttt agtctctcag caggaaactg ggccaacaac ctcccctagc   107640
ttcgcaggca ctgcagtctg ggtcaaaaca ctcatagagc tactgagttt cacaagtttt   107700
tgtttttcctt tttttgaaat attttgttca ggtaaagaat catttaaaaa tccactgttc   107760
tcttgcttat tatgaaatca ctccttgagt ctgttaaaat ctatttcatc actgaagtgg   107820
ctattggcat tctttttttt tttttttttt tttgagacag agtcttactc tgttgcccag   107880
gctggagtgc aatggcgcaa tctcagctca ctgcaacctc agcctcctg ttgaagtga    107940
ttcttctgtc tcagcctcct gagtagctgg gactacaggc gcgcaccacc atgcctggct   108000
aatttttgta ttttagtag agatggggtt tcactatgtt ggctaggctg gtctcgaact   108060
cctgacctcg ttatccgccc accttagcct cccaaagtcc tggtattata ggcatgagcc   108120
accgccctgg ccggctgtta gcattcttta gtaaatgtgt ttttctttt tttagcccag   108180
agcctactgt acatttattt caatatctgt gaccatttgc tgttttctct ttaaattata   108240
gtcatcttac agttttttctg ttctttggtt attaaaatgt ggcattcttg gagctccatc   108300
agaaatgttc agagtccccc acagtggggg ttggtaagca actaagactt cccttacttc   108360
accacaaacc cgggctaatg ggatcataaa gtttgcagaa ctacctccaa gaattgctac   108420
gtaacatgtg aaacctgtat tatttgctca aggtgccctc aacagttaga tgatccaaac   108480
tggtatatca gtaatttgga aacatgccca gagtattgat ctccacttgt ccaaacttct   108540
tattatcaca aagtaagccc acatgtattg tgtaaataaa atgtcctaca ggagctcata   108600
gcagagtggg atcttatttc aagtgtgaaa cctattgcca aagagttaga tttgatatcc   108660
tagcatgaag agatcctgaa tcatttttct gattaatttg tgttgttctt gttcttcttt   108720
ttgcagtgca ctaattcagt ttttccagat atttcctgta tataaaaata atgacttta    108780
tgtcactggg gaggtaagta gaagtcacgt ttccttgtgt gcttcaaaca tcaccagaac   108840
tgacatatat tatgagtgta gtttgttcat ttaaaatcta tatatgtata tacatgtaca   108900
catacatatc aatattgatt cagccttat tcaaaattct cccaattatc aaaatgccct    108960
tcatatatat atatattttt tttagttgg agttttgctc ttgttgccaa gggctggagt    109020
gcagtggcgt gatctcggct cactgcaacc tgcgcctcct gggttcaagc aattctcctg   109080
cctcagcctc ctgagtagct gagattacag gcgcctgcca ccatgcacgg ctaatttttg   109140
tatttttagt agagatatggg tttcaccatg ttggccaggc tggtcttgaa ctcctgacct   109200
catgatctgc ccgcctcggc ctcccaaagt gctgggatta caggcatgag ccaccatgcc   109260
cagccctttc ataacatttt ttaaatccca gggcccaatg catgctcaca tattaccatg   109320
ggtgcactag gtaggctcag tcatctgcct tgtttgttgt cctcatcatt catgatgatg   109380
atttgaagag tccaggccag gtgctttgta gaatgtccca ttttctgaat ttgtctgatt   109440
```

```
ttttcctcag tgcttaggtt atgtcaaaac atttgagcaa gatcattaca tagatggtgt   109500
gtactttctg gtgtgtcaca tcaggaggca catgaagtca gtttgtccca ctgttggtga   109560
tgctaaactg gatcactgcg tcaaggtggt gtctgccaga tcttgccatt gtgaaggcac   109620
ctgtttatgt ttgtaattaa ctcataatta aagaccattc aaacactgtt tcctcaaaaa   109680
atgccatcca gtagttttag catccactga tctctgtctg aatcagttat tacactgggg   109740
gtgataaaat ggtgatttt ctaatgtatc tttctgtgga tatcacctgg cattcttcca   109800
tagggaagat ttttcccttt tcctcctatt acttacattt aaaaatagta ctgtggattc   109860
acagattgtt atttctattt gatctgttaa aatttgtttt ttattttga tgtttacatt    109920
gctttaaatt tggtcactgg gaacccttc agttggctcc tgtgcccttt tgaccggtcc    109980
ccattagcct ccaagcatgt ccttgctttt tgacacaaag gtgtgttcca gaagcatctt   110040
gtacttcttg tactttccct gccctagcct tggaatcagt cagttcttca cagaatgctg   110100
tttcttttc ctggggaatg gcatttaaaa agcaagtgct aagcactaag tggcccattg    110160
ctgctgggat gtcattgctt ttagacagtc tgtgggcaga gctaggaaac aaaatgactt   110220
catactgata cccataattc taattccata ccacaaggct ctcttctctt ttctctgttc   110280
tgtatttttt tacccttct cccacattga gggctgtggt tcctaatggc atcagtgtgt    110340
ttcctctttt gattgctttt acaatatgcc caatatggtt tcagaattac tacatgtgta   110400
ccattaccaa caagaaacat caaaattact tttaatattt tttgctgcaa tgatttttat   110460
ccttaaattg tatctcacta cacacctata atcaaagtac tgtgtttaaa agttaaaaga   110520
attctatttt ttaagggaga ttatgttaaa atttaataca cagttacatt catttgtcta   110580
tgttggtttc agttttaggg tttgcttttt tcatccttt taagattatt ttaaaaatgt    110640
gtaccagcca atcatttgag aacacaggtg cagttctagg tgctaggaac ataatggtga   110700
ataacactga aaaacaacaa aaaaatccat gccctacatt ctagagaggt aggcagtgat   110760
aactaaaata tgtgctaggt accaccatca ggcagggaca agtgtcatga aaggatgcag   110820
tagggcaagg gctggagagt gaaggaggtg ctatttttgga taagattgtc tgacgagata   110880
atgagcagaa ccctgaatga tgtggtgggg taatttctgc agtatctgta agaagagctt   110940
tcctggcaga aggaacaatg aatgcaaaga ctctccagtg gggacaggct tggcaggttc   111000
aaggaaaagc acagagctgc tgtggtagga gctgagcaga aagaggccag tggatcctgc   111060
agggcccggc tgcctgtggc agagtttgga ctttattcta acggtaatgg gaaaccattg   111120
agggtccagt gttcactgaa agaacattta gaattgaatt caactgagca cagatatatt   111180
gagtatctgc tatgtttgag gcactggaca aatattagaa attcagttat ttatgagata   111240
ttgactctgc cctaaatctg aaggtcgaat aattacaata cagatgaaag gcacaattag   111300
agaaatatta tctctgatcc acgagtcttg aaaaaagaaa aaaaaggaa aaaattagac    111360
aagtaactgt aaagactaat agccccagga aaggtaccag tagctacctc agtgtgggat   111420
cctcaggaaa ggcaagcag aggaggtgaa aattaaaccg ggttttgaag gataaataag    111480
ggtgtgttag ttaaggctct tggttgcaag tgacagaaac cctatttaaa gcagctttag   111540
tgaaacaggg cattgattga tttaacgtca ggtgtggctg gacctgggtg cccttacttt   111600
gtcatcagga ttctgcctgt cattcttcc tgatctatgt acttggcttt gtacttttct    111660
ggtttcattc tcaggcaagt tcttttcatg tggtactcct gcttctccat ccatcccagg   111720
gcaggtagga cctatccatt caacttccct ttcccagtaa ttccagccct ccagattcct   111780
gaatctcaga tgatccactt ggatcccatg cctatcctag aaccaccagc tggacccagg   111840
tggttggaat atacaaattg gccagaatgg tgcctgaggc ccactccaca ccctgggagg   111900
gtagggacca ggatggggg ccctcacact ctgaatcata aggcctgaga gttggaaatg    111960
agtggtctcc agaggaagat ccaagtgatg atgccagagg aagggctgta aagatgctgg   112020
caagcacatc tgcaatgtcc accttcagcg agggaaagag aaaaatggtc cgagttttc    112080
catgggaatg gcaagtaact ggaactagca acttctctct ttcttctctt tataagctat   112140
ttggaaggga tgttctgact gattagcata ctacacttta ggttttttta agccagttat   112200
gcagtcagga caacttagaa cctctcctgg taatttctgc ctgttccttg tcttttaacc   112260
aatttcagag ccaggttagg gaagtgaata ggaagtgaca ctcccattat ttggcaacaa   112320
ccctggaaaa tgcccattct ccacctccca cagaagagtg gtctacttcg tgtgtaatgc   112380
cttgtcttgg aaataatgtg gtgatgttgt taaccatgat gttgatgttg atacaaacca   112440
tgatgtttgg caaaactgcc aaatcccaga tgaaaaattt gacttggtta tttcacatct   112500
gccttgtggt tttatgcata taatttccta atgtgtgtag aaaaggacag ttttcttttt   112560
accttccttg ctgccaggat gaatacttt aaggaaacct gtgcctttctg agtggtgaag    112620
gaagatgtga ggtagagatg ccattgtcag gagatatcat cctccccgaa ctacatggga   112680
tacgttcagt ctgggggcac tgctcttttc agaagaaaaa acactaaata atgatgcctt   112740
gatggtttat tatgaatatt agaatattat gaatatttat tcagtctagt ttgtcccatc   112800
tgggttgtct tctgttttaa ggccatgtgg cagaaaagag aagtggaagg cgttctggat   112860
taatcatttg gagacctggg attcagggct ggctttgctc ctccctggat gatttcagaa   112920
aagtcttca gcctccctgg gcctctgctt ttcatctaac aatcagatga gttgttaaac    112980
tagatcactt ccagggatat tttgctttac tagaaagttc aaattcagtt atctagactc   113040
actctttaag tatctgtatg taattgcagt tttaacgtaa tacctaccca ttttccctct   113100
cgctgctgcc accacacaaa aaaaaattgt tctagatttt tcaagaaaga aaattccttt   113160
ctcttctaaa ctcttaattt tctcacactc ttaggaaagc tgaatagtgc tgctgagttt   113220
gtagagccat cttcaaaaaa taaatgcaca aattcagtttctg cttttcaatg    113280
taaatgcacc agacctaaat atcttccat ttgtgtgcta tgaatgagag gagcctgatg    113340
ctcaagggt ctggagcagc tgttcagaac cttgatttgg tgtgaagcag tctgaaata    113400
ataatagtac ctactgcata gggttgtttt gagcatttaa ttagataacc ctcctcagat   113460
attacatag tgactggctg tggtgagtac ccaacacatg atgactatta ttaccattca    113520
tgctgaaag ctgggctaat atattatgac tcccaagcat acagcctaat gcctggagac    113580
aagagctgaa gtgttaatag aagctcgct aactcattgc tgggatatgg catttccccc    113640
tctactctgt gtctattatt ttgaaatcat ttttaaaagc aatagttact ttgtctaaaa   113700
aaaaatggag cttagcagtt gacattagaa gttgtgcttg ttttttatat ggacagcagc   113760
aaaatgtgtc aggacccacc ccaggctccc tgcctcaccg tgtggacgat ggtgtggcca   113820
caccagagaa agtggctgg gcctgccctc agtgcaaagg aaagggggag agctgctttg    113880
tcttcttcct cctcctcttc atttctgccc agaacaccaa ctggaattaa ttttctctaa   113940
aaagagacaa atgtgtctgt aaatcaccct cctcaaggca tgaaaaaac atacttcaaa    114000
aagagaaata agctgtgttt aattcccata attaactttc tttataagtg ttatcctttc   114060
tgagccagta gctattagtg agattgccct tgttcttgag gcacgacac atttagcatc    114120
ctctcaattg tacatgagcc caggtagaag ttaaagcaaa acagccctca cgggaaggca   114180
```

```
ggtaggtgac aggatcaggg ggaccgccca ttgttctctg agcctgtggc tttatgtgcc   114240
gctcaaggga aagagtcagt gcacgtggga gggttgtggca gtggatggga acgcttccaa   114300
actagcaggg catgtggtta aaacagaaca tctcttctcc atcagcaaaa acgggcagac   114360
tctctttata aacagttttg caaccataat ttatttgaga acccaataga gacaaaactt   114420
tgaagctatt taaaaatgaa ttagggagct taatgcgaca cttatctttc atctgcatgg   114480
gtgaagtccc tgttggaagt acagtgtctg acaaccttta ttgaaatcat catggcccat   114540
tgggttaggt ggcaagctcc cagtatgcga gagccatgtt tgtttcttat tcaatactaa   114600
gcacggtgct taatgaatat tatagaatgg agttcatgca tggctgcctt tagataaaat   114660
aaaaatattg atatttattt cctgcatctt ttcacctact ttttttttt ttttttttg    114720
agacaaagtg tcactctgat gcctaagctg gagtgcagca ttgccatctc agctcactgc   114780
accctccaat tcccgggttc aggtgattct cctgcctcag cctcccgagt agctgggatt   114840
acaggcacgt gccaccatgc ccgcctaatt tttgtatttt tagtagagat ggggtttcac   114900
tatgttggac aggctggcct tgaactcctg actgggtgat ctgcctacct cagtctccca   114960
aagtgctgag attacagatg taagccactg cgcccagccc cttctttt ttaaaattt     115020
tattttaggt ttgggtgtac atgtgaaggt ttgttacata gacaaacacg tgtcataggg   115080
gtttgttgta catattatta catcacccag gtattaagct cagtacccaa tagtgatctt   115140
ttctgctcct ctcgcctccc tttcattgcc cttctctccc tgtactatgt cccaggccct   115200
ggggactctc ctttggcctc cgttgttttc cagggccatc ttcccacctc agccatcctc   115260
tcctcagtct attgtgcaca gcttctattt ctccatgctt cttccatctg tatcatgatt   115320
gttctgtttc tgtcccccat tctgacttgt tgtcaactca ttgttccata gaaaggatct   115380
gataaattaa acccaatagg gtggactctc aacatgtttg catttgagta gagagcagag   115440
cctacctgat gggtagatat ttgtaatagg gcactaacat gcaaacagaa               115500
gggtggcaac caaggtgggg tgggagagcg attctagaag taggcttata attattagca   115560
ttctatgtaa gcctgtacca tcatcctgtt agcctgggct tgggatcatg taatttgatg   115620
gctagaagtg atacttcaag aacatctagt tcatgtattt tatctgtaga ttttactaga   115680
gaatatttat tgagaatgga tctgtatgta gacatcatgc taagcactgt tttatgcatt   115740
acctcgttta atcctaacag ctgccttatg aaataggtgc tatgattatt cttcccattt   115800
tacaggtgag gtgaccgagg cttagtgagg ttaggtatgc cttaccaagg tcacccagcc   115860
agaaagtgga ggagccagca ttggaaccta agcagtcaga ctccagggcc tgaagatggt   115920
ggtgaagaaa tgagctagtg gtgcagcctt gttcaccaaa atgcttgttc accaaactgg   115980
gtgctctcac cttgaacttg cactgtctct aggacctgct tcagattcac tttgtgtctg   116040
aagggggagtc aaacatcccc ttccatattt tatgctgaat ctctaaggtt attaacctta   116100
cacaaacaga aaagaagttc tctagcttct tgaatgtctc tgtctttctg gccaagactg   116160
ttttaatcat aaagacttgg ctttgatcat taagttttat agagtaagtg gaagtttcaa   116220
gtgatataag gacttgaagt ctttggaatg caattattc tcaaggcttg gaacttgctg    116280
aatttttatta gatagcattc aagctgtttt aactcttgaa cctatgacaa atctctattt   116340
tcagttatgt tcatctgcac ttgccaatat tttcttttg aattgaaaat ggatttgtga   116400
ctatttaatg atttttaatat tacaaaaatc aggggtttaag ctgcaaccga agaactgaac   116460
aagggcatat ggaaatgttt gcaagttgga tctctggctt ttggacagca tatccaaatc   116520
aaatcgatac atatgtactg aggttgcaca gaaaagaata tgagtaaatc agaagtcatt   116580
ataagctttg ttggaaatga attaccatgc tggagcaggc agcatagaga cataaatagt   116640
acctgattag atgagatgtt taggttgaga atgagaaatg ctaagttaca tccattatgc   116700
agcttcatcc ttctgaattg tatctacagt gagcaaacaa agattcagtt tgttgactgc   116760
ggcccagtgt gttcagactc tttatttaaa agtcaaatta actgtagtct ccattttaaa   116820
caaaagggtt tattcatctc attgagtcac ctggcttcac gctggatttc tccaaactgg   116880
cactgaactc agagtaggtg ggaaaaggat gcatcttgtt cacctatgcc tgtcaatgat   116940
ggctttttct ttttaagga tgatcttctc aatgaaaat aagaatatat catttgggaa    117000
gcagcatgta ttttttgcata agtttatgtg actaaaaatt ggctatagat caaaatgttt   117060
ttgctatatg tctatgcctg tagattttgc aagtttcttt ttaagcccat attaaaaaag   117120
aaatagatac tttgataaag tcatattctt gttggaaggc tcttttttttt aattgcagca   117180
gtatgtctt gaaattagat gacgcatggt ctggaaatgt ctaggaagtt atagcgatta   117240
ccacaacact gaaattccag ctttcctcat tcattaattt tctaaactgg ccattttaag   117300
gccacacttc tctcttcaga gaaaataatg gtactgagga agtaagattc taccctaggc   117360
tagatgaagc caaggtaggt cgccctagcc tagtcttgcc ctcatggtgc ccattacacc   117420
gaggttttca ccaggttttg tggctttcct ggggtgttca gtgtgtgtat aaagttctct   117480
gtgaggcatt gaagctgtct tcttccctct ggtcttctcc cataaatggg tggcagctct   117540
attgtagtct gtgcctggga tgagctggag aacaagggaa tgatatgact gattccagaa   117600
gggcagtgcg ccttgatgcc ttctggggat acaaaggagc tctcaccagc ccagtagtga   117660
attcttcaaa gaaggatttt ttttagttct gtgtagctgg ggagagtggg gttcaagcag   117720
ggcagggagc ttagaatgac cctcagggtc ctcagtgtac cattgctgaa gttgcaact    117780
ccctctttcc acctgccagg caaagggtag gaactaaggc ctgtggatgg tgaaactttg   117840
tgtcaagtt tagctgtgtc tcatttcaaa agccattgct cattatcact gacaaagttc    117900
tgaattttt ttccaccatgaaa tgtgtaccta gaagcaaggc agagaatgag tgtataagtg  117960
tatctatttt tttttttctac taaacttcag agaaatgtaa tcaactgaga 118020
caatagtaac tgctaccata tgtgaaattt ctgtaagagg acattgtttc catttttaata   118080
ttattctctg acactatttg ttttcctctg gaggagctga ttgaagctgg acttagcta    118140
tgaaatcttt ttcccttcct tgaaagtaac caaatggcag gttacagtaa gtaggctgtg   118200
aattgttg aaacataaaa gaaaagagag attcacgcaa aagcacgat tacaggtttt     118260
ctctacatcc aatttcattg tgtttttaca catctgaagata attaaccaaa cattgcattc   118320
tctctatttt tacaagtaca atgtgctcct cacgggattt ccattaggct ggaaaaaaaa   118380
atcgcaaacc aagattcaaa actactattc agctatgatg ttgaggcctt tttctctcct   118440
gggagaaata aagattgag agctgaattc tgagatcctt ctgatgtagg aggagaattg    118500
gaagtttata gcctctttaa gctccagcaa atacaagcat gtacaaacac accctaatac   118560
ctctgctcct tcttgttgga ggtgagctcg aaatatggtc accatgggaa aaattaacca    118620
agtaagagca gtgctggaaa tcgcagcttg aagctccttt aattattaga aaggaataat   118680
aagggcaccc taaaaattct gatgtgttga gtgctaacct agtttgaatt ctgttagatg   118740
tgttatgttt atccggctga gcttctcatt cgaaggtcac tgccaaatcc taaaataata   118800
tgtgttcagt tagtttctgg ccacacttt cctctcttct tttaaaattg ctttggtatt    118860
gctctgagct tttatgagac cagggtctga tcccatgtta ggtagtgtt aattcacaga    118920
```

```
cctcaggggc ttcattgacc agctgctgcc cacactggcg aacaccatgg ggaggtcaga   118980
gaagccacgg gaccaagagt tctggttgtt gttgctgttt tcattagaac tcagaacaaa   119040
agaagcaata gttcataaaa ttacagaatc actgttataa gcctaaggga ccatttagtt   119100
gatttctaat ccataaggca gtcacaccta aattcttctc ctgaaatatg gggttctata   119160
aaatatatac aggaaaaggc aaatgaggta aaataaaaca cacttgattt attacctggt   119220
tgtcttttga agtacttaat ggcggtcaga gaatcattaa attgagaaat aaatgattca   119280
agaagaataa atgagtctga tcttgccaaa aaaaaaaaaa ctatctcaac aaggagagtg   119340
aaaataactg aaattttatt acaatatttc agtgcctgtt ttccataaaa ataattctat   119400
aattgtcttc tctgtgacag cctgagtcac tcaaccaatg gaatgattaa tgaaaaaggc   119460
aatgacggat ttgtcacact gacacaaagc aaggaagtgt gatagtcatt agaaagttaa   119520
aaaaaaaaaa aagctaagat catcactgtg aggttggcag atgtggactg aatattgaag   119580
aatttcattt tggatatggt tatagtacta ctcatctgtt ttgtttttca taaatgatca   119640
gcttagcaag cttggagtag ataaacccaa gatgtagttc caccttgggg gacctcagac   119700
ccgtggtata ttccaggacc attgactgtc agtgatggct ttttttttt tttttttaag   119760
aagtatcttc tcaatagaaa agatttcgtt gactgaaatg caattagata tgacaaaggg   119820
gagctgcaga gacagccaag ccagggtaga attccagcca ggcatgtgaa tgaaatgcac   119880
gggcccttgt tttcatcact gtaaaatatt ggaaaacaat gtttatctta aattggctta   119940
aagtaggtga ggtagcctgg ctcatagtaa tgctcaaaaa ctgagtgggt gttccttctt   120000
aattccctgc ctggatatat cccagatacc cagatacaca tgatggtcac tggggggaaag   120060
tgccacaaaa atgcagatgt ttcagcctac gtttgtcatg actacctacc tagcaactta   120120
aagtacatgc ccttccatgt cagaaagggt caagagagat gtttttattac caggtcttat   120180
aacaagaaaa ttggagtgat aatatcactg gaagataaac tttttggcat ttgtaccaat   120240
ttctgatagg ggaaaagtat ttagaagtaa tgccagataa gtcattcatt tatcaagtgt   120300
gtttttattt acctattttg tgctaggcaa tgtatacatt atagaaattc taatctaaga   120360
aatcgtaaac tttgctctat catgtgtcag tcatggtttc cataatatag ttttgaaaga   120420
aattgtgacc tttatgaggg caagttttgt gctttattca tttttgtgtc tcctcaagta   120480
tctagtataa tgcctgtatt agttcatttt cacgctgctg taaaggtact acgagagaga   120540
gagagagaga gcatgggcag gggaaactgg ctcttttaaa accatcagct ctcgtgagaa   120600
ctccctcact atcatgagaa tagcatgggg gaaactgccc ccatgatcca atcacctccc   120660
accagatccc ttcctcaaca cataaggatt acagttggag atgagatttg gttggggaca   120720
cagaggcaaa ccatgtcaat gcctttgaca gaagaattgc ccaataaact atcattgaat   120780
aaagactata taacaataca ttttaccag taaaatggtt actcagggaa atgtgctttt    120840
ttgtcatttt acagaaattg tatttgataa atgttcactt attgtcacta caagagaat    120900
gtagcacagt tagacaacaa accaaatttc agacatatga acacaccttt atattacaca   120960
aggaagctaa aatgtactta caagtatgaa tggataaatt gctttgattc aatactttac   121020
ctaaataatt attattgcac aagagagctg tatcaatgag gagttcttgg ataaattaca   121080
taaatgatat tgttttatca ttgcttgaa ggagtttagg ttttggagtc ggtcagctca    121140
ggtgtaattc tggctctaca acttaacctc tctgagcctc agtgtcctca tcttgaaatg   121200
ggagtaatga ttatcttcag catatgatta tggtgtggat aaaataagag cttttcagggg   121260
ttcccagcct ttgaactaca gacccctgga gggccttgga gatgctgtga agggtctgtg   121320
aactcacagg tatccacata atgtctctag tctgttttga acatagatgc attgctcttt   121380
ttcagatgtc tgtagattca ttttaagatt cattcattca acaactattt attgagcact   121440
aacaaaata cgcatcagtc ataagtggact caagtaaaca aacagacaa atgtccctgt   121500
attcacggat cttatattct agtatgggta ggagaataac agtataaag ataagtaagt    121560
aaaagtttgt tggagaatga taagtattaa ggaaatactt aggaaagaaa aaatatagga   121620
cattgaggga atttgccata tggggggcctg tgagaagagc attccaggtg gagggaatgg   121680
ctggtccaaa ggcctggcag acatgtgcct ggtatgtgca aggaatagca tggaacccaa   121740
tgggctggaa aggaatgagc gagagggtgg caggggttga gggtagagaa gggagcagat   121800
catgtcagcc cttatgcctt tgcttttggg aagatgggaa gtcattaaag gataagggca   121860
aaagaaggag gccaatgagg agtctactgc agtcatccag gccagagatg atgtgatgga   121920
gaagggttg tgagaagaca ttggactctg gacagatttt gttagaatag gtagagctga    121980
caagcttggc tgattgactt ctgtggaata cgagacaaag agagatataa cgaatggcac   122040
caagattgtt ggcctgagca gggggagaaac agaattaaca tgagatgaaa gggaggctgc    122100
ctcagggttg gggattggga gctttatttt gaacatgtgc agtttaatat tagacataca   122160
agtgagata tcaagaaggc aacttttgat ggaaagaatg caaaatgcaa aattatttga   122220
aaaatactgc tgagtcaata gtagctcttc cagcacagtc ttaaagtaga accgttacca   122280
tgtttgttag gggaaatata tctacaaaat attctgacct tgaaaaagga ccttgtgctg   122340
gaaaagtttg gaaatagaga tgagttcaag tgaaaatttt agtggccaat aaatattatt   122400
ttcctttttct gcttctccta ttccttttagt acatgttgat ttcaaaattt gcagcattat   122460
cagattttga aatcttaatt ttaaacttga gatttttttc cctctaatct ttgaatagag   122520
ctttctggta agagatgcct aacacatggc agaattgtgt tctcccaagt tatttttattt   122580
tggaaggaaa ttagaatgtt cacttattac atgttcactt gtgatttttt gtgcatcgaa   122640
cctgttcatg tcatgtggtg ctatttgaga cgacaaaaga attggaagac agaggttttt   122700
gctattatgg aatctataat gtggggttaa gaaacagtag gtataccctca tgtgagaagaa  122760
ttgctccttc attgttattt taattagctt aagtacattt aatttacta gcatccattt    122820
gtgattggcc atttcaacat ctgtccttct cagtcttatg cagggaaata tgtgccagcc   122880
attgcacacc tcatccattc cctcaaccct gtgagagagg tgaagatcaa cctgaacgga   122940
attgctattg gagatggata ttctgatccc gaatcagtag gtttctcctt ctgactttct   123000
attttgtctc ttaggggggat taaatgcctt tttatcagat ggaaggctcc tcttagaggt   123060
ctaacttttg ataagggaaa caccagttga ctttatgact taaatctcct aattttacc    123120
aaatgtttca acgtatcaat ttactgtgtc agcttacatt ggctgtcagt gcaaatgtgt   123180
gtgtgtttgt attgtgttgt gttctgttgt gtgtgttgtg gggtgtatat gtgtgtgtgc   123240
atgtaattat cctacttggc taaccagcac aatattaaca attacaaagg attatttcac   123300
caagcaaatg ggcttcctta aggtctcttt ctctccctt gtcacattga tgtgtgtctt    123360
ttttgtcctc agattatagg gggctatgca gaattcctgt accaaattgg cttgttggat   123420
gagaagcaaa aaaagtactt ccagaagcag tgccatgaat gcatagaaca catcaggaag   123480
cagaactggt tgaggccctt tgaagtgagt tctgggggcc ctgtgctgcc cttgagcaat   123540
taaaaccatc tgggggaggga gggcgggtga gcaggaacac cttggtgctc aggcattttt   123600
ttgttaagaa ggtatatctg ttattccatt ggagatcggg aggcgagttg agtggcctca   123660
```

```
taatgaagaa aaggactgtc tgtgttcctt tgaatttact ttggctatat tttaagcctg   123720
agatcatctt ggagtgttta tctaactgtg tctttcatta accgttttga tttcttttaaa 123780
tgctgtggag gccctcaagg cagactctat catatggaaa tcagaagaaa ggcaacccag  123840
gaagtagagg catatgcttc accatctgct ctaaaccatg tagaagagtt ttatatccac  123900
aaacagggtt tcagctggga gaaatgacca cagtgtgtaa cagatgacat gtgacacacg  123960
tgtcaggaac aaagattata aagtgtagta atttgaaact cttacaaagg gccattggta  124020
tttgtgcata tcctttcatt gctcccctaa aattaaactt gagaatcaat aattacgttc  124080
ttcactcttt tctttctcag ttatttaaaa tgtaagaata tactaaatat taggatacag  124140
gaagttgggt ttttttttgtt tttttttgct tttttgcca atgcagacag agccatgtgt  124200
aaacaatctc cctgaggggc tttttgccgt atttactata cagccatcat gtttgacatg  124260
gtagtaaatg aggcaaggtc tgaatttcga gggctttaat ttgtttgtta ttagacacat  124320
attctgtaac agtatatcta atgtcgttat tgttattaaa gcagaaatct gatattaagt  124380
cttaagggca ttgcagatca gccagttcag atcaaaatag gagacatgca accttggaga  124440
aaagggtaga ggataataca aagttatttt tcattttaca agtagggtgt tgggacacta  124500
tcagaaatcc cccaaggcag tgaccgcccT tgccgtgaat tctgatagca gctagctgtg  124560
caaatggatg gagcaaaggg agtcctgagc catcctacag agctccacca ggctctcctt  124620
tctctgtgtc aggacactaa atgtggctgc aaagtgtgga ttcagaattt cttatgcaat  124680
tgtaaacaca aaggaagagg ggtctcctgg ggcacatgta ggatcatgct tccacttgca  124740
atgacagtat tttcaaggct ttctgctgtg gtagtcacag aggggacgaa ggagtgaaac  124800
ttcagtattt agaattaata ccaaattta tgtggcatga gaccaatttg caattgaaac  124860
atttgatatg ttttaaaga agcacacagg ataaagcaat tgtcaagagc aagagcattt  124920
gagaggccca tatttagaaa aaaagcagaa agatgactgg tacataatgc agcaggctaa  124980
acacctacag gattagtgaa gctgtagaaa agttcaggtg tgttgtgtat tcagagataa  125040
tgagaacatg acccacgagg tgagaatctc tcccaaaccg gatacgtcag aaaccggaac  125100
cccaagcagg taaaacgttt gaaggcttgg aatgtctttt tgaccattgg tcccgtatct  125160
tgagtgatga attaaaacaa gacctttgct tttcaagga aaatagataa aatgatactt  125220
aggacagtaa acaacttgtg gttgaaatgt gtttcagtga ctgcaaagga agactccaac  125280
aaatcctgaa acccaggga atataaatgt cagaatctca agcctaaaat gataaagcct  125340
gtttgacgct ctgatccttt aaaatgattt aattaatcaa agagtagtaa ctcagagctg  125400
gagagtactc tggagatagg tcatctactg tccctatgca tttacatgca cacacaca   125460
cacacacaca cacacacaca cacacacaca cacacacaca cacacatta ctggtgagtg   125520
gagaggatgc cgagcccag gggatagcaa tgaattgccg aaggatacac aaatagattg   125580
tggcaggctg aggactggaa ttgcttcccc catttccacc acagtattta tcctatggta  125640
attttcaggc atttctgtaaa aatcctggat cgtcttagat atttctgcaag atgtgaaatg 125700
actgatcctc tgtccagtat tacctcccct tccatgatga ttttctgaat cacaaagttc  125760
ttagtttcac aggtcttgac cacccatgtt attttttgac aacaactgac ttttttctttt 125820
tttttttttt tttttgaga cggagtctcg ctctcttgcc caggctggag tgcagtggca  125880
agatctcagc tcactgcaac ctccacctcc caggttcaag ccattctcct gcctcagcct  125940
cccgagtge tgggattaca ggcactcgcc accacgaatg gctaattttt cttattttta   126000
gtagagacgg gttttcaccg tgttggctgg gctggtctca aactccggac tcaagtgat   126060
ccgcccgcct cggccttcca aagtgctggg attacagctg tgagccacca tgcctggcca  126120
acaaatgact tttaactctt tctaaaagca aagttattct tcaaggttga cttatattc   126180
ccactggtgt tgaagataat ttctaacaat gagttccaaa aatgatgtgt gcattcagaa  126240
tgaccctggc ctatggtgcc ccatctgggg gaacaaatta gaaaaagaca cctcggccgg  126300
gcgcagtggc tcacgcctgt aatcccagca ctttgggagg ccgaggcggg cggatcacga  126360
ggtcaggaga tcgagaccac ggtgaaaccc cgtctctact aaaaatacaa aaagttagc   126420
cgggcgtagt ggcgggcgcc tgtagtccca gctactcggg aggctgaggc aggagaatg   126480
cgtgaaccca ggaggcggag cttgcagtga gccaagatcg cgccactgca ctccagcctg  126540
ggtgacagag cgagactcca tctcaaaaaa aaaaaaaaca aagaaaaaaaa aaagaaaaaa 126600
gacacctcct ctgtggtgat gcagtcctgt gggttcagga cggggcaggc agatgcctcc  126660
attgtgtgag gataagaggt ggccacttct ccagatgcag ccctgagcca ggctctccag  126720
ctcagcgagc agaactttgg ctggttcccc gtccctttgc acccttagc cacaggcatc   126780
gcatggagct gcacaaccag atgtggggcc ctgagcaatg gtagcattgg tagagaatac  126840
ttactaccac ctccaccca accgccttct atggtgataa ccctttcat tcttggcctc    126900
tagcccatg gcaataggaa cttgaataag ttctttcatg tttgaaaaag aatatgaata   126960
caggccgggg gcgtggctt acacctgtaa tcccagcact ttaggaggcc gaggtgggca   127020
gatcacaagg tcaggagttc gagaccagcc tgatcaacat ggtgaaaccc cgtctctatt  127080
aaaaatacac acacacaaaa aaaattagc tgggcgtggt ggcaggcgcc tttaatctca  127140
ggtactcggg aggctgaggc aggagaattg cttgaatccg ggaggcagaa gttgcagtga  127200
gctgagatct caccactgca ctccagcctg agtgacagtg cgagactcca tctcaaaaaa  127260
aaaaaaaaag aatatgaata taataattag tctattttct caagcattga agcatggcca  127320
gaaggaattg gcaagtagga agcattgcag gctgactgct gggagccagt gtgtgcgtgg  127380
ttgagtgtgc aggctcagga gtcgtggcct aatcatctca tctctgacat tattagtgag  127440
gtgtcctcgg caagttgctt aaactcatgt gtctcagttt tctcaccat aaaattagaa   127500
taataatacc ttatctgata agagaccctaa atttgtactt gatagattgt ttttaacatg  127560
tgctgacttc atttctttga attcttttgt aagaactcct tacaacttaa tatcatcatc  127620
aacaacccc ctccatgtct tcaacctctt ctgtgactat tttcttctct tcatcttctt   127680
gctttgccag aaacctggct ctccctgat gctgcagtcc ctgtggtcct cttgagtggg   127740
ggctgttctc tctcttagct tgtctgtatc acttggttca taggtgggagt aggtgtctca  127800
cttgctcatc atgtgacttt cagatcatgt tccctgcctc ctcctaaagc attgagctttt 127860
gactctcctg tcctcagaca gggcctctga ccacttccaa ctgtgtctgc ctaccaaccc  127920
ctggttactc cctctcattt gaatagctga gctccttcct ccctgtcact ctctgcagca  127980
ttattcttgt cataattcct ggtaactgca ggatccacat tgacgatcct tttgggacct  128040
ggttggt ggttcctcgg gcctcagcct cctcttttc aatgatcttg ttctcctcct catcttagct 128100
gctgattctc ataccctaaa atgctggcag ctgatccaca atcacacatt caaacatctt   128160
tctccaacta cccacctcctg tccgaatctc ttctgctaat gtactgatct tacagccctg  128220
caacctcact accttttcaat ccattgatcc tcctgcctct ccactatctc taacccctc   128280
aagtctccat ttctctaatt acctgtcttc aacccagggt cagtcattcc atacattcc   128340
aagcccaaag ctcttttgca tttcttccaa ctcctttggc tgaaccacag ccctggctca  128400
```

```
atctgcctct ctgtcaggct gtgcttgtct ccacacagct gacaatggct ggaggaaagc 128460
atgcaaccat gctgactgct ctcccgctca gctggtgact gggttttttta atgtcagccc 128520
aaagataact tccaccagct ccaggaacct gcatctgcac catatcctgc gtcttctctc 128580
catgtcatct ggtgagcagt tcatgatcca tgttaaggca cccttcccac aaggcttact 128640
cccataggca aggcctttga gcttactgtg tcctctgcct ggaaccttcc ttccctaga 128700
tgtctgcatg gctctattcc tctcatccaa tatgtctttta ctcaaatgcc accttctaag 128760
tgaggtcctc tgtgacctcc tctctacatt gtcccataca cacatgcaca cacatgacac 128820
ttcctactcc tctttagttt tctccttgtc attccctaac atactcaaga gtttatcact 128880
gtctaccata tgatataatt tacttagaaa tgcttgttgt cccccaccag aataaaagct 128940
ccatggggga ggaccattgg tctgtttttgt tgatggccat ttctccagtg ccatgacagt 129000
gtctagcaca gagaatatgc acaataagtg ggcgctggat gaaacaataa aggaatgaaa 129060
aagttgttga ataaatgaaa tgacaaatgt ctgtacattt ttatccacac tgatgttttc 129120
tttctttctt tctttctccc tctctcccaa cctagatact ggataaaacta ctagatggcg 129180
acttaacaag tgatccttct tacttccaga atgttacagg atgtagtaat tactataact 129240
ttttgcggtg cacggtaatg acattttaaa aaccataata atgtttgctt aaaacttttg 129300
gcaaaaccga acttccttttg atttgggaaa tattatagat gactttatac tagaccaaca 129360
tgtccaaact gtaccgcgtg atgtggtcta ctaacccata gaatcttttc ctcatcagtg 129420
ttgtatacgt tataatctga ccactgagaa tgtgtgatat ttcagataac tcaaaacaac 129480
ttctgatgaa catgatttcc cccaagtaga gcttgttata gaggcacttt tgtgaaggac 129540
acaggctggg attggagttc tgggtctcag gtcccagagc ttcaagtctg tttacgagtc 129600
tcttgaaaat gcccacattc tttgttctgt acttaagacg cttggataat caaaactgcc 129660
aaagccttaa tgaaaatatt tgctttgtct tacttttaag atgtttaatg catttagtat 129720
ggccctcact tcaagccttc tggaatattt ctcaaagtat tcaagtagtt tgtttcataa 129780
aagtaggcca aagttgatat cttttgtgta gaattagtca aacagaagga gccaaagtag 129840
gtgtttgaat ttgtataatc tttgtctaat gcttatgaca atgcattctg tttttaaaat 129900
tgcctgattt atgaactgat tgtaaataa agtataacgt tagtttcagt ggaattcgcc 129960
aatgctgcag ttttggattt agattctact aagagaaaaa catgtggtag acaagacaga 130020
aacaaaattt gtgatgatac ctttttttct ttacaacaat atattcacag ttagtaaaaa 130080
ttgttgatga agcacaaagt tgtcaaactc aaactttaac agttttttta atccttgtgt 130140
aactgttttt tttttaaagc atttactcct ttcttttcagt ataatgatta ttacagagac 130200
tttattgcag tttttttttt aataagcttc atggacaact tttcttctgt cttgtgtcct 130260
tcataaagta tcatctcttt tcacatttga catatttttcc cctttattat agtcaatcca 130320
attttgtgtg tgtgtgcggt ttttttttatt ttttaattttt attattatta tactttaagt 130380
tttagggtac atgtgcacaa cgtgcaggtt tgttacatat gtatacacat ggacacagtg 130440
tggggaacat cacacaccgg ggactgttgt ggggtggggg taggggggag ggatagcatt 130500
aggagatata cctgatgcta aatgacgagt taataagtgc agcacaccaa catggcacat 130560
gtatacatgt gtgtggtttt aataaacagc agaacacaga aaagaaattc ttagctttaa 130620
atccagcaca ccaccaacct ggcccttgtg atccatttga ccttctttcc aaagagccac 130680
caacaaggag tgaattgatt ttgataatct catctctttt gttttctctc tctttgcctc 130740
tagtgggggt gctaatggga gtcacagatt gcaaaagatt agtttctgca aaggaaaatc 130800
ctgtatttgc aaattgggta ttttaagagt attttaaggg tatttcagat ttctaattag 130860
taaaagatt ccacctaaat tatctcaaaa cctccgagtt aaaatttcaa gaatggcgac 130920
aagttaatag tcccgtcacg tttctccatg ttgtatgtta tgagaaattc acagcttttt 130980
ccaacatact gttcctgcca ccaatcatgt tccctatgtc tttccaatgc ccttctgcc 131040
aggaacctga ggatcagctt tactatgtga aattttttgtc actcccagag gtgagacaag 131100
ccatccacgt ggggaatcag acttttaatg atggaactat agttgaaaag tacttgcgag 131160
aagatacagt acagtcagtt aagccatggt taactgaaat catgaataat tataaggtaa 131220
gagagctact tcagttacta ttttaggaac tttcagatta cccagagcag aagtgatttg 131280
taatttgagt cctgccttttt tttttttttt aactttatg atgtgtcatt agcataaata 131340
acagccctt tctttgtttg attccaattc aaagttttat attgttcctt ttaatttaac 131400
cacttttgcc gttgtggtga cttatacctg taatcccagt gctttgggag cctgaggcgg 131460
gtggatcacc tgaggtcaag attttgagac cagcctggcc aacatggtga aaccttctct 131520
ctactaaaaa atacaaaaac tagctggaca tggtggcggg tgcctgtaat cccagctact 131580
tgggaggttg aggcgtgaga atcacttgaa cccgggaggc agaggttgca gtgagccaag 131640
atcgcaacat tgcactccag cctgggcaac agagcaaaaa ctctgtctca aaaaaataaa 131700
aataaaaataa aataatttaa ccactttccc ctgattattc cttaaaatga aattcccttt 131760
ggcacacacc acttctcatc ctttcttgag aaaggaagag ttgcagagcc aaaaagatga 131820
ctggccgtgt gtaagagcca gatttctctt atgtgttgct ttgttacatg aatcccaatg 131880
acgtcaggga taaatgaaat caactggtta ttctgaaaat gcattttgcc taatggttgt 131940
attcattcac tttacccaat cacagtgttt tgagtctctc cttagggtgt gaggttgaaa 132000
tgatgaatga gaaagggtcc ctgtttggaa gtaggtcaag tcaagccatt gtgctgtctg 132060
gttgaaatgc tctgcctttg ctgccagtgg aggtgccagt ggagagtgag gtcacagaaa 132120
aggagccctg gaggttcagg caaagaagac atgggccctg gaactccac tgggaaggag 132180
gacaccaaga gcaaatgaca tggggaaagt cagcctgtgt attattcctt tcctggtact 132240
acgctctcag ctcctcctct ggtcctccag tgctgttagc cttttgcccaa gggatcgtct 132300
ctagggcaac tccgaaggat gcctgtactg atgactgggg agaccaccac tgagtcgatcc 132360
acttcctccc tatatcctgt tttgaatgaa caaaaaacag ggcagtcggc agcccatagg 132420
attttttgtat gaattagaat aaaaggcatcc tctcctcaag tacatctttat tcgatctttc 132480
agaaattgtc ctgatatact gccttagtta aaaccagact cttttactgcc attttgctggc 132540
atgctgaata ttcatttcta caatgtgtat attaggaatg gtgtgtctta ggattgttca 132600
gtgcacaatc tgcaatacta tccaggcagt ccctggccaa tgcaccctaa ctagactgtg 132660
gtttagaata tgccagacct aggaggccca tttctgggtc ctgcttctag tacagtgttg 132720
gacacgtaac cattgttgaa aatgtttaaa gaccaattat atgccaagtc tacaaaccca 132780
ttataaacct gcaaaacttg atgaaaatact tactttctg gaaagaaaga gtctaactag 132840
gtcaggccag catttcagcc atccttgtgt ttggtttttct tggggacatg tagtggccct 132900
tagtgcttgc tgcttcaaga cttctcagag gacctccaga aggcactgct gtttgtcctc 132960
tcctctgagc tctcagaacg cgttgtcttt acccccatag gtgtacatgg cacactctaa 133020
cgtgcagact ctcagtctga cacccatacc accaccagcc tggagcagat gtcaggaatg 133080
aatgaatgat tagtgctgta tcaaaaatat atctataaac ctgtccataa tccattaggt 133140
```

```
gcttattatc cacaaattta ttaaaccaaa aagaggttag cgttcatgtc ttaaagatga   133200
tgttctgtaa tgtgatgtta aggaatggaa cgagtgaatt ttttgagag gagagcagat   133260
aagtttgata tgtgttattt gtgcccttgg gagatatatt ttctcactgt acacactttt   133320
ttttttttt tttgagatag agttttgctc ttgttgccca gctgtagtgc aatggtgcga   133380
ctggctcact gcaacctcca cctcctgggt tcaagcaatt ctcctgcctc agcctctcaa   133440
gtagctggga ttataggcat gtgccaccat gcccagctaa ttttgtattt ttaatagaa    133500
tgagttttct ccgtgttggt cagattggtc tcaaacttct gacctcaggt gatccgccca   133560
cctcggcctc ccaaagtgct aggattgcag gcatgaacca ccgcacctgg cctcactgta   133620
caaatttaac tagaatatga ttcctttctc agccatgtga gggtaaggtg ggacaaacag   133680
cttacctgat gacataaact ctccttatgt tttgactgat aaaggagaat atattgatta   133740
gaggtgatcc tgcattttga tatttaaact tctctgtccc tcttgcccat gtatcctaaa   133800
cttaccacta tgaattccaa taaaatcaaa atccagtatt ttctaaactt ttctttctt    133860
ttttgagaca gagtttcact ctgttgctca ggctggaatg cagtggcacg atctcggctc   133920
actgcaacct ccacatcccg ggttcaagtg attctcctgc ctcagcctcc tgagtagctg   133980
agattacagg cacatgccac catgcctggc taattttttt tccgtatttt tagtagagac   134040
agggtttcac catgttgccc aggctgattt caaactcctg acctcaggtg atccacccgc   134100
ctcggcctcc caaagtgctg ggattacagg tgtgagccac cgtgtctggc ataaactttt   134160
caactctgaa tcggttgcca gaaaaagaaa agagtttagt ggtatagata aaccatattt   134220
ccataaagaa acagaacaaa atatgccacc aaaaagtggc tgctgctaaa acagacagca   134280
tgttcactca cgcagctggc aaagcgcttg ggatagtgat tatctttggc ttgtctgtta   134340
atgatgttga acctcagtgt tcagaacggg aatcagaaca acctaggttg gcttaaaacg   134400
ttagtaccat taaagtcata tttatgtaag actcggtact aatttgtcat agaaaatagc   134460
atgcctgttt ctattcatag gaactagagg tcttttttcca gtactgggtt cattttggcc   134520
aatgtggagc atctctgatg gttgaaggaa gaccttcctg ggtttctgga attacgtttt   134580
catgtagttt ctgtataaaa attagcttct ctgtaaacta cgttagtttc tatgtaagct   134640
acgtgaaaac ataatccttt tcttacagtg atatacagga gatgcatact caaaagtcat   134700
tttccttttca gtaatttcag atgtttgggt ggtaaattga aatatcatat tggcagtttc   134760
aaaaataact agaaagagaa acaatctgtt gggctatttg aattcttttat gactgaatga   134820
agtcaaaaca tgatcaggac ttttaggagt tagctggtta atagagtatg gtggttatga   134880
acatgttctt aagttgcata tcttgagttt gagctctggt tacaccagtc actggctatg   134940
ctcctttggg agaggaaact taaactctct gcgctttggc ttccttgtct ataaaacagg   135000
aataaaaaca gtatttatgt gtgagtttct gtgaggttta aatgagatta tatatgtaaa   135060
cacacttaga agagtgcctg atggttagaa ggtgcttatt tatatatata taagctatta   135120
ccaaaaatgt tcaacaaatt ttgtgaaagt ctttaagatc ttgctacatt caaaagttat   135180
acaagaaacc ctgaaaaaca caaaaataaa aaagaatgga caggcttcca gtttccattc   135240
cagtgtgtaa gaagcttaga agtctccact ccattgtaac aacagtaaaa agccaaacaa   135300
actgaaatat aatcaagaac tcttttttaga tttgttgaaa ctgaggtcac agggcaaatt   135360
gctgccctcc aaaattagag agagagatga atatagggag tcaaaactta acaggagcaa   135420
acctgtaagt agaaccctcc atggaaacaa atggtgagga agggaaacct gaacagtaat   135480
tggtaaatta ctagaggctc catagggaca agtctgagag tttaaaacac catggggtggg  135540
gagaggactc agccaaaggt cacttgtaaa tgacctttat tatgttgagg gacttttctt   135600
gtatacccag actgttgagt gtttttatca agaaaggatg ttggatttttg ttgaatactt   135660
tttgtgtcaa ttgagatgat catgtggttt tgtctttcag tctgtgatgt gtcacttttga   135720
ttaacgtacc tatgttaaac cagtcttgca tgctaagggt aaatcccact tgatcatgct   135780
gtagaatctt tttggtgtat tgttgaattt ggattgctaa tattttatcg ataattttttg  135840
catgaatgtc agagttacag ccttgcagtt ttcttttttc ttatgatatc tttgcctggc   135900
ttaggaatca agataaatact tgccaaaaaa tctatgatta atatgctaag gattttaatg   135960
gaaaagtag acaacctgca agaacagatg gatattgaaa atagagatat ggagattata   136020
agaatcaaaa ggaactgtta gagatcaaaa acactgtaac agagataaag aatgtctttg   136080
gtgggctcac tagtagactg gacacagctg agctaagagt agcatgagga tgtaataaat   136140
aaaagcttcc aaaactgaaa agtaaagaga acaaagactt aaaaaaattt tttttgaata   136200
gccttaactg tgggacaact acaaaagatg taacatacac ataaagggaa taccagaaca   136260
agaagaaaga gaaggaaatg gaagcaatat ttaaagcaat aatgattgca aacttttccca   136320
gattaatgta aaacatcaaa gcacagattc cagaagctca gaaaacatgg agtcagataa   136380
atgccaaaac aaaataatca agaaaaggag gcaagtcata tggaagcttc aaaaaaatca   136440
aagataaaga aaaaaagtct caaaagaagc caagggggag aaaaaccta cctatagaga   136500
agcaaaggta agaattacat ctaggttctc tcagaaaatc atgccaacaa gaagagcatg   136560
gagtgaaata tttaaagtgt tgagagaata aaacccacca acttagaatt ctgcaccttg   136620
caaaagtatt cctcaaaagt gaaagagaaa taaagactt ctcagacaaa caaaaattga    136680
gggaatttgt tgctagtaga cctgctttgt aagaaatgtt aaagtaagtt ttcaaagaga   136740
agataagtga tataggtcag aaactcacat ctatataaag agaagaagag cattggataa   136800
tgattaaatg aagatgacat aattatttat gtagaaaatc cagaagaatc aacaaaaaag   136860
cctcttggaa ttaataagtg attaatcata acaaggttgc aggatataag gttaatatag   136920
aaaagttaat cactttccta tgtactccca ataaaacagt gaaatttgaa attaaacatg   136980
aggactattt acattagcac ccttcaaaaa tgaaatactt agatataaat acaacaaaat   137040
atgtataaga tctatattag gaaaactgca aaactctgat aaaagacatc aagaacaact   137100
aatagttgga gaaatatttt gtgtacatgg atatgaagac tcaatattgt caagatgtca   137160
gttcttccca acttgatcca tagattcaat acaatcccaa tcaaaatctc agtaacattt   137220
tgtagataag gataaattgt tctaaagttt ctaaggagag gcaaaagaca cagaataacc   137280
aacacaacat tgaacaagag gaataaaagtc agaagattga cattacccaa cttcaagact   137340
taccataaag ctacaataat taagatatta tttattgtaa taattaagta tggcattggc   137400
aaaagaatag gcaaataggt tgatggacta gaatagagag cccagaaata tacccacata   137460
aatatagtca accgatcttt gataaaggag caaaggttat acaatgtagc aaagatagtc   137520
tttacaacaa atggtgcagg aacaaatgga tatatccaca tcacaaaacaa aataatgaaa   137580
tagcacacaga tcttcacccc ctcacaaaaa tgttctctga atggattgta gacctaaagg   137640
taaaacataa aactataaca cttgtaggca ttaacttagg agaaaatcta aatgaccttg   137700
ggtatggtgt tgatgtttca gatacaatgc taaggaaca atccatgaaa gaataattg     137760
agaagctgga catcattaaa attaataact tctactttac caaaaacaat gtcaagtaaa   137820
tgagaagata agccacagag tgggagaaaa tatttgcaaa agacacatcc gataatggac   137880
```

```
tgttaaccaa aatatatttt taaaaaccct tatagctcaa caataagaaa atgaacaacc    137940
caatttagaa atgggaaaaa gacctgggca cctcaccagt gaaaatatac agatggtaag    138000
taaacatatg aaaagatgtt ggctggttgc cagtggctca tgtctataat cccagcactc    138060
caggaggcca aggcgagagg atcacccagg agtttgaaac cagcttggac aacatagaga    138120
gaccctgtct ctacaaaata aaaataatta attaatttat tagctggatg tggtggtgtg    138180
cacctgtagt catggctacc tgagaggctg aggtgggagg atcactcgac cccaagagtt    138240
caaggttgca gcaagtcatg actgtgccac cgtactctag cctaggcaac agagtgagac    138300
cctgtctcaa aaaaaaaaaa aaaaaagaa aaggaaaaga tgttcaacat catatgtcat    138360
tagggtatta caaattaaag ccatgagata ccacttccag acctattgga atagccaaaa    138420
tccaaaatac tgacaacact aaatgcttac aaggatgtgg agcaatagga actctcattc    138480
tggtgggaat gcaaaatgat acagccacct tggaagacaa tttgaaaatt tcttacaaaa    138540
tttaatatac tcttaccata ccattcagca gtcattctct ttggtattta cccaaatgaa    138600
ctgtaagctt gtgtccacac aaaaatctgt acagggctat ttataacagc tttattcata    138660
attgccaaaa cttggaaaca accaagatat tcttcagtag gtgaatgaat aaactagtcc    138720
agacaatgaa attttattca gtgctaaaaa aaacgagcta tcaagccatg aaaagacatg    138780
tagaaaactt aaatgcatat ttctgagtga aagaagccaa tctgaaaagg ctacgtactg    138840
tatgatccca actatgtgac attctctaaa aggcaaaact atggagactg aaaagatcag    138900
tggttgccag gagttgggg agggagggat caataggcag agcacagagg attttttaggg    138960
caatgaaact attctgtgtg atacttcaat ggtggataca agatgttatg catttgtcaa    139020
aacccatgga ccgcataaca ccaacagtga gttctaatgt gaactgtgga ctttaggtga    139080
tttgatgatg tttcagtgta gctttgttag tgtaacaaat acatcgctgt ggtgagggat    139140
attgatagtg gaggaggttg tatgggagag ggcataaggg gtgcatggga actctgtact    139200
ttacactcaa ttttgctatg aacctaaaac tgctctgaaa cacaaaattt actaatttat    139260
taatttacct ttttttaagt taattgtctt cctagtaaag gggatagatg ctagtatatt    139320
tgataatggg tagattcaat tcctacatcc agcagactgg taaagtagac tctgtgaagg    139380
aaaatacaac taaaatacaa ttgaattcag gataaatgac aacaaacata attgtaatgc    139440
ctttaataaa atgaaagtgg atctgaaaac aaaaacaaca ccagaaaaac aaaaggcaga    139500
gaagggaatt ctgtggagca agagcaataa ggcagggtgg ccctgagaac cagtgtcctc    139560
agtgctgggc tggcagctgg cagctgggct gtgggcccaa gtaaagtgac actgctgacc    139620
tgagagccca gcaccagggc tgggacatgt ggagggccca aactggtccc acagtgctag    139680
gaactctggc aactagcaga agcaaataca cttaacttag tggtagggcc gggcacggtg    139740
gctcatgcct gtaatctcag tgctttggga ggctgaggtg ggcacatgac ctgaggtcag    139800
gagttcaaga ccagcctggc caacatggtg aaacccatc tctactaaaa aagtaaaaaa    139860
ttagccaggt atggtggcgg gcgcctgtaa tcccagctac ttgggaggct gaagcagaag    139920
aattgcttga acctaggaag cagaggttgc agtgagccga gattgcacca ctgcactcca    139980
gtttgggtga cagagtgaga ctccctctca aataaataa ataaataat gaaaagaaaa    140040
tagaggtgtt tacagtctct cagatttttc aaaaatataa agccatttc aacaaaaatg    140100
taagcttgta atcaaaagtc acctaacaca aaagtaaaca ggctacagcc tgtgaataaa    140160
cagaaacaaa tataagagag aaagatagcc aaggcacttt cagatatagg acatatgaga    140220
gataaaacaa ctatgtatga aatatttgaa ggcataaaaa tggagttaca aaacaagcaa    140280
taaatgagaa actaataaat atggctaggc aaatttgaaa gagaacaaat tgtaatcatt    140340
aaaaatgaat gatacagttg ttgaatttaa aactcagtgc atgggttaaa gagtagatta    140400
gacagtgctg aagataaatt taatgaatca gaagatagt ctgaagaaat taccaaaatg    140460
gaacacagga agaaaagata aaagtttga agggagatta agaggcatta agaagagaat    140520
actatatgtc taagcagagt cagagagggt aagaacagaa agaatgaaaa aaagccattt    140580
ttaagaaaca gtggctgaaa atttgccata tctgataaag gttatgaatg cacagacaca    140640
tgtactgaag cacatataca ataagcagtg ggagagagaa aataaattca tattttaggt    140700
ggttttaatg aaattgaata atagcaaaaa gcaaagagaa tgttttaaaa gtcagaagga    140760
aaaggcaggc catctacaaa aggaggacaa tcagactgac agacttgtca gtgacagcaa    140820
tggaaggcat aatatcttca aagtgctaaa atgagataac aatctagaac tacatttcaa    140880
gtaaaatggt agaataaaag tattttcaga tttaacaaaa aaattattc aagtgcattt    140940
agaatcaaca gattttcact aaaggagctt ctaaagaata tatttaggaa aaataaatta    141000
ctccagaatt attccaggaa gaaaatctga gctacaagaa gaaatactaa ctatagaaat    141060
tgatagaaat aatattttat caatgttaat gttctggttt tgatcattgt acaatggttg    141120
tgtaaaatgt taacatttgt taaggctatg taaagggtat actatttatt taacagattt    141180
tgtttgtttt gttttgtttt gtttttgtgac aggatcttgc tctattacct aggctggagt    141240
acagtggtgt ggtcatatct tactgtctca aactcctagg ctcaagctct cctccagcct    141300
cagtccccca gtagctggga actataggca tgtgctggct aatgttggct tttcttttc    141360
tttttctttt ctttttttttt tttttttgta caaacagagt tttgttctat tgcccaggct    141420
ggtgtcaaac tcctggcctc aagcaatcct cccaccctga ccttccaaag tgctgggatt    141480
acaggtgtga gccattgcag ccagcctctg tagcagattg actgagatat aatttacata    141540
ccacagaatt cactcatttc aaatgtacaa gttagtggtt tttgcaactg caattttctc    141600
tgcagccatc accactatct aatttctgaa catcttcatc acatctgaaa gaaaaaagaa    141660
aaaatcccct attcattagc aatgatttcc acttcctctt ccagcccctg gcaaccacta    141720
atctactttc tgtctgtatg gatttgccta ttttggatat ttcttataaa tgaaattgtg    141780
cagtatatgg ccttttgtga ctgtttcttt cactttgtat gttttcaggg ttcatacatg    141840
ttatagcatg ttcattcttt ttactgcaaa ataatattcc tatgtatggt tataccacat    141900
tctattcatc cattcatcta ttgatgaca tttggcatgt ttccactttg tgattattgt    141960
gaaaatgttt gctatgaata ttcatgtaca gtgtggtgt gaacatatgt tttccattct    142020
cttgggtaga tagataccta agagtggaat tactgggtca tatgttaact ctatatttaa    142080
cattttgaag ttccagtttc tccacatcct tgtcagcact tgttattgtc tgacattttg    142140
attctagcca tcctagtgat ttaaagtgct atctcattgg ctttgattg gcatttccct    142200
aatgatgaac gatgaacatc tttctatgtg atttttattt tcatttttta tgttttttgg    142260
agaaatgtgt atccaaatac tttgcctatt aattgggttg ctaattaatt gggttatttg    142320
tttttttatta ttgaggtgtt aagagttttt ttgtttgttt gtttgtttga gatggagact    142380
tgctctgtcg cccaggctgc agtgcagtgg catgatcctg gctcactgca acctccacct    142440
cccgggttca gcaattctc ctgcctcagc tcctgaata gctgggatta caggtgcatg    142500
tcaccacacc tggctaattt tttatatttt tagtagagac agggtttcac cgtgtgagcc    142560
aggatggtct ggatgtcctg acctcatgat ccgcccgcct cgacctccca aagtgctggg    142620
```

```
attacaggcg tgagccaccg tgcccagcct gagagttctt tatacattct gaatacaagt   142680
cccttatcag atatgatttt ttttcctatt ctctggggttg tcttttttatt ttcttgatgt  142740
tgcccatcaa agtccaaaag ttttaatttt gataaaatcc aatttgtgtt ttctttcatc   142800
atttatgctt ttggtttggt ttttttttttt ttttttggaa ctgaatcttc atttcatttt  142860
agtcaagtta aaaataggtt taaaaactaa tactcgagtt ggttattgga aaacatccaa   142920
gtattcacaa tttgggtgtg tgaatctact ttttttttttc tgtctctatt ttataaaaat  142980
ttttttcccc ataggttatt ggggtacagt tagtatttgg ttacatgagt aagttcttta   143040
gtggtgattt gtgagatttt ggtgcaccca tcacccaagc agtacacaac acaccctgtt   143100
tgtagtattt tatcccttac caccctccca tcttccccca aagtccactg tatcattctt   143160
atgcctttgc gtcctcatag cttagttccc acacatcagt gagaacatat gatgtctgat   143220
tttccgttcc tgagttactt cgcttgatag tctccaatct catccaggtc actgcaaatg   143280
ccgttaattc attcctttt atggttgagt agtattcata tatatatatt catatatata   143340
tttggaatat atatatgtgg aatatatata tatatttata tttatatata ccacagtttc   143400
tttatccact cgttggttga tgggcatttg ggttggtttt ggttccacgg attttgcagt   143460
tgcgagttgt gctgctataa acctgtgtgc aagtatcttt ttcatataat gacttcttttt  143520
cctctggaca gataccccagt agtgggattg ctgatcaaat ggtagttcta cttttagttc   143580
tttaggaaac cacactgttt tccatagtgg ctatactagt ttacattccc accaacagtg   143640
tagaagtgtt ccctgatcac tgcatccacg ctaacatcta ctgtttttttg attttttgat   143700
tatgccatc cttgcaggag tgaggtggta tcgcatggtg gttttaattt gcatttccat    143760
aatcattagt cgatgttgagc gttttttcat atatttgttg gccatttgta tatcttcttt  143820
tgagaattgt ctattcatgt ccttagccca cttttttgatg ggattgttttg ttttttactt  143880
actgatttgt ttgttgtaga ttctggatat tagtccttttg tcagatgtat agattgtgaa   143940
gattttctcc cactctgtgg gttgtctgtt tactctgcag actgttcctt ttgccgtgca   144000
aaaagctctttt tgtttaattta agtcccagct attaatcttt gtttttattg catttgcttt 144060
tgggttcttg gtcactaaat cttgcctaag ccaatgtcta gaagggttttt tccaatgtta  144120
ccttctagaa tttttaagt ttcaggtttt agatttaagt ccttaatcaa tcttgagttg   144180
atttttatat aaggtgagag atgaggatcc agtttcattc tcctgcatgt ggctagccaa   144240
ttatcccagc accatttgtt gaaaagggtg tcctttcccc actttatgtt tttatttgct  144300
ttgtcaaaga tcaattggct gttagtatttt ggattttgtttt ctgggttctc tattctgttc 144360
catcagtcta tgtgcctatt tttataccag taccacgctg ttttggtgac tgtggcctta  144420
tagtatagtt tgaaatcagg tagtgtgatg cctccagatt tgttttttttt ttttgcttag  144480
tctcactttg gctttgtggg cttttttctgt tgttgttcca tatgaatttt agaattggct  144540
tttcgaattc tgtgaagaat gatggtggta ttttgatgag gattgcattg aatttgtaga  144600
ttgtttttgg caatatggtc atttttcacaa tgttgattcc acccatccat aagtatggga  144660
tgtgtttcta tttgtcttgt ttatttgtat ttatgatttc tttcagcagt gtttttgtagt 144720
tttccttaac attttgaaga actgccaaag tgtttattgc aaagtatctg ggccatttta   144780
caattccacc aaaatggatg agttccaatt tctccaggtc ttttgcctcc ttggttaggt  144840
gtattcctaa gtattttatt tttttttttt gcagctatcg taaaagggg tgagttcttg    144900
atttgattct cttgttggtc actgcgtata gaagagctac tgatttgtgt acattaatct   144960
tgtatccaga agctttgtcg aattatttta tcagttctag gagctttctg gagggggtctt 145020
cagtgttttc aaggtaaact atcataacat cagcaaacag tgcagtttg acttcctctt   145080
tactgatttg gatgcccttt attctttct cttgtctgat tgatctggct aggacttcca   145140
gtactatgtt gaagaggagt ggtgagaatg ggcatccttc tcttgttcca gttctcagag   145200
ggaatgtttt caacttttcc ctattcagta ttatgttggc tgttggcttt tattacattg   145260
aggtatgtcc cttgtatgcc aattttgctg agagttttaa tcataaaggg atgctggatt   145320
tgttgaatgc ttttttctgca tctgttgaga tgatcatgtg atttttgttt ttaattctgt   145380
ttatgtggtg tatcacattt attgatttgt gtatgttaaa ccatccctgc atccctggta   145440
tgaaacccac ttgatcacat gatggattat cttttttgata tgttgttgga ttcagttacc   145500
tagtattttg ttaaggattt tagtgtctat gttcatcagg tatatcagtc tgtagttttc   145560
tcttctggtt atgtccttttc ctggttttgg tattagggtg atgctggttt cctagaatgg  145620
attagggagg tttccctctt tctctatgtc gtggaatagt attaaaagga ttggtatcaa   145680
ttcttctttg aatgtctggc agaattctgt gtaaatctat ctggttctgg acttttttttt  145740
cgttggtaat tttttaatta ccattttcaat ctcgctgctt gttattggtc tgttcagggt  145800
atctaattct tcctgattta agctaggagg attgtattttt tccaggatttt tatccatctc  145860
ttctaggttt tctagtttat gtgtgtaaag tgttcatag tagccttgaa tgatctttta   145920
tatttcagtg gtgttggttg taatgtctcc cgttttgttt cttaatgagg tttattttggat 145980
tttctctctt cttgttaatc ttgctaatgg tctatcaatt ttattttatct tttcaaagaa   146040
ccagctcttt gtttcattta tcttttgcat ttttttcttgt ttcaatttca tttatttctg   146100
ttctgatctt ggttattgcc tttcttctgc tgggtttggg tttgggtttg gtttgttctt    146160
gtttctctag ttccttgagg tttgactttta ggatatcagt ttgtgctctt tcagtctttt    146220
tgatgtaggc gtttacggct atgaactttc ctcttagcac cgcctttgct gtatcccaga   146280
ggttttgata ggttgtgtca ttattgtcgt tcagcttgaa gaacttttaa atttccgtct    146340
tgatttcatt tttgacccaa tgatcaggtt atttaatttg catgtattca catggtttcg    146400
aaggttcctt ttggagttga tttccagttt tatcccactg ttgctgagaa gagtgcttga   146460
tataattca attttcttaa atttattgag gctcatttg tggcctgtcg tttggtctat     146520
cttgagaaaa gttccatgtg ctgttgaata gaatgtgtat tctttggttg ttggacgaaa   146580
tgttctgtat atatctgttt tttccaaggt atagtttaaa tccattgctt ctttgttgcc   146640
tttctctctt gatgacctgt ctagtgctgt cagtggagta ttgaaatccc ccactattaa    146700
tgtgttgctc tctgtctcat ttcttaggtc tattagtaat tgttttataa atttgggagc   146760
tccactgtta ggtgcatatg tgtttaggcc tttgactgtt atataatgtc cttctttgtc    146820
tcttttaact gcagttgctt taagtttgtt ttgtctgata taagaatagc tattcctgct    146880
cacttttggt gtctctttgc atgaaatgcc tttttccacc cctttactttt atgtgagtcc   146940
ttatgtgtta ggtgagtctc ctgaaggcag cagatagttg gttggtgagt tcttatccat   147000
tcc tgtatcttt aagtggagca tttaggccat ttgcattcaa tgttactatt 147060
gagatatgag gtaccattgc attcatcgtg ctatttgttg cctgtgtacc ttgtttttttt  147120
tgcctttatt ttttgccttt taaattgtat ttttgttttta taggtcccgt gtgatttatg  147180
ctttaaaaag gttctgttttt gatgtgtttc caggatttgt ttcaagatttt agagctcctt  147240
ttagcagttc ttgtagtggt ggcttggtag ttgtgaattc tctcagcatc tgtttgtctg   147300
aaaaagactg aatctttcct tcatatatga tgcttagttt cactggatac aaaattcttg   147360
```

```
gctgataatt gttttgtttg aggaggctga agatagggcc ccaatcccct gtagcttgtg   147420
tggtttctgc tgagaaatct gctgttaacc tgataggttt tcctttatag gttacctggt   147480
acttttgtct cacagctctt aagattcttt ctttcgtctt aactttggat aacctgattg   147540
gacaatgtga ctaggtgatg atcttttgt gataaatttc ccaggtgttc tttgtgcttc    147600
ttgtatttgg atgtctaggt ctctagcaag gccagggaag ttttcctcga ttattccccc   147660
aaatctcttt tccaaacttt tcgatttgtc tactttctca ggaacaccga ttattcttag   147720
gtttggtcat tcaacataat cccagacttc ttggaggctt tgttcatatt ttcttatttt   147780
ttaaaaattt atctttgctg gactgggtta atttgaagtc tttgtcatca agctctgaat   147840
ttctttttc tatttgttca gttctattgc tgagacttc gagagtattt tgcatttcta     147900
taagtgtgtc caatgtttcc caaagttttg atgttttttc tttatgcaat ctatttccct   147960
tgacttcttg tatcgtgctt aatacatttg actttattta atcttccctt ttccaaccat   148020
tctgaaactg catggtttct aatgcaaatg ctcccttg cattagaaac acctggggtg     148080
ctctaacaac acctaatcag gcccactcca ccaaagattc tgatttagct acctactata   148140
gcaaccagca catagtagta tgcaataaag ttggaaagaa ggaagggaag gaaaagaaag   148200
gatggaatga cggaagacaa atggcttgtt catttgtact ataaaccacc tttacaataa   148260
acatatattc aattataagt gcaaataatc caccacctca agtaccattg attatatcat   148320
gtatattcct tagtccttag tcttaatcag cagcattaaa aaaatgcgaa tgcactctca   148380
tacactgatt gtaagatgta tcctcatttt aaaaataatt aaacatgtgg atgaaaggat   148440
agggtatctc tagaatctag gaaatgcaac ccacagtctc caggagcttt ggctttgaaa   148500
tctctgctct ttgagaggt cccctggtcc cgtattcctt gtgatataga atttacattg    148560
ttattgtttt tcttgaagat tctgaaaatg ttttcaaccc ccttttctct gtctggttat   148620
agttcctgcc ttgcttaaaa aaaaaatcat ttgtgctatt tttcaaaga ccgtgtatga    148680
gtatgtgtgt gtgtgtgtgt gtgtgtgtgc acgcgcgcac gtgcatgtgt gtgtccttga   148740
atttgaggtt gtttgtgttt ctaagtggtc tggaaggaca ctgcagtttt aagaggaacc   148800
atctgcaaat gccaattctt acttgcactt gtgcttttga aggttaagtt gcctttgggt   148860
agggcttaat atgctgtatg taaaagttta cctggtcggg ccgggtggct gacgcctgta   148920
atcccagtac tttgggagtc cgaggctggc agatcacaag gtcaggagtt tgagaccagc   148980
ctggccaatg tggtgaaacc tgtgtctact aaaaatacaa aaaattagc cgggtgtggt    149040
ggtgcatgcc tttaatctca gctacttggg aggttgaggc aggagaagtg cttgaacccg   149100
ggaggtggaa gttgcagtga gccgcgatca cgccactgca ctccaacttg ggtgacagaa   149160
caagactcaa tctcaaaaaa aaaaaaaaaa aggttcatct agtcaggaaa tggtaaatat   149220
aaagttacat ttccctgtca cttatcattc tacagctcat taaatttcac ctaattgcat   149280
cttcagaatt caggatgtta gtgtttctta gcttcactac cagactgaaa tcttaacacc   149340
caggtcatta gagttctatt tacttatccc aggctatcaa aagatcttcc tttaggaatg   149400
gcgagttcct gagtaataaa tgtgacttag aagtttgaaa ggtaaatatt ccagcaaatc   149460
taactcattt tgttagtcat tctaattgct tgtggcattt tccatcataa catttttga    149520
tggcaaaatg ttgatggtaa tcatggccag gaaactagat tgataaatg tctagcatat    149580
caagaaaaat ttaacactta aatgatacta atttcttcaac tgttagttgg actttaagct   149640
tctgtccaac catgatggga aaagtctgac tgtgttgact gtgagctgta tgtgatttcc   149700
ccctagccct ttgaagacaa tgaagagaat gccagtatca tttcacgaaa acttctggga   149760
ggaggaagta gctcccagtg aagcatgact tctgcagaga aggaagctaa ctctaggaca   149820
tttatttat gtaactatag tctatagata agcaactgcc acattatagg cagataaaaa    149880
tagtgtacat tcgaaaacca atttatactg cagagttcct tgtgagttca ttttatctgt   149940
atccgttata atccaaatgc aagagtagca ttactttttt taatgaggca tacttctggg   150000
cttttttgat ttttaagcat ttcagagaat aaagggaaaa gagaatacct ataaattatg   150060
aaaattgattt cgattcacct aaacttgcca tgctttcgac atcttctctt gttcatactt   150120
tatgttagat gaaatgttca catgataacc cgtgtgtgtt tgtattttct cttcattctt   150180
tcattaagcc atttaataat atattcttcc ccatgagatg gttaagttg ttttttcttgg    150240
tgcacaccac catcatgtca taaaggcttt attttgttgt tgtttgaaag tgtccatgc    150300
ttaaaacatt agaaagtaca cttgtgattg tggctacagg aaatgtagaa tttcatctag   150360
agttacttaa acatggcatg gtgagagtgg ttcagagaga aagtaataaa atgacaatac   150420
catttgctat gcagattcca gagatctaaa acccagtaag ctaagaaatg tatatttaaa   150480
ttcagttgct atgaaaccca actggtatga aacacaggcg attacatccg ttgactttac   150540
tttgaaaaga caaatcgaga aagggtggag agagtattct tttctggata caattagtag   150600
tatctgttgt gcaataaatg tcacatgctg tagtggctac tccatcttta ttcctttatgt  150660
catagtataa taggagatgt aaaaagtcga cgtagatgtt ttaaaagact gggccactgg   150720
gaatcactgg gaatccaaag cagtgtgtgc ccaccaccat ctaataaagt gtgagaggat   150780
atacgaaagg tttaatttt taatttaaaa caaaaggaaa taaataagc tttgctgact     150840
cttttatta ttattttttt gagacagagt ctcactctgt cacccaggtt ggagtgcagt    150900
ggcataatct cagctcactg caacctccac ctcccgggtt caagtgattc tcatgcctca   150960
gcctcccaag tacctaggat taccggtgcc tgccaccata cctggttaat ttttgtattt   151020
ttagtaaaga tgggattttg ccatgttgac caggctggtc ttgaactcct cacttcaggt   151080
cttgaactcc tgcctcggcc tcccaaactg ctgggactaa agggatgagc caccatgccc   151140
agcctcatgt ataatgtaca gattgtcct aggggcttg tttggtctgt atgtcacggt     151200
cacacatcag atggtctaga gccagaatgg aaagccaatg cttttgtctt tgtttttcca   151260
tcatcatcat catcatcatc atgatttgag tctgttgcc atacagtctg actccaggcc    151320
ccatgctctt tccactccag tttcctcttc tttcgtgtga gagtggatga cttaattctg   151380
tggcagttga ccctggtctg ttatcaaaaa gagaaagcca cgttgtcaca cttcccactg   151440
ccgacagaag ccccagtcag atgttctggg ctcttcctag gtcttttccg ttggattttga  151500
ctggtctatg ttgtagaagt tgtctaacca cccacactcc tgccatgagt caatctgtgc   151560
catctacttg cttatgactg ttattattat cattgttccc aagtcttgtc attgggtaat   151620
gatcaacgca gcagcacaaa agcagaaact ttttgctctg ggcagaagct cctgatgccc   151680
tccttcttga tttctggctt tcccctctac tcttttcact ctgaagattc ttgtctgttt   151740
cttcagcctc ctgacagtcc ccatatttgt tacagtgatt tgtcagttcc ttctaagcct   151800
gtttgacatt ctctgaaaag aaagggaaa aggatgcttt agtctcccaa caggggagag    151860
ttgtgttttt ggaagaaaaa caacaccaaa aaacctaatt gcaaggtaat gggtggctt    151920
tgatgaatag aaccattgag agcatggggc agaaagtctt gcacctgact gataccaggt   151980
tttcctgtct agataaaaac ataaagaaca cagagcacag actttaaaaa aaaaaaaggt   152040
aaagaaaagt aagctgtgta accaggcact tgccttcttt tatgaggaga tcaacctggt   152100
```

```
tggaaacctt ccactaactt tgctatctac cagggagggg gtgtggggat tgataacaac  152160
aggtgggaat tagactcctg gcagtagctt ttctggttct ttggatgtgt gcctactact  152220
gtcgctctca gtcctcttct cagagaaagg caaagtaacc tttattcaaa ctggaatttt  152280
ctcaagctgg aaggcaagtt tgttatggga ggagagaatg ccaatgggtc agccagaatc  152340
caaggagggc tgcactttgc ggaatgctct gctccctgac cacactaggg cctccccgtc  152400
cactgtccat atccgttttg agagcttctg agcatctcta ggttaatgct ttttgcaggc  152460
tgtttagcat ttctcctgtg atgaggctgt cctgctctct gctggcattc gggaccactt  152520
tagctgggaa ggatcatttc cttcccatta gtgaaaggga gcacagcttt cctgttttat  152580
ttttccctt tcttcataat ccttaatgta ttcactcaat tactagtggt actattattt  152640
tttgttttt cttttgttgt tttgttttgt tttagagaca gggtctcact gttgcccagg  152700
ctagagtgca gtgtcataat catagctcac tgcaacctca acctcctggg ttcaaaagac  152760
cctctcacct cagcctccca agtagctggg actacaggag catgctgctg tgcttggctg  152820
atttttttaa cttttttgta gagagaggat attgctgtgt tgcccagact ggtctcaaac  152880
tcctggcctc aagtgatcct cctacctcag cttcccacag tgctaggatt aaaggtgtga  152940
gccatggcac ctggcccatt actattatat tttgaactta agtgacagta gtaatgttgg  153000
ggagcagaga gctggcaggg caagccaata gcaagcaggt tttcccatag ttcctgtctg  153060
ctcccctgta atgatagcta ttatgggagt atctgctgct cctcctccac atggacatag  153120
tttccaattt ccttaatcca gcttcatgaa ccgcagaccg ctcctccgag agtggctgtc  153180
cttggaagtt acttacttct gttacttcgc agctattgac agagaggacc aattttcttt  153240
ccagtatata ccaaacccaa ggtatagcag tgctgtccaa tagaaatata atgcaaggga  153300
gatatgtgca tttaaatttt ctagaaggca catgaaaact ataaagaaa caggtgaaat  153360
caatttttaac aatatattgt ccttaacact atatatatat aatgtcatca tattaatttt  153420
aattgatact aagaaattat tgaaatattt tacattcttt tctttgtact gagtcttcag  153480
aatcctgtgt gtatcttaga tgcacataac aattttgact agccacattt taagtgctta  153540
taatacactt tattgaagaa tgtaggtcga taccatagat ttaactgtct ataaattaaa  153600
gcattttttt ctttgctctt gcagggccgt ttcttattgg ttgggttgta tgcaaatgtg  153660
tgtttgttaa ttaaatatat ttaatgatgt ggagaaagaa agaaattggc tccttgaccc  153720
acctcctagt agggtaataa cttttgtcaag cacattgcag tctttggaga tgacccttag  153780
gtgtgacctt gaagctgacc ttctgacagg caggggtaca ttcctcctct ggagagattt  153840
gtctgtggga gtgggtgagc ttgctcctgg gacagtcagt ttattaaaat tcagttattg  153900
ggccaggcgc ggtggctcat gcctgtaatc ccagcacttt gggaggccaa ggcgggtgga  153960
tcacttgagg tccggtgttc aagaccagcc tgggaaacat ggtgaaacct tgtctctacc  154020
aaaaaataca aaaattagcc aggtgtaaac ccggggaggca gaagtcgcag tgagccgaga  154080
tcgcaccact gcactccagc ctgggtgaca gagcagagacc ctgtctcaaa aaaaaaaaa  154140
aaaaaaaaaa tccagttatt gatcatggtc agaggagatt cttgagaggc aaggggatca  154200
gaaagcagcc atgagagcag accctgaaac aagaagcaga gtaaaggact gactagaagg  154260
ggccccagga cttttatatt caagcaagag gacaagaatt attctggatc attcttaaaa  154320
gtcgtttaag tgtgctgttc taggtaggga gcttttttcc aaagatcatt gcatcagaat  154380
gatggctttc tggatccttt tcaagttggc tttgttgttc cccactaaaa gcagcaaaat  154440
aatttagagt taaggtgcaa gaaagcagga ataattttt ttggccaaaa gacattattt  154500
atataatcgc tggacactga ctcaaacttg ctgttccact tccattcttc tttattcatc  154560
ttgacaaaac cagctggtag ggggatggga ggcacatggg gctgtttatt ctaagttcac  154620
ttactctctt gtcttccctt ttccttaaaa cgtgaaagca aaatatgtct ctttttaaga  154680
acaacttggt tgcagaaatg actactgttt cattcaattt ttctaccagt cttcttcaag  154740
caggccttgg ggactcaggc ctcctgagta ttacatccct aagactctgc acaattacca  154800
ggaagaagta tggccaacag tgagagtgat ggacagctga ggtcaacgca ttatccatgg  154860
acagataaca agtctgcccc cagtcaggga catttcttaa atgtttatact cctcagctga  154920
attaaagttt tcttctgcag ctgagctttt gggaaaccca tgggaattat tgtttgttga  154980
gctggataat agtgaaatta attcttttct gcttaggggg aaggcactgg tgggacatgc  155040
taattgcttc agtccaaaag aactcctggc cacattagag tttgtaatag aagaatgata  155100
agtaaagcag ccagaagagg aagtttggag ggctgatttg caggagtttc attgatttag  155160
catctgtagg gaaaattccc ttaaaaaaga atttttttt tggattagtg aacaggagaa  155220
cattcaaaac taagacagat agaggccaac tgggaatgct gtgcagcctg aatagctta  155280
ggctgctgtt caatcatttc cccaaacagg aaaccacaga atgttagaga ttaaggtcac  155340
tagatcattg ggaaaaaagc ataactttgt ctgcaaagta ttatgatata ttgtaaatgg  155400
accagaatat aagcataaat ctttcgtcta aaaatgcaac aacaaaaatc catccttctc  155460
acaaaagcac aatttgcttt cctgttgtgc tgagatacca aagcctcctt ctctggtatt  155520
tctgtaattt tcctaataag taagagctgt aagcagggaa taaagagaaa agttttgtgt  155580
tctctgtcag taacatgtgt gcttttttt tttaaccaca acaaaaaatg gttaaagttt  155640
agaacagtaa gtggacctca catgatttat tttcagtctt agcctttcat gctagcaaca  155700
atgaaaataa actaaaatgc acacttatat acatttctgt ctctaatctc tcaggctgta  155760
ttaaaagcac agagttcttt tttcacctct gattatcatc atggcactgc ctgacttaaa  155820
ttttaagtga aaatctgtgc ttatagagtg tggaatcttt ctaggtgtct gtaaacgtac  155880
tcttctgcag gtatctttgg ctaaaatggt tgctttatat ctgccttaaa ttatttaccc  155940
ctcagaggca tactctattt aaaataaggg ttaattctca tctgattctg ttcattaggt  156000
ctttactagg agaaggtttt cttgctgaga tagttaaact catgaataaa ctgctgattt  156060
atgtgcatct agaacctgaa attcaattta tgatttgaat tgttaaaagg actagcattt  156120
tagaaaggtt taagtgaaac tgacttttct tggccccctct tctaaggaaa acttaaagaa  156180
tgaaagcata aatttcccctt tccttttctg agtattcact gcttttgaaaa gttaaaaaaa  156240
aatctgaagc atttgaaaga cagggggtcac agctttccat acctgttccc atggtactta  156300
gtccttagtc tctccataaa cgtgtctgtt gaataggcag agatctcata tgagtaaact  156360
aaaaaacaaa caaaacacac tacatacaca agtgagcatg ccctcttctc caactcagac  156420
aaaaggccac ttcccttcca tttcagatgg agggaacact taaccacctg caaatccagg  156480
aaggaagtga aataagtgga tagtgttgga ttgagaccta ctgatctttt tacccatga  156540
cagaggtatg gatacagaga atattttct cttctaagaa aaacagtagc ataagcattg  156600
aataaatgac aaccaccctg tgcctgtgtg tgtgaggata ccagggcagg ggtggggtg  156660
tgcctcaggg ttacagctcc gcaaagtgtt agctcattgt ggctgagagg aaatacaggc  156720
ccagcctggt cagatctccg aatattttaaa tgctgactgt cttagttcag gctgctgtaa  156780
catagtaaca tagactaagg gcttaaaaac aagaaaaaat tgtttcttac agttctggaa  156840
```

```
gctggaaatc tgagatgaga ttaccagcat gatcagttct ggtgaggatc tcctgggttg   156900
cagactactg acctcttttt gtatcctcac atggtggaaa gagtaataga gagctctctg   156960
aggtctcttt tgtaggggca ctaattccat tcatgagggc tctgctctta tccccta atc   157020
accctccaaa ggccccatct cctaacacca tcactttggc tgttaggttt tccacatttg   157080
agttttggga ggatacaaac atttggtcca taacactgga atctaaatgg aaaaacagtt   157140
acaacaacac catttggact aaccaaatac atctgcatgc tgaatgcaag cctcacacag   157200
ccaacttaag acctctgcac tccagtatag gaatttattt tttagtttat ctttgataaa   157260
gagcaataaa aacattggta aaacctgctc ttcaagttat aggaaatctt taggtttggt   157320
atcctatttg ccctcctgac agctgtggga tgtagctatt tccactattt agaggagaaa   157380
attaaagctc agagtgagta gatgacatat ccaagatcac tcagtgagca caggtcttgc   157440
ggggctgagg cagggccaga ggtcaagact tctgtctgaa agtgtcggct acttttataa   157500
gcttctgctg ttagttctgt ccagtcagtg gcgtgcctgg tgcagttatt tatggagttc   157560
taactcctcc atcctaagtc acaattctaa tccataggta acatttcatt tggaaattgt   157620
tgtaccgttg tgtactttat catgcttcac atgcatcatg tttcataaat actcccgatt   157680
catatgtgct tttcttttct tttcttttt ttttttt tttgagatg gagtctcact   157740
ctgtcaccca ggctggagtg cagtggtgcg atcgcagctc actgcaagct ccgcctccca   157800
ggttcactcc attctcctgc ctcagcctcc caagtagctg ggactacagg cgcccaccac   157860
catgcccggc taatttttt ttttgtatt tattttagta gagacggggt ttcaccgtgt   157920
tagccaggat ggtctccatc tcctgacctt gtgatccgcc cacctcggcc tcccaaagtg   157980
ctgggattat aggtgtgagc caccacgcct ggcacttttt cttatcccca ttgtgcagat   158040
gaagaaactg agctctagat gggctaactc aattaagata atactgccag ttagtggcag   158100
gggtcagatt caaacccagc catagagttt atgcacataa ctataaacat atatcctaa   158160
tgtcaaagag tcacacttta ggtttgccac ttgcttgtgg aattacaaat atagaataaa   158220
gcacctgttc aatgtgttct tatggaggtt agtgaccttta gacagtagtg aggcaatgtg   158280
gaagagcact tagaagcaca cagtttgggc tcaggtcgat ctgaacttga atttcagtca   158340
cctgttgggg gatcatggta cactgactta cctccttaca cctctgcctc cttgtgccta   158400
aaatgggata aataacacct gccttctgag aatgctgtaa aatgcttagc acagttcctg   158460
gaacataata agaaaaacaa caagagagtc ttattattac tcaaaaactt ccttttaaaa   158520
gccatagtct ttaccacact tttctagcat ttaagtgtgg gggaattcca tgtgattttg   158580
aattccaggc ttcagaatta gaagttcctt taaaagagta atacatgaat ttatggctct   158640
aactttcaag aaaagactga gatgcagtgg ccaatgcatg caaaattagt agtcaagggt   158700
gtgttattat ttcgagagct tgaatatata tagagttcag gtttatcctg gctggatttc   158760
ttcctacagt cggcctttt ctgaaagagt gagattgaca accaagtatt tgacacagaa   158820
agaccatccc tatattctga aggtttattt agaagaagtg ctgtgtcgag tctctccaat   158880
cattatcaga tgatcaactt gcttgagaag gaggaggacc taatactcac tgacctctta   158940
ttctgtgtca ggcactgtgc tgggaacttt tgtgtacatg g tctcattagt tctcgttaca   159000
attctgtata gttcgtcgca tcctcatgtc cagaaaggg gctgaagctc ttggaagttc   159060
acccacatgt ctacgagttc cagttatggt gtgttggcat gcactgcact ggtccgaagg   159120
tgtatgagtt tggatttcat ggtttcagtg acagaaataa ctctgcttac ttgaagcgtg   159180
aatgaaattg attggaagac aggataggtc ttagaattca tggaaaaact gaagaagtgg   159240
ggtgaagaaa gaacagcaga ttgggggaaaa ttctagggat ctaggaagca aaactaatga   159300
gtagacttat caatgaactc tgtgtcctct gcccatgatt ccaattccag ggaaagagca   159360
tttgagtgcc tttacttagg taatgtgctt atcctttgcc agaggaggca ggcactgtg   159420
attgacaact cccaccaggg ctgtatccac tgaaggtgtg ggtgacccac aaagtacagt   159480
ttccaggaga agggagagtg gacctgggca tgcaaaagca gcagatggtc actatacagc   159540
accacatgaa accattaaag agcagaatcc ataccctgta attgtccatc ggttttatgg   159600
ggtaccaggc actgtgcaag gcctggggat gtagcacgca ctcgggagct cctgttttta   159660
aggcactgct ggtatttcac agcggtttag caaggccact ccccaccaac tgtgagtaat   159720
gccctcacac acatcctgtc catagagcca aagtgagagg tgactaagag atgtcaccag   159780
ggccagacaa acagagcaag attgtttctg aaccggagat gtgaactgtg tctcatatgc   159840
aactaactct cagtttccag cagcttttg tagcactaaa tggttagctg cagggagtca   159900
ataaatgctt gttggtttga aggaacttta gctctttct taaggaaaaa ttttaggtag   159960
aagggtggaa gtcgggatct aggactcatt ctgttgcctc acagtatcac agtttccata   160020
acagtaaagt ggaggcggac agtggaacac ttctgttcct gaccttgtga agcagtacaa   160080
gaataaagct ctatgcacat gaaagcaggt tgaaaagcaa gaaagaatta ataataataa   160140
agatgctttt ctcatctctg ccttttgaca aagaggaaga aaaagatgct tgtggtccaa   160200
gtcaccaaat gccgtctctt ggaaaggctt gaattctgga atgagttttt aaagactgtc   160260
tatgaattaa aattaagctt tttacctagt tgtcatgaaa aaaaaaatga gagctggtat   160320
ggtagtattt gaattcttac aaattatttc tccaaaagac tcatcttttg ccaaactgag   160380
gtatccaacc tcatagcatt attgttcttt ttttttttt tttccattat aaaagcattc   160440
taggctgggt gcagtggctc atgcctgtaa tcccagcact ttaaggaggc aggtagatca   160500
cttgagccca gaagtttgag agcagccttg gcaacatggt gatacctgt tctaccaaa   160560
aatacgaaaa atagccagtc tcataacctg gtctctaaat taattaatta attaaacttt   160620
ttaaagaatt atttttgtaaa aaacgatgag acacacatga cacatgggga gaacaacaca   160680
tactggggcc tgtcaggagg gtgcaggggg agggaggtaa tggatgctgg gcttaatacc   160740
taggtgatga gatgatctgt acagcaaacc accatggcac acattgacct atgtaacaaa   160800
cctgcacata tacccctgaa cttaaaagtt gaagaaaaaat aaatcaataa ataaaaagca   160860
ttctatggcc aggtgcggtg gatcatacct gtaatcccag catttgggga aggaagctga   160920
ggtgggcaga ttgcttgagc ccaggagttc aagaccagcc tgggcaacat ggcgaaaccc   160980
cgtctctaca aaatatacaa aaaattagc tgggtgtagt ggcatgcacc tgtagtccca   161040
gctactcggg aggctgagat gggaggatgg cttgagtcca gcagttggag gttgcagtga   161100
gccaagattg tgccattgca ctccagctta ggggaacata gtgagactgt tcttaaaaa   161160
aaatttaaaa aaaggattgt aaccacattt gccaaaaaca aaacaaaaca gaaacctaga   161220
agatagccaa tctaaaataa atcaaccata gctcaaatac tgtattttg atttgttctt   161280
tccccaggtt tgaagcattt ttaaatatgt gataattaga tgtacaaacaa gtgaagtctc   161340
agttttcat tgatttttt cataagataa gcatttttct gtgacattgc ataaccatca   161400
gtttcactaa gctaagcagc cagccctcta aggagtaaaa gaagtctcta aaagcagtgg   161460
ctttgctccc ttaccagagg cctacagctg accagaaagg aaagtgagga aatgcatgtt   161520
cagggcactg cctagtacgt cgctggagac caactccaac cagctctttc cttgttcctt   161580
```

```
gttttgttcc aatcactatt gacaagggaa gtgtagctaa aagctgcatt catctctgtc  161640
tcctcccttc tgtctttaga ccttgttgct taaaatacca gcaagcctta ggggtaagtt  161700
tgctccagag tgtcccagtt ttagcactgc atgtcttgct gggcaactcc tgtccagggc  161760
aaaactggac agttggtcac cctaccgggg gagaagtggg atgagtgtgt agacatattt  161820
ggccaacctg tccttgtcag agctaagttc ctccctggaa cttttctatc aggatgtggg  161880
tagccagcgt gtgccttgg gcttcaggac caccccctatg ccgtgcccac ctgcttctca  161940
tgctcagcca ctgggtccta ggctatctca tccactcacc cagcctagag gcacctaact  162000
gggatattcc tataggggct catgagagta aatgtgacat ttaggtgcaa ataagagctc  162060
tggaattctt atatttaatg ctggcctgcc tttgaaatca cttctcatga tcgttattct  162120
gatttctttt ttgttgcatt tgacttatgt gcccttcaga aatacaaaat ggtttccttg  162180
ctttgcaaag gaaggatttc catttgtacc caaaagtaga ccttctacac attgcctgtg  162240
cgagattgtg caattcagct ctttgctgtt tcttggtcca gagagttggt gctcttgtta  162300
tgataagtct tgactaacaa gataagtctt gactaacaac tcagggatgg tcctcattcc  162360
atgtcagttc aacatgtaat ataatgctgt acatataaat gtgttttttgc tgtaacatgg  162420
ggactttgct attgtccctt aaggatgaaa aaaacatcac attgatttca aaatatagta  162480
atgattgtca gtaaagaaag ctgtgggaga cacatgagag atgcaagctg cctgtagtgg  162540
ccatggagag taaaattaaa tggatgcact atgaatttgc tgattgatca gcatctttta  162600
cactgaattc tagaagaaga atcacttttat gcttgatgat ctttgctaat cagctataat  162660
caggtcttcg tagaatggtg aagtaattaa gtcttgttca ctggtactaa tcatatataa  162720
ttgtttccat actgttggcc aaaacaacta taggagggttt tgcagaggcc atgagtactc  162780
aaggtctttg aggtaatttc tctatataaa caatgcaaat attttattac tggagttcag  162840
ttgaattttt ttaacaggct ttaaatctat caggatttttc ctgtgggttt cttcttagga  162900
gagtgggggt ggtgatgtg actgagtaac atgaaaggcc ccgtgttcct gcagtggggg  162960
cccagggctc tttcatctta gtctgactgc tgtcccactg ctgcttgagg atttggagtg  163020
tgtaaaagtc ctgggctttt taattatgtt tgagcctttc aagaacccgc accgtaaagg  163080
gaaagacgga aacttatgca gtgaaatatt ttatatccaa tttgaggatt caaccaaagg  163140
tctccactcg ggccaaatca gagccttcaa aatagatcaaa agtagcatgg agttgaggcc  163200
gacctctttg ttggaggtgg agtggcaata ctttatgata attaatatgt tagttgcata  163260
aaagtagcgt aagagtagaa aaaaaggaga gtatattact cagatttcca ccatctaaat  163320
attaacattt ttcaaacttt gtattccata tatgtgaata tgtacattga tttttatagt  163380
tatagttgtg atatacatta tacttgactt tctgcttttca tacttaacat tatgtgataa  163440
gtatttccca cattgcatca tggttcaatg aaacatttta aatggtctta taatatccta  163500
tagaattctt atactgttgt gcatttacct actcaattat aggacttctg gattgtgttt  163560
gagtttttca ttataagact caatgaatat atataatttt ttaaaatttc tttggacctg  163620
ttttcctaga atatattcta caagttgaaa ttactgggac aaggaatttc aacatttta  163680
agttgggggg cagaaaattg gctactgatt ttctgaaaag aagagccatt ttatactgtc  163740
cccattagtt ctacaacttt atcagaattg ggaattatct gaattatttt ttcaagcaaa  163800
ttgaaaattg ctttaggatt aatgaaaaga gttacctcag tgttgttttt cctatgataa  163860
acatcagttt gacacataca aaaaattgta ttctaggaag aaagaacatt cctcactgtt  163920
gacaagcagc tatcatattt ttaaaaagga agttttgcaa gtggcatggc aggcatagtt  163980
gcttccaata agaaacaaat ttgaggcacc tgaatctctc tgtctgctgc tgcaaaaaaa  164040
ttatacttgc tactgaaatc aatgtaggag aggagagcaa tatggattag caatacccaa  164100
gagaaagctc agcttgccag cgactgcact gcctgaagtt gaagttaatg aaatgcaggc  164160
ttcatgaaaa tcctaggggg tagtattcct tagttccact aaaatgtaac cacagtcttc  164220
cttcttaaca tagccataag tccaagtaaa acctgtatat atgtatcact gagtaataca  164280
acacaaatgt ttttgcaacc aagagaggcc tttatgcaga ttactatgaa gaattcagtg  164340
gtagagacaa ggcttgagtt tatttcggat tgttattctt tatggctaac tagaagaaaa  164400
tctcagagag attcatgtct ctttttctct ctcactggct cactatttat acctagctcg  164460
attcatgagc ttcacctcct gaatcttgca tttgctgatg gcttgatttc atttcaggtt  164520
ctgatctaca atggccaact ggacatcatc gtggcagctg ccctgacaga gcgctccttg  164580
atgggcatgg actggaaagg atcccaggaa tacaagaagg cagaaaaaaa agtttggaag  164640
atctttaaat ctgacagtga agtggctggt tacatccggc aagcgggtga cttccatcag  164700
gtaggaagat gcttgggagc aggcaggttg tgggaatggg agagcgggat tgaaaataaa  164760
gcctgaatag caatgagaca tggccgacct taagcaaagc catacaacag ccagtgtgtg  164820
tcttctgtgg ccctactttc cacagagaag ggtgtctga gttcagacat acataggact  164880
aaatataaaa ccagacaaaa gtttaggcat tgttcaagag gtaaggagac aattcattaa  164940
aaagacagtg ctcagtccaa agaggcaaat cattaatgag agaattgcag tctatttggg  165000
gagagaactt ggcaaattat aaaggaagtt tcaacacaat ctcctctggc aaatgtatga  165060
tcacattttt atattacatg tggagcctca ggacaaaatc tctctagctg acaccctagt  165120
gcaacttcca ctgcggggtc agatgttact ctcatcatct tccttttcttg caatgtcctc  165180
ttcaagtgtt ggaatcatgg ttatactggc ctcataaaat aagttgggaa gtgtttcctc  165240
tttctgttgt tggaaacggt atctttaagt gttaggagaa ttcactggtg aagccatctg  165300
ggcttggaga tttgtttgag ggaagggttt tgttgttgtt gtcgatatgt aagtgtacat  165360
ctttataga tacatgtaat attttgatac atgtatttaa tgttaatgac caaatcaggg  165420
tatttaggat atccatcacc tcaaacatgt atcatttcat tatattggga acatttcaaa  165480
tctcttctag ccattttgaa atatacaata tatcgttctt aactatagtc accctactgt  165540
gctattgaac actagaattt attccttcta tctaactgtc tgcacccctt aaccaatctc  165600
tcttcgtctt cccacccatc cccacttccc agcctctggt aactatcatt ctattctcta  165660
cctccatgaa attaacttttt tacgctccca catgtgagtg agaacatacg atatttgtct  165720
ttctttgcct ggcttatttc ctttaacata acgaccttcca gttccatcca tgtcactgca  165780
agtgatagga tttcattctt ttttatggct tagtaatatt ccattgtgtg tatatgccac  165840
attttttaaa tccattcatc tgttgatgga cacttagggt gattccatgt catggctatt  165900
gtgaatagta ctatgataaa catggcgtgc agatattcct ttaatatact gatttctttt  165960
cctttagaa aatatcaagt agtggaattg ctgcagcata tggtaattct atttgtagtt  166020
tttttagaa acctccatat tgttttctat aatggctgta ctaatttaca ttcctaccaa  166080
tagtgtatga gttcatttc tctgcatcct catcagcatc tgttatttt tgtcttttg  166140
gtaatagcca ttaaactcc aatgagatga tacctcattg tggttttaat ttgcgtttcc  166200
ctgatgatta gtgatgctga gatttttcca tatacctgtt gggcacctgt atgtcttctt  166260
ttgagaaatg tctattaaga tccttttctc acttttttttt tttttttttt gagatggagt  166320
```

```
cttgctctgt tgcccaggct ggagtgccgt ggcaggatct ctcggctcac tgcaagctcc    166380
accacaccgg ttcgcgccat tctcctgcct cagccttccg agtagctggg actacaggcg    166440
cctgccacca cacccggcta agttttcta ttttagtag agatggggtt tcaccgtgtt      166500
agccaggatg gtctcgatct cctgacctcg tgatctgccc caccttggcc tcccagtgtg    166560
ctggattac aggcttgagc caccacgcct ggcccttttc tcactttta atggtattat      166620
ttatggtttg tgctcttcag ttgcttgagt tgcttgtata ttctggatat tagtcttttgg   166680
tcagatggat agttggcaga tattttctcc tattctacag gttgtctctt cactctattg    166740
attgttccct ttgctgtgaa gaaacttttt agtttaatat agacccattt gtctgtttat    166800
ggttttatca cctatgcttt tggggtctta gccataaaag ctttacctac accagtgtcc    166860
taaagtgttt cccctgtttt cttctagtgg ttttatcatt ttgagtctta tgtttaagtc    166920
tttaatccat tttgagctta ttttacatgg atatggtgag agatagggggg ttcgttttttg  166980
agcttattct atgtgtatat ggtgagagat aggggtttag tttcattctt ctgcatatgg    167040
atcccagttt acccagcacc attcattgaa gagggtgtcc tttccccagt gtatgttctt    167100
gtcagctttg tcagagatta tttggctata aatatgtgga tttattctg ggttactat      167160
tctgtgccat tggtctatgt gcctgttttt gtactaatac cttgctgttt tggttgttat    167220
tgctttgtag tatattttga aatcaggtag tgtgatgcct ccagctttgt tcttttttgct   167280
cagtattgct ttcactattt ggggtctttt tatttctgtg acaaatgcca ttggtatttt    167340
aatagttatg cattgaacct gtagattgct ttattcagta tgatcatttt aacaatatta    167400
attttttccaa tccatgagca tgagatgtct tccattttgtt tgtgtcctct tcaacttctt  167460
acatcagcat tttatagttt tccttgtaga gatctttcac ctccttgatt aaatctattt    167520
taaggttatt tatttctttt gtagctattg taaatgggat tgctttcttg atttcttttt    167580
tagctagttc attattagta tatagaaatg ctagtagatt ttgtatgttg attttgtatc    167640
ctacaacttt actgaattca tttatcagtt ctaaaattgt tttggtggag tctttagttt    167700
tttctgtata aaagatcgtg tcagctgcaa agagaaacag tttgacttgc tcttttttcag   167760
tatgaatgcc ttttgtttct ttttcttacc cagttgctct ggctaggact tctggtacta    167820
tgttgaatag gagtggtgaa aggggacatt cttgtcttgt tccaattctt agaggaaatg    167880
ctttcagctt ttccctattc agtatgatga tgtttgttgt atatggcctt tattacgtta    167940
tggtatgttc cttctatgcc tgatttgttg acagttttta tcatgaaggg atgttggatt    168000
ttatcagatg ttttttcttaa tctattgaga tgaacttaca gtttttgtct ttcattctgt   168060
tgatgtgata tatcatgttt attgatttgc atatgttgaga ccatccttgg cctttctggga 168120
taaattccac ttgattatgg tgtattatct ttttgatgtg ttgttggatt ctgtttgcta   168180
gtattttgtt gaggatgttt acatctatat tcattaggga gattggctg tagttttctt    168240
cttgtgtgtg tccttgtctg gttttcgtat caggatgata gccttgtaga atgaattaga   168300
aagaattgcc tcctctttaa ttttaaagaa ttagtttgag aagagtttgt gttagctctt   168360
tcatataagt ttggtagaat ttggcagaaa agtcatccag tctagacttt cctttgttgg   168420
gagaattttt attactgatt caatctcatt attcttatt ggtctgttca agttttctat    168480
atcttcctgg ttcaatcttg gtaggctgta tatgtccagg aatttatcca ttccctagg    168540
tttccagtt tgttaggcta aagttgtcca taatagtctc tgatgatcct tcgtatttgt    168600
gtggtatcga ttgtaatgtc tccttttca tttctgattt tatttatttg ggttttctct    168660
cttttttttct tgattagtat agcctagtct agtttattga ttttatttat cttttttaaa  168720
aacaggcttt tttatttcat tgatcctttg tatttctttt tagtttctat tccatttagt   168780
tctgctctga ttgttattat tcctttgttc taatttttggg tttagaacaa aagataatgg  168840
gttttggtttg ttcttgcttt tctagttttt taaagatgca tctttaggt gtatatttaa   168900
acactttcta cttttttgat gtaggtattt attactataa acttccatct tagcactact   168960
tttgctgtat cctataggtt ttggtatttt gcgtttccat tttcatttgt ttcaagaaat   169020
gtttaaattt tcttcttgat ttcttaattg attcaatggt cattcaggag catgttttta   169080
attttcatgt gtttatacag tttccaaagt tttccttggt attgattttct agtttaattc 169140
cattgtagtc ttagaatata cttgatatga ttctgattat tttacatttg ttgagatttg   169200
tttaatggca taacaagtga tctgtcctag agaatgtttc ctgtgctgat gagaaaaaaa    169260
tgcattatgt agcagttgga taacatgttc tgtaaatgtc tgttagttcc attttgtcta    169320
aagtgcagtt taaatctgac gtttcttttct tattttttctg tctaaatgat ggcaattct   169380
gagactgttt gttgaagtcc tcgactatga ttgtattgga gcctatctct cccttttagat  169440
ccaatactat ttgctttata tatttgggtg ctccagtgtt ggctgcatat atttaatata    169500
attgggatgg ttatatcctc ttgctaaatt gaaaactttt ttttacaatt tttatcttga    169560
aatctgtttt atctaagtac agctactcct tctcactttt ggtttctgtt tacatggaat   169620
ataattgttt attcctttac tttcagtctg tatgtgtctt tgcagctgat gtgagtttct   169680
tgcaggtagc tgatatggtt tggatgtttg tcccctccaa gtctcaagct gaaatgtgat   169740
tcccaatatt ggagatgggg tctgatggga ggtgattgtg tgatggggaa gattcctcat   169800
gaatggcttt gcaccaatcc cttggtgata agtgagtttt cactcagttc atgtgagacc    169860
tggtatttaa cagagtctgg gacctcctcc atctctgtct cttgttcctg ctcttgtcat    169920
gtgaaacaca tgcacccact ttgccttctg ccataattgt aagcttcctg aagccctcat    169980
cagaagctga gcaaatgttg gtgccatact tgtatagcct acagaattgt aagccaatta    170040
aacctctttc ctttataaat tacccagcct caggtatgtt tttattatga tgcagaatgg    170100
cctaacgcag tagcatatag ttagatcata ttttattttt atccgttcag ccggttttatg  170160
tcttttatgt ggggaattta atccatttac attcaaagtt attactgata ggtgagaact    170220
tatttctgcc attttgttca ttgttttctg gttgttttat atatccttt ttccgttctt     170280
cctctttat tgcttatcat tgtggtttga tggttttctg tagtggtaac atttgaatct     170340
tttctcttc tcatttatga agccagtg agtttatact ttcatgtttt cttgatgcta       170400
ggtatcgtct tttcacttcc agttatagga ctgccttaag catttcttgt agggccagtc    170460
caatggtaat gaatgtcctc agttttttgct tgtctgggaa agactttctt tttccttctt   170520
ttttgaagga tggctttgtg ggtatagtaa tcttggttgt cagttttgtt ctttcagcac    170580
tttgaatata ccatctcatt ttctcgtggc ttataagttt ctgctgagaa aactgttagt    170640
ctgatgggga ttcccttata tgtgccttga caatttttctc ttgctaattt tagaattctt   170700
tctttgtactt tttga cagtataact ataatgtctc ggagaaga catttttgga           170760
ttgaatccat ttggagattt ttgagcttcc tgttctagat gcctatatct cttgcaagac    170820
tttggaagtt tggggctata atgtcattaa gtaagctttc tatgccttg cttacctctt     170880
cttcttctgg aacacccaaa atgtgaatat tggttgcct gctttatggt gttccatatg     170940
tcatgtaggc tttcttgtt cttattaaa cttatatat atgtacttttt ttgtctgagt      171000
tatttcaaaa gacatttctt ctacttcaaa aagtattctg cttgatctct attattgaag    171060
```

```
ctcttgatta tatttttttg tttcattcat tgaattcttc agttacagga tttctgattg    171120
gttcttcttt atgtatcagt ctctttgatg aatttctcat tctgattatg aactgttttt    171180
ctgatttcct tctattattt atctgtgtta tcttgtatct cgctaagctt ctttaataac    171240
actattatga aatctttacc agatatgtca tagatttatt tttcattgaa atctgtcact    171300
agggaattat tgttttttta cacatatcac atttccttgc tttttcatgt ttgtttgttt    171360
ttacattgat atctgtgaat ctggtgtaac agtcccttct tctgattttt tgaattgact    171420
tttgtaggaa agatgttttc caatagatgt gtctgtaggg ttggttgtgt agggcactttt   171480
ggttttgatt ttgggtgggc acagtaatgt agtcttcaga tgacttcttc agctataatc    171540
agtgtcagtg gtatcttcga gttcctcagt gggttaggct gtggttttta gtagacactg    171600
tagtgaggtt ttgctatgga ttgggacacc aggtgggcca gttctttggc accagtatgc    171660
tgtttcttgg gttccaggt ggcatacatg gaaactggta gaagcaggtc tgagtgggct     171720
gatccttggg ccttcatatt atttggctga gtccctaccc aaatctcatc ctgagttgta    171780
gctcccataa tccccacatg tcatggaagg gacccgtgg gaggtaattg aatcatggga     171840
gcaggtcttt cctgtgctat tctcgtgata gtgagtaagt cttgtgagat ctgatggttt    171900
tataaaagga gttcctccac acaagctctc ttgcctgctg ccctataaga tgggcctttg    171960
cttctccttt gccttccatc atgtttgtga gccccctgc cacagccatg tggaactgtg     172020
agcccattaa acctctttcc tttataaatt acccagtctc aggtatgtct ttattagcag    172080
catgagaaca gactaataca ggcttccagg tgacttgcta aagtgctggc agtggcagca    172140
gtaggccagg ctggcaagtg gatcactgaa ctcctgggca gtgtgcatgg catcaccaat    172200
ggcgatagca gtagtgggca ctagcactga tggcagcaaa cttggtgggc cagtccccca    172260
gccccaaggt ggtacatata caggtgactg ctcgtgagg tgatgcaac aggctgggag      172320
tggacatcct caggtccctg gaaggaatgc atgggctcca gcattggcgg gaaaggtgta    172380
ttgatctcta ggcctctgga taatgtgcat atgcactggc aggctgggga ggcctgtcct    172440
tagcacccc aggtgtggat gtgcagggca ggcatattcc caggcctctg gacaatgccc     172500
acaggcactg tgagggtgg ggccaggtga gctggagctg tcctcaggcc cctcaatggt     172560
gtgtgcatac aaaggctgtg gcaggcaggg ctgatcaatt cccaggcccc cagacaaacat   172620
gcacaggcac tggcaacctg tgcgggccca ttgtcagctc catagaaggc atgtatgcat    172680
gccagtggca gtgggtgggg taggtcaatc cctagactcc tggataatgt tcatgggcac    172740
aggtgaaggc agtgcagagg caggcctatg cttaggcctc tagatggcat atgtgggtga    172800
tgcgtgtggc agtgtgtgtg gttgatcaat ccccaggccc tcaaatggca cactaggatg    172860
ccagttgtag tagcaatggg tatctttagg cactttgatg atgtatgtgg gcaccagtgg    172920
cagtgggggt ggtaggtcgg cctcctggtt cccagatgat gcgtgtgggc actggtggtg    172980
gtggcagaca ggcagacctg ttttttaggtc tcctggtggc aagcagaccg ggttgatctc   173040
caggaccttg gatggtgtcc ttgggccaag aggcaggcta gatgggcctg tcctcaggtc    173100
cttggacagt gcctgggtga gccagttccc aggccctgtt aagatatgtg caggtgtgca    173160
gccaccctgc tgctgggggg taaggatttg ctgtcagtgg caacagcccc aggcaggcag    173220
ctctcaggct ctggagagta catgctttgg ctccctttgt ccctagggca gcctccccag    173280
tgtgtttcac tacccattcc ttggggcgta agacattgca tgagctaaag ttttggggac    173340
gcatctgcac tgctggctcc agccagtatc gtgatgctgt aaacctttga gtagatgtag    173400
gggggtgtct gcaggggttc agggatgtag atatgtagtg ggtattgggc cccaaaggtg    173460
tgatgtagtc tggtggggc cggcctctca aaatggcacc atgccgtagc tgcttgaatc     173520
tcaggggatg tgtgggaccc agtgtgaaca tcttctgtag aacaatgtca ttacatggac    173580
tccaggcatc tctttatact agtctcaggg ctttgtgaggg ctgagggggct ctcctgtggc   173640
taaaattata ggagtctgtg gtgggaatat ggactgctga ctgctgggaa tctctcatttt    173700
accttttacc cacagtggga gtttcccctg gctctgagtt gatcttggct gggttagctg     173760
cttcacttcc ctttccttct atgcctcaga agttcccagt cactttcctg ctgaattcca    173820
ttgtttttctt tagatgttct atttgacatc taattatcta tttgccattc tggtccttct   173880
tcgtgaagga ggtgacagcc aggtgcgtca ggcagccatc ttgaagcccc tccaacggag    173940
ggttttcaat tgcagattca atttctaaag tagatatggg attacttacc ttttctgttt    174000
cttcatgtgt cagtttcat aggctgtaat ttttttcag gaatttgtct atttcatcca      174060
aaatttcaga ttcattgaca taaagttgct ttataacatc atcttttttt tttcttgag     174120
acagaatccc actctgtctg ccagtcatga tcttggctca ctacaacctc cgccttctag    174180
gacatgaggt catatctcag cctcccaagt agctgggact acaggcatgt accaccacac    174240
ctggctaatt tatttgtatt tttagtagat acagggtttc accttgttgg ccaggctgtt    174300
ctcgaactcc tgacctcaag tgatccaccc accttggcct cccaaagtgc tgggattaca    174360
ggtatgagcc accacgctcg gcctgtaaca tcatccttaat atgatttaat gtttcttaag   174420
atctctggtg ttttttagtaa ttagcacctc tcttgcctga ggtttaacaa ttttattctt   174480
ttcaagaaac caatttttat cttattttt cttgattata tttttgcttt ctcttttatt    174540
aatttgtgct ttatccttat tatcttcctg ctattctttc cattgtgtgt gactattgtt    174600
ttttaaaaa caacatgaat tttagccttt tatttctaaa atatgcatcc aatgggagaa     174660
ataaattcct gttgtttaag ccatccacta tggtatcctt ataggactgt tgagagggtt    174720
tggataagtt aataagctta gagcaattcc tggctcatag taaattttgc tattttttatt  174780
tttattatta ttaccctgga ttgcttacaa gagtacatat aacgaagaaa aaattataaa    174840
tagtaatagt caggattcag gaaaatatgt ttattgaaag tcaacatata agggaaagtt    174900
ggaatattaa tattcaggcc attaaggca tatttgaatg ttgagctgcc agggagtggt     174960
ggacatgtta cctcccccca tctgctacac tactttgtga taaacatctc accaggcaca    175020
cacacgatct cctcaagatt atttgatggc tgcctccacc acctgttatt ttatatcccc    175080
tgaaccagcc ttgtgaaatg ctcccaggcc tggcatccca catgtgtcct gcttggctct    175140
ttgcataaaa cgtccagtca gggaggccag attgctgctt caggggcgaca agtcccacag   175200
aggtggtaaa aggaattggc cgccagtcag aaactggtgg caaatatcac actcaacccg    175260
ctgactcttc ttgtgaatgc aaaacacatt tagagatgaa atggtactcc tctggctgcc    175320
aaaaaaacaa gtaacaaaag aagcaaggcc cacatatgtt tgtgatagtg agtgttttac    175380
cacgcagcaa gggatctgca ttttgtatag gtgatttaa aatgttggca aagatcccttc    175440
ccccttagtg cctcagcgtt ggttttgggt ggtttgtgga gatgagggtt atgaggaggg    175500
aaaagcactc ccgtgtgaac aaaggcattc tctgtgaggt ttatctaaga atactgtcca    175560
agtgtcaagc gtctgataat gaagaaaacg gaccttagcc atggacttgc ttttcagcat    175620
tagacacaca aaacagaagc atgggtatgt gtctgccaaa aaagcaacct cattctctgc    175680
caaacactac agctcttaat ttaaaaaatt gaaaccaaag tagacttgtc tctggatggt    175740
tacctaaaat gtccacttaa agaaatgaca gctctcctag gggagcagta cggtaccgag    175800
```

```
agagggagca attttccctg tgtattcaca tcaagccatg cccagagaaa tcaaacacag   175860
ctcccaccag ccttcagaga tccgatgaag agcaagtgct tcttgttcct ccttgttggc   175920
tctgacctag aaggtaataa gttttttggta ttggtgccat tttaaggatt ggacactgcc   175980
ctgttatata atccgagcag cagactttct gagcgtctgt caaatttaga agttgtctgt   176040
caaatgcaag gtctggacta acttatttct aagtatatac ctaacaaaga tccaaaatat   176100
ctatatttca ttaatgccca gaggggctca gccagcaatg caatgtggaa tagtgtagtg   176160
tctttcagca aatgtcataa tgctctctat gcttacatag atatgtaaat atatatatat   176220
atatatttat acctatctct atataccata tacctatctc tagccactga gatagaaata   176280
tacacaaaat gtaaatctca ggctacgtga taaccaaagt catgggtagc ctctgcactg   176340
gcattgacca taaaccctta caagtgttat ctctgggtcc cagaagttga gtcctctttc   176400
tccttgtctg ttgacaaccc atggccattg ctctcaaggc cacccttttg ggatctttct   176460
gtgcctttct ccaaatatca aagttgctgt tcattatctg agttgatatt gtcactgcat   176520
ttgaaatgta ggacattta ttcttaacat gccagcccta aggaagtttt gactccacat   176580
taagaaattt aaaactttgg ccgggcaggg ttgctgacgc ctgtaatcca agcacttttgg   176640
gaggctaagg tgggtggatc acttgaggcc aggagttcga gaccagcctg gccaacatgg   176700
tgaaacttca tctctactaa aaatacaaaa attagccagg catggtggca cacgcctgta   176760
atcccagcta ctcgggagtc agaggcatga gaatcgcttg aacttgggag gcagaggttg   176820
cggtgagctg agatcgcgcc actgcactcc agattgggca acagagtgag accctgtctc   176880
aaaaaaaaaa aaaaaaagaa ttaaaaattt taatcggaat aataaccata ctgagaaatt   176940
gctttaagat tttttttttt agaataaatg tcattaagct gaatgtcctg gagaaagaaa   177000
acacttctgt tttttttcatc gttatttttat tgaaaatatc tttattgaca caaattattt   177060
ttcatataaa tattgaaaaa atgttgagtc attgagcagt tttcattttt accgaatctt   177120
actgggtgta gcttcatataa tcatgagttt tgcatgatct ccaacaggct gatttttcctg   177180
attgcaattt gagcccttac tattttttatt ttatgttttc actgtcaata tcaattccat   177240
tttcttccaa aactacaaga tggattatct cggctaggtt gtatttaatg gctggaatga   177300
attttaggtc tcattttcca gggaagggaa actgaaaccc agaggttaag tgacttccct   177360
gaagtatcct acccatttca tgtctgagct gaggttagag tcttggctta cagcccagag   177420
attctctact tcacaagcat atccactact ggaataatgg aatcacagca gtatgctggt   177480
acagttaaaa ttggagccta tatgcatgcc taccataatt aaagcagggc cgagaaataa   177540
tgtattttcac atctagtgtt agctctgaat ccacacccaa ggtgaccacc tcctatagac   177600
agagagaaga ttgggggtttt ttgtttcatt ttgttttgtt ttttgagagg gagtcctgct   177660
gtgttgccca ggctggaatg cagtggcatg atcttggctt actgcaacct ccacctccca   177720
ggtgcaagtg attctcctgt ctcagcctcc caagtagctg ggattacaga cacacaccat   177780
catgcccagc taattttttata tttttttagtag agatggggtt tcaccgtgtt ggccaggctg   177840
gtctcaaact cctgacctca agtgatccgc ctgcctcggc ctcccaaagt gctgggatta   177900
caggcgtgag ccaccacgcc cagccgattg gttttttttac aaaaggcacta agatttggtg   177960
gtgaggccag gttcatataa tgtcaagaaa agttatggct ttatcgggga acttgtgata   178020
ttaaaagaat gcatgctgaa attggccaaa atgagcagag agaatatggt gggcagtgtc   178080
atggataaga gaatatgggg cagggcacag ggcagagtgc atagtctggc tcatagcctg   178140
cagcttggag agtgagaggt gggagagaaa ccagaatggg aacatcaggc ctggatagta   178200
gacaaggagt gtgtgttcca ttgtttaagc agtggggagc catcagaggt ttgaaagcac   178260
attttaaaag ctgttcttttg ggaagtttat aatggtaact ttaggatgaa ttcagggtga   178320
ggaaactcta gaaataggaa gtcatataag gagcttttatt ggaagaagat tctccatcta   178380
tttaatacgt ccaccttctt gatattggtt tggaagtcct gaaatagagg tcgtggggaa   178440
taaggtttgg aatgcccaag ctgtgaggac tgattccctg tttgagagat ggtgttcact   178500
gtgtgtcccc accaacttaa gatcactgca tgctggcgtc cctggcactt cctcaatggc   178560
cctagtaggc atcctcagcc ccctaaagca caagccctgc accaagactt gcaccttgac   178620
cttgacctgg gtttagtata tggagcccctc aggcccgtgg tctgccacac tgtgctcagg   178680
ggcttctccc aaaatgtcct ggtttccaac aggaatcaga ccttcagcta gaggttacat   178740
ctagggaaac caaaggggaag gagcacgcca ccctgaagct tgactgttct ggaaagccct   178800
caccaattgg aggggggtcta tgacatgaga agaaggtgga gttagacaaa cctggttttaa   178860
actttcatttt tgccgcttgc tagctgtggg ctggttactg gtcctggaaa cttttttttttt   178920
ttttttgata tggagtctca ctctgtcatc caggctggag tgcagtggca tgatcttggc   178980
tcactgtaac ctccacctcc tgggttcaag cgattctcct gcctcagcct cccaagtagc   179040
tgggattaca ggtccccacc accacatctg gctgattttt gtgttttttag tagagacagg   179100
gtttcaccat attggccaag ctggtctcga actcgtgacc tcaggtgatc caccagcctt   179160
cgcctcccaa agttctggaa ttacaggcat gagccaccat gctggaaact cttgagtgag   179220
aacagttact tcatagggggt gatgggaagg tcaaagagaa tgataaggat ggcgaccgat   179280
gattccgcat ctgtgagctc tcaggccacg gtctaccaca cactttttta atccacaatt   179340
tgtggaatc acagtagcta tcctataaac tatgtcatgt tatttactaa ctcataactg   179400
aagaaacaga agcttcacct gaaaaacttg cttaaggctt tgaacagtaa tagtatctga   179460
gatttgaaaa ttcaaattct gacctttcca ccaccccaca gtgtctttaa gtacctgtga   179520
ggggagtgca gtgggaaggg atgaactgta gccggatcta ggctacatgc cccgctgtat   179580
tagtctgttc ttgtactgct ataaggaaat acctgagaca gggtaaattc taagaaaaga   179640
ggtttaattg gctcacagtt ctgcaggctg tacgggaagc atgacggcat ctccttctga   179700
agaggcctca gggagtttca cttatggcag agggcaaagc tggagcagat gagagctagc   179760
cggggagatg ccacacacct ttaaaccttt agatgacaag atctcgtgag aactcactca   179820
gtattgccag gacagcacca aggtagacat ggtgggaaa gcaccattca tgagaaatct   179880
gccccatgat ccaatcacct cccaccaggc cccacctcca aattgggat taccattaga   179940
caagcaattt gggtggggac acagatccaa accataccac tgcccttggg gtatgtggtg   180000
atggtggcaa ggcggtggtg tggtggtggt ggacagaata tttggcagca catgctaacc   180060
accatagaat acttgttccc taatgaaaag aagttcctt aaaaggagga ggatggagga   180120
ggcatggttc atctgcagaa agcagtaacg accacagctt cctaattgtg cttttctaaa   180180
actcacatta actttttgttt gtttcttgac tacacacaa tcaatgtgg aggaaagaat   180240
gactctagtc cttcgagtgg acgatcaggc taggatttga acattttcac agatagtcca   180300
cagaaggaat gacagacagc tagccacctg ccttttctcgg aattactgct gacaattcat   180360
tttttgtgtg ttttattaag aatttaaaac agcttaggaa gcattatgaa ttgtttctga   180420
aggaacagtt ccagaagggt cttcagcagg tccttgataa cattgacatg gtcagaggaa   180480
gcaacaagca aaaaaatgtc acttttgcat ttgactagat gagagggaaa gagaagttt   180540
```

```
caaaaacata ttgaatggag gaaaataact gttaaataag cttaaggcaa tgataatcaa    180600
atatagttaa ttccctggaa aaatgtttta gctttggctg ggcatggtgg ctcacaactg    180660
taatctcaac actttgggag gttgaggtgg gaggatcgct tgagcccagg agttcaagac    180720
tagcctgggt gggcaagata gtaagactct gtccctacaa aaaaaaaaat taaaagaatt    180780
aaccaggtgt ggtggtgcag gcctgtagtc ccagctactt gggaagctga gatgggagga    180840
tcacttgagc ccaggaggtc gaggcgcagt gagctatgtt cacgccactg caccccagcc    180900
tgggcgtcag agtaagaccc tgtctcaaac aaaacaaaac aaaacaaaac aaaaagcttt    180960
ggctttgtta aggaaatcgg caaacagagt cttcatctcc cccaccagca gtcgccttct    181020
acaatgatgg atgtcctctt tcacgggttc ttttgtctcta tcttccagac aggggcaaag    181080
ttcctctgtc cacttatgga aatctgactg tgggcagaaa accagaacac agtaatcaaa    181140
ccacaccca cctcccagcc agagagcttc tctgaagtca caggttaggt cctccaaaag     181200
caggcactga ggcaaagttt ggggtgcaaa tagtttgtta gagaccaaca cctgtggaag    181260
gaagggtata ggagcaagac tggaccaagg gagaaataaa actgtgatac aggccagaca    181320
aaccaggcag ggaactcttg ggagcatatt ttctatcaga gtgtcccaca ctgggccaaa    181380
atagtgagc cttttatgcc cagctcattg actcaccaaa tttgggctgc cccaggaagg     181440
tcatcatctt gggaaaggca gctctttgca gctgaggcag accccgaagg agctgacagc    181500
tgggggctgt ctgctgaatg cactccctgc agtggagcag caagtacatc cttgaagaga    181560
ggtccagtgg ggtgcatctc tatgtctacc acaaaggcca cccagataat gtacttgcta    181620
gctctcatgg atttgggggc agggagttgg gagcagcggg agctggtggt ttgcctaata    181680
tgggaacttg gtctttcttt gtttgcatga cataaaattt tgactaagct ctcagtgtaa    181740
ttatgtctta tatctgcctt agaaagatgg atcaggcctt ggttttaac tcatatcaag     181800
attccaagat aggcaagatg gatctttcag gaaaaggatt aaagaatcat cagaaaatat    181860
ttccctttt cagttattta tcatggaata ataaatcact ccaaaactta gtggcttcaa     181920
acaatttatt atttctcaca aatatgtgga ttgagtgagc tcagctgggt gggtctgatt    181980
cagatggggt aggctgaggt cacatgtgca gctgcattca gctgggagtt tggctaaagc    182040
tggacatcc aagatgatct cctctcctcc agtgctctct ccataccacc tctaatcatg     182100
tagtgtcctg gcctggactt ttccacaata cagcaggctg gtgttccaaa tggaaaagca    182160
gaagatgcca gtccttttaa ggcctgtact caaaagtccc agaacattat ttccatttca    182220
ttctctcctg gtcaatgcaa aacacagagc aaagcagatt cctttggtg ggaagaatgg     182280
caaagaatct ggagccattt ttaatctcct cctttgccct aaaccaatgt gtctcaacct    182340
ttgcagatac agatttccac acctgctctg tagatacct gattttattg gtctggggtg     182400
gaacctgggc attggtattg aagcttcaaa gaggtttcta atatgtagcc agtttgggaa    182460
ccctaaaacta tgatgtcttt tgtccctcta ttgataatga catggcttcc atctggcagg    182520
aaccccatg tggcatatgt ttggagaaac tttcattctg attcctgaag tatgttctaa     182580
atccatttt acttacaagc taaccagaaa tttgagaaca cagttttact ctttacaaat     182640
cagccattga cctgaagcat tgtctctgtc ttccagtcag tagtatcaac tggtatggca    182700
ctggttctct gaaatcatca gccaaaacct taatctaaat tgtagacttc agtccctgcc    182760
atgcactgca ggtttacaag tggtctttgt tcttttttaat tattgataga tcactggcaa    182820
tttagacttg taagaaaact ctttatttg tttaaaagca ttagtttcct tttcccagca     182880
gttttgtgct gtactgaaac aacgtgttcc tggtgtgcag tgctcttaga tagtagtgtg    182940
tctgtgttgc ctttcaacaa agaaaaaact accaagcact gtctgcttta aacatcatcc    183000
agagtgatgg tttgcagcaa agatgtccac tagccacagt gaatttttt tctggataat    183060
agattcatac aattccatgt caaagcaaag aaaaaaaag tgccacattt tagactgtga    183120
agtcttatta taagtaagct cagtatttcc attagttact cattaggcta tttaataagg     183180
attcttaacc tggagtaagg gtctgtggtt aggattcaag gagttgtcag tgaacttgga    183240
agggaaaaa ctgcatctttt atttttctcta acctctaact gaaatagcat ttcctttcat    183300
tatgaattgt gaaatttcac attttcttcc attataaatg taggcaacaa atcacagtgg    183360
cacagcagta cctttgactt ttgtcaccaa tagaaagcaa agacattctc ataccaaata    183420
ccacatacac tgttatagat atgttgaaaa cctttttatcc ttatcactaa aattaaaatt     183480
atagtagttt tcagaccctc tggttctcc tactgaatgt gctaatatac aagtatgtat     183540
gtgctatctc acaattttt tttactgttt tgatgatttc agtggagtgt ttcatttgca    183600
atcctagcaa agcctaggat ttgatttaa ttcactgtat attatctatg tatatgtgtg    183660
gatgcatatg cactctgtat taattatgta tgtatttatt ttaaggcagg gacttgccct    183720
gtcacctagg ctgaagtgct gtagcaccat catggctcac tttagccttg aactcccagg    183780
ctcaacaaat cctcccacct cagcatccca ggtatctggg accataggca catgatacca    183840
cacctgacta attttttgtat tttcttgtag atgggggtc ttgccatgct gttcagcctg     183900
gtttcaaact cctgagctca agtgatcctc ttgccttggc ctccaaagt cctaggatta    183960
tcggcatgag ccgccatgcc cagccagcat gcatttagaa acattattgt gagaaggtag    184020
tccacaggct gcaccagaca gtcataggag actgtagcac agaaacagat taagaaccca    184080
tgcattaggc tatttgaatt gttgaaaata atttatagat tctcccagc ccaaatcacc     184140
tatcacctt ggtgataca gacagatttt atgagctaaa ctatcaagta ggcttgaatt    184200
ttgtttctag ttgattacac tggcaattct aactactttt gttaccatat tcaagtgaca    184260
ttatagtata gggattaaga gaatggatac tgtgttagac ttggaataga tccctgctct    184320
accatgtacc agctgtatga ccttgggcaa gttacttaac ctctccaaga accccctcac    184380
ctgtgaaatg gggataatat tatcacccac cactctcaca ggagggttca ttattaggat    184440
gaattgagat aatgcttata aattacttga ccctctctct acctggcacc taataagcat    184500
aaaataaatg ttggtttcta ttgccattag ggagctctct tagcattaat ctatttcac     184560
agggcaagaa cctcttgctc tgttcataga gtccttaaga gacattttgt attaaagttt    184620
cagatgatga aatagttca atattgtctg tcagataggc ctgaaactac cacagctgta    184680
tccagtttta acttgacttt aacaaagaga ctgtcttgtc aaaaggtagt agtagcagag     184740
agggatgggg cggtgttgga cattttgcta tatgacagcc taataggaaa taaaagtggc    184800
tgaattgagt aatgagttgt ttctaaagca ttgagtccct tctagtttaa caataatttg    184860
aaacatccct gttgacaaca aatgaggtgc atccagcctt ttttttttc ttttttctcct     184920
gtttgtactg agcttctaac atatggaaga caggaaatat aggagcttac atttagaagg    184980
taaaaaacta tcaaaacaaa acaaaaaaaa aatttggcaa cttattgctc ttctgctgtc    185040
cagcatggag atgtgggtat ttattttgt tcctaatatt tatttttta tacagcaacc      185100
agagtcccaa ggtttagatt ctggcaccgg ctctgtcatc ttagagctgc ttgccagagg    185160
gggacttccc acttttgact ttgttccagt tcaattgctt ctccaggcct tccccacata    185220
ctgttttca gacatggggc caatctcatc atctctgtgt aggggagaag aaaaaagcac    185280
```

```
agcagagaac atgttaaatt tcctaaagat tcattttgc aaggatggca gcatcagcag    185340
gtggttttc ttttcttctt ttaaatttaa aattgaatac ataccaaaga atatttacca    185400
tgctgtctaa gataaaacag tgataaatga acacttttgt actcaccagc tggtttaaaa   185460
aatacgacat tgcccttcct aattacccct ggaggtagac tactgtcctg aattttgctt   185520
ttaccatccc ctttctttt tctttgttaa tagttttact gcagacatac gtatccatat    185580
ataatatttt acttttcatg tttaatttta tagaaaagaa attattctgt atgtattttg   185640
caaaaacata cttttgctat tcaacgctgt atgtgagatt cacccatgtt gatatgctca   185700
attgtgtctt attcttttc attgctgcat agtatttcat catatacgtg ttattcaccc    185760
attccactgc cgatggacat ttgggttgtt ttcagtattt tgcttctaca gatagtgctg   185820
ctatggacat ttttgcacat atctccttgt gtctgtgtca gcctcactag ataatgttaa   185880
actgttttcc aaattgatta ttcttgccgg taaagtataa gagttctgat tattccatga   185940
tctcagcaaa cacttggact tgcctctagt tctttcacct gagcttatta aattaaagga   186000
aggcttactg tcctttctca cgtctaaaag tcatggtttg tattctcttt ccatagctgt   186060
ctcctgtctt ttttttttt ttttttttta atgccataac attgaaggac tctggcatac   186120
acacacacag cgaaggcaga gtggacattt cacatccaag tccgggtggt tatgtaggtt   186180
cattttctt ctgggtgtcc tgtgctgagg ttggctagca aaatatccag ctcaaaaaaa    186240
aaatcagaaa gttattccct tagcaccttt tcaattcaac tctgccaaca gtggctcagt   186300
aagaagcagc aagtaaataa aatcaacaga tttcagctta tgccttgggc tcgccagcaa   186360
tccccagacc acaggagaa aatgaatctt tttctcacaa aattcctctc actcccatca    186420
cttttccatt gaaacaacaa ggcagagaag ttacttatt gacttgcttt cctgtgagtc    186480
ttaccagaaa atgaagaata atagtaattg gcaaatacta cccacccagt tccttagcta   186540
gcacttctca catctgcttt atgatatcct tgctggcctg attttattca tttcctagtg   186600
ctcggcatag aaaccacaag aactagcaaa aagaaaaac actgcattta tataaaccaa    186660
taaaactagt gagcattttg tggacattaa aagaaacatg agggctatcc cacattataa   186720
atttcaaaat gcaagttttt gccttgtggt attttaaaag ttttaagatg ctattcagga   186780
acactctcaa taactgtttt aaattgttgt cgttttaaat ttttttcctt ttccaatatc   186840
ccacttgcct agtcttaact agtctccttc ctcaccaatc tgcccttctg tgcttttcc    186900
aaaatgcaag tttaactgtg gttgttttcc ttgtttaaaa ccactcacta actctgatac   186960
ctgcaggata aagtcctaac tctacctgga ttaatgaaaa gatttgatct ggcctctgtt   187020
tcctttccca accttaactc ttaccctctc cctcctttgc aattaaaatg ttgaaaaaca   187080
aaataccata tcatccccca aacatgcacc cagaaattca catgggattc cctcctcttg   187140
ccttgtgagg ccctttgtac tcctctgaca cacctggaaa actcccattt gcctttcatt   187200
cttggcaatc ttggtatgct tgatctttcc ccacattacc tccttcttgg caactctctc   187260
catctacgta catctcctat tgtatgtact acactggggt ttcacacttc aactctttaa   187320
ttgccttcct ctctactcg atgctaagtt ccttgaggac aggaataatt tatttaaaa    187380
atattcattt atttttgtag catacccctt agcacagttc ttggcactga gtaaatgttc   187440
agtgaattaa aatcaaatcg gcctctacct cattcccatg cccctctcct ttgcctctga   187500
ctgtgtgtgt gtgtgtgtgt gtgttttaat actacatctc tcaaggagtg tcatgattgt   187560
tcaccagttg tacacaccaa agtgtcttgg aggaaacaga gagacatgc tgagataatg    187620
aacagttcaa aacaattccc ttcaaactaa agactacact gtttatgtca gctaaagact   187680
atttcctttc tgtgttgcat gggagaaaaa atgagaaata ttctgggaca caaatttata   187740
aaaggagttg tagaaatttc attacctcag tgctgactag agcatcctct cctttaaaaa   187800
taattgaatt cctggttttt gttttttcc cttctcttaa aaaccacaa gcttgcttcc    187860
tgaagacaaa ggaaataata aacaatagca actcccaatt tgactctgat tatttgccaa   187920
aagtcttctt agttcatgtg gttctatttc attagagagg accgattagc ataagaagaa   187980
tgcttctaaa ttaagctacc caaatatgca cttagttagt actctgggag ctaatttatt   188040
gtattattta aaatataaat tggctagcaa atctatttat tgaggtgtaa cagctaggca   188100
acaatgcgta acttctctt ggctgttgag tggtttttaa tcatctattg aaatttaaca    188160
gagagccatt tcattaaatg gaaagcggat aaatactgag aagtctgtat tttagagtat   188220
tatccacaca tggagaatga tatttgagga acaaagaggg aattgggatt tgcttttaa    188280
acagtaactt tttgttgttt taatttgaag tgtaaccaaa gactcacaaa atcacttgtg   188340
gggatgttaa agcaagaaat aaacaaataa ggcggaagat ggagtagggt agagaaatag   188400
agggatggaa aaaattgtgt taagatagtg ctacgttgtc aattagacta atgcagtatt   188460
tttgccttgt acagttttgg ggttggcagt aaaaactatg taccttgttt tatttaaca    188520
aatggcatca tgaaaatatc atgctattg gcatgctgtg tattctaaat tcccagaacc    188580
tagagacatt taggggttct gggttcct taggctgtga gtcgagaaca tagttgaatc    188640
cagatacct gtcggtctg gagttctcct aaacagatca gctctggagc atctcatggt    188700
gctctgatat aaatggaaga gtcttgtaga tgttgtagca tggtcttgaa attctatcat   188760
tgtcacttat actagaactc agtgagggta ggcagaaatg gaaacaagtg acaggccttt   188820
ctcacctttc tgcaaatttt tgaaatctgg ctcatctgat ttccagagcc aaggtttcaa   188880
agaagtttta gaccttgtaa tttacgatag gtggatgttc cttaggttca cgttggaaag   188940
aagaagaatg tcagaatgtt tcctctttcc ccaggacagc caaaatgtca gagaaccagg   189000
agtctgaggg taaactgaag agagagggca ctgatttgta gtatttgcca atttccatag   189060
tgtaaatact ctcacgcagc caatttcaag ctaccaactt cacaccacta aacatggagt   189120
tgggcagcaa tgtgcacagt tggttctcct gatccagtga gggagtgccc acacactgct   189180
gctagaacta tcttgcattg ctgtctgcag gaagtaaatc tttagcaggt tagccggctc   189240
ttgtttccat ggtacacaga agatgatgag tcaggatcta agtccttgca gcactcctgg   189300
cgagagcatt tactgctata acctctgccc cttcctcccc cactcttatt ctctcttcca   189360
aaagaaaact acaaatgtag atcataaagc tagatgtaaa gtaagtataa ataatgaact   189420
ggattgtgct ttttatcctc ttgtggatat caagtataaa aactggacag ggaaggagag   189480
aatgaggatg ggaaatcttg attactttt aattgcatca aatcctgtgt ggtaaagtgg    189540
gttcctaaaa ggggaaaaag acagaacagt ttttgccat tctgctacga caagtaaggt    189600
cttgctttcc tggcatttct gtgtaggaag aagagggtgt ttggcattgc atgtggtgaa   189660
agggagaga gggtggaggg aaagaatggg atggatcatg gcattggcag ggataaaact    189720
cactgtagac acagttaagt tgagtgcagt gacagaggtt tgctttcaca ttcaagctgc   189780
ttcattaatt tcattgggc cttttccaag gaaagggagg attcataaaa gggaaatcaa    189840
agaagcctgg aaaagaaaca tttccccttc tgaagactgt attataatcc tttttctga    189900
aaagtacag taatgaatgt tatatttatt agtgctgtaa tttctcctct tcacttctta    189960
aagggaaaaa aatactctgt ttgtcataaa aactctgata atagtagtag agtgaccact   190020
```

```
ggttgagtcc ttattatctt tgtaatacac tggcacatgg tacaaactta agacatattt    190080
gtaatgggcc aggcgcgatg ggtaatctca gcactttggg aggccgaggc aggaggatcc    190140
cttgagccca ggagtttgag accagcctgg ggaacatggt gaaacccgt  ttctactgaa    190200
aatacaaaaa aaattagctg gatgtagtgg cgtatgcctg taatcccagc tactcgggag    190260
gctgaggcac aagaatcact tgaactcagc aagcagaggc tgcagggagc caagatcaca    190320
tcactgcact ccagcctggg ccacagagtg agacctgtc  tcaaaaaaaa aaaaagaaaa    190380
gaaaagaaaa aaaagacata tttgtagacc agatgccctg catcatttta taagtattgt    190440
ctctgaatcc ttacaaaaag ttattcatag agtaagcaac cattccagat tgcctgaccc    190500
ttttttactt ttagcactca aagccctatg ttcccagaaa cctcttggtc ctaggcacag    190560
tgcgacaagt ggtcacccaa attcttatcc ccattttaca aatgagaaaa tagagatagt    190620
taagtcatta tgccaaagtc acagaactgg gctcaaaccc tgagctacca aatcccaagt    190680
ccgtgctctt aaccatcagg ccaaatggct tccattatc  ctgtactctg cttttagatt    190740
ttcattaact atactgccca aggaaagaga aagcttcaac ttcaataatt catcccaacc    190800
ttgctgaaat taacacagaa attcttggag ttaatacaga gaaaattttc catgactttt    190860
tttttaatag acacgttcaa agcacgtcta actgatctgg tgaaataagg ctaacagatt    190920
tgagtgaaag gtcttcacct ctcaggtgtt cattctgtat ctctctaaaa ggaaggaacg    190980
tatcacaaga tttcttctca tttgagtacc ctgattgtca gaagtctgtt tctcatatca    191040
tgcagtaatg cccccttccac ttactctcat ccttttattc aatctattat ttggaagtca    191100
tactgccctc ccctttacc  actattaact tgataatagt agattatttt atctatcctt    191160
tatgtttatg tagagattat gacatatatc ctgatttaag aaagtcagct ttgagtcaat    191220
acatttacca ttgtccagat ataaaagtgt acctacaac  aggggccccc aatccctcgg    191280
tcacagactg gtaactgttt gtggcctttt aggaagcagg ccacacagca ggaggtgagt    191340
gcaggcaagc attactgtct gagctccgcc tcctgtcaaa tcagtggcag cattagattc    191400
ttataggagg ggaaccctat tgtgaactgc gcatgtgagg gatctagttg tgcgcttctc    191460
atgagaatct aatgcctgat gatctgaagt ggaacagtgt catccccaaa ccatccccca    191520
ctcccaaca  ctgtgcatgg aaaaaccgtc tcccacaaaa ttggtccctg gtgtcagaaa    191580
ggttggggac tgctgcctta caacactta  actcacttta cacccttttt gtgcaagtac    191640
tgtcttttga aaaacttcta catagttcaa actccagaag acattattaa ttattgatac    191700
tccttacttg tgttcacata tgtaaattct cagttgctgt tcattctcct ctgcattttc    191760
atgtttccat tacggataat tttccttctg tctgaagaac agtctttcgt acttctttta    191820
gtgcaggtct gctgacaaaa acctttttcca attttttgtt tccttgaaaa tatctttaca    191880
aggtcttcat ttctatacaa gttctaggtt ggcagatatt ttatttaaga actttcaaga    191940
tattattttca ctgtcttcca gctttcattg tttctgttga atagtcagtt ttcttgctgc    192000
tttgaaggta ctgaaagtac tgtttccttt tctgtgacag cttttaagat tttctctgtc    192060
tttgctttta gcaaaatgct attctctctg tgtgtgtgtg tgtgtgtgtg tgtgtgtgtg    192120
tgcacataca catactatag tgtaatatac tattactaat atactattat gtgtactatg    192180
atgtggttag tttgctttgt gtttattcta tctaggattc atagagcttc tcaaaactgg    192240
cttggtaact tttgtcaatt ttggaaattt ttcagtcagt atctctgaat gttactattt    192300
gtttcttttg ccccatttct tccttatcat tttatcctaa aattccagtt aaacataagt    192360
taaatgtttc atggtttcat gtcgtcttct tcttctttt  ttttttttt  gaattttcat    192420
accttattc  tccatgcttc agtctggata tcctctactg acctaacttc cagttcatat    192480
agtgtttctt ctgcatgcct aatctattgc taaaacatcg atcgagttct taatttcaat    192540
gaacaatgaa tgagtaactt tttagttaaa gaacttccat ttgattctct tgtatatatt    192600
ctaattatct tgtgaattat ttttctatac ctaacatctt gcatattttg ttcacagttta    192660
cttaaaatg  tgtacctggt aactctaata tctggatcat ttgtggtctc tgttatcttt    192720
ttttctcctt aaatttagt  cattgctctt gttctttgtc atgcctatta aattttatta    192780
aatgttgaag aaaatgtaca aaaaatatat gaagaaaaat gttattttc  ttccaaaagg    192840
atttaatttt ttctagaagg catacagagt agaggcatat caccttgata aagtttggga    192900
ttgagacgat tgattcagtg cttgatttca aggtttgtga ggactaacct gtttctggtt    192960
tgttattact tccaaggcat tgtctttcac ggatctgatg gaaagcctgc agtgcttacc    193020
agtgctgtcc ctccttgaca ggcttgcaac tccaattttt tgttgttgtt gtttcttttg    193080
gggttttctt tgtttttgtt ttttggtctc tcaagcaccg taagactaat gagcttttca    193140
ttctcttatc tgccgctttt gacttggcgt cttggtcaga gaagcttaaa aattggtgaa    193200
tttcccaaag ggaaaagcag cacaaaatgt taggctcact tccttgtgat tccctttct     193260
ctacgatcat ggcctctctc aaggcttggt tgctctctga tacctttaaa cagcttattt    193320
tcttttttaat tcagcttcta ttgttttctg tggaataaga ttggtttggt acatgctatt    193380
gtgtcacagt cagaagtgga agtcctaaat tacaaacagt attgttgcaa ctgattaaga    193440
tggtgtacat aggaagcccc ttggggatgt tgtaaaggag caccaaaagt tttaactgct    193500
ctagaaatatg taccattatg atggctacat gtgggtctcc tgaagcacct agaagctcct    193560
tttctcattc tattcaataa ccatttgcta caccagaggt gtacagtggg agacctcaag    193620
aatcgttttcc ctgagtgctg ttgaagcaac tcccagcctt gatctctgct gttttttcat    193680
tctttcgaaa gtgacttatt gcattcttttg ttaggaagtg tctgctaaca agctttggct    193740
tgtttttat  tctcgttccc aagtaccttt tcaatatatt tttatttgaa tgctatttac    193800
gttattcta  cttatagtta gtgtctgaaa gcaaactaaa agataagatt tagtaaatgt    193860
ggaatggcat aaaaagtagtg aaaagaactt acatgtaaat cagaaaccac aacaagcaga    193920
ttctcttgag ggtatgcatc tttctatact ggaaagcaga aacaatcaaac caatcctaca    193980
tattctgcct gccaaacttg cagctcccat gtggctcttt tctcttcct  ggtgagtagc    194040
accaccttg  caaatctgcc catgtcagaa gcctgaaatg gggaggattt gttggggatg    194100
ggtagagaaa gtctcactta aacttttat  cggattaatc actgatttta ttggttccat    194160
cttactaccc tcttctccctt cccttctcc  ccatccctcc catgagccca catcctctca    194220
cctgatttgg tagtctccta attgcctcc  ttgtaccagt atgactccct tccaaattag    194280
ccttctcctt agacattaag tcatttttct acaatgcaaa cataagcatg tcactaccct    194340
acttaaaacc ctctaggata tatccagaat aggcaagtct atagagacag aaagcagatt    194400
aatggttgcc agggggctgat gggggagagg gagtgggaga gtgattacta atgatatgg    194460
gtttcctttg gggtggtgaa atattctgc  aacaagatat tgtgaatata ctaaatgcta    194520
ccgaatcata cgctttaaaa tggttaaagt ggtaattta  tgttaagtgt attttaccac    194580
agttgctttt aaagcccgat aggataaggt ccactcatcc cagcatgtca cttgggcat     194640
cacatggtcc cactagcgtt tgcctgttca tctgtctctt ctgtttccct ctattcctgc    194700
atgaatggga cgacatacag actgctgcat gcgcccgcag cttcacggcc cctgcatttc    194760
```

```
cacacagaat ttcctttgtc tgcggtgatc cctctgctgc acgtgcccac agtttcatgc   194820
ccctgcattt ccatgcctcc tgcatttcca cgcctcctgc atttccacac acagtttcct   194880
ctgtctgcgg tgatccctcc acccccaccc cacccaccca ccactctccg tccagtgatc   194940
tccttcaaga cccccaagaa gcttcccctg acacatctac atcaacaagc ccactgtgaa   195000
cttccctctc ttttctgtca tctaaacagg cacaactggg aaaccttttc tggcaggtct   195060
ttgtttctag ttccagggag aattatattg ttttctaaaa aataaagtgg aatgaagctt   195120
taaagtgttt gtataaccct gttgaaattc atgacacatt tgtgaccccc tggaacatct   195180
ggaacacatg aagttagagg ctgcagctct agtgtggagg cacccaaaat agacagttct   195240
attcagggag ccctgagatt aatcttgtca catttaaata cgtaattaca gccctgacac   195300
attttgttac tcacctctaa aagctgccaa gtggtctgtt atctttgatt tgtgaatgat   195360
gagtggcttg attataaaca agagtggttt attttttccac actcaaaaat atatttattt   195420
ttgaagttaa tatcagtaaa atgctgtatg tgaatctgct taagaatatg ctttgtttgg   195480
gaattttgtg gcatgtgaaa caactttgtc ccttaacaag ctttctcttc ccgcaatatt   195540
aatgacacaa tttacaatgc cattagggtc attacatg gcagctcaga aattggacca   195600
gggtcaggta ggtcactgag aggaagagta agaacacctg accccttcag cgctccttca   195660
ccacttgata attatggaca gggaaggtgt gtgtgagtgc gcatgtgcgt gagtaaatac   195720
caggagagcg gatacccagg aagtgaggtc atgagtaggg attaaacaaa tttctacttg   195780
tattcatgag taggtgttaa tcaaattacc ttgatgtaaa cagagaattc cctggtttgc   195840
cacagagtag aaaaaaaattc tcaacagtgg ttttcaacaa gcagttggaa caacagcatc   195900
agcattgctt tggaattgtt agatatgcaa attcttaggc cctgccctgg accttccgaa   195960
ttggaaagtc tggaggtgat gcctcacgat ctcttttaat gagctcaggt attttttatgc   196020
acgttcaaat ttgagagtca ttgtttttgtt ttttcgtttg ttttttgaggt ggagtctcac   196080
tctgtcgccc aggctggagt gcagtggtgc catcttagct cactgcaacc tctgcctccc   196140
aggttcaagt gattctcctg cttcagcctc cccagtagtt gggattacag gcgtgcatca   196200
ccatgcctgg ctaattttttt tttttttaat ttttagtaga ggcagggttt cgccatgttg   196260
gccagctct ttcaaactcc tgacctcaaa tgatccgacc acctcagcct cccaaagtgt   196320
tgggattaca ggcatgagcc actgcaccca gccaagaacc attgttttaa acaaccttt   196380
ttaaaccaag gtttttttatg aaaatgtagg aacaccatgt tctagggtag tttaggttca   196440
tataagcata tatacatata tattcattta tatttagaga tgggatctcc ttttgttgcc   196500
caggctggag tgcagtggct cagtcagctc actgtagcc caaactcctg caatcaagcg   196560
atcctcctga tctcaagcaa tcctcctgat ataggcattt tgattctgga ttttcaatat   196620
agataagtgt tggaagaata acgaaaatga ccaatattta ctgaagacca tcccaggccg   196680
ggcactgtgc taagtattcc agggacatta ttccactaac tcctcacaca actcacaact   196740
accccacgag gtaatacttg tttcccaatt gtaaagtaaa ggaacctgag gctcagtgag   196800
gttaagttcc ttgcccaagg tcacacaacg tgcagtgcct cttgccatgc tcctgcactc   196860
tgacttctga gcccaggctg tgaagcactg tgctatcctt tgtttgtcct ttgttagctg   196920
cagcactggt tctgggggca ggatgacctt tagctcttgg gtattcaatt tattggtgtt   196980
ccggaccatt gctgccaaac tcatttccag ttgaagcagc tgggttttgt cacacatatg   197040
actttgttaa gtgtcctcag ctgagctgaa gctgcacaga aatcactcat cagattcctg   197100
ccagggccaa agatatggat gaaaatctgc aggaagaaat gtctagcctg ggattgcggg   197160
gcggcaaaag tttccctctg gagtcctatg aaggggttct tgtcacacat gtttactttc   197220
agtttgtgat aaaaagtggg catgctgggt ttccagttgc aagcttctac acaaatggta   197280
gatgggttc acagtcattg cagtgaggca caaatgacca ttgatcaact gcagcaaaac   197340
acaaagtttt cacatttgca tgtgaaagag ttaagtctgg tcccacatct gcaaatggga   197400
tctgcctccc tcactgtaat atgtgaaata caaaaataca gaaaaattatg tttatatctg   197460
caataatttt tttcatcaat aaacctcaga gggctattga gaggtgaata aaaatgttcc   197520
gtgactaagc tgcaaatttc agttcaaaga taaggaatga ttgagtagag ggtttgatta   197580
aaaacaccac accggtgttt gcatcagaag tcagggttct agctagttat ctcacttaac   197640
aattgtgtga cttggacaag ccactgaata attccaaata gctcagtcat ctcaatgctc   197700
atgtgaatgg tgctccctgt agttgttcag tgcacagctt gtatagctgc gagctgcaag   197760
gtaaatatca tctaatagtg ttaatcctac ttactgcacg tcaaggttgt aagatgggag   197820
gtgttgggat ataggggcag attttcaata taataaatgt actatccaaa tatactttt   197880
ctgcctcagt ttccttcaga ttgagacaag tagaagaacc cagcctctta ggaagggcct   197940
tgtgaaggtg accttttaatt gctgatcgtg attctgcagc tagaagttac tgaaagtgat   198000
gtcctttttg catacgttta ttcacttcat gcactggtac ctcctgtca ttctccacat   198060
atggaacgag acatctcagg ccaggctgac ctctcctgca tgtaacttcc caacactcag   198120
tgtcagtcct tgcccttttg gcactgaatc atgacagctt cccgtttccc tctacttgga   198180
atattagctg acgctagagg cttaacgagt acagagacca gtccccttttt gctgattgga   198240
tctcatcatt agagatgttt taggaatgct ttatatcacc caacaagggc ttgggttacg   198300
taggtgtctg catttgtcag aactggtgag tctacactta agactagcgc atttcattgt   198360
atcttaactt gactcaaaag aagaaaatct gtaaacacat gttgaactct gatgaataat   198420
gtgatgctga agtgtgtggg ggaagtgcac tacatgccca ttttactttg agatgtgtca   198480
aaaatataag atggattagt ggatgggtgt gggatgcata gaggcaccct tatgtgagaa   198540
agcaagtaaa gtgaaagttc atgactcaaa atcgtcacta tatgaattgt tttcgaattt   198600
gctatgtttt aaaatgtttt ataatccaat attaggaaaa aaaagaatgt tctaactcta   198660
tgctgctcaa aacatgactt tctttcattt caagtgtcaa gttttttgtt ttgttttttt   198720
ttttttttgtt ttttggtttt tttttttaag atgggggtc tcattctgtc aaccaggctg   198780
gagtgcagtg catgtggcat gatcctagct cactgcagac tccaactcct gggttcaggt   198840
catcttcctg cctcagtcaa ggatgtttta ggttttttaa tttttttgag aaccaaaatt   198900
tccccttcat tactgataaa ggctaaaatg gaaggtatgg ctcagtgtga gggacaattg   198960
ggctggctaa ctgaagggtg gaattaagta gacaatccac cccattgcag gcagacctca   199020
catacccccag aagtagtggg ctggaggtgg gcctcaccag gtaacacttg cagtgcagca   199080
ctctcaactg cggggagcag gcagatcact tctctagagga aaaagacaag gaataatttt   199140
caattttttac actcatgaga aaagaataca actttgcgta aaattaacta agctttaaaa   199200
cttttctacc ttaacatgcc tgttacaaaa gccatcaaca gccagatagg cagcttgtcc   199260
aaaggcatgc attgggagaa tatgttctgt atttcatgtg agtttaaaat agagtttaat   199320
ctgaatgaaa actttccatg tatttagaat atccatttct ctaaatttcc gttcttttac   199380
ttttttcttt taaggtaatt attcgaggtg gaggacatat tttaccctat gaccagcctc   199440
tgagagcttt tgacatgatt aatcgattca tttatggaaa aggatgggat ccttatgttg   199500
```

```
gataaactac cttcccaaaa gagaacatca gaggttttca ttgctgaaaa gaaaatcgta   199560
aaaacagaaa atgtcatagg aataaaaaaa ttatcttttc atatctgcaa gattttttc    199620
atcaataaaa attatccttg                                               199640

SEQ ID NO: 2           moltype = RNA   length = 2213
FEATURE                Location/Qualifiers
source                 1..2213
                       mol_type = genomic RNA
                       organism = Homo sapiens
SEQUENCE: 2
gctcctttcg cttttcgctc gctgcactcc aagcccggga acacccgcgt ccgcacacta    60
agggcaccac cgctctccca cctctgcgct gtcagatgtc aggcgcggag gtgctctggg   120
caccgaggtg ctggcgaacc aaacaagtat caccccggac gcctgccccc attccgagag   180
agcgggcggg atggccacag gctgcaatac agtgacacga tcacagctca ctgctacagc   240
ctctacctcc tgggcttaat ccatcctccc tcctcagcct cccaagcagc tgggactaca   300
ggtgattttg atatgctgct aaggtttgat aagagaaatg agattcagag aacagattat   360
attgttgaag agcttgactg gaaatgatcc aaacggaaac attggctctt cctggggttc   420
cagcctgctg tcttgacagg aactatacca tcagctctcc tgggtctctt acatgccaag   480
tcatcctgca gatctgggac tcactccgta atcagcttga ttgctgtaag ttgaacacgt   540
cagtggcatg gcaccagct gcacaaccct aggagccacc aaacacagta tattctatat   600
aaatgttgct gccaggagcc ccagttcaaa ctacaatacc ctgagagatg gttggtgcca   660
tgtggaaggt gattgtttcg ctggtcctgt tgatgcctgt ccctgtgat gggctgtttc   720
gctccctata cagaagtgtt tccatgccac ctaaggagga ctcaggacag ccattatttc   780
tcacccctta cattgaagct gggaagatcc aaaaaggaag agaattgagt ttggtcggcc   840
cttcccagg actgaacatg aagagttatg ccggcttcct caccgtgaat aagacttaca   900
acagcaacct cttcttctgg ttcttcccag tcagatca gccagaagat gccccagtag   960
ttctctggct acagggtggg ccgggaggtt catccatgtt tggactcttt gtggaacatg  1020
ggccttatgt tgtcacaagt aacatggacct tgcgtgacag agacttcccc tggaccacaa  1080
cgctctccat gctttacatt gacaatccag tgggcacagg cttcagtttt actgatgata  1140
cccacggata tgcagtcaat gaggacgata tagcacggga tttatacagg gcactaattc  1200
agttttccca gatatttcct gaatataaaa ataatgactt ttatgtcact ggggagtctt  1260
atgcagggaa atatgtgcca gccattgcac acctcatcca ttccctcaac cctgtgagag  1320
aggtgaagat caacctgaac ggaattgcta ttggagatgg atattctgat cccgaatcaa  1380
ttataggggg ctatgcagaa ttcctgtacc aaattggctt gttggatgag aagcaaaaaa  1440
agtacttcca gaagcagtgc catgaatgca tagaacacat caggaagcag aactggtttg  1500
aggcctttga aatactggat aaactactag atggcgactt aacaagtgat ccttcttact  1560
tccagaatgt tacaggatgt agtaattact ataacttttt gcggtgcacg gaacctgagg  1620
atcagcttta ctatgtgaaa ttttttgtcac tcccagaggt gagacaagcc atccacgtgg  1680
ggaatcagac ttttaatgat ggaactatag ttgaaaagta cttgcgagaa gatacagtac  1740
agtcagttaa gccatggtta actgaaatca tgaataatta taaggttctg atctacaatg  1800
gccaactgga catcatcgtg gcagctgccc tgacagagcg ctccttgatg ggcatggact  1860
ggaaaggatc ccaggaatac aagaaggcag aaaaaaaagt ttggaagatc tttaaatctg  1920
acagtgaagt ggctggttac atccggcaag cgggtgcctt ccatcaggta attattcgag  1980
gtggaggaca tattttaccc tatgaccagc ctctgagagc ttttgacatg attaatcgat  2040
tcatttatgt aaaaggatgg gatccttatg ttggataaac taccttccca aaagagaaca  2100
tcagaggttt tcattgctga aaagaaaatc gtaaaaacag aaaatgtcat aggaataaaa  2160
aaattatctt ttcatatctg caagattttt ttcatcaata aaaattatcc ttg          2213

SEQ ID NO: 3           moltype = RNA   length = 2087
FEATURE                Location/Qualifiers
source                 1..2087
                       mol_type = genomic RNA
                       organism = Homo sapiens
SEQUENCE: 3
gtgactgggt ggggctgcct cacttctgcc tgatttggga agcgctgcaa ggacaaccgg    60
ctggggtcct tgcgcgccgc ggctcaggga ggagcaccga ctgcgccgca ccctgagaga   120
tggttggtgc catgtggaag gtgattgttt cgctggtcct gttgatgcct ggcccctgtg   180
atgggctgtt tcgctcccta tacagaagtg tttccatgcc acctaaggga gactcaggac   240
agccattatt tctcacccct tacattgaag ctgggaagat ccaaaaagga agagaattga   300
gtttggtcgg ccctttccca ggactgaaca tgaagagtta tgccggcttc ctcaccgtga   360
ataagactta caacagcaac ctcttcttct ggttcttccc agctcagata cagccagaag   420
atgccccagt agttctctgg ctacaggtg gccgggagg ttcatccatg tttggactct   480
tgtgtggaaca tgggccttat gttgtcacaa gtaacatgac cttgcgtgac agagacttcc   540
cctggaccac aacgctctcc atgctttaca ttgacaatcc agtgggcaca ggcttcagtt   600
ttactgatga tacccacgga tatgcagtca atgaggacga tgtagcacgg gatttataca   660
gtgcactaat tcagtttttc cagatatttc ctgaatataa aaataatgac ttttatgtca   720
ctggggagtc ttatgcaggg aaatatgtgc cagccattgc acacctcatc cattccctca   780
accctgtgag agaggtgaag atcaacctga acggaattgc tattggagat ggatattctg   840
atcccgaatc aattataggg gctatgcag aattcctgta ccaaattggc ttgttggata   900
agaagcaaaa aaagtacttc cagaagcagt gccatgaatg catagaacac atcaggaagc   960
agaactggtt tgaggccttt gaaatactgg ataaactact agatgcgac ttaacaagtg  1020
atccttctta cttccagaat gttacaggat gtagtaatta ctataacttt ttgcggtgca  1080
cggaacctga ggatcagctt tactatgtga aattttttgtc actcccagag gtgagacaag  1140
ccatccacgt gggaatcag acttttaatg atggaactat agttgaaaag tacttgcgaa  1200
agatacagt acagtcagtt aagccatggt taactgaaat catgaataat tataaggttc  1260
tgatctacaa tggccaactg gacatcatcg tggcagctgc cctgacagag cgctccttga  1320
tgggcatgga ctggaaagga tcccaggaat acaagaaggc agaaaaaaaa gtttggaaga  1380
tctttaaatc tgacagtgaa gtggctggtt acatccggca agcgggtgac ttccatcagg  1440
taattattcg aggtggagga catattttta ccctatgacca gcctctgaga gcttttgaca  1500
```

```
tgattaatcg attcatttat ggaaaaggat gggatcctta tgttggataa actaccttcc  1560
caaaagagaa catcagaggt tttcattgct gaaaagaaaa tcgtaaaaac agaaaatgtc  1620
ataggaataa aaaaattatc ttttcatatc tgcaagattt ttttcatcaa taaaaattat  1680
ccttgaaaca agtgagcttt tgtttttggg gggagatgtt tactacaaaa ttaacatgag  1740
tacatgagta agaattacat tatttaactt aaaggatgaa aggtatggat gatgtgacac  1800
tgagacaaga tgtataaatg aaattttagg gtcttgaata ggaagtttta atttcttcta  1860
agagtaagtg aaaagtgcag ttgtaacaaa caaagctgta acatcttttt ctgccaataa  1920
cagaagtttg gcatgccgtg aaggtgtttg gaaatattat tggataagaa tagctcaatt  1980
atcccaaata aatggatgaa gctataatag ttttggggaa aagattctca aatgtataaa  2040
gtcttagaac aaaagaattc tttgaaataa aatattata tataaaa            2087
```

SEQ ID NO: 4          moltype = RNA    length = 1739
FEATURE               Location/Qualifiers
source                1..1739
                      mol_type = genomic RNA
                      organism = Homo sapiens
SEQUENCE: 4
```
agcgctgcaa ggacaaccgg ctggggtcct tgcgcgccgc ggctcaggga ggagcaccga   60
ctgcgccgcg taagtgccgc ctgccctgcg tgggtcgtgc cagctcagcg ggacaggtcc  120
tcgcctcggt ccctcggact tagggagcgc ggggcagacc ctgagagatg gttggtgcca  180
tgtggaaggt gattgtttcg ctggtcctgt tgatgcctgg ccctgtgat  gggctgtttc  240
gctccctata cagaagtgtt tccatgccac ctaagggaga ctcaggacag ccattattc   300
tcaccccttä cattgaagct gggaagatcc aaaaaggaag agaattgagt ttggtcggcc  360
cttttcccagg actgaacatg aagagttatg ccggcttcct caccgtgaat aagacttaca  420
acagcaacct cttcttctgg ttcttcccag ctcagataca gccagaagat gccccagtag  480
ttctctgget acagggtggg ccgggaggtt catccatgtt tggactcttt gtggaacatg  540
ggccttatgt tgtcacaagt aacatgacct tgcgtgacga agacttcccc tggaccacaa  600
cgctctccat gctttacatt gacaatccag tgggcacagg cttcagtttt actgatgata  660
cccacgggta tgcagtcaat gaggacgatg tagcacggga tttatacagt gcactaattc  720
agttttcca gatatttcct gaatataaaa ataatgactt ttatgtcact ggggagtctt  780
atgcagggaa atatgtgcca gccattgcac acctcatcca ttccctcaac cctgtgagag  840
aggtgaagat caacctgaac ggaattgcta ttggagatgg atattctgat cccgaatcaa  900
ttataggggg ctatgcagaa ttcctgtacc aaattggctt gttggatgag aagcaaaaaa  960
agtacttcca gaagcagtgc catgaatgca tagaacacat caggaagcag aactggtttg 1020
aggcctttga aatactggat aaactactag atggcgactt aacaagtgat ccttcttact 1080
tccagaatgt tacaggatgt agtaattact ataacttttt gcggtgcacg gaacctgagg 1140
atcagcttta ctatgtgaaa tttttgtcac tcccagaggt gagacaagcc atccacgtgg 1200
ggaatcagac ttttaatgat ggaactatag ttgaaaagta cttgcgagaa gatacagtac 1260
agtcagttaa gccatggtta actgaaatca tgaataatta taaggttctg atctacaatg 1320
gccaactgga catcatcgtg gcagctgccc tgacagagcg ctccttgatg ggcatggact 1380
ggaaggatc ccaggaatac aagaaggcag aaaaaaaagt ttggaagatc tttaaatctg 1440
acagtgaagt ggctggttac atccggcaag cgggtgactt ccatcaggta attattcgag 1500
gtgggaggaca tattttaccc tatgaccagc ctctgagagc tttgacatg attaatcgat 1560
tcatttatgg aaaaggatgg gatccttatg ttggataaac taccttccca aaagagaaca 1620
tcagaggttt tcattgctga aaagaaaatc gtaaaacag aaaatgtcat aggaataaaa 1680
aaattatctt tcatatctg caagattttt ttcatcaata aaaattatcc ttgaaacaa  1739
```

SEQ ID NO: 5          moltype = RNA    length = 3219
FEATURE               Location/Qualifiers
source                1..3219
                      mol_type = genomic RNA
                      organism = Homo sapiens
SEQUENCE: 5
```
gtgcacagac ggcccaggat gggttaatga gcaggcagct cagacgccgc aggtagcggc   60
cctgcctctg aacaaagagg agtccacacc tgggtgcag acaaagggag gccgcctctg  120
ctacccaatt cccagttcac atcgcctgct gctggggacc cctagtggcg cacacgacg   180
caggcacagg tgattttgat atgctgctaa ggtttgataa gagaaatgag attcagagaa  240
cagattatat tgttgaagag cttgactgga aatgatccaa acggaaacat tggctcttcc  300
tggggttcca gcctgctgtc ttgacaggaa ctataccatc agctctcctg ggtctcttac  360
atgccaagtc atcctgcaga tctgggactc actccgtaat cagcttgatt gctgtaagtt  420
gaacacgtca gtggcatggg caccagctgc acaaccctag gagccaccaa acacagtata  480
ttctatataa atgttgctgc caggagcccc agttcaaact acaatacct gagagatggt  540
tggtgccatg tggaaggtga ttgtttcgct ggtcctgttg atgcctggcc cctgtgatgg  600
gctgtttcgc tccctataca gaagtgtttc catgccactt aagggagact caggacagcc  660
attatttctc acccttaca ttgaagctgg gaagatccaa aagaatctt gctctgttgc  720
caggctggag tgcagtggtg cagcctcggc tcactgcgct ctgcacctcc tgcgttcaag  780
cgattctcct gcctcagcct cctgagtagc tggaactaca ggaagagaat tgagtttggt  840
cggcccttc ccaggactga acatgaagag ttatgccggc ttcctcaccg tgaataagac  900
ttacaacagc aacctcttct tctggttctt cccagctcag atacagccag aagatgcccc  960
agtagttctc tggctacagg gtgggccggg aggttcatcc atgtttggac tctttgtgga 1020
acatgggcct tatgttgtca caagtaacat gaccttgcgt gacagagact cccctggac 1080
cacaacgctc tccatgcttt acattgacaa tccagtgggc acaggcttca gttttactga 1140
tgatacccac gggtatgcag tcaatgagga cgatgtagca cgggatttat acagtgcact 1200
aattcagttt tccagatat ttcctgaata taaaaataat gacttttatg tcactggggga 1260
gtcttatgca gggaaatatg tgccagccat tgcacacctc atccattccc tcaaccctgt 1320
gagagaggtg aagatcaacc tgaacggaat tgctattgga gatggatatt ctgatcccga 1380
atcaattata gggggctatg cagaattcct gtaccaaatt ggcttgttgg atgagaagca 1440
aaaaaagtac ttccagaagc agtgccatga atgcatagaa cacatcagga agcagaactg 1500
gtttgaggcc tttgaaatac tggataaact actagatggc gacttaacaa gtgatccttc 1560
```

```
ttacttccag aatgttacag gatgtagtaa ttactataac ttttttgcggt gcacggaacc  1620
tgaggatcag ctttactatg tgaaattttt gtcactccca gaggtgagac aagccatcca  1680
cgtggggaat cagacttta atgatggaac tatagttgaa aagtacttgc gagaagatac   1740
agtacagtca gttaagccat ggttaactga aatcatgaat aattataagg ttctgatcta  1800
caatgccaa ctggacatca tcgtggcagc tgccctgaca gagcgctcct tgatgggcat   1860
ggactggaaa ggatcccagg aatacaagaa ggcagaaaaa aagtttgga agatctttaa   1920
atctgacagt gaagtggctg gttacatccg gcaagcgggt gacttccatc aggtaattat  1980
tcgaggtgga ggacatattt taccctatga ccagcctctg agagcttttg acatgattaa  2040
tcgattcatt tatggaaaag gatggatcc ttatgttgga taaactacct tcccaaaaga   2100
gaacatcaga ggttttcatt gctgaaaaga aaatcgtaaa aacagaaaat gtcataggaa  2160
taaaaaaatt atcttttcat atctgcaaga ttttttttcat caataaaaat tatccttgaa  2220
acaagtgagc ttttgttttt gggggggagat gtttactaca aaattaacat gagtacatga  2280
gtaagaatta cattatttaa cttaaaggat gaaaggtatg gatgatgtga cactgagaca  2340
agatgtataa atgaaatttt agggtcttga ataggaagtt ttaatttctt ctaagagtaa  2400
gtgaaaagtg cagttgtaac aaacaaagct gtaacatctt tttctgccaa taacagaagt  2460
ttggcatgcc gtgaaggtgt ttggaaatat tattggataa gaatagctca attatcccaa  2520
ataaatggat gaagctataa tagttttggg gaaaagattc tcaatgtat aaagtcttag   2580
aacaaaagaa ttctttgaaa taaaaatatt atatataaaa gtaatgatga gtcaattctt  2640
gataagcaga tgctcttatg cagagaacaa acttaatctt tgccttttca ttttctttt   2700
ccttctttga gtttgaggtg tacacacttc tgaaagagcc tgcaggctac attagttata  2760
agagccattt taatttgggc ttcaaattct ctacttcttt tccccaaata aagaacaacc  2820
taattttgta tcattgttag aatatcaaaa aaaattaaga taagctggca tcaatatata  2880
catttataaa tatacattca ttagcagttt tctgactaaa atgtcacatc ctggcacatc  2940
ttttcgattt atgcatcatg tgctcacatc tctgaaattc tacaagacgt gtggattttt  3000
ccacatcact tccttctcat attcccatc tatgaactgg ctcactggag aattaaattt   3060
aaaaagtcaa agcctgttct tgcggcaaat agtttatgga gtttattctt ttaatttctc  3120
atgttgtgcc tgattacgtt caggtttgtg atcttccttt ttaaattgtt cattgtaccc  3180
atgtcctaga agtcattaaa tcaaatattc tgatcaaaa                        3219

SEQ ID NO: 6           moltype = RNA  length = 2889
FEATURE                Location/Qualifiers
source                 1..2889
                       mol_type = genomic RNA
                       organism = Homo sapiens
SEQUENCE: 6
gtgcacagac ggcccaggat gggttaatga gcaggcagct cagacgccgc aggtagcggc    60
cctgcctctg aacaaagagg agtccacacc tggggtgcag acaaagggag gccgcctctg   120
ctacccaatt cccagttcac atcgcctgct gctggggacc cctagtggcg gcacacgacg   180
caggcacagg cttgattgct gtaagttgaa cacgtcaggt gcatgggcac cagctgcaca   240
accctaggag ccaccaaaca cagtatattc tatataaatg ttgctgccag gagccccagt   300
tcaaactaca atacccctgag agatggttgg tgccatgtgg aagtgattg tttcgctggt   360
cctgttgatg cctggcccct gtgatgggct gtttcgctcc ctatacagaa gtgtttccat   420
gccacctaag ggagactcag gacagccatt atttctcacc ccttacattg aagctgggaa   480
gatccaaaaa ggaagagaat tgagtttggt cggccctttc ccaggactga acatgaagag   540
ttatgccggc ttcctcaccg tgaataagac ttacaacagc aacctcttct tctgttctt    600
cccagctcag atacagccag aagatgcccc agtagttctc tggctacagg gtgggccggg   660
aggttcatcc atgtttggac tcttttgtgga acatgggcct tatgttgtca caagtaaacat  720
gaccttgcgt gacagagact tccctggac cacaacgctc tccatgcttt acattgacaa    780
tccagtggc acaggcttca gttttactga tgatacccac ggatatgcag tcaatgagga    840
cgatgtagca cgggatttat acagtgcact aattcagttt ttccagatat ttcctgaata    900
taaaaataat gacttttatg tcactgggga gtcttatgca gggaaatatg tgccagccat    960
tgcacacctc atccattccc tcaacccgt gagagaggtg aagatcaacc tgaacggaat    1020
tgctattgga gatggatatt ctgatcccga atcaattata gggggctatg cagaattcct   1080
gtaccaaatt ggcttgttgg atgagaagca aaaaagtac ttccagaagc agtgccatga    1140
atgcatagaa cacatcagga agcagaactg gtttgagcc tttgaaatac tggataaact   1200
actagatggc gacttaacaa gtgatccttc ttacttccag aatgttacag gatgtagtaa   1260
ttactataac ttttttgcggt gcacggaacc tgaggatcag ctttactatg tgaaattttt   1320
gtcactccca gaggtgagac aagccatcca cgtggggaat cagactttta atgatggaac   1380
tatagttgaa aagtacttgc gagaagatac agtacagtca gttaagccat ggttaactga   1440
aatcatgaat aattataagg ttctgatcta caatgccaa ctggacatca tcgtggcagc    1500
tgccctgaca gagcgctcct tgatgggcat ggactggaaa ggatcccagg aatacaagaa   1560
ggcagaaaaa aagtttgga agatctttaa atctgacagt gaagtggctg gttacatccg    1620
gcaagcgggt gacttccatc aggtaattat tcgaggtgga ggacatattt taccctatga   1680
ccagcctctg agagcttttg acatgattaa tcgattcatt tatggaaaag gatgggtcca   1740
ttatgttgga taaactacct tcccaaaaga gaacatcaga ggttttcatt gctgaaaaga   1800
aaatcgtaaa aacagaaaat gtcataggaa taaaaaaatt atcttttcat atctgcaaga   1860
ttttttttcat caataaaaat tatccttgaa acaagtgagc ttttgttttt gggggggagat  1920
gtttactaca aaattaacat gagtacatga gtaagaatta cattatttaa cttaaaggat   1980
gaaaggtatg gatgatgtga cactgagaca agatgtataa atgaaatttt agggtcttga   2040
ataggaagtt ttaatttctt ctaagagtaa gtgaaaagtg cagttgtaac aaacaaagct   2100
gtaacatctt tttctgccaa taacagaagt ttggcatgcc gtgaaggtgt ttggaaatat   2160
tattggataa gaatagctca attatcccaa ataaatggat gaagctataa tagttttggg   2220
gaaaagattc tcaatgtat aaagtcttag aacaaaagaa ttctttgaaa taaaaatatt    2280
atatataaaa gtaatgatga gtcaattctt gataagcaga tgctcttatg cagagaacaa   2340
acttaatctt tgccttttca ttttctttt ccttctttga gtttgaggtg tacacacttc    2400
tgaaagagcc tgcaggctac attagttata agagccattt taatttgggc ttcaaattct   2460
ctacttcttt tccccaaata aagaacaacc taattttgta tcattgttag aatatcaaaa   2520
aaaattaaga taagctggca tcaatatata catttataaa tatacattca ttagcagttt   2580
tctgactaaa atgtcacatc ctggcacatc ttttcgattt atgcatcatg tgctcacatc   2640
```

```
tctgaaattc tacaagacgt gtggattttt ccacatcact tccttctcat attacccatc    2700
tatgaactgg ctcactggag aattaaattt aaaaagtcaa agcctgttct tgcggcaaat    2760
agtttatgga gtttattctt ttaatttctc atgttgtgcc tgattacgtt caggtttgtg    2820
atcttccttt ttaaattgtt cattgtaccc atgtcctaga agtcattaaa tcaaatattc    2880
tgatcaaaa                                                            2889

SEQ ID NO: 7           moltype = RNA   length = 3380
FEATURE                Location/Qualifiers
source                 1..3380
                       mol_type = genomic RNA
                       organism = Homo sapiens
SEQUENCE: 7
gcttttcgct cgctgcactc caagccccgg aacacccgcg tccgcacact aagggcacca     60
ccgctctccc acctctgcgc tgtcagatgt caggcgcgga ggtgctctgg gcaccgaggt    120
gctggcgaac caaacaagta tcaccccgga cgcctgcccc cattccgaga gagcgggcgg    180
gatggccaca ggctgcaata cagtgacacg atcacagctc actgctacag cctctacctc    240
ctgggcttaa tccatcctcc ctcctcagcc tcccaagcag ctgggactac aggtgatttt    300
gatatgctgc taaggtttga taagagaaat gagattcaga gaacagatta tattgttgaa    360
gagcttgact ggaaatgatc caaacgaaa cattggctct tcctggggtt ccagcctgct    420
gtcttgacag gaactatacc atcagctctc tgggtctct tacatgccaa gtcatcctgc    480
agatctggga ctcactccgt aatcaagaat gccaccaatt cagcacttaa aaaattctgg    540
gccaggtgtg gtggctcaca cctgtaatcc tagtactttg ggaggccaag accggcagac    600
cacttgaggc cagaagtttg agaccagcct ggccaacatg gtgaaaccct gtctctacta    660
aaaatacaaa agttagccag gcttgattgc tgtaagttga acacgtcagt ggcatgggca    720
ccagctgcac aaccctagga gccaccaaac acagtatatt ctatataaat gttgctgcca    780
ggagccccag ttcaaactac aatacctga gagatgtttg gtgccatgtg gaaggtgatt     840
gtttcgctgg tcctgttgat gcctggcccc tgtgatgggc tgtttcgctc cctatacaga    900
agtgtttcca tgccacctaa gggagactca ggacagccat tatttctcac cccttacatt    960
gaagctggga agatccaaaa aggaagagaa ttgagtttgg tcggcccttt cccaggactg   1020
aacatgaaga gttatgccgg cttcctcacc gtgaataaga cttacaacag caacctcttc   1080
ttctggttct tcccagctca gatacagcca gaagatgccc cagtagttct ctggctacag   1140
ggtgggccgg gaggttcatc catgtttgga ctctttgtgg aacatgggcc ttatgttgtc   1200
acaagtaaca tgaccttgcg tgacagagac ttccccttgga ccacaacgct ctccatgctt   1260
tacattgaca atccagtggg cacaggcttc agttttactg atgatacca cggatatgca   1320
gtcaatgagg acgatgtagc acgggattta tacagtgcac taattcagtt tttccagata   1380
tttcctgaat ataaaaataa tgacttttat gtcactgggg agtcttatgc agggaaatat   1440
gtgccagcca ttgcacacct catccattcc ctcaaccctg tgagagaggt gaagatcaac   1500
ctgaacggaa ttgctattgg agatggatat tctgatcccg aatcaattat aggggggctat  1560
gcagaattcc tgtaccaaat tggcttgttg gatgagaagc aaaaaaagta cttccagaag   1620
cagtgccatg aatgcataga acacatcagg aagcagaact ggtttgaggc ctttgaaata   1680
ctggataaac tactagatgg cgacttaaca agtgatcctt cttacttcca gaatgttaca   1740
ggatgtagta attactataa cttttgcgg tgcacggaac ctgaggatca gctttactat   1800
gtgaaatttt tgtcactccc agaggtgaga caagccatac acgtgggaa tcagacttgt   1860
aatgatggaa ctatagttga aaagtacttg cgagaagata cagtacagtc agttaagcca   1920
tggttaactg aaatcatgaa taattataag gttctgatct acaatggcca actggacatc   1980
atcgtggcag ctgccctgac agagcgctcc ttgatgggca tggactggaa aggatcccag   2040
gaatacaaga aggcagaaaa aaaagtttgg aagatctta aatctgacag tgaagtggct   2100
ggttacatcc ggcaagcggg tgacttccat caggtaatta ttcgaggtgg aggacatatt   2160
ttacccctatg accagcctct gagagctttt gacatgatta atcgattcat ttatggaaaa   2220
ggatgggatc cttatgttgg ataaactacc ttcccaaaag agaacatcag aggttttcat   2280
tgctgaaaag aaaatcgtaa aaacagaaaa tgtcataga ataaaaaat tatcttttca    2340
tatctgcaag atttttttca tcaataaaaa ttatccttga aacaagtgag cttttgtttt   2400
tgggggagaa tgttactac aaaattaaca tgagtacatg agtaagaatt acattattta   2460
acttaaagga tgaaaggtat ggatgatgtg acactgagac aagatgtata aatgaaattt   2520
tagggtcttg ataggaagt tttaatttct tctaagagta agtgaaaagt gcagttgtaa   2580
caaacaaagc tgtaacatct ttttctgcca ataacagaag tttggcatgc cgtgaaggtg   2640
tttgaaata ttattggata agaatagctc aattatccca aataaatgga tgaagctata   2700
atagttttgg ggaaagatt ctcaaatgta taagtcttta gaacaaaaga attctttgaa   2760
ataaaaatat tatatataaa agtaatgatg agtcaattct tgataagcag atgctcttat   2820
gcagagaaca aacttaatct ttgccttttc attttcttt tccttctttg agtttgaggt   2880
gtacacactt ctgaaagagc ctgcaggcta cattagttat aagagccatt ttaatttggg   2940
cttcaaattc tctacttctt ttccccaaat aagaacaac ctaattttgt atcattgtta   3000
gaatatcaaa aaaattaag ataagctggc atcaatatat acatttataa atatacattc   3060
attagcagtt ttctgactaa aatgtcacat cctggccatt cttttcgatt tatgcatcat   3120
gtgctcacat ctctgaaatt ctacaagacg tgtggatttt tccacatcac ttccttctca   3180
tattacccat ctatgaactg gctcactgga gaattaaatt taaaaagtca aagcctgttc   3240
ttgcggcaaa tagtttatgg agtttattct tttaatttct catgttgtgc ctgattacgt   3300
tcaggtttgt gatcttcctt tttaaattgt tcattgtacc catgtcctag aagtcattaa   3360
atcaaatatt ctgatcaaaa                                              3380

SEQ ID NO: 8           moltype = RNA   length = 3401
FEATURE                Location/Qualifiers
source                 1..3401
                       mol_type = genomic RNA
                       organism = Homo sapiens
SEQUENCE: 8
gcttttcgct cgctgcactc caagccccgg aacacccgcg tccgcacact aagggcacca     60
ccgctctccc acctctgcgc tgtcagatgt caggcgcgga ggtgctctgg gcaccgaggt    120
gctggcgaac caaacaagta tcaccccgga cgcctgcccc cattccgaga gagcgggcgg    180
```

```
gatggccaca ggctgcaata cagtgacacg atcacagctc actgctacag cctctacctc    240
ctgggcttaa tccatcctcc ctcctcagcc tcccaagcag ctgggactac aggtgatttt    300
gatatgctgc taaggtttga taagagaaat gagattcaga gaacagatta tattgttgaa    360
gagcttgact ggaaatgatc caaacggaaa cattggctct tcctggggtt ccagcctgct    420
gtcttgacag gaactatacc atcagctctc ctgggtctct tacatgccaa gtcatcctgc    480
agatctggga ctcactccgt aatcagcttg attgctgtaa gttgaacacg tcagtggcat    540
gggcaccagc tgcacaaccc taggagccac caaacacagt atattctata taaatgttgc    600
tgccaggagc cccagttcaa actacaatat ggagttttgc tcttttttgc ccaggctgga    660
gtgcgatggc acaatcttgg ctcactgcaa cctccacctc ttgggttcaa gcaatgcttc    720
tgcctcagcc tcccaagtag ctgggattac agagacaggg tttcaccatg ttggacaggc    780
cgggcacctg acctcaagtg atctgcccgc tcagcctgc caaaaccctg agagatggtt    840
ggtgccatgt ggaaggtgat tgtttcgctg tcctgttga tgcctggccc ctgtgatggg    900
ctgtttcgct ccctatacag aagtgtttcc atgccaccta agggagactc aggacagcca    960
ttatttctca cccttacat tgaagctggg aagatccaaa aaggaagaga attgagtttg   1020
gtcggccctt tccaggact gaacatgaag agttatgccg gcttcctcac cgtgaataag   1080
acttacaaca gcaacctctt cttctggttc ttcccagctc agatacagcc agaagatgcc   1140
ccagtagttc tctggctaca gggtgggccg ggaggttcat ccatgtttgg actctttgtg   1200
gaacatgggc cttatgttgt cacaagtaac atgaccttgc gtgacagaga cttcccctgg   1260
accacaacgc tctccatgct ttacattgac aatccagtgg gcacaggctt cagttttact   1320
gatgataccc acggatatgc agtcaatgag gacgatgtag cacgggattt atacagtgca   1380
ctaattcagt ttttccagat atttcctgaa tataaaaata atgactttta tgtcactggg   1440
gagtcttatg cagggaaata tgtgccagcc attgcacacc tcatccattc cctcaaccct   1500
gtgagagagg tgaagatcaa cctgaacgga attgctattg gagatggata ttctgatccc   1560
gaatcaatta taggggcta tgcagaattc ctgtaccaaa ttggcttgtt ggatgagaag   1620
caaaaaaagt acttccagaa gcagtgccat gaatgcatag aacacatcag gaagcagaac   1680
tggtttgagg cctttgaaat actggataaa tactacagtg gcgacttaac aagtgatcct   1740
tcttacttcc agaatgttac aggatgtagt aattactata acttttttgcg gtgcacggaa   1800
cctgaggatc agctttacta tgtgaaattt ttgtcactcc cagaggtgag acaagccatc   1860
cacgtgggga atcagacttt taatgatgga actatagttg aaaagtactt gcgagaagat   1920
acagtacagt cagttaagcc atggttaact gaaatcatga ataattataa ggttctgatc   1980
tacaatggcc aactggacat catcgtggca gctgccctga cagagcgctc cttgatgggc   2040
atggactgga aaggatccca ggaatacaag aaggcagaaa aaaagtttg gaagatcttt   2100
aaatctgaca gtgaagtggc tggttacatc cggcaagcgg gtgacttcca tcaggtaatt   2160
attcgaggtg gaggacatat tttaccctat gaccagccgc tgagagcttt tgacatgatt   2220
aatcgattca tttatggaaa aggatgggat ccttatgttg gataaactac cttcccaaaa   2280
gagaacatca gaggttttca ttgctgaaaa gaaaatcgta aaaacagaaa atgtcatagg   2340
aataaaaaaa ttatcttttc atatctgcaa gattttttc atcaataaaa attatccttg   2400
aaacaagtga gcttttgttt ttgggggagg atgtttacta caaattaac atgagtacat   2460
gagtaagaat tacattattt aacttaaagg atgaaaggta tggatgatgt gacactgaga   2520
caagatgtat aaatgaaatt ttagggtctt gaataggaag ttttaatttc ttctaagagt   2580
aagtgaaaag tgcagttgta acaaacaaag ctgtaacatc tttttctgcc aataacagaa   2640
gtttggcatg ccgtgaaggt gtttggaaat attattggat aagaatagct caattatccc   2700
aaataaatgg atgaagctat aatagttttg gggaaaagat tctcaaatgt ataaagtctt   2760
agaacaaaag aattctttga aataaaaata ttatatataa aagtaatgat gagtcaattc   2820
tgataagca gatgctctta tgcagagaac aaacttaatc tttgccttttt cattttcttt   2880
ttccttcttt gagtttgagg tgtacacact tctgaaagag cctgcaggct acattagtta   2940
taagagccat tttaatttgg gcttcaaatt ctctacttct ttttccccaaa taaagaacaa   3000
cctaattttg tatcattgtt agaatatcaa aaaaaattaa gataagctgg catcaatata   3060
tacatttata aatatacatt cattagcagt tttctgacta aaatgtcaca tcctggcaca   3120
tcttttcgat ttatgcatca tgtgctcaca tctctgaaat tctacaagac gtgtggattt   3180
ttccacatca cttccttctc atattcccca tctatgaact ggctcactgg agaattaaat   3240
ttaaaaagtc aaagcctgtt cttgcggcaa atagtttatg gagtttattc ttttaatttc   3300
tcatgttgtg cctgattacg ttcaggtttg tgatcttcct ttttaaattg ttcattgtac   3360
ccatgtccta gaagtcatta aatcaaatat tctgatcaaa a                       3401

SEQ ID NO: 9          moltype = RNA   length = 3205
FEATURE               Location/Qualifiers
source                1..3205
                      mol_type = genomic RNA
                      organism = Homo sapiens
SEQUENCE: 9
gcttttcgct cgctgcactc caagcccgg aacaccgcg tccgcacact aagggcacca     60
ccgctctccc acctctgcgc tgtcagatgt caggcgcgga ggtgctctgg gcaccgaggt    120
gctggcgaac caaacaagta tcaccccgga cgcctgccca cattccgaga gagcgggcgg    180
gatggccaca ggctgcaata cagtgacacg atcacagctc actgctacag cctctacctc    240
ctgggcttaa tccatcctcc ctcctcagcc tcccaagcag ctgggactac aggtgatttt    300
gatatgctgc taaggtttga taagagaaat gagattcaga gaacagatta tattgttgaa    360
gagcttgact ggaaatgatc caaacggaaa cattggctct tcctggggtt ccagcctgct    420
gtcttgacag gaactatacc atcagctctc ctgggtctct tacatgccaa gtcatcctgc    480
agatctggga ctcactccgt aatcagcttg attgctgtaa gttgaacacg tcagtggcat    540
gggcaccagc tgcacaaccc taggagccac caaacacagt atattctata taaatgttgc    600
tgccaggagc cccagttcaa actacaatac cctgagagat ggttggtgcc atgtggaagg    660
tgattgtttc gctggtcctg ttgatgcctg gccctgtga tgggctgttt cgctccctat    720
acagaagtgt ttccatgcca cctaaggag actaggaca gccattattt ctcacccctt    780
acattgaagc tgggaagatc caaaaggaa gagaattgag tttggtcggc cctttcccag    840
gactgaacat gaagagttat gccggcttcc tcaccgtgaa taagacttac aacagcaacc    900
tcttcttctg gttcttccca gctcagatac agccagaaga tgcccagta gttctctggc    960
tacagggtgg gccggaggt tcatccatgt ttggactctt gtggaacat gggccttatg   1020
ttgtcacaag taacatgacc ttgcgtgaca gagacttccc ctgaccaca acgctctcca   1080
```

```
tgctttacat tgacaatcca gtgggcacag gcttcagttt tactgatgat acccacggat    1140
atgcagtcaa tgaggacgat gtagcacggg attttatacag tgcactaatt cagttttcc    1200
agatatttcc tgaatataaa aataatgact tttatgtcac tggggagtct tatgcaggga    1260
aatatgtgcc agccattgca cacctcatcc attccctcaa ccctgtgaga gaggtgaaga    1320
tcaacctgaa cggaattgct attggagatg gatattctga tcccgaatca attatagggg    1380
gctatgcaga attcctgtac caaattggct tgttggatga gaagcaaaaa aagtactcc     1440
agaagcagtg ccatgaatgc atagaacaca tcaggaagca gaactggttt gaggcctttg    1500
aaatactgga taaactacta gatggcgact taacaagtga tccttcttac ttccagaatg    1560
ttacaggatg tagtaattac tataactttt tgcggtgcac ggaacctgag gatcagcttt    1620
actatgtgaa attttttgtca ctcccagagg tgagacaagc catccacgtg gggaatcaga   1680
cttttaatga tggaactata gttgaaaagt acttgcgaga agatacagta cagtcagtta    1740
agccatggtt aactgaaatc atgaataatt ataaggttct gatctacaat ggccaactgg    1800
acatcatcgt ggcagctgcc ctgacagagc gctccttgat gggcatggac tggaaaggat    1860
cccaggaata caagaaggca gaaaaaaaag tttggaagat ctttaaatct gacagtgaag    1920
tggctggtta catccggcaa gcgggtgact tccatcaggt aattattcga ggtggaggac    1980
atattttacc ctatgaccag cctctgagag cttttgacat gattaatcga ttcatttatg    2040
gaaaaggatg ggatccttat gttggataaa ctaccttccc aaaagagaac atcagaggtt    2100
ttcattgctg aaaagaaaat cgtaaaaaca gaaaatgtca taggaataaa aaaattatct    2160
tttcatatct gcaagatttt tttcatcaat aaaaattatc cttgaaacaa gtgagctttt    2220
gttttttgggg ggagatgttt actacaaaat taacatgagt acatgagtaa gaattacatt    2280
atttaactta aaggatgaaa ggtatggatg atgtgacact gagacaagat gtataaatga    2340
aattttaggg tcttgaatag gaagttttaa tttcttctaa ggtaagtga aaagtgcagt     2400
tgtaacaaac aaagctgtaa catctttttc tgccaataac agaagtttgg catgccgtga    2460
aggtgtttgg aaatattatt ggataagaat agctcaatta tcccaaataa atggatgaag    2520
ctataatagt tttggggaaa agattctcaa atgtataaag tcttagaaca aaagaattct    2580
ttgaaataaa aatattatat ataaaagtaa tgatgagtca attcttgata agcagatgtt    2640
cttatgcaga gaacaaactt aatctttgcc ttttcatttt cttttccctt ctttgagttt    2700
gaggtgtaca cacttctgaa agagcctgca ggctacatta gttataagag ccatttaat    2760
ttgggcttca aattctctac ttcttttccc caaataaaga acaacctaat tttgtatcat    2820
tgttagaata tcaaaaaaa ttaagataag ctggcatcaa tatatacatt tataaatata    2880
cattcattag cagttttctg actaaaatgt cacatcctgg cacatctttt cgatttatgc    2940
atcatgtgct cacatctctg aaattctaca agacgtgtgg atttttccac atcacttcct    3000
tctcatatta cccatctatg aactggctca ctggagaatt aaatttaaaa agtcaaagcc    3060
tgttcttgcg gcaaatagtt tatggagttt attcttttaa tttctcatgt tgtgcctgat    3120
tacgttcagg tttgtgatct tccttttaa attgttcatt gtacccatgt cctagaagtc    3180
attaaatcaa atattctgat caaa                                           3205

SEQ ID NO: 10              moltype = RNA   length = 3162
FEATURE                    Location/Qualifiers
source                     1..3162
                           mol_type = genomic RNA
                           organism = Homo sapiens
SEQUENCE: 10
gcttttcgct cgctgcactc caagccccgg aacacccgcg tccgcacact aagggcacca     60
ccgctctccc acctctgcgc tgtcagatgt caggcgcgga ggtgctctgg gcaccgaggt    120
gctggcgaac caaacaagta tcaccccgga cgcctgcccc cattccgaga gagcgggcgg    180
gatggccaca ggctgcaata cagtgacacg atcacagctc actgctacag cctctacctc    240
ctgggcttaa tccatcctcc ctcctcagcc tccaagcag ctgggactac agatccaaac    300
ggaaacattg gctcttcctg gggttccagc ctgctgtctt gacaggaact ataccatcag    360
ctctcctggg tctcttacat gccaagtcat cctgcagatc tgggactcac tccgtaatca    420
gcttgattgc tgtaagttga acacgtcagt ggcatgggca ccagctgcca aaccctagga    480
gccaccaaac acagtatatt ctatataaat gttgctgcca ggagcccag ttcaaactac     540
aatacctga gagatggttg gtgccatgtg aaggtgatt gtttcgctgg tcctgttgat      600
gcctggcccc tgtgatgggc tgtttcgctc cctatacaga agtgtttcca tgccacctaa    660
gggagactca ggacagccat tatttctcac ccttacatt gaagctggga agatccaaaa    720
aggaagagaa ttgagtttgg tcggcccttt cccaggactg aacatgaaga gttatgccgg    780
cttcctcacc gtgaataaga cttacaacag caacctcttc ttctggttct tcccagctca    840
gatacagcca gaagatgccc cagtagttct ctggctacag ggtgggccgg gaggttcatc    900
catgtttgga ctctttgtgg aacatgggcc ttatgttgtc acaagtaaca tgaccttgcg    960
tgacagagac ttcccctgga ccacaacgct ctccatgctt tacattgaca atccagtcag    1020
cacaggcttc agttttactg atgatacacca cggatatgca gtcaatgagg acgatgtagc    1080
acgggatttta tacagtgcac taattcagtt ttttccagata tttcctgaat ataaaaataa    1140
tgactttttat gtcactgggg agcatccatt tgtgattggc catttcaaca tctgtccttc    1200
tcagtcttat gcagggaaat atgtgccagc cattgcacat ctcatcc cctcaaccc         1260
tgtgagagag gtgaagatca acctgaacgg aattgctatt ggagatggat attctgatcc    1320
cgaatcaatt ataggggct atgcagaatt cctgtaccaa attggcttgt tggatgagaa    1380
gcaaaaaag tacttccaga agcagtgcca tgaatgcata gaacacatca ggaagcagaa    1440
ctggtttgag gcctttgaaa tactggataa actactagat ggcgacttaa caagtgatcc    1500
ttcttacttc cagaatgtta caggatgtag taattactat aattttttgc ggtgcacgga    1560
acctgaggat cagctttact atgtgaaatt tttgtcactc ccagaggtga gacaagccat    1620
ccacgtgggg aatcagactt ttaatgatgg aactatagtt gaaagtact tgcgagaaga    1680
tacagtacag tcagttaagc catggttaac tgaaatcatg aataattata aggttctgat    1740
ctacaatggc caactggaca tcatcgtggc agctgccctg acagagcgct ccttgatggg    1800
catgactgg aaaggatccc aggaatacaa gaaggcagaa aaaaaagttt ggaagatccc    1860
taaatctgac agtgaagtgg ctggttacat ccggcaagcg ggtgacttcc atcaggtaat    1920
tattcgaggt ggaggacata ttttacccta tgaccagcct ctgagagctt ttgacatgat    1980
taatcgattc atttatggaa aaggatggga tccttatgtt ggataaacta ccttcccaaa    2040
agagaacatc agaggttttc attgctgaaa agaaaatcgt aaaacagaa aatgtcatag    2100
gaataaaaaa attatcttttt catatctgca agattttttt catcaataaa aattatcctt    2160
```

```
gaaacaagtg agcttttgtt tttgggggga gatgtttact acaaaattaa catgagtaca    2220
tgagtaagaa ttacattatt taacttaaag gatgaaaggt atggatgatg tgacactgag    2280
acaagatgta taaatgaaat tttagggtct tgaataggaa gttttaattt cttctaagag    2340
taagtgaaaa gtgcagttgt aacaaacaaa gctgtaacat cttttctgc caataacaga    2400
agtttggcat gccgtgaagg tgtttggaaa tattattgga taagaatagc tcaattatcc    2460
caaataaatg gatgaagcta taatagtttt ggggaaaaga ttctcaaatg tataaagtct    2520
tagaacaaaa gaattctttg aaataaaaat attatatata aaagtaatga tgagtcaatt    2580
cttgataagc agatgctctt atgcagagaa caaacttaat ctttgccttt tcattttctt    2640
tttccttctt tgagtttgag gtgtacacac ttctgaaaga gcctgcaggc tacattagtt    2700
ataagagcca ttttaatttg ggcttcaaat tctctacttc ttttcccaa ataaagaaca     2760
acctaatttt gtatcattgt tagaatatca aaaaaatta agataagctg gcatcaatat     2820
atacatttat aaatatacat tcattagcag ttttctgact aaaatgtcac atcctggcac    2880
atcttttcga tttatgcatc atgtgctcac atctctgaaa ttcacaaga cgtgtggatt     2940
tttccacatc acttccttct catattaccc atctatgaac tggctcactg gagaattaaa    3000
tttaaaaagt caaagcctgt tcttgcggca aatagtttat ggagtttatt cttttaattt    3060
ctcatgttgt gcctgattac gttcaggttt gtgatcttcc ttttttaaatt gttcattgta   3120
cccatgtcct agaagtcatt aaatcaaata ttctgatcaa aa                       3162

SEQ ID NO: 11          moltype = RNA   length = 2869
FEATURE                Location/Qualifiers
source                 1..2869
                       mol_type = genomic RNA
                       organism = Homo sapiens
SEQUENCE: 11
gcttttcgct cgctgcactc caagcccgg aacaccgcg tccgcacact aagggcacca      60
ccgctctccc acctctgcgc tgtcagatgt caggcgcgga ggtgtctgg gcaccgaggt     120
gctggcgaac caaacaagta tcaccccgga cgcctgcccc cattccgaga gagcgggcgg    180
gatgccaca ggctgcaata cagtgacacg atcacagctc actgctacag cctctacctc     240
ctgggcttaa tccatcctcc ctcctcagcc tcccaagcag ctgggactac agaccctgag    300
agatggttgg tgccatgtgg aaggtgattg tttcgctgt cctgttgatg cctggcccct     360
gtgatgggct gtttcgctcc ctatacagaa gtgtttccat gccacctaag ggagactcag    420
gacagccatt atttctcacc ccttacattg aagctgggaa gatccaaaaa ggaagagaat    480
tgagtttggt cggcccttc ccaggactga acatgaagag ttatgccggc ttcctcaccg     540
tgaataagac ttacaacagc aacctcttct tctggttctt cccagctcag atacagccag    600
aagtgccccc agtagttctc tggctacagg gtgggccggg aggttcatcc atgtttggac    660
tctttgtgga acatgggcct tatgttgtca caagtaacat gaccttgcgt gacagagact    720
tccctggac cacaacgctc tccatgcttt acattgacaa tccagtgggc acaggcttca    780
gttttactga tgatacccac ggatatgcag tcaatgagga cgatgtagca cgggatttat    840
acagtgcact aattcagttt ttccagatat ttcctgaata taaaaaataat gacttttatg    900
tcactgggga gtcttatgca gggaaatatg tgccagccat tgcacacctc atccattccc    960
tcaaccctgt gagagaggtg aagatcaacc tgaacgaaat tgctattgga gatggatatt    1020
ctgatcccga atcaattata gggggctatg cagaattcct gtaccaaatt ggcttgttgg    1080
atgagaagca aaaaaagtac ttccagaagc agtgccatga atgcataaga cacatcggaa    1140
agcagaactg gtttgaggcc tttgaaatac tggataaact actagatggc gacttaacaa    1200
gtgatccttc ttacttccag aatgttacag gatgtagtaa ttactataac ttttttcgt     1260
gcacggaacc tgaggatcag cttttactatg tgaaattttt gtcactccca gaggtgagac    1320
aagccatcca cgtggggaat cagacttta atgatgaaat tatagtigaa aagtacttgc     1380
gagaagatac agtacagtca gttaagccta ggttaactga aatcatgaat aattataagg    1440
ttctgatcta caatgccaa ctggacatca tcgtggcagc tgccctgaca gagcgctcct     1500
tgatgggcat ggactggaaa ggatcccagg aatacaagaa ggcagaaaaa aaagtttgga    1560
agatctttaa atctgacagt gaagtggctg gttacatccg gcaagcgggt gacttccatc    1620
aggtaattat tcgaggtgga ggacatattt taccctatga ccagcctctg agagcttttg    1680
acatgattaa tcgattcatt tatgaaaag gatgggatcc ttatgttgga taaactacct    1740
tcccaaaaga gaacatcaga ggttttcatt gctgaaaaga aaatcgtaaa aacagaaaat    1800
gtcataggaa taaaaaaatt atctttcat atctgcaaga ttttttttcat caataaaaat    1860
tatccttgaa acaagtgagc ttttgttttt ggggggagag gtttactaca aaattaacat    1920
gagtacatga gtaagaatta cattatttaa cttaaaggat gaaaggtatg atgatgatgt    1980
cactgagaca agatgtataa atgaaatttt agggtcttga ataggaagtt taatttctt    2040
ctaagagtaa gtgaaaagtg cagttgtaac aaacaaagct gtaacatctt tttctgccaa    2100
taacagaagt ttggcatgcc gtgaaggtgt tggaaatat tattggataa gaatagctca    2160
attatcccaa ataaatggat gaagctataa tagttttggg gaaaagattc tcaaatgtat    2220
aaagtcttag aacaaaagaa ttctttgaaa taaaaatatt atataaaatg taatgatgatga    2280
gtcaattctt gataagcaga tgctcttatg cagagaacaa acttaatctt tgccttttca    2340
ttttcttttc cttctttgag tttgaggtgt acacacttc tgaaagagcc tgcaggctac      2400
attagttata agagccattt aatttgggc ttcaaattct ctacttcttt tccccaaata    2460
aagaacaacc taattttgta tcattgttag aatatcaaaa aaattaagaa taagctggca   2520
tcaatatata catttataaa tatacattca ttagcagttt tctgactaaa atgtcacatc    2580
ctggcacatc ttttcgattt atgcatcatg tgctcacatc tctgaaattc tacaagacgt    2640
gtggattttt ccacatcact tccttctcat attacccatc tatgaactgg ctcactggag    2700
aattaaattt aaaaagtcaa agcctgttct tgcggcaaat agtttatgga gtttattctt    2760
ttaatttctc atgttgtgcc tgattacgtt caggtttgtg atcttccttt ttaaaattgtt   2820
cattgtaccc atgtcctaga agtcattaaa tcaaatattc tgatcaaaa                2869

SEQ ID NO: 12          moltype = RNA   length = 3380
FEATURE                Location/Qualifiers
source                 1..3380
                       mol_type = genomic RNA
                       organism = Homo sapiens
```

```
SEQUENCE: 12
gcttttcgct cgctgcactc caagccccgg aacacccgcg tccgcacact aagggcacca    60
ccgctctccc acctctgcgc tgtcagatgt caggcgcgga ggtgctctgg gcaccgaggt   120
gctggcgaac caaacaagta tcaccccgga cgcctgcccc cattccgaga gagcgggcgg   180
gatggccaca ggtgattttg atatgctgct aaggtttgat aagagaaatg agattcagag   240
aacagattat attgttgaag agcttgactg gaaatgatcc aaacggaaac attggctctt   300
cctggggttc cagcctgctg tcttgacagg aactatacca tcagctctcc tgggtctctt   360
acatgccaag tcatcctgca gatctgggac tcactccgta atcagcttga ttgctgtaag   420
ttgaacacgt cagtggcatg ggcaccagct gcacaaccct aggagccacc aaacacagta   480
tattctatat aaatgttgct gccaggagcc ccagttcaaa ctacaatacc ctgagagatg   540
gttggtgcca tgtggaaggt gattgtttcg ctggtcctgt tgatgcctgg ccctgtgat    600
gggctgtttc gctccctata cagaagtgtt tccatgccac ctaagggaga ctcaggacag   660
ccattatttc tcacccctta cattgaagct gggaagatcc aaaaagggtc tcgctgtgtt   720
atccaggctg gagtgcagtg gcatgatcat ggctcactgc agccttgacc tcctgggctc   780
aagtgatcct cccacctcag cctcccgagt tgctgggact acaagcactg ccaccatgct   840
cagctaagag gcatgccact actttccctt ccactccttg ccacctgcac cttctgactc   900
actctagttg aaagccctgg gggaaggaac aaactctgca gcctgactgc tgtgtttaat   960
cccagctctc ctctactagc tggaagagaa ttgagtttgg tcggcccttt cccaggactg  1020
aacatgaaga gttatgccgg cttcctcacc gtgaataaga cttacaacag caacctcttc  1080
ttctggttct tcccagctca gatacagcca gaagatgccc cagtagttct ctggctacag  1140
ggtgggccgg gaggttcatc catgtttgga ctctttgtgg aacatgggcc ttatgttgtc  1200
acaagtaaca tgacctgcg tgacagagac ttccccctgga ccacaacgct ctccatgctt  1260
tacattgaca atccagtggg cacaggcttc agttttactg atgatacca cggatatgca  1320
gtcaatgagg acgatgtagc acgggattta tacagtgcac taattcagtt tttccagata  1380
tttcctgaat ataaaaataa tgacttttat gtcactgggg agtcttatgc agggaaatat  1440
gtgccagcca ttgcacacct catccattcc ctcaaccctg tgagagaggt gaagatcaac  1500
ctgaacggaa ttgctattgg agatgatatt tctgatcccg aatcaattat aggggctat   1560
gcagaattcc tgtaccaaat tggcttgttg gatgagaagc aaaaaaagta cttccagaag  1620
cagtgccatg aatgcataga acacatcagg aagcagaact ggtttgaggc ctttgaaata  1680
ctggataaac tactagatgg cgacttaaca agtgatcctt cttacttcca gaatgttaca  1740
ggatgtagta attactataa ctttttgcgg tgcacggaac ctgaggatca gctttactat  1800
gtgaattttt tgtcactccc agaggtgaga caagccatcc acgtggggaa tcagactttt  1860
aatgatggaa ctatagttga aaagtacttg cgagaagata cagtacagtc agttaagcca  1920
tggttaactg aaatcatgaa taattataag gttctgatct acaatggcca actgacatc   1980
atcgtggcag ctgccctgac agagcgctcc ttgatgggca tggactggaa aggatcccag  2040
gaatacaaga aggcagaaaa aaaagttggg aagatcttta aatctgacag tgaagtggct  2100
ggttacatcc ggcaagcggg tgacttccat caggtaatta ttcgaggtgg aggacatatt  2160
ttaccctatg accagcctct gagagcttt gacatgatta tcgattcat ttatggaaaa    2220
ggatggatcc cttatgttgg ataaactacc ttcccaaaag agaacatcag aggttttcat  2280
tgctgaaaag aaaatcgtaa aacagaaaa tgtcatagga ataaaaaat tatcttttca    2340
tatctgcaag atttttttca tcaataaaa ttatccttga aacaagtgag cttttgtttt   2400
tgggggagaa tgtttactac aaaattaaca tgagtacatg agtaagaatt acattattta  2460
acttaaagga tgaaaggtat ggatgatgtg acactgaagc aagtagtata aatgaaattt  2520
tagggtcttg aataggaagt tttaatttct tctaagagta agtgaaaagt gcagttgaa   2580
caaacaaagc tgtaacatct ttttctgcca ataacagaag tttggcatgc cgtgaaggtg  2640
tttgaaaata ttattggata agaatagctc aattatccca aataaatgga tgaagctata  2700
atagtttttgg ggaaaagatt tcaaatgta taaagtctta gaacaaaaga attctttgaa  2760
ataaaaatat tatatataaa agtaatgatg agtcaattct tgataagcag atgctcttat  2820
gcagagaaca aacttaatct ttgccttttc attttctttt tccttctttg agtttgaggt  2880
gtacacactt ctgaaagagc ctgcaggcta cattagttat aagagccatt ttaatttggg  2940
cttcaaattc tctacttctt ttccccaaat aaagaacaac ctaattttgt atcattgtta  3000
gaatatcaaa aaaattaag ataagctggc atcaatatat acatttataa atatacattc   3060
attagcagtt ttctgactaa aatgtcacat cctggcacat cttttcgatt tatgcatcat  3120
gtgctcacat ctctgaaatt ctacaagacg tgtggatttt tccacatcac ttccttctca  3180
tattacccat ctatgaactg gctcactgga gaattaaatt taaaaagtca aagcctgttc  3240
ttgcggcaaa tagtttatgg agtttattct tttaatttct catgttgtgc ctgattacgt  3300
tcaggtttgt gatcttcctt ttttaaattgt tcattgtacc catgtcctag aagtcattaa  3360
atcaaatatt ctgatcaaaa                                              3380

SEQ ID NO: 13           moltype = RNA  length = 3248
FEATURE                 Location/Qualifiers
source                  1..3248
                        mol_type = genomic RNA
                        organism = Homo sapiens
SEQUENCE: 13
gcttttcgct cgctgcactc caagccccgg aacacccgcg tccgcacact aagggcacca    60
ccgctctccc acctctgcgc tgtcagatgt caggcgcgga ggtgctctgg gcaccgaggt   120
gctggcgaac caaacaagta tcaccccgga cgcctgcccc cattccgaga gagcgggcgg   180
gatggccaca ggtgattttg atatgctgct aaggtttgat aagagaaatg agattcagag   240
aacagattat attgttgaag agcttgactg gaaatgatcc aaacggaaac attggctctt   300
cctggggttc cagcctgctg tcttgacagg aactatacca tcagctctcc tgggtctctt   360
acatgccaag tcatcctgca gatctgggac tcactccgta atcagcttga ttgctgtaag   420
ttgaacacgt cagtggcatg ggcaccagct gcacaaccct aggagccacc aaacacagta   480
tattctatat aaatgttgct gccaggagcc ccagttcaaa ctacaatacc ctgagagatg   540
gttggtgcca tgtggaaggt gattgtttcg ctggtcctgt tgatgcctgg ccctgtgat    600
gggctgtttc gctccctata cagaagtgtt tccatgccac ctaagggaga ctcaggacag   660
ccattatttc tcacccctta cattgaagct gggaagatcc aaaaagggtc tcgctgtgtt   720
atccaggctg gagtgcagtg gcatgatcat ggctcactgc agccttgacc tcctgggctc   780
aagtgatcct cccacctcag cctcccgagt tgctgggact acaagcactg ccaccatgct   840
```

```
cagctaagag gaagagaatt gagtttggtc ggcccttttcc caggactgaa catgaagagt    900
tatgccggct tcctcaccgt gaataagact tacaacagca acctcttctt ctggttcttc    960
ccagctcaga tacagccaga agatgcccca gtagttctct ggctacaggg tgggccggga   1020
ggttcatcca tgtttggact ctttgtgaaa catgggcctt atgttgtcac aagtaacatg   1080
accttgcgtg acagagactt ccctgacc acaacgctc ccatgcttta cattgacaat     1140
ccagtgggca caggcttcag ttttactgat gatacccacg gatatgcagt caatgaggac   1200
gatgtagcac gggatttata cagtgcacta attcagtttt tccagatatt tcctgaatat   1260
aaaaataatg acttttatgt cactggggag tcttatgcag ggaaatatgt gccagccatt   1320
gcacacctca tccattccct caaccctgtg agagaggtga agatcaacct gaacggaatt   1380
gctattggag atggatattc tgatcccgaa tcaattatag ggggctatgc agaattcctg   1440
taccaaattg gcttgttgga tgagaagcaa aaaaagtact tccagaagca gtgccatgaa   1500
tgcatagaac acatcaggaa gcagaactgg tttgaggcct tgaaatact ggataaacta    1560
ctagatggcg acttaacaag tgatccttct tacttccaga atgttacagg atgtagtaat   1620
tactataact ttttgcggtg cacggaacct gaggatcgac tttactatgt gaaattttg    1680
tcactcccag aggtgagaca agccatccac gtggggaatc agactttaa tgatggaact    1740
atagttgaaa agtacttgcg agaagataca gtacagtcag ttaagccatg gttaactgaa   1800
atcatgaata attataaggt tctgatctac aatggccaac tggacatcat cgtggcagct   1860
gccctgacag agcgctcctt gatgggcatg gactggaaga tcccagga atacaagaag    1920
gcagaaaaaa aagtttggaa gatctttaaa tctgacagtg aagtggctgg ttacatccgg   1980
caagcgggtg acttccatca ggtaattatt cgaggtggag gacatatttt accctatgac   2040
cagcctctga gagcttttga catgattaat cgattcattt atggaaaagg atgggatcct   2100
tatgttggat aaactacctt cccaaaagag aacatcagag ttttcattg ctgaaaagaa    2160
aatcgtaaaa acagaaaatg tcataggaat aaaaaaatta tcttttcata tctgcaagat   2220
tttttttcatc aataaaaatt atccttgaaa caagtgagct tttgttttg ggggagatg    2280
tttactacaa aattaacatg agtacatgag taagaattac attatttaac ttaaggatg    2340
aaaggtatgg atgatgtgac actgagacaa gatgtataaa tgaaatttta gggtcttgaa   2400
taggaagttt taatttcttc taagagtaag tgaaaagtgc agttgtaaca aacaaagctg   2460
taacatcttt ttctgccaat aacagaagtt tggcatgccg tgaaggtgtt tggaaatatt   2520
attggataag aatagctcaa ttatcccaaa taatggatg aagctataat agttttgggg    2580
aaaagattct caaatgtata aagtcttaga acaaaagaat tctttgaaat aaaaatatta   2640
tatataaaag taatgatgag tcaattcttg ataagcagat gctcttatgc agagaacaaa   2700
cttaatctt gccttttcat tttcttttc cttcttgag tttgaggtgt acacacttct     2760
gaaagagcct gcaggctaca ttagttataa gagccatttt aatttgggct tcaaattctc   2820
tacttcttt ccccaaataa agaacaacct aattttgtat cattgttaga atatcaaaaa   2880
aaattaagat aagctggcat caatatatac atttataaat atacattcat tagcagtttt   2940
ctgactaaaa tgtcacatcc tggcacatct ttcgattta tgcatcatgt gctcacatct   3000
ctgaaattct acaagacgtg tggatttttc cacatcactt cctctcata ttacccatct    3060
atgaactggc tcactggaga attaaattta aaaagtcaaa gcctgttctt gcggcaaata   3120
gtttatggag tttattcttt taatttctca tgttgtgcct gattacgttc aggtttgtga   3180
tcttccttt taaattgttc attgtaccca tgtcctagaa gtcattaaat caaatattct   3240
gatcaaaa                                                            3248
SEQ ID NO: 14         moltype = RNA   length = 3215
FEATURE               Location/Qualifiers
source                1..3215
                      mol_type = genomic RNA
                      organism = Homo sapiens
SEQUENCE: 14
gcttttcgct cgctgcactc caagcccggg aacacccgcg tccgcacact aagggcacca     60
ccgctctccc acctctgcgc tgtcagatgt caggcgcgga ggtgctctgg gcaccgaggt    120
gctgcgaac caaacaagta tcaccccgga cgcctgcccc cattccgaga gacgggcgg     180
gatggccaca gatccaaacg gaaacattgg ctcttcctgg ggttccagcc tgctgtcttg   240
acaggaacta taccatcagc tctcctgggt ctcttacatg ccaagtcatc ctgcagatct   300
gggactcact ccgtaatcag cttgattgct gtaagttgaa cacgtcagtg gcatgggcac   360
cagctgcaca accctaggag ccaccaaaca cagtatattc tatataaatg ttgctgccag   420
gagcccagt tcaaactaca atatggagtt ttgctctttt ttgcccaggc tggagtgcga    480
tggcacaatc ttggctcact gcaacctcca cctcttgggt tcaagcaatg cttctgcctc   540
agcctcccaa gtagctggga ttacagagac agggtttcac catgttggac aggccgggca   600
cctgacctca agtgatctgc cgcctcagc tgccaaaac cctgagagat ggtggtgcc      660
atgtggaagg tgattgtttc gctggtcctg ttgatgcctg gccctgtga tgggctgttt    720
cgctccctat acagaagtgt ttccatgcca cctaagggag actcaggaca gccatattt    780
ctcaccccctt acattgaagc tgggaagatc aaaaaggaa gagaattgag tttggtcggc   840
cctttccag gactgaacat gaagagttat gccggcttcc tcaccgtgaa taagacttac    900
aacagcaacc tcttcttctg gttcttccca gctcagtaa agccagaaga tgcccagta     960
gttctctggc tacagggtgg gccgggaggt tcatcatgt ttggactctt tgtgaacat    1020
gggccttatg ttgtcacaag taacatgacc ttgcgtgaca gagacttccc ctggaccaca   1080
acgctctcca tgctttacat tgacaatcca gtgggcacag gcttcagttt tactgatgat   1140
acccacggat atgcagtcaa tgaggacgat gtagcacggg atttatacag tgcactaatt   1200
cagttttttcc agatatttcc tgaatataaa aataatgact tttatgtcac tgggagtct   1260
tatgcaggga aatatgtgcc agccattgca cacctcatcc attccctcaa ccctgtgaga   1320
gaggtgaaga tcaacctgaa cggaattgct attggagatg gatattctga tcccgaatca   1380
attatagggg gctatgcaga attcctgtac caaattggct gttggatga agcaaaaa      1440
aagtacttcc agaagcagtg ccatgaatgc atagaacaca tcaggaagca gaactggttt   1500
gaggccttg aaatactgga taaactacta gatggcgact taacaagtga tccttcttac   1560
ttccagaatg ttacaggatg tagtaattac tataactttt tgcggtgcac ggaacctgag   1620
gatcagcttt actatgtgaa attttgtca ctcccagagg tgagacaagc catccacgtg   1680
gggaatcaga cttttaatga tggaactata gttgaaagt acttgcgaga agatacagta    1740
cagtcagtta agccatggtt aactgaaatc atgaataatt ataaggttct gatctacaat   1800
ggccaactgg acatcatcgt ggcagctgcc ctgacagagc gctccttgat gggcatggac   1860
```

```
tggaaaggat cccaggaata caagaaggca gaaaaaaaag tttggaagat ctttaaatct    1920
gacagtgaag tggctggtta catccggcaa gcgggtgact tccatcaggt aattattcga    1980
ggtggaggac atattttacc ctatgaccag cctctgagag cttttgacat gattaatcga    2040
ttcatttatg gaaaaggatg ggatccttat gttggataaa ctaccttccc aaaagagaac    2100
atcagaggtt ttcattgctg aaaagaaaat cgtaaaaaca gaaaatgtca taggaataaa    2160
aaaattatct tttcatatct gcaagatttt tttcatcaat aaaaattatc cttgaaacaa    2220
gtgagctttt gttttgggg ggagatgttt actacaaaat taacatgagt acatgagtaa     2280
gaattacatt atttaactta aaggatgaaa ggtatggatg atgtgacact gagacaagat    2340
gtataaatga aattttaggg tcttgaatag gaagttttaa tttcttctaa gagtaagtga    2400
aaagtgcagt tgtaacaaac aaagctgtaa catcttttc tgccaataac agaagtttgg     2460
catgccgtga aggtgtttgg aaatattatt ggataagaat agctcaatta tcccaaataa    2520
atggatgaag ctataatagt tttggggaaa agattctcaa atgtataaag tcttagaaca    2580
aaagaattct ttgaaataaa aatattatat ataaaagtaa tgatgagtca attcttgata    2640
agcagatgct cttatgcaga gaacaaactt aatctttgcc tttcatttt cttttttcctt    2700
ctttgagttt gaggtgtaca cacttctgaa agagcctgca ggctacatta gttataagag    2760
ccattttaat ttgggcttca aattctctac ttcttttccc caaataaaga acaacctaat    2820
tttgtatcat tgttagaata tcaaaaaaaa ttaagataag ctggcatcaa tatatacatt    2880
tataaatata cattcattag cagtttctg actaaaatgt cacatcctgg cacatctttt     2940
cgatttatgc atcatgtgct cacatctctg aaattctaca agacgtgtgg atttttccac    3000
atcacttcct tctcatatta cccatctatg aactggctca ctggagaatt aaatttaaaa    3060
agtcaaagcc tgttcttgcg gcaaatagtt tatgagtttt attctttaa tttctcatgt     3120
tgtgcctgat tacgttcagg tttgtgatct tccttttaa attgttcatt gtacccatgt     3180
cctagaagtc attaaatcaa atattctgat caaaa                              3215

SEQ ID NO: 15          moltype = RNA   length = 3087
FEATURE                Location/Qualifiers
source                 1..3087
                       mol_type = genomic RNA
                       organism = Homo sapiens
SEQUENCE: 15
gcttttcgct cgctgcactc caagccccgg aacacccgcg tccgcacact aagggcacca      60
ccgctctccc acctctgcgc tgtcagatgt caggcgcgga ggtgctctgg gcaccgaggt     120
gctggcgaac caaacaagta tcaccccgga cgcctgcccc cattccgaga gagcgggcgg    180
gatggccaca ggcttgattg ctgtaagttg aacacgtcag tggcatgggc accagctgca    240
caacccctagg agccaccaaa cacagtatat tctatataaa tgttgctgcc aggagcccca   300
gttcaaacta caatatggag ttttgctctt ttttgcccag gctggagtgc gatggcacaa    360
tcttggctca ctgcaacctc cacctcttgg gttcaagcaa tgcttctgcc tcagcctccc    420
aagtagctgg gattacagag acagggtttc accatgttgg acaggccggg cacctgacct    480
caagtgatct gcccgcctca gcctgccaaa accctgagag atggttggtg ccatgtggaa    540
ggtgattgtt tcgctggtcc tgttgatgcc tggcccctgt gatgggctgt ttcgctcccc    600
atacagaagt gtttccatgc cacctaaggg agactcagga cagccattat ttctcacccc    660
ttacattgaa gctgggaaga tccaaaaagg aagagaattg agtttggtcg gccctttccc    720
aggactgaac atgaagagtt atgccggctt cctcaccgtg aataagactt acaacagcaa    780
cctcttcttc tggttcttcc cagctcagat acagccagaa gatgccccag tagttctctg    840
gctacagggt gggccgggag gttcatccat gtttggactc tttgtggaac atgggcctta    900
tgttgtcaca agtaacatga ccttgcgtga cagagacttc ccctgaccaa caccgctctc   960
catgctttac attgacaatc cagtgggcac aggcttcagt tttactgatg ataccacgg    1020
atatgcagtc aatgaggacg atgtagcacg ggatttatac agtgcactaa ttcagtttttt  1080
ccagatattt cctgaatata aaaataatga cttttatgtc actgggggagt cttatgcagg   1140
gaaatatgtg ccagccattg cacacctcat ccattccctc aaccctgtga gagaggtgaa    1200
gatcaacctg aacggaattg ctattggaga tggatattct gatcccgaat caattatagg    1260
gggctatgca gaattcctgt accaaattgg cttgttggat gagaagcaaa aaagtactt    1320
ccagaagcag tgccatgaat gcatagaaca catcaggaag cagaactggt ttgaggcctt    1380
tgaaatactg gataaactac tagatggcga cttaacaagt gatccttctt acttccagaa    1440
tgttacagga tgtagtaatt actataactt tttgcggtgc acggaacctg aggatcagct    1500
ttactatgtg aaatttttgt cactcccaga ggtgagacaa gccatccacg tgggaatca     1560
gactttaat gatggaacta tagttgaaa gtacttgcga gaagatacag tacagtcagt     1620
taagccatgg ttaactgaaa tcatgaataa ttataaggtt ctgatctaca atggccaact    1680
ggacatcatc gtgcagctg ccctgacaga gcgctccttg atgggcatgg actggaaagg    1740
atcccaggaa tacaagaagg cagaaaaaaa agtttggaag atcttttaaat ctgcagtga    1800
agtggctggt tacatccggc aagcgggtga cttccatcag gtaattattc gaggtggagg    1860
acatatttta ccctatgacc agcctctgag gcttttgac atgattaatc gattcattta    1920
tggaaaagga tgggatcctt atgttggata aactacctttc ccaaaagaga acatcagagg    1980
ttttcattgc tgaaaagaaa atcgtaaaaa cagaaaatgt cataggaata aaaaaaatatt    2040
cttttcatat ctgcaagatt ttttcatca ataaaaatta ccttgaaac aagtgagctt     2100
ttgtttttgg gggagatgt ttactacaaa attaacatga gtacatgagt aagaattaca    2160
ttattttaact taaggatga aaggtatgga tgatgtgaca ctgagacaag atgtataaat    2220
gaaattttag ggtcttgaat aggaagttttt aattcttct aagagtaagt gaaaagtgca    2280
gttgtaacaa acaaagctgt aacatctttt ctgccaata acagaagttt ggccatgcca    2340
gaaggtgttt ggaaatatta ttggataaga atagctcaat tatcccaaat aaatggatga    2400
agctataata gttttgggga aaagattctc aaatgtataa agtcttagaa caaaagaatt    2460
ctttgaaata aaaatattat atataaaaagt aatgatgagt caattcttga taagcagatg    2520
ctcttatgca gagaacaaac ttaatctttg ccttttcatt ttcttttcc ttctttgagt    2580
ttgaggtgta cacacttctg aaagagcctg caggctacat tagttataag agccatttta    2640
atttgggctt caaattctct acttcttttc cccaaataaa gaacaaccta attttgtatc    2700
attgttagaa tatcaaaaaa aattaagata agctggcatc aatatataca tttataaata    2760
tacattcatt agcagtttc tgactaaaat gtcacatcct ggcacatctt ttcgatttat    2820
gcatcatgtg ctcacatctc tgaaattcta caagacgtgt ggatttttcc acatcacttc    2880
cttctcatat tacccatcta tgaactggct cactggagaa ttaaatttaa aaagtcaaag    2940
```

```
cctgttcttg cggcaaatag tttatggagt ttattctttt aatttctcat gttgtgcctg   3000
attacgttca ggtttgtgat cttccttttt aaattgttca ttgtacccat gtcctagaag   3060
tcattaaatc aaatattctg atcaaaa                                       3087

SEQ ID NO: 16           moltype = RNA   length = 2418
FEATURE                 Location/Qualifiers
source                  1..2418
                        mol_type = genomic RNA
                        organism = Homo sapiens
SEQUENCE: 16
gcttttcgct cgctgcactc caagcccggg aacacccgcg tccgcacact aagggcacca     60
ccgctctccc acctctgcgc tgtcagatgt caggcgcgga ggtgctctgg gcaccgaggt    120
gctggcgaac caaacaagta tcaccccgga cgcctgcccc cattccgaga gagcgggcgg    180
gatggccaca ggcttgattg ctgtaagttg aacagtcagg tggcatgggc accagctgcc    240
caaccctagg agccaccaaa cacagtatat tctatataaa tgttgctgcc aggagcccca    300
gttcaaacta caatacactg agagatggtt ggtgccatgt ggaaggtgat tgtttcgctg    360
gtcctgttga tgcctggccc ctgtgatggg ctgtttcgct ccctacacag aagtgttttcc   420
atgccaccta agggagactc aggacagcca ttatttctca ccccttacat tgaagctggg    480
aagatccaaa aagatacagc cagaagatgc cccagtagtt ctctggctac agggtgggcc    540
gggaggttca tccatgtttg gactctttgt ggaacatggg ccttatgttg tcacaagtaa    600
catgaccttg cgtgacagag acttcccctg gaccacaacg ctctccatgc tttacattga    660
caatccagtg ggcacaggct tcagttttac tgatgataca cacggatatg cagtcaaatga   720
ggacgatgta gcacgggatt tatacagtgc actaattcag ttttttccaga tatttcctga   780
atataaaaat aatgactttt atgtcactgg ggaggaacct gaggatcagc tttactatgt    840
gaaatttttg tcactcccag aggtgagaca agccatccac gtgggaatc agacttttaa    900
tgatgaaact atagttgaaa gtacttgcg agaagataca gtacagtcag ttaagccatg    960
gttaactgaa atcatgaata attataaggt tctgatctac aatggccaac tggacatcat   1020
cgtggcagct gccctgacag agcgctcctt gatgggcatg gactggaaag gatcccagga   1080
atacaagaag gcagaaaaaa aagtttggaa gatctttaaa tctgacagtg aagtggctgg   1140
ttacatccgg caagcgggtg acttccatca ggtaatttat cgaggtggag gacatatttt   1200
accctatgac cagcctctga gagcttttga catgattaat cgattcattt atggaaaagg   1260
atgggatcct tatgttggat aaactacctt cccaaaagag aacatcagag gttttcattg   1320
ctgaaaagaa aatcgtaaaa acagaaaatg tcataggaat aaaaaaatta tcttttcata   1380
tctgcaagat tttttttcatc aataaaaatt atccttgaaa tgaatgagct tttgtttttg   1440
gggggagatg tttactacaa aattaacatg agtacatgag taagaattac attatttaac   1500
ttaaaggatg aaaggtatgg atgatgtgac actgagacaa gatgtataaa tgaaatttta   1560
gggtcttgaa taggaagttt taatttcttc taagagtaag tgaaaagtgc agttgtaaca   1620
aacaaagctg taacatcttt ttctgccaat aacagaagtt tggcatgccg tgaaggtgtt   1680
tggaaatatt attggataag aatagtcaa ttatcccaaa taaatggatg aagctataat   1740
agtttttgggg aaaagattct caagtgtata aagtcttaga acaaaagaat tctttgaaat   1800
aaaaatatta tatataaaag taatgatgag tcaattcttg ataagcagat gctcttatgc   1860
agagaacaaa cttaatcttt gcctttcat tttctttttc cttctttgag tttgaggtgt   1920
acacacttct gaaagagcct gcaggctaca ttagttataa gagccatttt aatttgggct   1980
tcaaattctc tacttctttt ccccaaataa agaacaacct aattttgtat cattgttaga   2040
atatcaaaaa aaattaagat aagctggcat caatatatac atttataaat atacattcat   2100
tagcagtttt ctgactaaaa tgtcacatcc tggcacatct tttcgattta tgcatcatgt   2160
gctcacatct ctgaaattct acaagacgtg tggatttttc cacatcactt ccttctcata   2220
ttacccatct atgaactggc tcactggaga attaaattta aaaagtcaaa gcctgttctt   2280
gcggcaaata gtttatggag tttattcttt taatttctca tgttgtgcct gattacgttc   2340
aggtttgtga tcttcctttt taaattgttc attgtaccca tgtcctagaa gtcattaaat   2400
caaatattct gatcaaaa                                                 2418

SEQ ID NO: 17           moltype = RNA   length = 2179
FEATURE                 Location/Qualifiers
source                  1..2179
                        mol_type = genomic RNA
                        organism = Homo sapiens
SEQUENCE: 17
gtgactgggt ggggctgcct cacttctgcc tgatttggga agcgctgcaa ggacaaccgg     60
ctggggtcct tgcgcgccgc ggctcaggga ggagcaccga ctgcgccgcg taagtgccgc    120
ctgccctgcg tgggtcgtgc cagctcagcg ggacaggtcc tcgcctcggt ccctcggact    180
tagggagcgc ggggcagacc ctgagagatg gttggtgcca tgtggaaggt gattgtttcg    240
ctggtcctgt tgatgcctgg cccctgtgat gggctgtttc gctccctata cagaagtgtt    300
tccatgccac ctaagggaga ctcaggacag ccattatttc tcaccccta cattgaagct    360
gggaagatcc aaaaaggaag agaattgagt ttggtcggcc cttttcccagg actgaacatg    420
aagagttatg ccggcttcct caccgtgaat aagacttaca cagcaacct cttcttctgg    480
ttcttcccag ctcagataca gccagaagat gccccagtag ttctctggct acagggtggg    540
ccgggaggtt catccatgtt tggactcttt gtggaacatg ggccttatgt tgtcacaagt    600
aacatgacct tgcgtgacag agacttcccc tggaccacaa cgctctccat gctttacatt    660
gacaatccag tgggcacagg cttcagtttt actgatgata cccacggata tgcagtcaat    720
gaggacgatg tagcacggga tttatacagt gcactaattc agtttttcca gatatttcct    780
gaatataaaa ataatgactt tatgtcact ggggagtctt atgcagggaa atatgtgcca    840
gccattgcac acctcatcca ttccctcaac cctgtgagag aggtgaagat caacctgaac    900
ggaattgcta ttggagtgg atattctgat cccgaataa ttatagggg ctatgcagaa    960
ttcctgtacc aaattggctt gttgatgag aagcaaaaaa agtacttcca gaagcagtgc   1020
catgaatgca tagaacacat caggaagcag aactggtttg aggcctttga aatactggat   1080
aaaactacta gatgcgactt aacaagtgat ccttcttact tccagaatgt tacaggatgt   1140
agtaattact ataactttttt gcggtgcacg gaacctgagg atcagcttta ctatgtgaaa   1200
tttttgtcac tcccagaggt gagacaagcc atccacgtgg gaatcagac tttaatgat    1260
```

```
ggaactatag ttgaaaagta cttgcgagaa gatacagtac agtcagttaa gccatggtta   1320
actgaaatca tgaataatta taaggttctg atctacaatg gccaactgga catcatcgtg   1380
gcagctgccc tgacagagcg ctccttgatg ggcatggact ggaaaggatc ccaggaatac   1440
aagaaggcag aaaaaaaagt ttggaagatc tttaaatctg acagtgaagt ggctggttac   1500
atccggcaag cgggtgactt ccatcaggta attattcgag gtggaggaca tattttaccc   1560
tatgaccagc ctctgagagc ttttgacatg attaatcgat tcatttatgg aaaaggatgg   1620
gatcctatg ttggataaac taccttccca aagagaaca tcagaggttt tcattgctga   1680
aaagaaaatc gtaaaacag aaaatgtcat aggaataaaa aaattatctt ttcatatctg   1740
caagattttt ttcatcaata aaaattatcc ttgaaacaag tgagctttg tttttggggg   1800
gagatgttta ctacaaaatt aacatgagta catgagtaag aattacatta tttaacttaa   1860
aggatgaaag gtatggatga tgtgacactg acaagatg tataaatgaa atttagggt   1920
cttgaatagg aagttttaat ttcttctaag agtaagtgaa agtgcagtt gtaacaaaca   1980
aagctgtaac atctttttct gccaataaca gaagtttggc atgccgtgaa ggtgtttgga   2040
aatattattg gataagaata gctcaattat cccaaataat tggatgaagc tataaatagtt   2100
ttggggaaaa gattctcaaa tgtataaagt cttagaacaa aagaattctt tgaaataaaa   2160
atattatata taaaagtaa                                                 2179

SEQ ID NO: 18           moltype = RNA  length = 2608
FEATURE                 Location/Qualifiers
source                  1..2608
                        mol_type = genomic RNA
                        organism = Homo sapiens
SEQUENCE: 18
aaacaaagaa aatcaagtct gcgaggagcg agggtttgct cccctctgct ccggatttgg    60
gtgtccaggg tagcgggcgc ggcacggcaa acaggtcggg gcgctctgct tcaccccaac   120
cttctccgcc ccgccagccc ccgctccagc tgcgccagaa agtgcgagcc tgcccgctcc   180
tttcgctttt cgctcgctgc actccaagcc ccggaacacc cgcgtccgca cactaagggc   240
accaccgctc tcccacctct gcgctgtcag atgtcaggcg cggaggtgct ctgggcaccg   300
aggtgctggc gaaccaaaca agtatcaccc cggacgcctg cccccattcc gagagagcgg   360
gcgggatgca cacagatcca aacggaaaca ttggctcttc ctgggggttcc agcctgactg   420
cttgacagga actataccat cagctctcct gggtctctta catgccaagt catcctgcag   480
atctgggact cactccgtaa tcagcttgat tgctgtaagt tgaacacgtc agtggcatgg   540
gcaccagctc cacaaccta ggagccacca acacagtat attctatata aatgttgctg   600
ccaggagccc cagttcaaac tacaataccc tgagagatgg ttggtgccat gtggaaggtg   660
attgtttcgc tggtcctgtt gatgcctggc ccctgtgatg ggctgtttcg ctccctatac   720
agaagtgttt ccatgccacc taaggggac tcaggacagc cattatttct cacccttac   780
attgaagctg gaagatcca aaaggaaga gaattgagtt tggtcggccc tttcccagga   840
ctgaacatga agagttatgc cggcttcctc accgtgaata agacttacaa cagcaacctc   900
ttcttctggt tcttccage tcagatacag ccagaagatg cccagtagt tctctggcta   960
cagggtgggc cggaggttc atccatgttt ggactctttg tggaacatgg gccttatgtt   1020
gtcacaagta acatgacctt gcgtgacaga gacttcccct ggaccacaac gctctccatg   1080
ctttacattg acaatccagt gggcacaggc ttcagttta ctgatgatac ccacggatat   1140
gcagtcaatg aggacgatgt agcacggat ttatacgtg cactaattca gtttttccag   1200
atatttcctg aatataaaaa taatgacttt tatgtcactg gggagtctta tgcagggaaa   1260
tatgtgccag ccattgcaca cctcatccat tccctcaacc ctgtgagaga ggtgaagatc   1320
aacctgaacg gaattgctat tggagatgga tattctgatc ccgaatcaat tataggggggc   1380
tatgcagaat tcctgtacca aattggcttg ttggatgaga agcaaaaaaa gtacttccag   1440
aagcagtgcc atgaatgcat agaacacatc aggaagcaga actggtttga ggcctttgaa   1500
atactggata aactactaga tggcgactta acaagtgatc cttcttactt ccagaatgtt   1560
acaggatgta gtaattacta taactttttg cggtgcacgg aacctgagga tcagcttac   1620
tatgtgaaat ttttgtcact cccagaggtg agacaagcca tccacgtggg gaatcagact   1680
tttaatgatg gaactatagt tgaaaagtac ttgcgagaag atacagtaca gtcagttaag   1740
ccatggttaa ctgaaatcat gaataattat aaggttctga tctacaatgg ccaactggac   1800
atcatcgtgg cagctgccct gacagagcgc tccttgatgg gcatggactg gaaaggatcc   1860
caggaataca agaaggcaga aaaaaaagtt tggaagatct taaatctga cagtgaagtg   1920
gctggttaca tccggcaagc gggtgacttc catcaggtaa ttattcgagg tggaggacat   1980
attttacct atgaccagcc tctgagagct tttgacatga ttaatcgatt catttatgga   2040
aaaggatggg atccttatgt tggataaact accttcccaa agagaacat cagaggtttt   2100
cattgctgaa aagaaaatcg taaaacaga aaatgtcata ggaataaaaa aattatcttt   2160
tcatatctgc aagattttt ttcatcaataa aaattatcct tgaaacaagt gagctttgt   2220
ttttggggg agatgtttac tacaaaatta acatgagtac atgagtaaga attacattat   2280
ttaacttaaa ggatgaaagg tatggatgat gtgacactga acaagatgt ataaatgaaa   2340
ttttagggtc ttgaatagga agttttaatt tcttctaaga gtaagtgaaa agtgcagttg   2400
taacaaacaa agctgtaaca tctttttctg ccaataacag aagtttggca tgccgtgaag   2460
gtgtttggaa atattattgg ataagaatag ctcaattatc ccaaataaat ggatgaagct   2520
ataatagttt tggggaaaag attctcaaat gtataaagtc ttagaacaaa agaattcttt   2580
gaaataaaaa tattatatat aaaagtaa                                      2608

SEQ ID NO: 19           moltype = RNA  length = 2480
FEATURE                 Location/Qualifiers
source                  1..2480
                        mol_type = genomic RNA
                        organism = Homo sapiens
SEQUENCE: 19
aaacaaagaa aatcaagtct gcgaggagcg agggtttgct cccctctgct ccggatttgg    60
gtgtccaggg tagcgggcgc ggcacggcaa acaggtcggg gcgctctgct tcaccccaac   120
cttctccgcc ccgccagccc ccgctccagc tgcgccagaa agtgcgagcc tgcccgctcc   180
tttcgctttt cgctcgctgc actccaagcc ccggaacacc cgcgtccgca cactaagggc   240
accaccgctc tcccacctct gcgctgtcag atgtcaggcg cggaggtgct ctgggcaccg   300
```

```
aggtgctggc gaaccaaaca agtatcaccc cggacgcctg cccccattcc gagagagcgg    360
gcgggatggc cacaggcttg attgctgtaa gttgaacacg tcagtggcat gggcaccagc    420
tgcacaaccc taggagccac caaacacagt atattctata taaatgttgc tgccaggagc    480
cccagttcaa actacaatac cctgagagat ggttggtgcc atgtggaagg tgattgtttc    540
gctggtcctg ttgatgcctg gccctgtga tgggctgttt cgctccctat acagaagtgt    600
ttccatgcca cctaagggag actcaggaca gccattattt ctcaccccctt acattgaagc   660
tgggaagatc caaaaaggaa gagaattgag tttggtcggc cctttcccag gactgaacat    720
gaagagttat gccggcttcc tcaccgtgaa taagacttac aacagcaacc tcttcttctg    780
gttcttccca gctcagatac agccagaaga tgccccagta gttctctggc tacagggtgg    840
gccgggaggt tcatccatgt ttggactctt tgtggaacat gggccttatg ttgtcacaag    900
taacatgacc ttgcgtgaca gagacttccc ctgaccaca acgctctcca tgctttacat    960
tgacaatcca gtgggcacag gcttcagttt tactgatgat acccacggat atgcagtcaa   1020
tgaggacgat gtagcacggg atttatacag tgcactaatt cagtttttcc agatatttcc   1080
tgaatataaa aataatgact tttatgtcac tggggagtct tatgcaggga aatatgtgcc   1140
agccattgca cacctcatcc attccctcaa ccctgtgaga gaggtgaaga tcaacctgaa   1200
cggaattgct attggagatg gatattctga tcccgaatca attataggg gctatgcaga   1260
attcctgtac caaattggct tgttggatga aagcaaaaa aagtacttcc agaagcagtg   1320
ccatgaatgc atagaacaca tcaggaagca gaactggttt gaggccttttg aaatactgaa   1380
taaactacta gatggcgact taacaagtga tccttcttac ttccagaatg ttacaggatg   1440
tagtaattac tataactttt tgcggtgcac ggaacctgag gatcagcttt actatgtgaa   1500
attttttgtca ctcccagagg tgagacaagc catccacgtg gggaatcaga cttttaatga   1560
tggaactata gttgaaaagt acttgcgaga agatacagta catcagtta agccatggtt   1620
aactgaaatc atgaataatt ataaggttc gatctacaat ggccaactgg acatcatcgt   1680
ggcagctgcc ctgacagagc gctccttgat gggcatggac tggaaggat cccaggaata   1740
caagaaggca gaaaaaaaag tttggaagat ctttaaatct gacagtgaag tggctggtta   1800
catccggcaa gcgggtgact tccatcaggt aattattcga ggtggaggac atattttacc   1860
ctatgaccag cctctgagag cttttgacat gattaatcga ttcatttatg gaaaaggatg   1920
ggatccttat gttggataaa ctaccttccc aaaagagaac atcagaggtt tcattgctg    1980
aaaagaaaat cgtaaaaaca gaaatgtca taggaataaa aaaattatct tttcatatct   2040
gcaagattt tttcatcaat aaaaaatatc cttgaaacaa gtgagctttt gtttttgggg   2100
ggagatgttt actacaaaat taacatgagt acatgagtaa gaattacatt atttaactta   2160
aaggatgaaa ggtatggatg atgtgacact gagacaagat gtataaatga aattttaggg   2220
tcttgaatag gaagttttaa tttcttctaa gagtaagtga aagtgcagt tgtaacaaac    2280
aaagctgtaa catctttttc tgccaataac agaagtttgg catgccgtga aggtgtttgg   2340
aaatattatt ggataagaat agctcaatta tcccaaataa atggatgaag ctataatagt   2400
tttggggaaa agattctcaa atgtataaag tcttagaaca aagaattct ttgaaataaa    2460
aatattatat ataaaagtaa                                               2480
SEQ ID NO: 20         moltype = RNA   length = 2021
FEATURE               Location/Qualifiers
source                1..2021
                      mol_type = genomic RNA
                      organism = Homo sapiens
SEQUENCE: 20
gcggctcagg gaggagcacc gactgcgccg caccctgaga gatggttggt gccatgtgga     60
aggtgattgt ttcgctggtc ctgttgatgc ctggccctg tgatgggctg tttcgctccc    120
tatacagaag tgtttccatg ccacctaagg gagactcagg acagccatta tttctcaccc    180
cttacattga agctgggaag atccaaaaag gaagagaatt gagtttggtc ggcccttttcc   240
caggactgaa catgaagagt tatgccggct tcctcaccgt gaataagact tacaacagca    300
acctcttctt ctggttcttc cagctcaga tacagccaga gatgccccca gtagttctct    360
ggctacaggg tgggccggga ggttcatcca tgtttggact ctttgtggaa catgggcctt    420
atgttgtcac aagtaacatg accttgcgtg acagagactt ccctggacc acaacgctct    480
ccatgcttta cattgacaat ccagtgggca caggcttcag ttttactgat gatacccacg    540
gatatgcagt caatgaggac gatgtagcac gggatttata cagtgcacta attcagtttt    600
tccagatatt tcctgaatat aaaaataatg acttttatgt cactggggag tcttatgcag    660
ggaaatatgt gccagccatt gcacacctca tccattccct caaccctgtg agagaggtga    720
agatcaacct gaacggaatt gctattggag atggatattc tgatcccgaa tcaattatag    780
ggggctatgc agaattcctg taccaaattg gcttgttgga tgagaagcaa aaaaagtact    840
tccagaagca gtgccatgaa tgcatagaac acatcaggaa gcagaactgg tttgaggcct    900
ttgaaatact ggataaacta ctagatggcg acttaacaag tgatccttct tacttccaga    960
atgttacagg atgtagtaat tactataact ttttgcggtg cacggaacct gaggatcagc   1020
tttactatgt gaaattttg tcactcccag aggtgagaca agccatccac gtggggaatc    1080
agacttttaa tgatggaact atagttgaaa agtacttgcg agaagataca gtacagtcag   1140
ttaagccatg gttaactgaa atcatgaata attataaggt tctgatctac aatggccaac   1200
tggacatcat cgtggcagct gccctgacag agcgctcctt gatgggcatg gactggaaag   1260
gatcccagga atacaagaag gcagaaaaaa agtttggaa gatctttaaa tctgacagtg    1320
aagtggctgg ttcatccgg caagcgggtg acttccatca ggtaattatt cgaggtggag    1380
gacatatttt accctatgac cagcctctga gacttttga catgattaat cgattcattt    1440
atggaaaagg atgggatcct tatgttggat aaactaccttt cccaaaagag aacatcagag   1500
gttttcattg ctgaaaagaa atcgtaaaa acagaaaatg tcataggaat aaaaaaatta   1560
tcttttcata tctgcaagat tttttcatc aataaaaatt atccttgaaa caagtgagct   1620
tttgtttttg gggggagatg tttactacaa aattaacatg agtacatgag taagaattac   1680
attatttaac ttaaaggatg aaaggtatgg atgatgtgac actgagacaa gatgtataaa   1740
tgaaatttta gggtcttgaa taggaagttt taatttcttc taagagtaag tgaaagtgca    1800
gttgtaaca aacaaagctg taacatcttt ttctgccaat aacagaagtt tggcatgccg   1860
tgaaggtgtt tggaaatatt attggataag aatagctcaa ttatcccaaa taatggatg     1920
aagctataat agttttgggg aaaagattct caaatgtata aagtcttaga acaaaagaat   1980
tctttgaaat aaaaatatta tatataaaag taaaaaaaaa a                        2021
```

```
SEQ ID NO: 21           moltype = RNA   length = 1581
FEATURE                 Location/Qualifiers
source                  1..1581
                        mol_type = genomic RNA
                        organism = Homo sapiens
SEQUENCE: 21
gagagatggt tggtgccatg tggaaggtga ttgtttcgct ggtcctgttg atgcctggcc    60
cctgtgatgg gctgtttcgc tccctataca gaagtgtttc catgccacct aagggagact   120
caggacagcc attatttctc accccttaca ttgaagctgg gaagatccaa aaaggaagag   180
aattgagttt ggtcggccct ttcccaggac tgaacatgaa gagttatgcc ggcttcctca   240
ccgtgaataa gacttacaac agcaacctct cttctggtt cttcccagct cagatacagc    300
cagaagatgc cccagtagat tctctggcta cagggtgggc cgggaggttc atccatgttt   360
ggactctttg tggaacatgg gccttatgtt gtcacaagta acatgacctt gcgtgacaga   420
gacttcccct ggaccacaac gctctccatg ctttacattg acaatccagt gggcacagtc   480
ttcagttttta ctgatgatac ccacggatat gcagtcaatg aggacgatgt agcacgggat  540
ttatacagtg cactaattca gtttttccag atatttcctg aatataaaaa taatgacttt   600
tatgtcactg gggagtctta tgcagggaaa tatgtgccag ccattgcaca cctcatccat   660
tccctcaacc ctgtgagaga ggtgaagatc aacctgactg aattgctat tggagatgga    720
tattctgatc ccgaatcaat tataggggc tatgcagaat tcctgtacca aattggcttg    780
ttggatgaga agcaaaaaaa gtacttccag aagcagtgcc atgaatgcat agaacacatc   840
aggaagcaga actggtttga ggcctttgaa atactgata aactactaga tggcgactta    900
acaagtgatc cttcttactt ccagaatgtt acaggatgta gtaattacta taactttttg   960
cggtgcacgg aacctgagga tcagcttac tatgtgaaat ttttgtcact cccagaggtg   1020
agacaagcca tcccacgtgg ggaatcgac ttttaatgat ggaactatag ttgaaaagta   1080
cttgcgagaa gatacagtac agtcagttaa gccatggtta actgaaatca tgaataatta   1140
taaggttctg atctacaatg gccaactgga catcatcgtc gcagctgccc tacagagcg   1200
ctccttgatg ggcatggact ggaaaggatc ccaggaatac aagaaggcag aaaaaaaagt   1260
ttggaagatc tttaaatctg acagtgaagt ggctggttac atccggcaag tgggtgactt   1320
ccatcaggta attattcgag gtgaggaca tattttaccc tatgaccagc ctctgagagc   1380
ttttgacatg attaatcgat tcatttatgg aaaaggatgg gatccttatg ttggataaac   1440
taccttccca aaagagaaca tcagaggttt tcattgctga aaagaaaatc gtaaaaacag   1500
aaaatgtcat aggaataaaa aaattatctt tcatatctg caagatttt ttcatcaata    1560
aaaattatcc ttgaaaaaaa a                                            1581

SEQ ID NO: 22           moltype = RNA   length = 1638
FEATURE                 Location/Qualifiers
source                  1..1638
                        mol_type = genomic RNA
                        organism = Homo sapiens
SEQUENCE: 22
ggacaaccgg ctgggtcct tgcgcgccgc ggctcaggga ggagcaccga ctgcgccgca     60
ccctgagaga tggttggtgc catgtggaag gtgattgttt cgctggtcct gttgatgcct   120
ggccccgtgt gatgggctgtt tcactccta tacagaagtg tttccatgcc acctaaggga   180
gactcaggac agccattatt tctcacccct tacattgaag ctgggaagat ccaaaaagga   240
agagaattga gtttggtcgg ccctttccca ggactgaaca tgaagagtta tgccggcttc   300
ctcaccgtga taagactta caacagcaac ctcttcttct ggttcttccc agctcagata   360
cagccagaag atgcccagt agttctctgg ctacagggtg ggcgggttca tccatcatg    420
tttggactct tgtggaaca tgggccttat gttgtcacaa gtaacatgac cttgcgtgac   480
agagacttcc cctggaccac aacgctctcc atgctttaca ttgacaatcc agtgggcaca   540
ggcttcagtt ttactgatga tacccacgga tatgcagtca atgaggacga tgtagcacgg   600
gatttataca gtgcactaat tcagtttttc cagatatttc ctgaatataa aaataatgac   660
tttatgtca ctggggagtc ttatgcaggg aaatatgtgc cagccattgc acacctcatc    720
cattccctca accctgtgag agaggtgaag atcaacctga acggaattgc tattggagat   780
ggatattctg atcccgaatc aattatagg ggctatgcag aattcctgta ccaaattggc    840
ttgttggaga agaagcaaaa aaagtacttc cagaagcagt gccatgaatg catagaacac   900
atcaggaagc agaactggct tgaggccttt gaaatactgg ataaactact agatggcgac   960
ttaacaagtg atccttctta cttccagaat gttacaggat gtagtaatta ctataacttt  1020
ttgcggtgca cggaacctga ggatcagctt actatgtga aattttgtc actcccagag    1080
gtgagacaag ccatccacgt ggggaatcag acttttaatg atggaactat agttgaaaag  1140
tacttgcgag aagatacagt acagtcagtt aagccatggt taactgaaat catgaataat  1200
tataaggttc tgatctacaa tggccaactg gacatcatcg tggcagctgc cctgacagag  1260
cactccttga tgggcatgga ctggaaagga tcccaggaat acaagaaggc agaaaaaaaa  1320
gtttggaaga tccttaaatc tgacagtgaa gtggctggtt acatccggca agcgggtgac  1380
tcccatcagg taattattcg aggtggagga catattttac ctatgaccac ggctctgaga  1440
gcttttgaca tgattaatcg attcatttat ggaaaaggat gggatcctta tgttggataa  1500
actaccttcc cgaaagagaa catcagaggt ttcattgct gaaagaaaa tcgtaaaaac    1560
agaaaatgtc ataggaataa aaaattatc ttttcatatc tgcaagattt ttttcatcaa   1620
taaaaattat ccttgaaa                                                1638

SEQ ID NO: 23           moltype = RNA   length = 1672
FEATURE                 Location/Qualifiers
source                  1..1672
                        mol_type = genomic RNA
                        organism = Homo sapiens
SEQUENCE: 23
aggacaaccg gctgggtcc ttgcgcgccg cggctcaggg aggagcaccg actgcgccgc     60
accctgagag atggttggtg ccatgtggaa ggtgattgtt tcgctggtcc tgttgatgcc   120
tggcccctgt gatgggctgt ttcgctccct atacagaagt gttccatgc cacctaaggg    180
agactcagga cagccattat ttctcacccc ttacattgaa gctgggaaga tccaaaaagg   240
```

```
aagagaattg agtttggtcg gccctttccc aggactgaac atgaagagtt atgccggctt 300
cctcaccgtg aataagactt acaacagcaa cctcttcttc tggttcttcc cagctcagat 360
acagccagaa gatgccccag tagttctctg gctacagggt gggccgggag gttcatccat 420
gtttggactc tttgtggaac atgggcctta tgttgtcaca agtaacatga ccttgcgtga 480
cagagacttc ccctgaccaa caacgctctc catgctttac attgacaatc cagtgggcac 540
aggcttcagt tttactgatg atacccacgg atatgcagtc aatgaggacg atgtagcacg 600
ggatttatac agtgcactaa ttcagttttt ccagatattt cctgaatata aaaataatga 660
cttttatgtc actggggagt cttatgcagg gaaatatgtg ccagccattg cacacctcat 720
ccattccctc aaccctgtga gagaggtgaa gatcaacctg aacggaattg ctattggaga 780
tggatattct gatcccgaat caattatagg gggctatgca gaattcctgt accaaaattg 840
cttgttggat gagaagcaaa aaagtactcc cagaagcag tgccatgaat gcatagaaca 900
catcaggaag cagaactggt tgaggcctt tgaaatactg gataaactac tagatggcga 960
cttaacaagt gatccttctt acttccagaa tgttacagga tgtagtaatt actataactt 1020
tttgcggtgc acggaacctg aggatcagct ttactatgtg aaatttttgt cactcccaga 1080
ggtgagacaa gccatccacg tggggaatca gacttttaat gatggaacta tagttgaaaa 1140
gtacttgcga gaagatacag tacagtcagt taagccatgg ttaactgaaa tcatgaataa 1200
ttataaggtt ctgatctaca atggccaact ggacatcatc gtggcagctg ccctgacaga 1260
gcactccttg atgggcatgg actgaaagg atcccaggaa tacaagaagg cagaaaaaaa 1320
agtttgaaag atctttaaat ctgacagtga agtggctggt tacatccggc aagcgggtga 1380
cttccatcag gtaattattc gaggtggagg acatatttta ccctatgacc agcctctgag 1440
agcttttgac atgattaatc gattcattta tggaaaagga tgggatcctt atgttggata 1500
aactaccttc ccaaaagaga acatcagagg tttcattgg tgaaaagaaa atcgtaaaaa 1560
cagaaaatgt cataggaata aaaaaattat cttttcatat ctgcaagatt ttttcatca 1620
ataaaaatta tccttgaaaa aaaaaaaaa aaaaaaaaaa aaaaaaaaaa aa 1672

SEQ ID NO: 24          moltype = RNA   length = 1772
FEATURE                Location/Qualifiers
source                 1..1772
                       mol_type = genomic RNA
                       organism = Homo sapiens
SEQUENCE: 24
agcgctgcaa ggacaaccgg ctggggtcct tgcgcgccgc ggctcaggga ggagcaccga 60
ctgcgccgcg taagtgccgc ctgccctgcg tgggtcgtgc cagctcagcg ggacaggtcc 120
tcgcctcggt ccctcggact tagggagcgc ggggcagacc ctgagagatg gttgggtgcc 180
tgtggaaggt gattgtttcg ctggtcctgt tgatgcctgg ccctgtgat gggctgtttc 240
gctcccatat cagaagtgtt tccatggcac ctaaggagga ctcaggacag ccattatttc 300
tcacccctta cattgaagct gggaagatcc aaaaaggaag agaattgagt ttggtcggcc 360
ctttcccagg actgaacatg aagagttatg ccggcttcct caccgtgaat aagacttaca 420
acagcaacct cttcttctgg ttcttcccag ctcagataca gccagaagat gccccagtag 480
ttctctggct acagggtggg ccgggaggtt catccatgtt tggactcttt gtggaacatg 540
ggccttatgt tgtcacaagt aacatgacct tgcgtgacag agacttcccc tggaccacaa 600
cgctctccat gctttacatt gacaatccag tgggcacagg cttcagtttt actgatgata 660
cccacggata tgcagtcaat gaggacgatg tagcacggga tttatacagt gcactaattc 720
agttttccca gatatttcct gaatataaaa ataatgactt ttatgtcact ggggagtctt 780
atgcagggaa atatgtgcca gccattgcac acctcatcca ttccctcaac cctgtgagag 840
aggtgaagat caacctgaac ggaattgcta ttggagatgg atattctgat cccgaatcaa 900
ttatagggg ctatgcagaa ttcctgtacc aaattgcctt gttggatgag aagcaaaaa 960
agtacttcca gaagcagtgc catgaatgca tagaacacat caggaagcag aactggtttg 1020
aggcctttga aatactggat aaactactag atggcgactt aacaagtgat ccttcttact 1080
tccagaatgt tacaggatgt agtaattact ataacttttt gcggtgcacg gaacctgagg 1140
atcagcttta ctatgtgaaa tttttgtcac tcccagagga gacaagcc atccacgtgg 1200
ggaatcagac ttttaatgat ggaactatag ttgaaaagta cttgcgagaa gatacagtac 1260
agtcagttaa gccatggtta actgaaatca tgaataatta taaggttctg atctacaatg 1320
gccaactgga catcatcgtg gcagctgccc tgacagagcg ctccttgatg gcatggact 1380
ggaaaggatc ccaggaatac aagaaggcag aaaaaaaagt ttggaagatc tttaaatctg 1440
acagtgaagt ggctggttac atccggcaag tgggtgactt ccatcaggta attattcgag 1500
gtggaggaca tattttaccc tatgaccagc ctctgagagc ttttgacatg attaatcgat 1560
tcatttatgg aaaggatgg gatccttatg ttgataaac taccttccca aaagagaaca 1620
tcagaggttt tcattgctga aagaaaatc gtaaaaacag aaaatgtcat aggaataaaa 1680
aaattatctt tcatatctg caagatttt ttcatcaata aaattatcc ttgaaaaaaa 1740
aaaaaaaaaa aaaaaaaaaa aaaaaaaa aa 1772

SEQ ID NO: 25          moltype = RNA   length = 1605
FEATURE                Location/Qualifiers
source                 1..1605
                       mol_type = genomic RNA
                       organism = Homo sapiens
SEQUENCE: 25
ggctcaggga ggagcaccga ctgcgccgca ccctgagaga tggttggtgc catgtggaag 60
gtgattgttt cgctggtcct gttgatgcct ggccctgtg atgggctgtt tcgctcccta 120
tacagaagtg ttttccatgcc acctaaggga gactcaggac agccattatt tctcaccct 180
tacattgaag ctgggaagat ccaaaaagga agagaattga gtttggtcgg cccttttcca 240
ggactgaaca tgaagagtta tgccggcttc tcaccgtga taagactta caacagcaac 300
ctcttcttct ggttcttccc agctcagata cagccagaag atgccccagt agttctctgg 360
ctacaggggt ggccgggagg ttcatccatg tttggactct tgtggaaca tgggccttat 420
gttgtcacaa gtaacatgac cttgcgtgac agagacttcc cctggaccac aacgctctcc 480
atgctttaca ttgacaatcc agtgggcaca ggcttcagtt ttactgatga tacccacgga 540
tatgcagtca atgaggacga tgtagcacgg gatttataca gtgcactaat tcagttttc 600
cagatatttc tgaatataa aaataatgac ttttatgtca ctggggagtc ttatgcaggg 660
```

```
aaatatgtgc cagccattgc acacctcatc cattccctca accctgtgag agaggtgaag    720
atcaacctga acggaattgc tattggagat ggatattctg atcccgaatc aattataggg    780
ggctatgcag aattcctgta ccaaattggc ttgttggatg agaagcaaaa aaagtacttc    840
cagaagcagt gccatgaatg catagaacac atcaggaagc agaactggct tgaggccttt    900
gaaatactgg ataaactact agatggcgac ttaacaagtg atccttctta cttccagaat    960
gttacaggat gtagtaatta ctataacttt ttgcggtgca cggaacctga ggatcagctt   1020
tactatgtga aatttttgtc actcccagag gtgagacaag ccatccacgt ggggaatcag   1080
acttttaatg atggaactat agttgaaaag tacttgcgag aagatacagt acagtcagtt   1140
aagccatggt taactgaaat catgaataat tataaggttc tgatctacaa tggccaactg   1200
gacatcatcg tggcagctgc cctgacagag cactccttga tgggcatgga ctggaaagga   1260
tcccaggaat acaagaaggc agaaaaaaaa gtttggaaga tctttaaatc tgacagtgaa   1320
gtggctggtt acatccggca agcgggtgac ttccatcagg taattattcg aggtggagga   1380
catattttac cctatgacca gcctctgaga gcttttgaca tgattaatcg attcattat    1440
ggaaaaggat gggatcctta tgttggataa actaccttcc caaaagagaa catcagaggt   1500
tttcattgct gaaagaaaa tcgtaaaaac agaaaatgtc ataggaataa aaaaattatc    1560
ttttcatatc tgcaagattt ttttcatcaa taaaaattat ccttg                  1605

SEQ ID NO: 26            moltype = RNA    length = 1686
FEATURE                  Location/Qualifiers
source                   1..1686
                         mol_type = genomic RNA
                         organism = Homo sapiens
SEQUENCE: 26
ggtgactggg tggggctgcc tcacttctgc ctgatttggg aagcgctgca aggacaaccg     60
gctgggctcc ttgcgcgccg cggctcaggg aggagcaccg actgcgccgc accctgagag    120
atggttggtg ccatgtggaa ggtgattgtt tcgctggtcc tgttgatgcc tggccctgt    180
gatgggctgt ttcgctccct atacagaagt gtttccatgc cacctaaggg agactcagga    240
cagccattat ttctcacccc ttacattgaa gctgggaaga tccaaaaagg aagagaattg    300
agtttggtcg gccctttccc aggactgaac atgaagagtt atgccggctt cctcaccgtg    360
aataagactt acaacagcaa cctcttcttc tggttcttca gagcagccga atacagccagaa   420
gatgccccag tagttctctg gctacagggt gggccgggag gttcatccat gtttggactc    480
tttgtggaac atgggcctta tgttgtcaca agtaacatga ccttgcgtga cagagacttc    540
ccctggacca caacgctctc catgctttac attgacaatc cagtgggcac aggcttcagt    600
tttactgatg atacccacgg atatgcagtc aatgaggacg atgtagcacg ggatttttac    660
agtgcactaa ttcagttttt ccagatattt cctgaatata aaaataatga ctttttatgtc   720
actggggagt cttatgcagg gaaatatgtg ccagccattg cacacctcat ccattccctc    780
aaccctgtga gagaggtgaa gatcaacctg aacggaattg ctattggaga tggatattct    840
gatcccgaat caattatagg gggctatgca gaattcctgt accaaattgg cttgttggat    900
gagaagcaaa aaagtacttc ccagaagcag tgccatgaat gcatagaaca catcaggaat    960
cagaactggt tgaggccct tgaaatactg gataaactac tagatggcga cttaacaagt   1020
gatccttctt acttccagaa tgttacagga tgtagtaatt actataactt tttgcggtgc   1080
acggaacctg aggatcagct ttactatgtg aaatttttgt cactcccaga ggtgagacaa   1140
gccatccacg tggggaatca gacttttaat gatggaacta tagttgaaag tacttgcga    1200
gaagatacag tacagtcagt taagccatgg ttaactgaaa tcatgaataa ttataaggtt   1260
ctgatctaca atggccaact ggacatcatc gtggcagctg ccctgacaga gcgctccttg   1320
atgggcatgg actggaaagg atcccaggaa tacaagaagg cagaaaaaaa agtttggaag   1380
atctttaaat ctgacagtga agtggctggt tacatccggc aagcgggtga cttccatcag   1440
gtaattattc gaggtggagg acatattta ccctatgacc agcctctgag agcttttgac    1500
atgattaatc gattcattta tggaaaagga tgggatcctt atgttggata aactaccttc   1560
ctaaaagaga acatcagagg ttttcattgc tgaaagaaaa tcgtaaaaaa cagaaaatgt   1620
cataggaata aaaaaattat cttttcatat ctgcaagatt ttttcatca ataaaatta    1680
tccttg                                                             1686

SEQ ID NO: 27            moltype = DNA    length = 2213
FEATURE                  Location/Qualifiers
source                   1..2213
                         mol_type = genomic DNA
                         organism = Homo sapiens
SEQUENCE: 27
gctcctttcg cttttcgctc gctgcactcc aagccccgga acaccgcgct ccgcacacta     60
agggcaccac cgctctccca cctctgcgct gtcagatgtc aggcgcggag gtgctctggg    120
caccgaggtg ctggcgaacc aaacaagtat cacccccgga gcctgccccc attccgagag    180
agcgggcggg atggccacag gctgcaatac agtgacacga tcacagctca ctgctacagc    240
ctctacctcc tgggcttaat ccatcctccc tcctcagcct ccaagcagct gggactaca    300
ggtgattttg atatgctgct aaggtttgat aagagaaatg agattcagag aacagattat    360
attgttgaag agcttgactg gaaatgatcc aaacggaaac attggctctt cctgggttc    420
cagcctgctg tcttgacagg aactatacca tcagctctcc tgggtctctt acatgccaag    480
tcatcctgca gatctgggac tcactccgta atcagcttga ttgctgtaag ttgaacacgt    540
cagtggcatg ggcaccagct gcacaaccct aggagccacc aacacagta tattctatat    600
aaatgttgct gccaggagcc ccagttcaaa ctacaatacc ctgagagatg ttggtgcca    660
tgtgaaggt gattgtttcg ctggtcctgt tgatgcctgg ccctgtgat gggctgtttc    720
gctccctata cagaagtgtt tccatgccac taagggaga ctcaggacag ccattattc    780
tcaccccctta cattgaagct gggaagatcc aaaaaggaag agaattgagt ttggtcggcc    840
ctttccagg actgaacatg aagagttatg ccggcttcct caccgtgaat aagacttaca    900
acagcaacct cttcttctgg ttcttccag ctcagataca gccagaagat gcccagtag    960
ttctctggct acagggtggg ccgggaggtt catccatgtt tggactcttt gtggaacatg   1020
ggccttatgt tgtcacaagt aacatgacct tgcgtgacag agacttcccc tggaccacaa   1080
cgctctccat gctttacatt gacaatccag tgggcacagg cttcagtttt actgatgata   1140
cccacggata tgcagtcaat gaggacgatg tagcacggga tttatacagt gcactaattc   1200
```

```
agtttttcca gatatttcct gaatataaaa ataatgactt ttatgtcact ggggagtctt   1260
atgcagggaa atatgtgcca gccattgcac acctcatcca ttccctcaac cctgtgagag   1320
aggtgaagat caacctgaac ggaattgcta ttgagatgg atattctgat cccgaatcaa    1380
ttataggggg ctatgcagaa ttcctgtacc aaattggctt gttggatgag aagcaaaaaa   1440
agtacttcca gaagcagtgc catgaatgca tagaacacat caggaagcag aactggtttg   1500
aggcctttga aatactggat aaactactag atgcgactt aacaagtgat ccttcttact    1560
tccagaatgt tacaggatgt agtaattact ataactttt gcggtgcacg gaacctgagg   1620
atcagcttta ctatgtgaaa tttttgtcac tcccagaggt gagacaagcc atccacgtgg   1680
ggaatcagac ttttaatgat ggaactatag ttgaaaagta cttgcgagaa gatacagtac   1740
agtcagttaa gccatggtta actgaaatca tgaataatta taaggttctg atctacaatg   1800
gccaactgga catcatcgtg gcagctgccc tgacagagcg ctccttgatg ggcatggact   1860
ggaaaggatc ccaggaatac aagaaggcag aaaaaaagt ttggaagatc tttaaatctg     1920
acagtgaagt ggctggttac atccggcaag cgggtgactt ccatcaggta attattcgag   1980
gtggaggaca tatttaccc tatgaccagc tctgagagg ttttgacatg attaatcgat     2040
tcatttatgg aaaaggatgg gatccttatg ttggataaac taccttccca aaagagaaca   2100
tcagaggttt tcattgctga aaagaaaatc gtaaaaacag aaaatgtcat aggaataaaa   2160
aaattatctt ttcatatctg caagatttt ttcatcaata aaaattatcc ttg            2213

SEQ ID NO: 28          moltype = DNA  length = 2087
FEATURE                Location/Qualifiers
source                 1..2087
                       mol_type = genomic DNA
                       organism = Homo sapiens
SEQUENCE: 28
gtgactgggt ggggctgcct cacttctgcc tgatttggga agcgctgcaa ggacaaccgg   60
ctggggtcct tgcgcgccgc ggctcaggga ggagcaccga ctgccccgca cctgagaga    120
tggttggtgc catgtggaag gtgattgttt cgctggtcct gttgatgcct ggccctgtg    180
atgggctgtt tcgctcccta tacagaagtg tttccatgcc acctaaggga gactcaggac   240
agccattatt tctcaccct tacattgaag ctgggaagat ccaaaaagga agagaattga    300
gtttggtcgg ccctttccca ggactgaaca tgaagagtta tgccggcttc ctcaccgtga   360
ataagactta caacagcaac ctcttcttct ggttcttccc agctcagata cagccagaag   420
atgcccagt agttctctgg ctacagggtg ggccgggagg ttcatccatg tttggactct    480
ttgtggaaca tgggccttat gttgtcacaa gtaacatgac cttgcgtgac agagacttcc   540
cctgaccac aacgctctcc atgctttaca ttgacaatcc agtgggcaca ggcttcagtt    600
ttactgatga taccccacgga tatgcagtca atgaggacga tgtagcacgg gatttataca   660
gtgcactaat tcagtttttc cagatatttc ctgaatataa aataatgac ttttatgtca    720
ctggggagtc ttatgcaggg aaatatgtgc cagccattgc acacctcatc cattccctca   780
accctgtgag agaggtgaag atcaacctga acggaattgc tattggagat ggatattctg   840
atcccgaatc aattataggg ggctatgcag aattcctgta ccaaattggc ttgttggata   900
agaagcaaaa aaagtacttc cagaagcagt gccatgaatg catagaacac atcaggaagc   960
agaactggtt tgaggccttt gaaatactgg ataaactact agatgcgac ttaacaagtg    1020
atccttctta cttccagaat gttacaggat gtagtaatta ctataacttt tgcggtgca    1080
cggaacctga ggatcagctt tactatgtga atttttgtca actcccagag gtgagacaag   1140
ccatccacgt ggggaatcag acttttaatg atggaactat agttgaaaag tacttgcgag   1200
aagatacagt acagtcagtt aagccatggt taactgaaat catgaataat tataaggttc   1260
tgatctacaa tggccaactg gacatcatcg tggcagctgc cctgacagag cgctccttga   1320
tgggcatgga ctggaaagga tcccaggaat acaagaaggc agaaaaaaag ttttggaaga   1380
tctttaaatc tgacagtgaa gtggctggtt acatccggca agcgggtgac ttccatcagg   1440
taattattcg aggtggagga catattttac cctatgacca gcctctgaga gcttttgaca   1500
tgattaatcg attcatttat ggaaaaggat gggatcctta tgttggataa actaccttcc   1560
caaaagagaa catcagaggt tttcattgct gaaaagaaa tcgtaaaaac agaaaatgtc   1620
ataggaataa aaaattatc ttttcatatc tgcaagattt ttttcatcaa taaaaattat    1680
ccttgaaaca agtgagcttt tgtttttggg gggagatgtt tactacaaaa ttaacatgag   1740
tacatgagta agaattacat tatttaactt aaaggatgaa aggtatggat gatgtgacac   1800
tgagacaaga tgtataaatg aaattttagg gtcttgaata ggaagtttta atttcttcta   1860
agagtaagtg aaaagtgcag ttgtaacaaa caaagctgta acatcttttt ctgccaataa   1920
cagaagtttg gcatgccgtg aaggtgtttt gaaatatat tggataagaa tagctcaatt    1980
atcccaaata aatggatgaa gctataatag ttttggggaa aagattctca aatgtataaa   2040
gtcttagaac aaaagaattc tttgaaataa aaatattata tataaaa                  2087

SEQ ID NO: 29          moltype = DNA  length = 1739
FEATURE                Location/Qualifiers
source                 1..1739
                       mol_type = genomic DNA
                       organism = Homo sapiens
SEQUENCE: 29
agcgctgcaa ggacaaccgg ctggggtcct tgcgcgccgc ggctcaggga ggagcaccga   60
ctgccgcgcg taagtgccgc ctgccctgcg tgggtcgtga cagctcagcg ggacaggtcc   120
tcgcctcggt ccctcggact tagggagcgc ggggcagaca ctgagagatg gttggtgcca   180
tgtggaaggt gattgtttcg ctggtcctgt tgatgcctgg ccctgtgat gggctgtttc    240
gctcccctata cagaagtgtt tccatgccac ctaaggggaga ctcaggacag ccattatttc   300
tcaccccctta cattgaagct gggaagatcc aaaaaggaag agaattgagt ttggtcggcc   360
ctttcccagg actgaacatg aagagttatg ccggcttcct caccgtgaat aagacttaca   420
acagcaacct cttcttctgg ttcttcccag ctcagataca gccagaagat gcccagtagt   480
tctctggca caggtgtggg ccgggaggtt catccatgtt tggactcttt gtggaacatg    540
gccttatgt tgtcacaagt aacatgacct tgcgtgacag agacttcccc tgaccacaa     600
cgctctccat gctttacatt gacaatccag tgggcacagg cttcagtttt actgatgata   660
ccccacggata tgcagtcaat gaggacgatg tagcacggga tttatacagt gcactaattc   720
agtttttcca gatatttcct gaatataaaa ataatgactt ttatgtcact ggggagtctt   780
```

```
atgcaggaa atatgtgcca gccattgcac acctcatcca ttccctcaac cctgtgagag    840
aggtgaagat caacctgaac ggaattgcta ttgagatgg atattctgat cccgaatcaa    900
ttataggggg ctatgcagaa ttcctgtacc aaattggctt gttggatgag aagcaaaaaa    960
agtacttcca gaagcagtgc catgaatgca tagaacacat caggaagcag aactggtttg   1020
aggcctttga aatactggat aaactactag atggcgaact aacaagtgat ccttcttact   1080
tccagaatgt tacaggatgt agtaattact ataactttt gcggtgcacg gaacctgagg   1140
atcagcttta ctatgtgaaa ttttgtcac tcccagaggt gagacaagcc atccacgtgg   1200
ggaatcagac ttttaatgat ggaactatag ttgaaaagta cttgcgagaa gatacagtac   1260
agtcagttaa gccatggtta actgaaatca tgaataatta taaggttctg atctacaatg   1320
gccaactgga catcatcgtg gcagctgccc tgacagagcg ctccttgatg ggcatggact   1380
ggaaaggatc ccaggaatac aagaaggcag aaaaaaaagt ttggaagatc tttaaatctg   1440
acagtgaagt ggctggttac atccggcaag cgggtgactt ccatcaggta attattcgag   1500
gtggaggaca tattttaccc tatgaccagc ctctgagagc ttttgacatg attaatcgat   1560
tcatttatgg aaaaggatgg gatccttatg ttggataaac taccttccca aaagagaaca   1620
tcagaggttt tcattgctga aaagaaaatc gtaaaaacag aaaatgtcat aggaataaaa   1680
aaattatctt ttcatatctg caagatttt ttcatcaata aaaattatcc ttgaaacaa    1739

SEQ ID NO: 30        moltype = DNA   length = 3219
FEATURE              Location/Qualifiers
source               1..3219
                     mol_type = genomic DNA
                     organism = Homo sapiens
SEQUENCE: 30
gtgcacagac ggcccaggat gggttaatga gcaggcagct cagacgccgc aggtagcggc     60
cctgcctctg aacaaagagg agtccacacc tggggtgcag acaaagggag gccgcctctg    120
ctacccaatt cccagttcac atcgcctgct gctgggacc cctagtggcg gcacacgacg    180
caggcacagg tgattttgat atgctgctaa ggtttgataa gagaaatgag attcagaaga   240
cagattatat tgttgaagag cttgactgga aatgatccaa acggaaacat tggctcttcc   300
tggggttcca gcctgctgtc ttgacaggaa ctataccatc agctctcctg ggtctcttac   360
atgccaagtc atcctgcaga tctgggactc actccgtaat cagcttgatt gctgtaagtt   420
gaacacgtca gtggcatggg caccagctgc acaaccctag gagccaccaa acacagtata   480
ttctatataa atgttgctgc caggagcccc agttcaaact acaataccct gagagatggt   540
tggtgccatg tggaaggtga ttgtttcgct ggtcctgttg atgcctggcc cctgtgatgg   600
gctgtttcgc tccctataca gaagtgtttc catgccacct aagggagact caggacagcc   660
attatttctc accccttaca ttgaagctgg gaagatccaa aaagaatctt gctctgttgc   720
caggctggag tgcagtggtg cagcctcggc tcactgcgct ctgcacctcc tgcgttcaag   780
cgattctcct gcctcagcct cctgagtagc tggaactaca ggaagagaat tgagtttggt   840
cggccctttc ccaggactga acatgaagag ttatgccggc ttcctcaccg tgaataagac   900
ttacaacagc aacctcttct tctggttctt cccagctcag atacagccag aagatgcccc   960
agtagttctc tggctacagg gtgggccggg aggttcatcc atgtttggac tctttgtgga  1020
acatgggcct tatgttgtca caagtaacat gaccttgcgt gacagagact tcccctgcac  1080
cacaacgctc tccatgcttt acattgacaa tccagtggc acaggcttca gtttttactga  1140
tgatacccac ggatatgcag tcaatgagga cgatgtagca cggatttat acagtgcact  1200
aattcagttt ttccagatat ttcctgaata taaaaataat gactttttatg tcactgggga  1260
gtcttatgca gggaaatatg tgccagccat tgcacacctc atccattccc tcaaccctgt  1320
gagagaggtg aagatcaacc tgaacggaat tgctattgga gatgatatt ctgatcccga  1380
atcaattata gggggctatg cagaattcct gtaccaaatt ggcttgttgg atgagaagca  1440
aaaaaagtac ttccagaagc agtgccatga atgcatagaa cacatcagga agcagaactg  1500
gtttgaggcc tttgaaatac tggataaact actagatggc gacttaacaa gtgatccttc  1560
ttacttccag aatgttacag gatgtagtaa ttactataac tttttgcggt gcacggaacc  1620
tgaggatcag ctttactatg tgaaattttt gtcactccca gaggtgagac aagccatcca  1680
cgtggggaat cagactttta atgatgaac tatagttgaa aagtacttgc gagaagatac  1740
agtacagtca gttaagccat ggttaactga aatcatgaat aattataagg ttctgatcta  1800
caatggccaa ctggacatca tcgtggcagc tgccctgaca gagcgctcct tgatgggcat  1860
ggactggaaa ggatcccagg aatacaagaa ggcagaaaaa aagtttgga agatctttaa  1920
atctgacagt gaagtggctg gttacatccg gcaagcggac gacttccatc aggtaattat  1980
tcgaggtgga ggacatattt taccctatga ccagcctctg agagcttttgt acatgattaa  2040
tcgattcatt tatggaaaag gatgggatcc ttatgttgga taaactacct tcccaaaaga  2100
gaacatcaga ggttttcatt gctgaaaaga aaatcgtaaa aacagaaaat gtcataggaa  2160
taaaaaaatt atcttttcat atctgcaaga tttttttcat caataaaaat tatccttgaa  2220
acaagtgagc tttgtgtttt gggggagat gtttactaca aaattaactagtacatga  2280
gtaagaatta cattatttaa cttaaaggat gaaaggtatg gatgatgtga cactgagaca  2340
agatgtataa atgaaatttt agggtcttga ataggaagtt ttaattctt ctaagagtaa  2400
gtgaaaagtg cagttgtaac aaacaaagct gtaacatctt tttctgccaa taacagaagt  2460
ttggcatgcc gtgaaggtgt ttggaaatat tattggataa gaatagctca attatcccaa  2520
ataaatggat gaagctataa tagttttggg gaaaagattc tcaaatgtat aaagtcttag  2580
aacaaaagaa ttctttgaaa taaaaatatt atatataaaa gtaatgatga gtcaattcta  2640
gataagcaga tgctcttatg cagagaacaa acttaatctt tgccttttca ttttcttttt  2700
ccttctttga gttgaggtg tacacacttc tgaaagagcc tgcaggctac attagttata  2760
agagccattt taatttgggc ttcaaattct ctacttcttt tccccaaata agaacaacc   2820
taattttgta tcattgttag aatatcaaaa aaaattaaga taagctggca tcaatatata  2880
cattataaaa tatacattca ttagcagttt tctgactaaa atgtcacatc ctggcacatc  2940
ttttcgattt atgcatcatg tgctcacatc tctgaaattc tacaagacgt gtggattttt  3000
ccacatcact tccttctcat attcccatc tatgaactgg ctcactggag aattaaattt   3060
aaaaagtcaa agcctgttct tgcggcaaat agtttatgga gttattctt ttaatttctc  3120
atgttgtgcc tgattacgtt caggtttgtg atcttccttt ttaaattgtt cattgtaccc  3180
atgtcctaga agtcattaaa tcaaatattc tgatcaaaa                         3219
```

```
SEQ ID NO: 31            moltype = DNA  length = 2889
FEATURE                  Location/Qualifiers
source                   1..2889
                         mol_type = genomic DNA
                         organism = Homo sapiens
SEQUENCE: 31
gtgcacagac ggcccaggat gggttaatga gcaggcagct cagacgccgc aggtagcggc   60
cctgcctctg aacaaagagg agtccacacc tggggtgcag acaaagggag gccgcctctg  120
ctacccaatt cccagttcac atcgcctgct gctggggacc cctagtggcg gcacacgacg  180
caggcacagg cttgattgct gtaagttgaa cacgtcagtg gcatgggcac cagctgcaca  240
accctaggag ccaccaaaca cagtatattc tatataaatg ttgctgccag gagcccccagt  300
tcaaactaca atacccctgag agatggttgg tgccatgtgg aaggtgattg tttcgctggt  360
cctgttgatg cctggcccct gtgatgggct gtttcgctcc ctatacagaa gtgtttccat  420
gccacctaag ggagactcag gacagccatt atttctcacc ccttacattg aagctgggaa  480
gatccaaaaa ggaagagaat tgagtttggt cggccctttc ccaggactga acatgaagag  540
ttatgccggc ttcctcaccg tgaataagac ttacaacagc aacctcttct tctggttctt  600
cccagctcag atacagccag aagatgccc agtagttctc ttgctacagg gtgggccggg  660
aggttcatcc atgtttggac tctttgtgga acatgggcct tatgttgtca caagtaacat  720
gaccttgcgt gacagagact tcccctggac cacaacgctc tccatgcttt acattgacaa  780
tccagtgggc acaggcttca gttttactga tgatacccac ggatatgcag tcaatgagga  840
cgatgtagca cggatttat acagtgcact aattcagttt ttccagatat ttcctgaata  900
taaaaataat gacttttatg tcactgggga gtcttatgca gggaaatatg tgccagccat  960
tgcacacctc atccattccc tcaaccctgt gagagaggtg aagatcaacc tgaacggaat 1020
tgctattgga gatggatatt ctgatcccga atcaattata gggggctatg cagaattcct 1080
gtaccaaatt ggcttgttgg atgagaagca aaaaagtac ttccagaagc agtgccatga 1140
atgcatagaa cacatcagga agcagaactg gtttgaggcc tttgaaatac tggataaact 1200
actagatggc gacttaacaa gtgatccttc ttacttccag aatgttacag gatgtagtaa 1260
ttactataac tttttgcggt gcacggaacc tgaggatcag cttactatg tgaaattttt 1320
gtcactccca gaggtgagac aagccatcca cgtggggaat cagacttta atgatggaac 1380
tatagttgaa aagtacttgc gagaagatac agtacagtca gttaagccat ggttaactga 1440
aatcatgaat aattataagg ttctgatcta caatggccaa ctggacatca tcgtggcagc 1500
tgccctgaca gagcgctcct tgatgggcat ggactgaaaa ggatcccagg aatacaagaa 1560
ggcagaaaaa aaagtttgaa agatctttaa atctgacagt gaagtggctg gttacatccg 1620
gcaagcgggt gacttccatc aggtaattat tcgaggtgga ggacatattt taccctatga 1680
ccagcctctg agagcttttg acatgattaa tcgattcatt tatggaaaag gatgggatcc 1740
ttatgttgga taaactacct tcccaaaaga gaacatcaga ggttttcatt gctgaaaaga 1800
aaatcgtaaa aacagaaaat gtcataggaa taaaaaatt atcttttcat atctgcaaga 1860
ttttttttcat caataaaaat tatccttgaa acaagtgagc ttttgttttt gggggggagat 1920
gtttactaca aaattaacat gagtacatga gtaagaatta cattatttaa cttaaaggat 1980
gaaaggtatg gatgatgtga cactgagaca agatgtataa atgaaatttt agggtcttga 2040
ataggaagtt ttaatttctt ctaagagtaa gtgaaaagtg cagttgtaac aaacaaagct 2100
gtaacatctt tttctgccaa taacagaagt ttggcatgcc gtgaaggtgt ttggaaatat 2160
tattggataa gaatagctca attatcccaa ataaatggat gaagctataa tagttttggg 2220
gaaaagattc tcaaatgtat aaagtcttag aacaaaagaa ttctttgaaa taaaaatatt 2280
atatataaaa gtaatgatga gtcaattctt gataagcaga tgctcttatg cagagaacaa 2340
acttaatctt tgccttttca ttttctttt ccttctttga gttgaggtg tacacacttc 2400
tgaaagagcc tgcaggctac attagttata agagccattt taatttgggc ttcaaattct 2460
ctacttcttt tccccaaata aagaacaacc taattttgta tcattgttag aatatcaaaa 2520
aaaattaaga taagctggca tcaatatata catttataaa tatacattca ttagcagttt 2580
tctgactaaa atgtcacatc ctggcacatc ttttcgattt atgcatcatg tgctcacatc 2640
tctgaaattc tacaagacgt gtggattttt ccacatcact tccttctcat attcccatc 2700
tatgaactgg ctcactggag aattaaattt aaaaagtcaa agcctgttct tgcggcaaat 2760
agtttatgga gtttattctt ttaatttctc atgttgtgcc tgattacgtt caggtttgtg 2820
atcttccttt ttaaattgtt cattgtaccc atgtcctaga agtcattaaa tcaaatattc 2880
tgatcaaaa                                                         2889

SEQ ID NO: 32            moltype = DNA  length = 3380
FEATURE                  Location/Qualifiers
source                   1..3380
                         mol_type = genomic DNA
                         organism = Homo sapiens
SEQUENCE: 32
gcttttcgct cgctgcactc caagcccgg aacacccgcg tccgcacact aagggcacca    60
ccgctctccc acctctgcgc tgtcagatgt caggcgcgga ggtgctctgg gcaccgaggt   120
gctggcgaac caaacaagta tcaccccgga cgcctgcccc cattccgaga gagcgggcgg  180
gatggccaca ggctgcaata cagtgacacg atcacagctc actgctacag cctctacctc  240
ctgggcttaa tccatcctcc ctcctcagcc tcccaagcag ctgggactac agtgattt    300
gatatgctgc taaggtttga taagagaaat gagattcaga gaacagatta tattgttgaa  360
gagcttgact ggaaatgatc caaacgaaa cattggctct tcctgggggtt ccagcctgct  420
gtcttgacag gaactatacc atcagctctc ctggtctct tacatgccaa gtcatcctgc  480
agatctggga ctcactccgt aatcaagaat gccaccaatt cagcacttaa aaaattctgg  540
gccaggtgtg gtggctcaca cctgtaatcc tagtactttg gaggccaag accggcagac  600
cacttgaggc cagaagtttg agaccagcct ggccaacatg tgaaaccct gtctctacta  660
aaaatacaaa agttagccag gcttgattgc tgtaagttga acacgtcagt ggcatgggca  720
ccagctgcac aaccctagga gccaccaaac acagtatatt ctatataaat gttgctgcca  780
ggagcccac ttcaaactac aatacctga gagatggttg gtgccatgtg aaggtgatt    840
gtttcgctgg tcctgttgat gcctggcccc tgtgatgggc tgtttcgctc cctatacaga  900
agtgtttcca tgccacctaa gggagactca ggacagccat tatttctcac ccttacattg  960
```

```
gaagctggga agatccaaaa aggaagagaa ttgagtttgg tcggcccttt cccaggactg 1020
aacatgaaga gttatgccgg cttcctcacc gtgaataaga cttacaacag caacctcttc 1080
ttctggttct tcccagctca gatacagcca gaagatgccc cagtagttct ctggctacag 1140
ggtgggccgg gaggttcatc catgtttgga ctctttgtgg aacatgggcc ttatgttgtc 1200
acaagtaaca tgaccttgcg tgacagagac ttccccTGga ccacaacgct ctccatgctt 1260
tacattgaca atccagtggg cacaggcttc agttttactg atgatacccA cggatatgca 1320
gtcaatgagg acgatgtagc acgggattta tacagtgcac taattcagtt tttccagata 1380
tttcctgaat ataaaaataa tgactttTAt gtcactgggg agtcttatgc agggaaatat 1440
gtgccagcca ttgcacacct catccattcc ctcaaccctg tgagagaggt gaagatcaac 1500
ctgaacggaa ttgctattgg agatggatat tctgatcccg aatcaattat aggggggctat 1560
gcagaattcc tgtaccaaat tggcttgttg gatgagaagc aaaaaaagta cttccagaag 1620
cagtgccatg aatgcataga acacatcagg aagcagaact ggtttgaggc cttTGaaata 1680
ctggataaac tactagatgg cgacttaaca agtgatcctt cttacttcca gaatgttaca 1740
ggatgtagta attactataa cttttttgcgg tgcacggaac ctgaggatca gcttTActat 1800
gtgaaatttt tgtcactccc agaggtgaga caagccatcc acgtggggaa tcagacttTT 1860
aatgatggaa ctatagttga aaagtacttg cgagaagata cagTACAGtc agttaagcca 1920
tggttaactg aaatcatgaa taattataag gttctgatct caatggcca actggacatc 1980
atcgtggcag ctgccctgac agagcgctcc ttgatgggca tggactggaa aggatcccag 2040
gaatacaaga aggcagaaaa aaaagttTGG aagatcttTA aatctgacag tgaagtggct 2100
ggttacatcc ggcaagcggg tgacttccat caggtaatta ttcgaggtgg aggacatatt 2160
ttaccctatg accagcctct gagagctttt gacatgatta atcgattcat ttatggaaaa 2220
ggatggatc cttatgttgg ataaactacc ttcccaaaag agaacatcag aggttttCAt 2280
tgctgaaaag aaaatcgtaa aaacagaaaa tgtcataggA AtAaaaaaat tatctttTca 2340
tatctgcaag attttttTca tcaataaaaa ttatccttga aacaagtgag cttttgttTT 2400
tgggggggaga tgtttactac aaaattaaca tgagtacatg agtaagaatt acattattta 2460
acttaaagga tgaaagtat ggatgatgtg acactgagac aagatgtata aatgaaattt 2520
tagggtcttg aataggaagt tttaattTcT tctaagagta agtgaaaagt gcagttgtaa 2580
caaacaaagc tgtaacatct ttttctgcca ataacagaag tttggcatgc cgtgaaggtg 2640
tttgaaaata ttattggata agaatagctc aattatccca aataaatgga tgaagctata 2700
atagttttgg ggaaaagatt tcaaatgta taagtctta gaacaaaaga attctttgaa 2760
ataaaaatat tatatataaa agtaatgatg agtcaattct tgataagcag atgctcTTAT 2820
gcagagaaca aacttaatct ttgccTTTtc attttctttt tccttctttg agtttgaggt 2880
gtacacactc ctgaaagagc ctgcaggcta cattagttat aagagccatt ttaattTGGG 2940
cttcaaattc tctacttctt ttccccaaat aaagaacaac ctaattttgt atcattgtta 3000
gaatatcaaa aaaattaag ataagctggc atcaatatat acatttataa atatacattc 3060
attagcagtt ttctgactaa aatgtcacat cctggcacat cttttcgatt tatgcatcat 3120
gtgctcacat ctctgaaatt ctacaagacg tgtggatttt tccacatcac ttccttctca 3180
tattacccat ctatgaactg gctcactgga gaattaaatt taaaaagtca aagcctgttc 3240
ttgcggcaaa tagtttatgg agtttattct tttaatttct catgttgtgc ctgattacgt 3300
tcaggtttgt gatcttcctt tttaaattgt tcattgtacc catgtcctag aagtcattaa 3360
atcaaatatt ctgatcaaaa                                             3380
SEQ ID NO: 33           moltype = DNA   length = 3401
FEATURE                 Location/Qualifiers
source                  1..3401
                        mol_type = genomic DNA
                        organism = Homo sapiens
SEQUENCE: 33
gcttttcgct cgctgcactc caagcccgg aacaccgcg tccgcacact aagggcacca   60
ccgctctccc acctctgcgc tgtcagatgt caggcgcgga ggtgctctgg gcaccgaggt  120
gctgcgaac caaacaagta tcaccccgga cgcctgcccc cattccgaga cgacgggcgg  180
gatggccaca ggctgcaata cagtgacacg atcacagctc actgctacag cctctacctg  240
ctgggcttaa tccatcctcc ctcctcagcc tcccaagcag ctgggactac aggtgatttt  300
gatatgctgc taaggtttga taagagaaat gagattcaga gaacagatta tattgttgaa  360
gagcttgact ggaaatgatc caaacggaaa cattggctct tcctggggct ccagcctgct  420
gtcttgacag gaactatacc atcagctctc ctgggtctct tacatgccaa gtcatcctgg  480
agatctggga ctcactccgt aatcagcttg attgctgtaa gttgaacacg tcagtggcat  540
gggcaccagc tgcacaaccc taggagccac caaacacagt atattctata taatgttgc   600
tgccaggagc cccagttcaa actacaatat ggagttttgc tcttttTTgc ccaggctgga  660
gtgcgatgg acaatcttgg ctcactgcaa cctccacctc ttgggttcaa gcaatgcttc  720
tgcctcagcc tcccaagtag ctgggattac agagacaggg tttcaccatg ttggacaggc  780
cgggcacctg acctcaagtg atctgcccgc ctcagcctgc caaacccTG agagatggtt  840
ggtgccatgt ggaaggtgat tgtttcgctg gtcctgttga tgcctggccc ctgtgatggg  900
ctgtttcgct ccctatacag aagtgtttcc atgccaccta agggagactc aggacagcca  960
ttatttctca ccccttacat tgaagctggg aagatccaaa aggaagaga ttgagtttg  1020
gtcggccctt tcccaggact gaacatgaag agttatgccg cttcctcac cgtgaataag  1080
acttacaaca gcaacctctt cttctggttc ttcccagctc agatacagcc agaagatgcc  1140
ccagtagttc tctggctaca gggtgggccg gaggttcat ccatgtttgg actctttgtg  1200
aacatgggcc ttatgttgt cacaagtaac atgaccttgc gtgacagaga cttccccTG  1260
accacaacgc tctccatgct ttacattgac aatccagtgg gcacaggctt cagttttact  1320
gatgataccc acggatatgc agtcaatgag gacgatgtag cacgggattt atacagtgca  1380
ctaattcagt ttttccagat atttcctgaa tataaaaata tgacttTTta tgtcactggg  1440
gagtcttatg cagggaaata tgtgccagcc attgcacacc tcatccattc cctcaaccct  1500
gtgagagagg tgaagatcaa cctgaacgga attgctattg gagatggata ttctgatccc  1560
gaatcaatta gggggctA tgcagaattc ctgtaccaaa ttggcttgtt ggatgagaag  1620
caaaaaaagt acttccagaa gcagtgccat gaatgcataga acacatcag gaagcagaac  1680
tggtttgagg cctttgaaat actggataaa ctactagatg gcgacttaac aagtgatcct  1740
tcttacttcc agaatgttac aggatgtagt aattactata cttttttgcg gtgcacggaa  1800
cctgaggatc agctTTActa tgtgaaattt ttgtcactcc cagaggtgag acaagccatc  1860
```

```
cacgtgggga atcagacttt taatgatgga actatagttg aaaagtactt gcgagaagat  1920
acagtacagt cagttaagcc atggttaact gaaatcatga ataattataa ggttctgatc  1980
tacaatggcc aactggacat catcgtggca gctgccctga cagagcgctc cttgatgggc  2040
atggactgga aaggatccca ggaatacaag aaggcagaaa aaaagtttg gaagatcttt   2100
aaatctgaca gtgaagtggc tggttacatc cggcaagcgg gtgacttcca tcaggtaatt  2160
attcgaggtg gaggacatat tttaccctat gaccagcctc tgagagcttt tgacatgatt  2220
aatcgattca tttatggaaa aggatgggat ccttatgttg gataaactac cttcccaaaa  2280
gagaacatca gaggttttca ttgctgaaaa gaaaatcgta aaacagaaa atgtcatagg   2340
aataaaaaaa ttatcttttc atatctgcaa gattttttc atcaataaaa attatccttg   2400
aaacaagtga gcttttgttt ttgggggag atgtttacta caaaattaac atgagtacat   2460
gagtaagaat tacattattt aacttaaagg atgaaaggta tggatgatgt gacactgaga  2520
caagatgtat aaatgaaatt ttagggtctt gaataggaag ttttaatttc ttctaagagt  2580
aagtgaaaag tgcagttgta acaaacaaag ctgtaacatc tttttctgcc aataacagaa  2640
ggtttggcatg ccgtgaaggt gtttggaaat attattggat aagaatagct caattatccc  2700
aaataaatgg atgaagctat aatagttttg gggaaaagat tctcaaatgt ataaagtctt   2760
agaacaaaag aattctttga aatagaaaata ttatatataa aagtaatgat gagtcaattc  2820
ttgataagca gatgctctta tgcagagaac aaacttaatc tttgcttttt cattttcttt   2880
ttccttcttt gagtttgagg tgtacacact tctgaaaagg cctgcaggct acattagtta   2940
taagagccat tttaatttgg gcttcaaatt ctctacttct tttccccaaa taagaacaa   3000
cctaattttg tatcattgtt agaatatcaa aaaaaattaa gataagctgg catcaatata   3060
tacatttata aatatacatt cattagcagt tttctgacta aaatgtcaca tcctggcaca   3120
tcttttcgat ttatgcatca tgtgctcaca tctctgaaat tctacaagac gtgtggattt   3180
ttccacatca cttccttctc atattaccca tctatgaact ggctcactgg agaattaaat   3240
ttaaaaagtc aaagcctgtt cttgcggcaa atagtttatg gagtttattc ttttaatttc   3300
tcatgttgtg cctgattacg ttcaggtttg tgatcttcct ttttaaattg ttcattgtac   3360
ccatgtccta gaagtcatta atcaaatat tctgatcaaa a                      3401

SEQ ID NO: 34          moltype = DNA   length = 3205
FEATURE                Location/Qualifiers
source                 1..3205
                       mol_type = genomic DNA
                       organism = Homo sapiens
SEQUENCE: 34
gcttttcgct cgctgcactc caagccccgg aacacccgcg tccgcacact aagggcacca   60
ccgtctccc acctctgcgc tgtcagatgt caggcgcgcg ggtgctctgg gcaccgaggt   120
gctggcgaac caaacaagta tcaccccgga cgcctgcccc cattccgaga gagcgggcgg  180
gatgccaca ggctgcaata cagtgacacg atcacagctc actgctacag cctctacctc   240
ctgggcttaa tccatcctcc ctcctcagcc tcccaagcag ctgggactac aggtgatttt   300
gatatgctgc taagtttga taagagaaat gagattcaga gaacagatta tattgttgaa   360
gagcttgact ggaaatgatc caaacgaaa cattggctct tcctgggtt ccagcctgct    420
gtcttgacag gaactatacc atcagctctc ctgggtctct tacatgccaa gtcatcctgc   480
agatctggga ctcactccgt aatcagcttg attgctgaa gttgaacacg tcagtggcat    540
gggcaccagc tgcacaaccc taggaccac caaacagt atattctata taaatgttgc      600
tgccaggagc cccagttcaa actacaatac cctgagagat ggttggtgcc atgtggaagg   660
tgattgtttc gctggtcctg ttgatgcctg gccctgtga tgggctgttt cgctccctat    720
acagaagtgt ttccatgcca cctaaggag actcaggaca gccattattt ctcacccctt    780
acattgtgga tgggaagatc caaaaaggaa gagaattgga tttggtcggc ccttttcccag  840
gactgaaacat gaaagagttat gccggcttcc tcaccgtgaa taagacttac aacagcaacc  900
tcttcttctg gttcttccca gctcagatac agccagaaga tgcccagta gttctctggc   960
tacagggtgg gccgggaggt tcatccatgt ttggactctt tgtggaacat gggccttatg   1020
tgtgcacaag taacatgacc ttgcgtgaca gagacttccc ctggaccaca acgctctcca   1080
tgctttacat tgacaatcca gtgggcacag gcttcagttt tactgatgat acccacggat   1140
atgcagtcaa tgaggacgat gtagcacggg atttataacag tgcactaatt cagttttcc    1200
agatattcc tgaatataaa aataatgact tttatgtcac tggggagtct tatgcaggga   1260
aatatgtgcc agccattgca cacctcatcc attccctcaa ccctgtgaga gaggtgaaga   1320
tcaacctgaa cggaattgct attggagatg gatattctga tccgaatca attatagggg   1380
gctatgcaga attcctgtac caaattggct tgttggatga aagcaaaaa aagtacttcc    1440
agaagcagtg ccatgaatgc atagaacaca tcaggaagca gaactggttt gaggcctttg   1500
aaatactgga taaactacta gatggcgact taacaagtga tccttcttac ttccagaatg   1560
ttacaggatg tagtaattac tataactttt tgcggtgcac ggaacctgag gatcagcttt   1620
actatgtgaa attttttgtca ctcccagagg tgagacaagc catccacgtg gggaatcaga   1680
cttttaatga tggaactata gttgaaaagt acttgcgaga agatacagta cagtcagtta   1740
agccatggtt aactgaaatc atgaataatt ataaggttct gatctacaat ggccaactgg   1800
acatcatcgt ggcagctgcc ctgacagagc gctccttgat gggctgaaggat tggaaggat    1860
cccaggaata caagaaggca gaaaaaaaag tttaaatct gacagtgaag                1920
tggctggtta tcatccggcaa gcgggtgact ccatcaggt aattattcga ggtggaggac    1980
atatttacc ctatgaccag cctctgagag cttttgacat gattaatcga ttcatttatg    2040
gaaaaggatg ggatccttat gttggataaa ctaccttccc aaaagagaac atcagaggtt   2100
ttcattgctg aaaagaaaat cgtaaaaaca gaaatgtca taggaataaa aaattatct    2160
tttcatatct gcaagatttt tttcatcaat aaaattatc cttgaaacaa gtgagctttt   2220
gttttttggg ggagatgttt actacaaaat taacatgagt acatgagtaa gaattacatt   2280
atttaactta aaggatgaaa ggtatggatg atgtgacact gagacaagat gtaaaatga    2340
aattttaggg tcttgaatag gaagttttaa tttcttctaa gagtaagtga aaagtgcagt   2400
tgtaacaaac aaagctgtaa catctttttc tgccaataac agaaggtttgg catgccgccgtga 2460
aggtgtttgg aaatattatt ggataagaat agctcaatta tcccaaataa atggatgaag   2520
ctataatagt tttggggaaa agattctcaa atgtataaag tctagaaca aaagaattct    2580
ttgaaataaa aatattatat ataaagtaa tgatgagtca attcttgata agcagatgct    2640
cttatgcaga gaacaaactt aatctttgcc ttttcatttt ctttttcctt ctttgagttt   2700
gaggtgtaca cacttctgaa agagcctgca ggctacatta gttataagag ccattttaat   2760
```

```
ttgggcttca aattctctac ttcttttccc caaataaaga acaacctaat tttgtatcat    2820
tgttagaata tcaaaaaaaa ttaagataag ctggcatcaa tatatacatt tataaatata    2880
cattcattag cagttttctg actaaaatgt cacatcctgg cacatctttt cgatttatgc    2940
atcatgtgct cacatctctg aaattctaca agacgtgtgg attttttccac atcacttcct   3000
tctcatatta cccatctatg aactggctca ctggagaatt aaattttaaaa agtcaaagcc   3060
tgttcttgcg gcaaatagtt tatggagttt attcttttaa tttctcatgt tgtgcctgat    3120
tacgttcagg tttgtgatct tcctttttaa attgttcatt gtacccatgt cctagaagtc    3180
attaaatcaa atattctgat caaaa                                          3205

SEQ ID NO: 35           moltype = DNA   length = 3162
FEATURE                 Location/Qualifiers
source                  1..3162
                        mol_type = genomic DNA
                        organism = Homo sapiens
SEQUENCE: 35
gcttttcgct cgctgcactc caagcccgg aacaccgcg tccgcacact aagggcacca     60
ccgctctccc acctctgcgc tgtcagatgt caggcgcgga ggtgctctgg gcaccgaggt    120
gctggcgaac caaacaagta tcaccccgga cgcctgcccc cattccgaga gagcgggcgg    180
gatggccaca ggctgcaata cagtgacacg atcacagctc actgctacag cctctacctc    240
ctgggcttaa tccatcctcc ctcctcagcc tcccaagcag ctgggactac agatccaaac    300
ggaaacattg gctcttcctg gggttccagc ctgctgtctt gacaggaact ataccatcag    360
ctctcctggg tctcttacat gccaagtcat cctgcagatc tgggactac tccgtaatca     420
gcttgattgc tgtaagttga acacgtcagt ggcatgggca ccagctgcac aaccctagga    480
gccaccaaac acagtatatt ctatataaat gttgctgcca ggagcccag ttcaaactac      540
aatacccctga gagatggttg gtgccatgtg aaggtgatt gtttcgctgg tcctgttgat     600
gcctggcccc tgtgatgggc tgtttcgctc cctatacaga agtgttttcca tgccacctaa    660
gggagactca ggacagccat tatttctcac cccttacatt gaagctggga agatccaaaa    720
aggaagagaa ttgagtttgg tcggccttt cccaggactg aacatgaaga gttatgccgg     780
cttcctcacc gtgaataaga cttacaacag caacctcttc ttctggttct tcccagctca    840
gatacagcca gaagatgccc cagtagttct ctggctacag ggtgggccgg gaggttcatc    900
catgtttgga ctctttgtgg aacatgggcc ttatgttgtc acaagtaaca tgaccttgcg    960
tgacagagac ttcccctgga ccacaacgct ctccatgctt tacattgaca atccagtggg   1020
cacaggcttc agttttactg atgatacccca cggatatgca gtcaatgagg acgatgtagc   1080
acgggattta tacagtgcac taattcagtt ttttccagata tttcctgaat ataaaaataa   1140
tgacttttat gtcactgggg agcatccatt tgtgattggc catttcaaca tctgtccttc   1200
tcagtcttat gcagggaaat atgtgccagc cattgcacac ctcatccatt ccctcaaccc   1260
tgtgagagag gtgaagatca acctgaacgg aattgctatt ggagatggat attctgatcc   1320
cgaatcaatt atagggggct atgcagaatt cctgtaccaa attggcttgt tggatgagaa   1380
gcaaaaaaag tacttccaga agcagtgcca tgaatgcata gaaccacatca ggaagcagaa   1440
ctggtttgag gcctttgaaa tactggataa actactagat ggcgacttaa caagtgatcc   1500
ttcttacttc cagaatgtta caggatgtag taattactat aacttttttgc ggtgcacgga   1560
acctgaggat cagctttact atgtgaaatt tttgtcactc ccagaggtga gacaagccat   1620
ccacgtgggg aatcagactt ttaatgatgg aactatagtt gaaaagtact tgcgagaaga   1680
tacagtacag tcagttaagc catggttaac tgaaatcatg aataattata aggttctgat   1740
ctacaatggc caactggaca tcatcgtggc agctgccctg acagagcgct ccttgatggg   1800
catggactgg aaaggatccc aggaatacaa gaaggcagaa aaaaaagttt ggaagatctt   1860
taaatctgac agtgaagtgg ctggttacat ccggcaaggc ggtgacttcc atcaggtaat   1920
tattcgaggt ggaggacata ttttaccta tgaccagcct ctgagagctt ttgactgat      1980
taatcgattc atttatggaa aaggatggga tccttatgtt ggataaacta ccttcccaaa   2040
agagaacatc agaggttttc attgctgaaa agaaaatcgt aaaaacagaa aatgtcatag   2100
gaataaaaaa attatctttt catatctgca agatttttttt catcaataaa aattatccttt  2160
gaaacaagtg agcttttgtt tttggggggaa gatgtttact acaaaattaa catgagtaca   2220
tgagtaagaa ttacattatt aacttaaag gatgaaaggt atgggatgatg tgacactgag    2280
acaagatgta taaatgaaat tttagggtct tgaataggaa gttttaattt cttctaagag   2340
taagtgaaaa gtgcagttgt aacaaacaaa gctgtaacat ctttttctgc caataacaga   2400
agtttggcat gccgtgaagg tgtttgaaaa tattattgga taagaatagc tcaattatcc   2460
caaataaatg gatgaagcta taatagtttt ggggaaaga ttctcaaatg tataaagtct     2520
tagaacaaaa gaattcttttg aaataaaaat attatatata aagtaatga tgagtcaatt    2580
cttgataagc agatgctctt atgcagagaa caaacttaat ctttgccttt tcatttttctt  2640
tttccttctt tgagtttgag gtgtacacac ttctgaaaga gcctgcaggc tacattagtt   2700
ataagagcca ttttaatttg ggcttcaaat tctctacttc ttttcccaa ataaagaaca     2760
acctaattt gtatcattgt tagaatatca aaaaaatta agataagctg gcatcaatat     2820
atacatttat aaatatacat tcattagcag ttttctgact aaaatgtcac atcctggcac   2880
atcttttcga tttatgcatc atgtgctcac atctctgaaa ttctacaaga cgtgtggatt   2940
ttccacatc acttccttct catattaccc atctatgaac tggctcactg gagaattaaa     3000
tttaaaagt caaagcctgt tcttgcggca aatagtttat ggagtttatt cttttaattt    3060
ctcatgttgt gcctgattac gttcaggttt gtgatcttcc ttttttaaatt gttcattgta   3120
cccatgtcct agaagtcatt aaatcaaata ttctgatcaa aa                       3162

SEQ ID NO: 36           moltype = DNA   length = 2869
FEATURE                 Location/Qualifiers
source                  1..2869
                        mol_type = genomic DNA
                        organism = Homo sapiens
SEQUENCE: 36
gcttttcgct cgctgcactc caagcccgg aacaccgcg tccgcacact aagggcacca     60
ccgctctccc acctctgcgc tgtcagatgt caggcgcgga ggtgctctgg gcaccgaggt    120
gctggcgaac caaacaagta tcaccccgga cgcctgcccc cattccgaga gagcgggcgg    180
gatggccaca ggctgcaata cagtgacacg atcacagctc actgctacag cctctacctc    240
```

```
ctgggcttaa tccatcctcc ctcctcagcc tcccaagcag ctgggactac agaccctgag    300
agatggttgg tgccatgtgg aaggtgattg tttcgctggt cctgttgatg cctggcccct    360
gtgatgggct gtttcgctcc ctatacagaa gtgtttccat gccacctaag ggagactcag    420
gacagccatt atttctcacc ccttacattg aagctgggaa gatccaaaaa ggaagagaat    480
tgagttttggt cggcccttc ccaggactga acatgaagag ttatgccggc ttcctcaccg    540
tgaataagac ttacaacagc aacctcttct tctggttctt cccagctcag atacagccag    600
aagatgcccc agtagttctc tggctacagg gtgggccggg aggttcatcc atgtttggac    660
tctttgtgga acatgggcct tatgttgtca caagtaacat gaccttgcgt gacagagact    720
tccccctggac cacaacgctc tccatgcttt acattgacaa tccagtgggc acaggcttca    780
gttttactga tgatacccac ggatatgcag tcaatgagga cgatgtagca cgggatttat    840
acagtgcact aattcagttt ttccagatat ttcctgaata taaaataat gacttttatg    900
tcactgggga gtcttatgca gggaaatatg tgccagccat tgcacacctc atccattccc    960
tcaaccctgt gagagaggtg aagatcaacc tgaacggaat tgctattgga gatggatatt   1020
ctgatcccga atcaattata gggggctatg cagaattcct gtaccaaatt ggcttgttgg   1080
atgagaagca aaaaaagtac ttccagaagc agtgccatga atgcatgaa cacatcagga   1140
agcagaactg gtttgaggcc tttgaaatac tggataaact actagatggc gacttaacaa   1200
gtgatccttc ttacttccag aatgttacag gatgtagtaa ttactataac ttttgcggt   1260
gcacggaacc tgaggatcag ctttactatg tgaaatttt gtcactccca gaggtgagac   1320
aagccatcca cgtggggaat cagacttta atgatgaac tatagttgaa agtacttgc    1380
gagaagatac agtacagtca gttaagccat ggttaactga aatcatgaat aattataagg   1440
ttctgatcta caatggccaa ctggacatca tcgtggcagc tgccctgaca gagcgctcct   1500
tgatgggcat ggactggaaa ggatcccagg aatacaagaa gcagaaaaa aaagttgga    1560
agatctttaa atctgacagt gaagtggctg gttacatccg gcaagcgggt gacttccatc   1620
aggtaattat tcgaggtgga ggacatattt tacccctatga ccagcctctg agagcttttg   1680
acatgattaa tcgattcatt tatggaaaag gatgggatcc ttatgttgga taaactacct   1740
tcccaaaaga gaacatccaga ggtttcatt gctgaaaaga aaatcgtaaa acagaaaat   1800
gtcataggaa taaaaaaatt atcttttcat atctgcaaga ttttttttcat caataaaaat   1860
tatccttgaa acaagtgagc ttttgttttt gggggggagat gtttactaca aaattaacat   1920
gagtacatga gtaagaatta cattatttaa cttaaaggat gaaaggtatg gatgatgtga   1980
cactgagaca agatgtataa atgaaatttt agggtcttga ataggaagtt ttaatttctt   2040
ctaagagtaa gtgaaaagtg cagttgtaac aaacaaagct gtaacatctt tttctgccaa   2100
taacagaagt ttggcatgcc gtgaaggtgt ttggaaatat tattggataa gaatagctca   2160
attatcccaa ataatggat gaagctataa tagttttggg gaaaagattc tcaaatgtat    2220
aaagtcttag aacaaaagaa ttctttgaaa taaaaatatt atatataaaa gtaatgatga   2280
gtcaattctt gataagcaga tgctcttatg cagagaacaa acttaatctt tgcctttca   2340
ttttcttttt cctcttttga gtttgaggtg tacacacttc tgaaagagcc tgcaggctac   2400
attagttata agagccattt taatttgggc ttcaaattct ctacttcttt tccccaaata   2460
aagaacaacc taattttgta tcattgttag aatatcaaaa aaattaaga taagctggca   2520
tcaatatata catttataaa tatacattca ttagcagttt tctgactaaa atgtcacatc   2580
ctggcacatc tttttcgattt atgcatcatg tgctcacatc tctgaaattc tacaagacgt   2640
gtggattttt ccacatcact tccttctcat attcccatc tatgaactgg ctcactggag    2700
aattaaattt aaaaagtcaa agcctgttct tgcggcaaat agtttatgga gtttattctt   2760
ttaatttctc atgttgtgcc tgattacgtt caggtttgtg atcttccttt ttaaattgtt   2820
cattgtaccc atgtcctaga agtcattaaa tcaaatattc tgatcaaaa               2869

SEQ ID NO: 37          moltype = DNA   length = 3380
FEATURE                Location/Qualifiers
source                 1..3380
                       mol_type = genomic DNA
                       organism = Homo sapiens
SEQUENCE: 37
gcttttcgct cgctgcactc caagccccgg aacacccgcg tccgcacact aagggcacca     60
ccgctctccc acctctgcgc tgtcagatgt caggcgcgga ggtgctctgg gcaccgaggt    120
gctggcgaac caaacaagta tcaccccgga cgcctgcccc cattccgaga gagcgggcgg    180
gatgcgcaca ggtgattttg atatgctgct aaggtttgat aagagaaatg agattcagag    240
aacagattat attgttgaag agcttgactg gaaatgatcc aaacggaaac attggctctt    300
cctggggttc cagcctgctg tcttgacagg aactataccc tcagctctcc tgggtctctt    360
acatgccaag tcatcctgca gatctgggac tcactccgta atcagcttga ttgctgtaag    420
ttgaacacgt cagtggcatg ggcaccagct gcacaaccct aggagccacc aaacacagta    480
tattctatat aaatgttgct gccaggagcc ccagttcaaa ctacaatacc ctgagagatg    540
gttggtgcca tgtggaaggt gattgtttcg ctggtcctgt tgatgcctgg ccctgtgat   600
gggctgtttc gctccctata cagaagtgtt ccatgccac ctaagggaga ctcaggacag    660
ccattatttc tcacccctta cattgaagct gggaagatcc aaaaagggtc tcgctgtgtt   720
atccaggctg gagtgcagtg gcatgatcat ggctcactgc tcctgggctc   780
aagtgatcct cccacctcag cctcccgagt tgctgggact acaagcactg ccaccatgct    840
cagctaagag gcatgccact actttccttc ccactccttg ccacctgcac cttctgactc    900
actctagtta aaagccctgg gggaaggaac aaactctgca gcctgactgc tgtgtttaat    960
cccagctctc ctctactagc tggaagagaa ttgagtttgg tcggcccttt ccaggactg   1020
aacatgaaga gttatgccgg cttcctcacc gtgaataaga cttacaacag caacctcttc   1080
ttctggttct tcccagctca gatacagcca gaagatgccc cagtagttct ctggctacag   1140
ggtgggccgg gaggttcatc catgtttgga ctctttgtgg aacatgggcc ttatgttgtc   1200
acaagtaaca tgaccttgcg tgacagagac ttccccttgga ccacaacgct ctccatgctt    1260
tacattgaca atccagtggg cacaggcttc agttttactg atgatacccca cggatatgca   1320
gtcaatgagg acgatgtagc acgggattta tacagtgcac taattcagtt tttccagata   1380
tttcctgaat ataaaaataa tgactttta tgtcactggg gagtcttatg cagggaaatat   1440
gtgccagcca ttgcacacct catccattcc ctcaaccctg tgagagaggt gaagatcaac   1500
ctgaacggaa ttgctattgg agatggatat tctgatcccg aatcaattat aggggggctat   1560
gcagaattcc tgtaccaaat tggcttgttg gatgagaagc aaaaaaagta cttccagaag   1620
cagtgccatg aatgcataga acacatcagg aagcagaact ggtttgaggc ctttgaaata   1680
```

```
ctggataaac tactagatgg cgacttaaca agtgatcctt cttacttcca gaatgttaca   1740
ggatgtagta attactataa cttttttgcgg tgcacggaac ctgaggatca gctttactat   1800
gtgaaatttt tgtcactccc agaggtgaga caagccatcc acgtggggaa tcagactttt   1860
aatgatggaa ctatagttga aaagtacttg cgagaagata cagtacagtc agttaagcca   1920
tggttaactg aaatcatgaa taattataag gttctgatct acaatggcca actggacatc   1980
atcgtggcag ctgccctgac agagcgctcc ttgatgggca tggactggaa aggatcccag   2040
gaatacaaga aggcagaaaa aaaagtttgg aagatcttta aatctgacag tgaagtggct   2100
ggttacatcc ggcaagcggg tgacttccat caggtaatta ttcgaggtgg aggacatatt   2160
ttaccctatg accagcctct gagagctttt gacatgatta atcgattcat ttatggaaaa   2220
ggatgggatc cttatgttgg ataaaactacc ttcccaaaag agaacatcag aggttttcat   2280
tgctgaaaag aaaatcgtaa aaacagaaaa tgtcataggaa taaaaaaat tatctttca    2340
tatctgcaag atttttttca tcaataaaaa ttatccttga aacaagtgag cttttgtttt   2400
tgggggggaga tgtttactac aaaattaaca tgagtacatg agtaagaatt acattattta  2460
acttaaagga tgaaaggtat ggatgatgtg acactgagac aagatgtata aatgaaattt   2520
tagggtcttg aataggaagt tttaattct tctaagagta agtgaaaagt gcagttgtaa    2580
caaacaaagc tgtaacatct ttttctgcca ataacagaag tttggcatgc cgtgaaggtg   2640
tttggaaata ttattggata agaatagctc aattatccca aataaatgga tgaagctata   2700
atagttttgg ggaaaagatt ctcaaatgta taaagtctta gaacaaaaga attctttgaa   2760
ataaaaatat tatatataaa agtaatgatg agtcaattct tgataagcag atgctcttat   2820
gcagagaaca aacttaatct ttgccttttc attttctttt tccttctttg agtttgaggt   2880
gtacacactt ctgaaagagc ctgcaggcta cattagttat aagagccatt ttaatttggg   2940
cttcaaattc tctacttctt ttccccaaat aaagaacaac ctaattttgt atcattgtta   3000
gaatatcaaa aaaattaag ataagctggc atcaatatat acatttataa atatacattc    3060
attagcagtt ttctgactaa aatgtcacat cctggcacat cttttcgatt tatgcatcat   3120
gtgctcacat ctctgaaatt ctacaagacg tgtggatttt tccacatcac ttccttctca   3180
tattacccat ctatgaactg gctcactgga gaattaatt taaaaagtca aggcctgttc    3240
ttgcggcaaa tagtttatgg agtttattct tttaattttct catgttgtgc ctgattacgt   3300
tcaggttttgt gatcttcctt tttaaattgt tcattgtacc catgtcctag aagtcattaa   3360
atcaaatatt ctgatcaaaa                                                3380
```

SEQ ID NO: 38        moltype = DNA   length = 3248
FEATURE              Location/Qualifiers
source               1..3248
                     mol_type = genomic DNA
                     organism = Homo sapiens
SEQUENCE: 38

```
gcttttcgct cgctgcactc caagcccgg aacaccgcg tccgcacact aagggcacca     60
ccgctctccc acctctgcgc tgtcagatgt caggcgcgga ggtgctctgg gcaccgaggt   120
gctggcgaac caaacaagta tcaccccgga cgcctgccc cattccgaca gagcgggcgg   180
gatggccaca ggtgattttg atatgctgct aaggtttgat aagagaaatg agattcagag   240
aacagattat attgttgaag agcttgactg gaaatgatcc aaacggaaac attggctctt   300
cctgggggtc cagcctgctg tcttgacagg aactatacca tcagctctcc tgggtctctt   360
acatgccaag tcatcctgca gatctgggac tcactccgta atcacttga ttgctgtaag    420
ttgaacacgt cagtggcatg ggcaccagct gcacaaccc aggagccacc aaacacagta   480
tattctatat aaatgttgct gccaggagcc cagttcaaa ctacaatacc ctgagagatg    540
gttggtgcca tgtggaaggt gattgtttcg ctggtcctgt tgatgcctgg ccctgtgat    600
gggctgtttc gctccctata cagaagtgtt tccatgccac ctaagggaga ctcaggacag   660
ccattatttc tcacccctta cattgaagct gggaagatcc aaaaagggtc tcgctgtgtt   720
atccaggctg gagtgcagtg gcatgatcat ggctcactgc agccttgacc tcctgggctc   780
aagtgatcct cccacctcag cctcccgagt tgctgggact acaagcactg ccaccatgct   840
cagctaaggag gaagagaatt gagtttggtc ggcccttttcc caggactgaa catgaagagt   900
tatgccggct tcctcaccgt gaataagact tacaacagca acctcttctt ctggttcttc   960
ccagctcaga tacagccaga agatgcccca gtagttctct ggctacaggg tgggccggga  1020
ggttcatcca tgtttggact cttttgtgaa catgggcctt atgttgtcac aagtaacatg  1080
accttgcgtg acagagactt cccctgacc acaacgtctc catgtcttta cattgacaat   1140
ccagtgggca caggcttcag ttttactgat gatacccacg gatatgcagt caatgaggac  1200
gatgtagcac gggatttata cagtgcacta attcagtttt tccagatatt tcctgaatat  1260
aaaaataatg acttttatgt cactggggag tcttatgcag ggaaatatgt gccagccatt  1320
gcacacctca tccattccct caaccctgtg agagaggtga agatcaacct gaaccggaatt 1380
gctattggag atggatattc tgatcccgaa tcaattatag ggggctatgc agaattcctg  1440
taccaaattg gcttgttgga tgagaagcaa aaaaagtact tccagaagca gtgccatgaa  1500
tgcatagaac acatcaggaa gcagaactgg tttgaggcct ttgaaatact ggataaacta  1560
ctagatggcg acttaacaag tgatccttct tacttccaga atgttacagg atgtagtaat  1620
tactataact ttttgcggtg cacggaacct gaggatcagc tttactattg gaaatttttg  1680
tcactcccag aggtgagaca agccatccac gtggggaatc agactttaa tgatggaact   1740
atagttgaaa agtacttgcg agaagataca gtacagtcag ttaagccatg gttaactgaa  1800
atcatgaata attataaggt tctgatctac aatggcaaac tggacatcat cgtggcagct  1860
gccctgacag agcgctcctt gatgggcatg gactggaaag gatcccagga atacaagaag  1920
gcagaaaaaa aagtttggaa gatctttaaa tctgacagtg aagtggctgg ttacatcaag  1980
caagcgggtg acttccatca ggtaattatt cgaggtggag gacatatttt acccctatgac 2040
cagcctctga gagcttttga catgattaat cgattcattt atggaaaagg atgggatcct  2100
tatgttggat aaaactacct tcccaaaagag aacatcagag gttttcattg ctgaaaagaa  2160
aatcgtaaaa acagaaaatg tcataggaat aaaaaaatta tcttttcata tctgcaagat  2220
ttttttcatc aataaaaatt atccttgaaa caagtgagct tttgtttttg ggggagatg    2280
tttactacaa aattaacatg agtacatgag taagaattac attatttaac ttaaggatg    2340
aaaggtatgg atgatgtgac actgagacaa gatgtataaa tgaaatttta gggtcttgaa  2400
taggaagttt taatttcttc taagagtaag tgaaaagtgc agttgtaaca aacaaagctg  2460
taacatcttt tctgccaata acagaagtt ggcatgccg tgaaggtgtt tggaaatatt    2520
attggataag aatagctcaa ttatcccaaa taaatggatg aagctataat agttttgggg  2580
```

```
aaaagattct caaatgtata aagtcttaga acaaaagaat tctttgaaat aaaaatatta    2640
tatataaaag taatgatgag tcaattcttg ataagcagat gctcttatgc agagaacaaa    2700
cttaatcttt gccttttcat tttcttttc cttctttgag tttgaggtgt acacacttct    2760
gaaagagcct gcaggctaca ttagttataa gagccatttt aatttgggct tcaaattctc    2820
tacttcttt ccccaaataa agaacaacct aatttgtat cattgttaga atatcaaaaa     2880
aaattaagat aagctggcat caatatatac atttataaat atacattcat tagcagtttt    2940
ctgactaaaa tgtcacatcc tggcacatct tttcgattta tgcatcatgt gctcacatct    3000
ctgaaattct acaagacgtg tggattttc cacatcactt ccttctcata ttacccatct    3060
atgaactggc tcactggaga attaaattta aaaagtcaaa gcctgttctt gcggcaaata    3120
gtttatggag tttattcttt taatttctca tgttgtgcct gattacgttc aggtttgtga    3180
tcttcctttt taaattgttc attgtaccca tgtcctagaa gtcattaaat caaatattct    3240
gatcaaaa                                                             3248

SEQ ID NO: 39           moltype = DNA   length = 3215
FEATURE                 Location/Qualifiers
source                  1..3215
                        mol_type = genomic DNA
                        organism = Homo sapiens
SEQUENCE: 39
gcttttcgct cgctgcactc caagcccgg aacaccgcg tccgcacact aagggcacca     60
ccgctctccc acctctgcgc tgtcagatgt caggcgcgga ggtgctctgg gcaccgaggt    120
gctggcgaac caaacaagta tcaccccgga cgcctgcccc cattccgaga gagcgggcgg    180
gatggccaca gatccaaacg gaaacattgg ctcttcctgg ggttccagcc tgctgtcttg    240
acaggaacta taccatcagc tctcctgggt ctcttacatg ccaagtcatc ctgcagatct    300
gggactcact ccgtaatcag cttgattgct gtaagttgaa cacgtcagtg gcatgggcac    360
cagctgcaca accctaggag ccaccaaaca cagtatattc tatataaatg ttgctgccag    420
gagcccagt tcaaactaca atatggagtt ttgctctttt ttgcccaggc tggagtgcga    480
tggcacaatc ttggctcact gcaacctcca cctcttgggt tcaagcaatg cttctgcctc    540
agcctcccaa gtagctggga ttacagagac agggtttcac catgttggac aggccgggca    600
cctgacctca agtgatctgc ccgcctcagc tgccaaaac cctgagagat ggttggtgcc    660
atgtggaagg tgattgtttc gctggtcctg ttgatgcctg gcccctgtga tgggctgttt    720
cgctccctat acagaagtgt ttccatgcca cctaagggag actcaggaca gccattattt    780
ctcaccctt acattgaagc tgggaagatc caaaaggaa gagaattgag tttggtcggc    840
ccttcccag gactgaacat gaagagttat gccggcttcc tcaccgtgaa taagacttac    900
aacagcaacc tcttcttctg gttcttccca gctcagatac agccagaaga tgccccagta    960
gttctctggc tacagggtgg gccgggaggt tcatccatgt ttggactctt tgtggaacat    1020
gggccttatg ttgtcacaag taacatgacc ttgcgtgaca gagacttccc ctggaccaca    1080
acgctctcca tgctttacat tgcaatcca gtgggcacag gcttcagttt tactgatgat    1140
acccacggat atgcagtcaa tgaggacgat gtagcacgg atttatacag tgcactaatt    1200
cagttttcc agatatttcc tgaatataaa aataatgact tttatgtcac tggggagtct    1260
tatgcaggga aatatgtgcc agccattgca cacctcatcc attccctcaa ccctgtgaga    1320
gaggtgaaga tcaacctgaa cggaattgct attggagatg gatattctga tcccgaatca    1380
attatagggg gctatgcaga attcctgtac caaattggat tgttggatga gaagcaaaaa    1440
aagtactcc agaagcagtg ccatgaatgc ataggaacaca tcaggaagca gaactggttt    1500
gaggcctttg aaatactgga taaactacta gatggcgact taacaagtga tcctttcttac    1560
ttccagaatg ttacaggatg tagtaattac tataactttt tgcggtgcac ggaacctgag    1620
gatcagcttt actatgtgaa attttgtca ctcccagagg tgacacaagc catccacgtg    1680
gggaatcaga cttttaatga tggaactata gttgaaaagt acttgcgaga agatacagta    1740
cagtcagtta agccatggtt aactgaaaat atgaataatt ataaggttct gatctacaat    1800
ggccaactga acatcatcgt ggcagctgcc ctgacagagc gctccttgat gggcatggac    1860
tggaaaggat cccaggaata caagaaggca gaaaaaaaag tttggaagat ctttaaatct    1920
gacagtgaag tggctggtta catccggcaa gcgggtgact tccatcaggt aattattcga    1980
ggtgaggac atattttacc ctatgaccag cctctgagag cttttgacat gattaatcga    2040
ttcatttatg gaaaaggatg ggatccttat gttggataaa ctaccttccc aaaagagaac    2100
atcagaggtt ttcattgctg aaaagaaaat cgtaaaaaca gaaaatgtca taggaataaa    2160
aaaattatct tttcatatct gcaagatttt tttcatcaat aaaaattatc cttgaaacaa    2220
gtgagctttt gtttttgggg ggagatgttt actacaaaat taacatgagt acatgagtaa    2280
gaattacatt atttaactta aaggatgaaa ggtatggatg atgtgacact gagacaagat    2340
gtataaatga aattttaggg tcttgaatag gaagttttaa tttcttctaa gagtaagtga    2400
aaagtgcagt tgtaacaaac aaagctgtaa catcttttc tgccaataac agaagtttgg    2460
catgccgtga aggtgtttgg aaatattatt ggataagaat agctcaatta tcccaaataa    2520
atggatgaag ctataatagt tttggggaaa agattctcaa atgtataaag tcttagaaca    2580
aaagaattct ttgaaataaa atattat ataaagtaa tgatgagtca attcttgata       2640
agcagatgc cttatgcaga gaacaactt aatctttgcc ttttcatttt catttt cttttcttt   2700
ctttgagttt gaggtgtaca cacttctgaa agagcctgca ggctacatta gttataagag    2760
ccatttaat ttgggcttca aattctctac ttcttttccc caataaaga acaacctaat    2820
tttgtatcat tgttagaata tcaaaaaaa ttaagataag ctggcatcaa tatatacatt    2880
tataaatata cattcattag cagttttctg actaaaatgt cacatcctgg cacatctttt    2940
cgatttatgc atcatgtgct cacatctctg aaattctaca agacgtgtgg attttccac    3000
atcacttcct tctcatatta cccatctatg aactggctca ctggagaatt aaatttaaaa    3060
agtcaaagcc tgttctgcg gcaaatagtt tatggagttt attctttaa ttctcatgt     3120
tgtgcctgat tacgttcagg tttgtgatct tccttttaa attgttcatt gtacccatgt    3180
cctagaagtc attaaatcaa atattctgat caaaa                               3215

SEQ ID NO: 40           moltype = DNA   length = 3087
FEATURE                 Location/Qualifiers
source                  1..3087
                        mol_type = genomic DNA
                        organism = Homo sapiens
```

```
SEQUENCE: 40
gcttttcgct cgctgcactc caagccccgg aacacccgcg tccgcacact aagggcacca    60
ccgctctccc acctctgcgc tgtcagatgt caggcgcgga ggtgctctgg gcaccgaggt   120
gctggcgaac caaacaagta tcaccccgga cgcctgcccc cattccgaga gagcgggcgg   180
gatgccaca ggcttgattg ctgtaagttg aacacgtcag tggcatgggc accagctgca    240
caaccctagg agccaccaaa cacagtatat tctatataaa tgttgctgcc aggagcccca   300
gttcaaacta caatatggag ttttgctctt ttttgcccag gctggagtgc gatggcacaa   360
tcttggctca ctgcaacctc cacctcttgg gttcaagcaa tgcttctgcc tcagcctccc   420
aagtagctgg gattacagag acagggtttc accatgttgg aaggccggg cacctgacct    480
caagtgatct gcccgcctca gcctgccaaa accctgagag atggttggtg ccatgtggaa   540
ggtgattgtt tcgctggtcc tgttgatgcc tggcccctgt gatgggctgt ttcgctccct   600
atacagaagt gtttccatgc cacctaaggg agactcagga cagccattat ttctcacccc   660
ttacattgaa gctgggaaga tccaaaaagg aagagaattg agtttggtcg gcccttttcc   720
aggactgaac atgaagagtt atgccggctt cctcaccgtg aataagactt acaacagcaa   780
cctcttcttc tggttcttcc cagctcagat acagccagaa gatgccccag tagttctctg   840
gctacagggt gggccgggag gttcatccat gtttggactc tttgtggaac atgggcctta   900
tgttgtcaca agtaacatga ccttgcgtga cagagacttc ccctgaccca aacgctctc    960
catgctttac attgacaatc cagtgggcac aggcttcagt tttactgatg ataccccacgg  1020
atatgcagtc aatgaggacg atgtagcacg ggatttatac agtgcactaa ttcagttttt  1080
ccagatattt cctgaatata aaaataatga cttttatgtc actggggagt cttatgcagg  1140
gaaatatgtg ccagccattg cacacctcat ccattccctc aaccctgtga gagaggtgaa  1200
gatcaacctg aacggaattg ctattggaga tggatattca gatcccgaat caattatagg  1260
gggctatgca gaattcctgt accaaattgg cttgttggat gagaagcaaa aaaagtactt  1320
ccagaagcag tgccatgaat gcatagaaca catcaggaag cagaactggt ttgaggcctt  1380
tgaaatactg ataaactac tagatggcga cttaacaagt gatccttctt acttccagaa   1440
tgttacagga tgtagtaatt actataactt tttgcggtgc acggaacctg aggatcagct  1500
ttactatgtg aaattttttgt cactcccaga ggtgagacaa gccatccacg tgggaatca   1560
gacttttaat gatggaacta tagttgaaaa gtacttgcga gaagatacag tacagtcagt  1620
taagccatgt ttaactgaaa tcatgaataa ttataaggtt ctgatctaca atggccaact  1680
ggacatcatc gtgcagctg ccctgacaga gcgctccttg atgggcatgg actggaaagg   1740
atcccaggaa tacaagaagg cagaaaaaaa agtttggaag atctttaaat ctgacagtga  1800
agtggctggt tacatccggc aagcgggtga cttccatcag gtaattattc gaggtggagg  1860
acatattta ccctatgacc agcctctgag agcttttgac atgattaatc gattcattta   1920
tggaaaagga tgggatcctt atgttggata aactaccttc ccaaaagaga acatcagagg  1980
ttttcattgc tgaaaagaaa atcgtaaaaa cagaaatgtg catagaaata aaaaattat   2040
cttttcatat ctgcaagatt ttttttcatca ataaaaatta tccttgaaac aagtgagctt  2100
ttgttttgg ggggagatgt ttactacaaa attaacatga gtacatgagt aagaattaca   2160
ttatttaact taaggatga aaggtatgga tgatgtgaca ctgagacaag atgtataaat   2220
gaatttttag ggtcttgaat aggaaagtttt aatttcttct aagagtaagt gaaaagtgca   2280
gttgtaacaa acaaagctgt aacatctttt tctgccaata acagaagttt ggcatgccgt   2340
gaaggtgttt ggaaatatta ttggataaga atagctcaat tatcccaaat aaatggatga   2400
agctataata gttttgggga aaagattctc aaatgtataa agtcttagaa caaaagaatt   2460
ctttgaaata aaatattat atataaaagt aatgatgagt caattcttga taagcagatg   2520
ctcttatgca gagaacaaac ttaatctttg cctttttcatt ttcttttttcc ttctttgagt  2580
ttgaggtgta cacacttctg aaagagcctg caggctacat tagttataag agccatttta   2640
atttgggctt caaattctct acttcttttc cccaaataaa gaacaaccta attttgtatc   2700
attgttagaa tatcaaaaaa aattaagata agctggcatc aatatataca tttataaata   2760
tacattcatt agcagttttc tgactaaat gtcacatcct ggcacatctt ttcgatttat   2820
gcatcatgtg ctcacatctc tgaaattcta caagacgtgt ggattttttcc acatcacttc  2880
cttctcatat tacccatcta tgaactggct cactggagaa ttaaatttaa aaagtcaaag   2940
cctgttcttg cggcaaatag tttatggagt ttattctttt aatttctcat gttgtgcctg   3000
attacgttca ggtttgtgat cttccttttt aaattgttca ttgtacccat gtcctagaag   3060
tcattaaatc aaatattctg atcaaaa                                      3087

SEQ ID NO: 41           moltype = DNA   length = 2418
FEATURE                 Location/Qualifiers
source                  1..2418
                        mol_type = genomic DNA
                        organism = Homo sapiens
SEQUENCE: 41
gcttttcgct cgctgcactc caagccccgg aacacccgcg tccgcacact aagggcacca    60
ccgctctccc acctctgcgc tgtcagatgt caggcgcgga ggtgctctgg gcaccgaggt   120
gctggcgaac caaacaagta tcaccccgga cgcctgcccc cattccgaga gagcgggcgg   180
gatgccaca ggcttgattg ctgtaagttg aacacgtcag tggcatgggc accagctgca    240
caaccctagg agccaccaaa cacagtatat tctatataaa tgttgctgcc aggagcccca   300
gttcaaacta caataccctg agagatggtt ggtgccatgt ggaaggtgat tgtttcgctg   360
gtcctgttga tgcctggccc ctgtgatggg ctgtttcgct ccctatacag aagtgttttcc  420
atgccaccta agggagactc aggacagcca ttatttctca ccccttacat tgaagctggg   480
aagatccaaa aaggaagagaa ttgagtttggtcg gcccagtagt ctctggctac agggtgggcc  540
gggaggttca tccatgtttg gactcttttgt ggaacatggg ccttatgttg tcacaagtaa    600
catgaccttg cgtgacagag acttcccctg acccaacg ctctccatgc tttacattga     660
caatccagtg ggcacaggct tcagtttac tgatgatacc cacggatatg cagtcaatga   720
ggacgatgta gcacgggatt tatacagtgc actaattcag ttttttccaga tatttcctga  780
atataaaat aatgactttt atgtcactgg ggagtcttat gcagggaaat atgtgccagc   840
cattgcacac ctcatccatt ccctcaaccc tgtgagagag tcaaccatccac gtgggaatc  900
agacttttaa tgatggaact atagttgaaa gtacttgcg agaagataca gtacagtcag   960
ttaagccatg gttaactgaa atcatgaata attataaggt tctgatctac aatggccaac   1020
cgtgcagctg ccctgacag agcgctcctt gatgggcatg actggaaag atcccagga     1080
atacaagaag gcagaaaaaa aagtttggaa gatctttaaa tctgacagtg aagtggctgg   1140
```

-continued

```
ttacatccgg caagcgggtg acttccatca ggtaattatt cgaggtggag gacatatttt    1200
accctatgac cagcctctga gagcttttga catgattaat cgattcattt atggaaaagg    1260
atgggatcct tatgttggat aaactacctt cccaaaagag aacatcagag gttttcattg    1320
ctgaaaagaa aatcgtaaaa acagaaaatg tcataggaat aaaaaaatta tcttttcata    1380
tctgcaagat ttttttcatc aataaaaatt atccttgaaa caagtgagct tttgtttttg    1440
gggggagatg tttactacaa aattaacatg agtacatgag taagaattac attatttaac    1500
ttaaaggatg aaaggtatgg atgatgtgac actgagacaa gatgtataaa tgaaattta    1560
gggtcttgaa taggaagttt taatttcttc taagagtaag tgaaaagtgc agttgtaaca    1620
aacaaagctg taacatcttt ttctgccaat aacagaagtt tggcatgccg tgaaggtgtt    1680
tggaaatatt attggataag aatagctcaa ttatcccaaa taaatggatg aagctataat    1740
agttttgggg aaaagattct caaatgtata aagtcttaga acaaaagaat tctttgaaat    1800
aaaaatatta tatataaaag taatgatgag tcaattcctg ataagcagat gctcttatgc    1860
agagaacaaa cttaatcttt gccttttcat tttcttttc cttctttgag tttgaggtgt    1920
acacacttct gaaagagcct gcaggctaca ttagttataa gagccatttt aatttgggct    1980
tcaaattctc tacttctttt ccccaaataa agaacaacct aattttgtat cattgttaga    2040
atatcaaaaa aaattaagat aagctggcat caatatatac atttataaat atacattcat    2100
tagcagtttt ctgactaaaa tgtcacatcc tggcacatct tttcgattta tgcatcatgt    2160
gctcacatct ctgaaattct acaagacgtg tggattttc cactcactt cctctcata     2220
ttacccatct atgaactggc tcactggaga attaaattta aaaagtcaaa gcctgttctt    2280
gcggcaaata gtttatggag tttattcttt taatttctca tgttgtgcct gattacgttc    2340
aggtttgtga tcttccttt taaattgttc attgtaccca tgtcctagaa gtcattaaat    2400
caaatattct gatcaaaa                                                 2418

SEQ ID NO: 42         moltype = DNA  length = 2179
FEATURE               Location/Qualifiers
source                1..2179
                      mol_type = genomic DNA
                      organism = Homo sapiens
SEQUENCE: 42
gtgactgggt ggggctgcct cacttctgcc tgatttggga agcgctgcaa ggacaaccgg    60
ctggggtcct tgcgcgccgc ggctcaggga ggagcaccga ctgcgccgcg taagtgccgc    120
ctgccctgcg tgggtcgtgc cagctcagcg ggacaggtcc tcgcctcggt ccctcggact    180
tagggagcgc ggggcagacc ctgagagatg gttggtgcca tgtggaaggt gattgtttcg    240
ctggtcctgt tgatgcctgg cccctgtgat gggctgtttc cctccctata cagaagtgtt    300
tccatgccac ctaaggagag ctcaggacag ccattatttc tcacccctta cattgaagct    360
gggaagatcc aaaaaggaag agaattgagt ttggtcggcc cttccccagg actgaacatg    420
aagagttatg ccggcttcct caccgtgaat aagacttaca acagcaacct cttcttctgg    480
ttcttcccag ctcagataca gccagaagat gccccagtag ttctctggct acagggtggg    540
ccgggaggtt catccatgtt tggactcttt gtggaaacgt ggccttatgt tgtcacaagt    600
aacatgacct tgcgtgacag agacttcccc tggaccacaa cgctctccat gctttacatt    660
gacaatccag tgggcacagg cttcagtttt actgatgata cccacggata tgcagtcaat    720
gaggacgatg tagcacggga tttatacagt gcactaattc agttttttcca gatatttcct    780
gaatataaaa ataatgactt ttatgtcact ggggagtctt atgcagggaa atatgtgcca    840
gccattgcac acctcatcca ttccctcaac cctgtgagag aggtgaagat caacctgaac    900
ggaattgcta ttggagatgg atattctgat cccgaatcaa ttataggggg ctatgcagaa    960
ttcctgtacc aaattggctt gttggatgag aagcaaaaaa agtacttcca gaagcagtgc    1020
catgaatgca tagaacacat caggaagcag aactggtttg aggcctttga aatactggat    1080
aaactactag atgcgacttt aacaagtgat ccttcttact tccagaatgt tacaggatgt    1140
agtaattact ataacttttt gcggtgcacg gaacctgagg atcagcttta ctatgtgaaa    1200
tttttgtcac tcccagaggt gagacaagcc atccacgtgg ggaatcagac ttttaatgat    1260
ggaactatag ttgaaagta cttgcgagaa gatacagtac agtcagttaa gccatggtta    1320
actgaaatca tgaataatta taggttctgt atctacaatg gccaactgga catcatcgtg    1380
gcagctgccc tgacagagcg ctccttgatg ggcatggact ggaaaggatc ccaggaatac    1440
aagaaggcag aaaaaaagt ttggaagatc tttaaatctg acagtgaagt ggctggttac    1500
atccggcaag cgggtgactt ccatcaggta attattcgag gtggaggaca tattttaccc    1560
tatgaccagc ctctgagagc ttttgacatg attaatcgat tcatttatgg aaaaggatgg    1620
gatccttatg ttggataaac taccttccca aagagaaca tcagaggttt tcattgctga    1680
aaagaaaatc gtaaaacag aaaatgtcat aggaataaaa aattatctt ttcatatctg    1740
caagatttt ttcatcaata aaaattatcc ttgaaacaag tgagctttg ttttggggg    1800
gagatgttta ctacaaaatt aacatgagta catgagtaag aattacatta tttaacttaa    1860
aggatgaaag gtatgatga tgtgacactg agacaagatg tataaatgaa attttagggt    1920
cttgaatagg aagttttaat ttcttctaag agtaagtgaa agtgcagtt gtaacaaaca    1980
aagctgtaac atctttttct gccaataaca gaagtttggc atgccgtgaa ggtgtttga    2040
aatattattg gataagaata gctcaattat cccaaatgg tgatgaagc tataagtt    2100
ttggggaaaa gattctcaaa tgtataagt cttagaacaa aagaattctt tgaaataaaa    2160
atattatata taaaagtaa                                                2179

SEQ ID NO: 43         moltype = DNA  length = 2608
FEATURE               Location/Qualifiers
source                1..2608
                      mol_type = genomic DNA
                      organism = Homo sapiens
SEQUENCE: 43
aaacaaagaa aatcaagtct gcgaggagcg agggtttgct cccctctgct ccggatttgg    60
gtgtccaggg tagcgggcgc ggcacggcaa acaggtcggg gcgctctgct tcaccccaac    120
cttctccgcc ccgccagccc ccgctccagc tgcgccagaa agtgcgagcc tgcccgctcc    180
tttcgctttt cgctcgctgc actccaagcc ccggaacacc cgcgtccgca cactaagggc    240
accaccgctc tcccacctct gcgctgtcag atgtcaggcg cggaggtgct ctgggcaccg    300
aggtgctggc gaaccaaaca agtatcaccc cggacgcctg cccccattcc gagagagcgg    360
```

```
gcgggatggc cacagatcca aacggaaaca ttggctcttc ctggggttcc agcctgctgt    420
cttgacagga actataccat cagctctcct gggtctctta catgccaagt catcctgcag    480
atctgggact cactccgtaa tcagcttgat tgctgtaagt tgaacacgtc agtggcatgg    540
gcaccagctg cacaaccca ggagccacca aacacagtat attctatata aatgttgctg    600
ccaggagccc cagttcaaac tacaataccc tgagagatgg ttggtgccat gtggaaggtg    660
attgtttcgc tggtcctgtt gatgcctggc ccctgtgatg ggctgtttcg ctccctatac    720
agaagtgttt ccatgccacc taagggagac tcaggacagc cattatttct cacccttac    780
attgaagctg ggaagatcca aaaggaaga gaattgagtt tggtcggccc tttcccagga    840
ctgaacatga agagttatgc cggcttcctc accgtgaata agacttacaa cagcaacctc    900
ttcttctggt tcttcccagc tcagatacag ccagaagatg cccagtagt tctctggcta    960
cagggtgggc cggaggttc atccatgttt ggactctttg tggaacatgg gccttatgtt   1020
gtcacaagta acatgacctt gcgtgacaga gacttcccct ggaccacaac gctctccatg   1080
cttacattg acaatccagt gggcacaggc ttcagttta ctgatgatac ccacggatat    1140
gcagtcaatg aggacgatgt agcacgggat ttatacagtg cactaattca gtttttccag   1200
atatttcctg aatataaaa taatgacttt tatgtcactg gggagtctta tgcagggaaa   1260
tatgtgccag ccattgcaca cctcatccat tccctcaacc ctgtgagaga ggtgaagatc   1320
aacctgaacg gaattgctat tggagatgga tattctgatc ccgaatcaat tatagggggc   1380
tatgcagaat tcctgtacca aattggcttg ttggatgaga agcaaaaaa gtacttccag   1440
aagcagtgcc atgaatgcat agaacacatc aggaagcaga actggtttga ggcctttgaa   1500
atactggata aactactaga tggcgactta acaagtgatc cttcttactt ccagaatgtt   1560
acaggatgta gtaattacta aactttttg cggtgcacgg aacctgagga tcagctttac   1620
tatgtgaaat ttttgtcact cccagaggtg agacaagcca tccacgtgtg ggaatcagact   1680
tttaatgatg gaactatagt tgaaagtac ttgcgagaag atacagtaca gtcagttaag   1740
ccatggttaa ctgaaatcat gaataattat aaggttctga tctacaatgg ccaactggac   1800
atcatcgtgg cagctgccct gacagagcgc tccttgatgg gcatggactg gaaaggatcc   1860
caggaataca agaaggcaga aaaaaaagtt tggaagatct ttaaatctga cagtgaagtg   1920
gctggttaca tccggcaagc gggtgacttc catcaggtaa ttattcgagg tggaggacat   1980
attttaccct atgaccagcc tctgagagct tttgacatga ttaatcgatt catttatgga   2040
aaaggatggg atccttatgt tggataaact accttcccaa aagagaacat cagaggtttt   2100
cattgctgaa aagaaaatcg taaaaacaga aaatgtcata aaaaaaaa aattatcttt   2160
tcatatctgc aagatttttt tcatcaataa aaattatcct tgaaacaagt gagcttttgt   2220
ttttgggggg agatgtttac tacaaaatta acatgagtac atgagtaaga attacattat   2280
ttaacttaaa ggatgaaagg tatggatgat gtgacactga acaagatgt ataaatgaaa   2340
ttttagggtc ttgaatagga agttttaatt tcttctaaga gtaagtgaaa agtgcagttg   2400
taacaaacaa agctgtaaca tctttttctg ccaataacag aagtttggca tgccgtgaag   2460
gtgtttggaa atattattgg ataagaatag ctcaattatc ccaaataaat ggatgaagct   2520
ataatagttt tggggaaaag attctcaaat gtataaagtc ttagaacaaa agaattcttt   2580
gaaataaaaa tattatatat aaaagtaa                                     2608

SEQ ID NO: 44         moltype = DNA   length = 2480
FEATURE               Location/Qualifiers
source                1..2480
                      mol_type = genomic DNA
                      organism = Homo sapiens
SEQUENCE: 44
aaacaaagaa aatcaagtct gcgaggagcg agggtttgct ccctctgct ccggatttgg     60
gtgtccaggg tagcgggcgc ggcacggcaa acaggtcggg gcgctctgct tcaccccaac   120
cttctccgcc ccgccagccc ccgctccagc tgccgcagaa agtgcgagcc tgcccgctcc   180
tttcgctttt cgctcgctgc actccaagcc ccggaacacc cgcgtccgca cactaagggc   240
accaccgctc tcccacctct gcgctgtcag atgtcaggcg cggaggtgct ctgggcaccg   300
aggtgctggc gaaccaaaca agtatccacc cggacgcgtc cccccattcc gagagagcgg   360
gcgggatggc cacaggcttg attgctgtaa gttgaacacg tcagtggcat gggcaccagc    420
tgcacaaccc taggagccac caaacacagt atattctata taaatgttgc tgccaggagc    480
cccagttcaa actacaatac cctgagagat ggttggtgcc atgtgaagg tgattgtttc    540
gctggtcctg ttgatgcctg gcccctgtga tgggctgttt cgctccctat acagaagtgt    600
ttccatgcca cctaagggag actcaggaca gccattattt ctcacccctt acattgaagc    660
tgggaagatc caaaaggaa gagaattgag tttggtcggc cctttcccag gactgaacat    720
gaagagttat gccggcttcc tcaccgtgaa taagacttac aacagcaacc tcttcttctg    780
gttcttccca gctcagatac agccagaaga tgccccagta gttctctggc tacagggtgg    840
gccgggaggt tcatccatgt ttggactctt tgtggaacat gggccttatg ttgtcacagg    900
taacatgacc ttgcgtgaca gagacttccc ctggaccaca acgctctcca tgctttacat    960
tgacaatcca gtgggcacag gcttcagttt tactgatgat acccacggat atgcagtcaa   1020
tgaggacgat gtagcacggg atttatacag tgcactaatt cagttttttcc agatatttcc   1080
tgaatataaa aataatgact tttatgtcac tggggagtct tatgcaggga aatatgtgcc   1140
agccattgca cacctcatcc attccctcaa cctgtgaga gaggtgaaga tcaacctgaa   1200
cggaattgct attggagatg gatattctga tcccgaatca attataggg gctatgcaga   1260
attcctgtac caaattggct tgttggatga gaagcaaaaa aagtacttcc agaagcagtg   1320
ccatgaatgc atagaacaca tcaggaagca gaactggttt gaggcctttg aaatactgga   1380
taaactacta gatggcgact taacaagtga tccttcttac ttccagaatg ttacaggatg   1440
tagtaattac tataactttt tgcggtgcac ggaacctgag gatcagcttt actatgtgaa   1500
attttttgtca ctcccagagg tgagacaagc catccacgtg gggaatcaga cttttaatga   1560
tggaactata gttgaaaagt acttgcgaga agatacagta cagtcagtta agccatggtt   1620
aactgaaatc atgaataatt ataaggttct gatctacaat ggccaactgg acatcatcgt   1680
ggcagctgcc ctgacagagc gctccttgat gggcatggac tggaaaggat cccaggaata   1740
caagaaggca gaaaaaaag tttgaagat ctttaaatct gacagtgaag tggctggtta    1800
catccggcaa gcgggtgact tccatcaggt aattattcga ggtggaggac atattttacc   1860
ctatgaccag cctctgagag cttttgacat gattaatcga ttcatttatg gaaaaggatg   1920
ggatccttat gttggataaa ctaccttccc aaaagagaac atcagaggtt tcattgctg   1980
aaaagaaaat cgtaaaaaca gaaaatgtca taggaataaa aaaattatct tttcatatct   2040
```

```
gcaagattttt tttcatcaat aaaaattatc cttgaaacaa gtgagctttt gttttttgggg    2100
ggagatgttt actacaaaat taacatgagt acatgagtaa gaattacatt atttaactta    2160
aaggatgaaa ggtatggatg atgtgacact gagacaagat gtataaatga aattttaggg    2220
tcttgaataG gaagttttaa tttcttctaa gagtaagtga aaagtgcagt tgtaacaaac    2280
aaagctgtaa catcttttc tgccaataac agaagtttgg catgccgtga aggtgtttgg    2340
aaatattatt ggataagaat agctcaatta tcccaaataa atggatgaag ctataatagt    2400
tttggggaaa agattctcaa atgtataaag tcttagaaca aaagaattct ttgaaataaa    2460
aatattatat ataaaagtaa                                                2480
```

| SEQ ID NO: 45 | moltype = DNA length = 2021 |
|---|---|
| FEATURE | Location/Qualifiers |
| source | 1..2021 |
| | mol_type = genomic DNA |
| | organism = Homo sapiens |

SEQUENCE: 45
```
gcggctcagg gaggagcacc gactgcgccg caccctgaga gatggttggt gccatgtgga    60
aggtgattgt ttcgctggtc ctgttgatgc ctggcccctg tgatgggctg tttcgctccc    120
tatacagaag tgtttccatg ccacctaagg gagactcagg acagccatta tttctcaccc    180
cttacattga agctgggaag atccaaaaag gaagagaatt gagtttggtc ggcccttttcc   240
caggactgaa catgaagagt tatgccggct cctcaccgt gaataagact tacaacagca    300
acctcttctt ctgttcttc ccagctcaga tacagccaga gatgcccca gtagttctct    360
ggctacaggg tgggccggga ggttcatcca tgtttggact ctttgtggaa catgggcctt    420
atgttgtcac aagtaacatg accttgcgtg acagagactt ccctggacc acaacgctct    480
ccatgcttta cattgacaat ccagtggca caggcttcag ttttactgat gatacccacg    540
gatatgcagt caatgaggac gatgtagcac gggatttata cagtgcacta attcagtttt    600
tccagatatt tcctgaatat aaaaataatg acttttatgt cactgggag tcttatgcag    660
ggaaatatgt gccagccatt gcacacctca tccattccct caaccctgtg agagaggtga    720
agatcaacct gaacggaatt gctattgag atggatattc tgatcccgaa tcaattatag    780
ggggctatgc agaattcctg taccaaattg gcttgttgga tgagaagcaa aaaaagtact    840
tccagaagca gtgccatgaa tgcatagaac acatcaggaa gcagaactgg tttgaggcct    900
ttgaaatact ggataaacta ctagatggcg acttaacaag tgatccttct tacttccaga    960
atgttacagg atgtagtaat tactataact ttttgcggtg cacggaacct gaggatcagc    1020
tttactatgt gaaattttg tcactcccag aggtgagaca agccatccac gtggggaatc    1080
agacttttaa tgatgaact atagttgaaa gtacttgcg agaagataca gtacagtgga    1140
ttaagccatg gttaactgaa atcatgaata attataagt tctgatctac aatgccaac    1200
tggacatcat cgtggcagct gccctgacag agcgctcctt gatgggcatg gactggaaag    1260
gatcccagga atacaagaag gcagaaaaaa agtttggaa gatctttaaa tctgacagtg    1320
aagtggctgg ttacatccgg caagcgggtg acttccatca ggtaattatt cgaggtggag    1380
gacatatttt accctatgac cagcctctga gagcttttga catgattaat cgattcattt    1440
atggaaaagg atgggatcct tatgttggat aaactacctt cccaaaagag aacatcagag    1500
gttttcattg ctgaaaagaa aatcgtaaaa acagaaaatg tcataggaat aaaaaaatta    1560
tcttttcata tctgcaagat ttttttcatc aataaaaatt atccttgaaa caagtgagct    1620
tttgtttttg gggggagatg tttactacaa aattaacatg agtacatgg taagaattac    1680
attatttaac ttaaaggatg aaaggtatgg atgatgtgac actgagacaa gatgtataaa    1740
tgaaatttta gggtcttgaa taggaagttt taatttcttc taagagtaag tgaaaagtgc    1800
agttgtaaca aacaaagctg taacatcttt ttctgccaat aacagaagtt tggcatgccg    1860
tgaaggtgtt tggaaatatt attggataag aatagctcaa ttatcccaaa taaatggatg    1920
aagctataat agtttttggg aaaagattct caaatgtata aagtcttaga acaaaagaat    1980
tctttgaaat aaaaatatta tatataaaag taaaaaaaaa a                       2021
```

| SEQ ID NO: 46 | moltype = DNA length = 1581 |
|---|---|
| FEATURE | Location/Qualifiers |
| source | 1..1581 |
| | mol_type = genomic DNA |
| | organism = Homo sapiens |

SEQUENCE: 46
```
gagagatggt tggtgccatg tggaaggtga ttgtttcgct ggtcctgttg atgcctggcc    60
cctgtgatgg gctgtttcgc tccctataca gaagtgtttc catgccacct aagggagact    120
caggacagcc attatttctc accccttaca ttgaagctgg ggagatccaa aaaggaagag    180
aattgagttt ggtcggccct tttccaggac tgaacatgaa gagttatgcc ggcttcctca    240
ccgtgaataa gacttacaac agcaacctct cttctggtt cttcccagct cagatacagc    300
cagaagatgc cccagtagat tctctggcta cagggtggc cggaggttc atccatgttt    360
ggactctttg tggaacatgg gccttatgtt gtcacaagta acatgacctt gcgtgacaga    420
gacttcccct ggaccacaac gctctccatg ctttacattg acaatccagt gggcaggct    480
tcagtttta ctgatgatac ccacggatat gcagtcaatg aggacgatgt agcacgggat    540
ttatacagtg cactaattca gttttttccag atatttctg aatataaaa taatgacttt    600
tatgtcactg gggagtctta tgcagggaaa tatgtgccag ccattgcaca cctcatccat    660
tccctcaacc ctgtgagaga ggtgaagatc aacctgaacg gaattgctat tggagatgga    720
tattctgatc ccgaatcaat tatagggggc tatgcagaat tcctgtacca aattggcttg    780
ttggatgaga agcaaaaaaa gtacttccag aagcagtgcc atgaatgcat agaacacatc    840
aggaagcaga actggtttga ggcctttgaa atactggata aactactaga tggcgactta    900
acaagtgatc cttcttactt ccagaatgtt acaggatgta gtaattacta taactttttg    960
cggtgcacgg aacctgagga tcagctttac atgtgaaat ttttgtcact cccagaggtg    1020
agacaagcca tccacgtgg gaatcagac tttaatgatg aaacttaagg aagatacagt    1080
acagtgatt aagccatggt taactgaaat catcgtggc agctgccc tgacagcg    1140
ctccttgatg ggcatggact ggaaaggatc ccaggaatac aagaaggcag aaaaaaagt    1260
ttggaagatc tttaaatctg acagtgaagt ggctggttac atccgcaag tgggtgactt    1320
ccatcaggta attattcgag gtggaggaca tattttaccc tatgaccagc ctctgagagc    1380
```

```
ttttgacatg attaatcgat tcatttatgg aaaaggatgg gatccttatg ttggataaac  1440
taccttccca aaagagaaca tcagaggttt tcattgctga aaagaaaatc gtaaaaacag  1500
aaaatgtcat aggaataaaa aaattatctt tcatatctg  caagattttt ttcatcaata  1560
aaaattatcc ttgaaaaaaa a                                            1581

SEQ ID NO: 47           moltype = DNA   length = 1638
FEATURE                 Location/Qualifiers
source                  1..1638
                        mol_type = genomic DNA
                        organism = Homo sapiens
SEQUENCE: 47
ggacaaccgg ctggggtcct tgcgcgccgc ggctcaggga ggagcaccga ctgcgccgca   60
ccctgagaga tggttggtgc catgtggaag gtgattgttt cgctggtcct gttgatgcct  120
ggcccctgtg atgggctgtt tcactcccta tacagaagtg tttccatgcc acctaaggga  180
gactcaggac agccattatt tctcacccct tacattgaag ctgggaagat ccaaaaagga  240
agagaattga gtttggtcgg cccttttccca ggactgaaca tgaagagtta tgccggcttc  300
ctcaccgtga ataagactta caacagcaac ctcttcttct ggttcttcc  agctcagata  360
cagccagaag atgccccagt agttctctg  ctacagggtg ggccgggagg ttcatccatg  420
tttggactct ttgtggaaca tgggccttat gttgtcacaa gtaacatgac cttgcgtgac  480
agagacttcc cctggaccac aacgctctcc atgctttaca ttgacaatcc agtgggcaca  540
ggcttcagtt ttactgatga tacccacgga tatgcagtca atgaggacga tgtagcacgg  600
gatttataca gtgcactaat tcagtttttc cagatatttc ctgaatataa aaataatgac  660
ttttatgtca ctggggagtc ttatgcaggg aaatatgtgc cagccattgc acacctcatc  720
cattccctca accctgtgag agaggtgaag atcaacctga acggaattgc tattggagat  780
ggatattctg atcccgaatc aattataggg gctatgcag  aattcctgta ccaaattggc  840
ttgttggatg agaagcaaaa aaagtacttc cagaagcagt gccatgaatg catagaacac  900
atcaggaagc agaactggct tgaggccttt gaaatactgg ataaactact agatggcgac  960
ttaacaagtg atccttctta cttccagaat gttacaggat gtagtaatta ctataacttt  1020
ttgcggtgca cggaacctga ggatcagctt tactatgtga aatttttgtc actcccagag  1080
gtgagacaag ccatccacgt ggggaatcag acttttaatg atggaactat agttgaaaag  1140
tacttgcgag aagatacagt acagtcagtt aagccatggt taactgaaat catgaataat  1200
tataaggttc tgatctacaa tggccaactg gacatcatcg tggcagctgc cctgacagag  1260
cactccttga tgggcatgga ctggaaagga tcccaggaat acaagaaggc agaaaaaaaa  1320
gtttggaaga tccttaaatc tgacagtgaa gtggctggtt acatccggca agcgggtgac  1380
tcccatcagg taattattcg aggtggagga catatttac  cctatgacca gcctctgaga  1440
gcttttgaca tgattaatcg attcatttat ggaaaaggat gggatcctta tgttggataa  1500
actaccttcc gaaagagaaa catcagaggt tttcattgct gaaagaaaaa tcgtaaaaac  1560
agaaaatgtc ataggaataa aaaattatc  ttttcatatc tgcaagattt ttttcatcaa  1620
taaaaattat ccttgaaa                                                1638

SEQ ID NO: 48           moltype = DNA   length = 1672
FEATURE                 Location/Qualifiers
source                  1..1672
                        mol_type = genomic DNA
                        organism = Homo sapiens
SEQUENCE: 48
aggacaaccg gctggggtcc ttgcgcgccg cggctcaggg aggagcaccg actgcgccgc   60
accctgagag atggttggtg ccatgtggaa ggtgattgtt tcgctggtcc tgttgatgcc  120
tggcccctgt gatgggctgt ttcgctccct atacagaagt gtttccatgc cacctaaggg  180
agactcagga cagccattat ttctcacccc ttacattgaa gctgggaaga tccaaaaagg  240
aagagaattg agtttggtcg gcccttttcc aggactgaac atgaagagtt atgccggctt  300
cctcaccgtg aataagactt acaacagcaa cctcttcttc tggttcttcc cagctcagat  360
acagccagaa gatgccccag tagttctctg gctacagggt gggccgggag gttcatccat  420
gtttggactc tttgtggaac atgggcctta tgttgtcaca agtaacatga ccttgcgtga  480
cagagacttc cctggacca  aacgctctc  atgctttac  attgacaatc agtgggcac   540
aggcttcagt tttactgatg atacccacgg atatgcagtc aatgaggacg atgtagcacg  600
ggatttatac agtgcactaa ttcagttttt ccagatattt cctgaatata aaaataatga  660
cttttatgtc actggggagt cttatgcagg gaaatatgtg ccagccattg cacacctcat  720
ccattccctc aaccctgtga gagaggtgaa gatcaacctg aacggaattg ctattggaga  780
tggatattct gatcccgaat caattatagg ggctatgcag aattcctgt  accaaattgg  840
cttgttggat gagaagcaaa aaagtactt  ccagaagcag tgccatgaat gcatagaaca  900
catcaggaag cagaactggt tgaggcctt  tgaaatactg gataaactac tagatggcga  960
cttaacaagt gatccttctt acttccagaa tgttacagga tgtagtaatt actataactt  1020
tttgcggtgc acggaacctg aggatcagct ttactatgtg aaatttttgt cactcccaga  1080
ggtgagacaa gccatccacg tggggaatca gacttttaat gatggaacta gttgaaaa    1140
gtacttgcga agatacag   tacagtcagt taagccatgg ttaactgaaa tcatgaataa  1200
ttataaggtt ctgatctaca atggccaact ggacatcatc gtggcagctg ccctgacaga  1260
gcactccttg atgggcatgg actggaaagg atcccaggaa tacaagaagg cagaaaaaaa  1320
agtttggaag atctttaaat ctgacagtga agtggctggt tacatccggc aagcgggtga  1380
cttccatcag gtaattattc gaggtggagg acatatttta cctatgacc  agcctctgag  1440
agcttttgac atgattaatc gattcattta tggaaaagga tgggatcctt atgttggata  1500
aactaccttc cgaaagaga  acatcagagg ttttcattgc tgaaagaaa  atcgtaaaa   1560
acagaaaatg tcataggaat aaaaaattat cttttcatat ctgcaagatt ttttcatca   1620
ataaaaatta ccttgaaaa  aaaaaaaaaa aaaaaaaaa  aaaaaaaa aa            1672
```

```
SEQ ID NO: 49           moltype = DNA  length = 1772
FEATURE                 Location/Qualifiers
source                  1..1772
                        mol_type = genomic DNA
                        organism = Homo sapiens
SEQUENCE: 49
agcgctgcaa ggacaaccgg ctggggtcct tgcgcgccgc ggctcaggga ggagcaccga    60
ctgcgccgcg taagtgccgc ctgccctgcg tgggtcgtgc cagctcagcg ggacaggtcc   120
tcgcctcggt ccctcggact tagggagcgt ggggcagacc ctgagagatg gttggtgcca   180
tgtggaaggt gattgtttcg ctggtcctgt tgatgcctgg ccctgtgat gggcgtgttc    240
gctccctata cagaagtgtt tccatgccac ctaagggaga ctcaggacag ccattatttc   300
tcaccccta cattgaagct gggaagatcc aaaaaggaag agaattgagt ttggtcggcc    360
ctttcccagg actgaacatg aagagttatg ccggcttcct caccgtgaat aagacttaca   420
acagcaacct cttcttctgg ttcttcccag ctcagataca gccagaagat gccccagtag   480
ttctctggct acagggtggg ccgggaggtt catccatgtt tggactcttt gtggaacatg   540
ggccttatgt tgtcacaagt aacatgacct tgcgtgacag agacttcccc tggaccacaa   600
cgctctccat gctttacatt gacaatccag tgggcacagg cttcagtttt actgatgata   660
cccacggata tgcagtcaat gaggacgatg tagcacggga tttatacagt gcactaattc   720
agtttttcca gatatttcct gaatatataa aaataatgact ttatgtcact ggggagtctt   780
atgcaggaa atatgtgcca gccattgcac acctcatcca ttccctcaac cctgtgagag    840
aggtgaagat caacctgaac ggaattgcta ttggagatgag atattctgat cccgaatcaa   900
ttataggggg ctatgcagaa ttcctgtacc aaattggctt gttggatgag aagcaaaaaa   960
agtacttcca gaagcagtgc catgaatgca tagaacacat caggaagcag aactggtttg  1020
aggccttga aatactggat aaactactag atggcgactt aacaagtgat ccttcttact  1080
tccagaatgt tacaggatgt agtaattact ataacttttt gcggtgcacg gaacctgagg  1140
atcagcttta ctatgtgaaa tttttgtcac tcccagaggt gagacaagcc atccacgtgg  1200
ggaatcagac ttttaatgat ggaactatag ttgaaaagta cttgcgagaa gatacagtac  1260
agtcagttaa gccatggtta actgaaatca tgaataatta taaggttctg atctacaatg  1320
gccaactgga catcatcgtg gcagctgccc tgacagagcg ctccttgatg ggcatggact  1380
ggaaaggatc ccaggaatac aagaaggcag aaaaaaaagt ttggaagatc tttaaatctg  1440
acagtgaagt ggctggttac atccggcaag tgggtgactt ccatcaggta attattcgag  1500
gtggaggaca tattttaccc tatgaccagc ctctgagagc ttttgacatg attaatcgat  1560
tcatttatgt aaaaggatgg gatccttatg ttggataaac taccttccca aaagagaaca  1620
tcagaggttt tcattgctga aaagaaaatc gtaaaaacag aaaatgtcat aggaataaaa  1680
aaattatctt ttcatatctg caagattttt ttcatcaata aaaattatcc ttgaaaaaa   1740
aaaaaaaaaa aaaaaaaaaa aa                                            1772

SEQ ID NO: 50           moltype = DNA  length = 1605
FEATURE                 Location/Qualifiers
source                  1..1605
                        mol_type = genomic DNA
                        organism = Homo sapiens
SEQUENCE: 50
ggctcaggga ggagcaccga ctgcgccgca ccctgagaga tggttggtgc catgtggaag    60
gtgattgtttt cgctggtcct gttgatgcct ggccctgtg atgggctgtt tcgctccta   120
tacagaagtg tttccatgcc acctaaggga gactcaggac agccattatt tctcacccct   180
tacattgaag ctgggaagat ccaaaaagga agagaattga gtttggtcgg cccttttcca   240
ggactgaaca tgaagagtta tgccggcttc ctcaccgtga ataagactta caacagcaac   300
ctcttcttct ggttcttccc agctcagata cagccagaag atgccccagt agttctctgg   360
ctacagggtg ggccggggag gttcatccat gtttggactc tttgtggaac atgggccttat  420
gttgtcacaa gtaacatgac cttgcgtgac agagacttcc cctggaccac aacgctctcc   480
atgctttaca ttgacaatcc agtgggcaca ggcttcagtt ttactgatga tacccacgga   540
tatgcagtca atgaggacga tgtagcacgg gatttataca gtgcactaat tcagtttttc   600
cagatatttc tgaatataaa aataatgact tttatgtca ctggggagtc ttatgcaggg    660
aaatatgtgc cagccattgc acacctcatc cattccctca accctgtgag agaggtgaag   720
atcaacctga acggaattgc tattggagat ggatattctg atcccgaatc aattataggg   780
ggctatgcag aattcctgta ccaaattggc ttgttggatg agaagcaaaa aaagtacttc   840
cagaagcagt gccatgaatg catagaacac atcaggaagc agaactggct tgaggccttt   900
gaaatactgg ataaactact agatggcgac ttaacaagtg atccttctta cttccagaat   960
gttacaggat gtagtaatta ctataacttt ttgcggtgca cggaacctga ggatcagctt  1020
tactatgtga aatttttgtc actcccagag gtgagacaag ccatccacgt ggggaatcag  1080
acttttaatg atggaactat agttgaaaag tacttgcgag aagatacagt acagtcagtt  1140
aagccatggt taactgaaat catgaataat tataaggttc tgatctacaa tggccaactg  1200
gacatcatcg tggcagctgc cctgacagag cactccttga gggcatgga ctggaaagga  1260
tcccaggaat acaagaaggc agaaaaaaag ttttggaaga tctttaaatc tgacagtgaa  1320
gtggctggtt acatccggca agcgggtgac ttccatcagg taattattcg aggtggagga  1380
catatttttac cctatgacca gcctctgaga gcttttgaca tgattaatcg attcatttat  1440
ggaaaaggat gggatcctta tgttggataa actaccttcc caaaagagaa catcagaggt  1500
tttcattgct gaaaagaaaa tcgtaaaaac agaaaatgtc ataggaataa aaaaattatc  1560
ttttcatatc tgcaagattt ttttcatcaa taaaaattat ccttg                   1605

SEQ ID NO: 51           moltype = DNA  length = 1686
FEATURE                 Location/Qualifiers
source                  1..1686
                        mol_type = genomic DNA
                        organism = Homo sapiens
```

```
SEQUENCE: 51
ggtgactggg tggggctgcc tcacttctgc ctgatttggg aagcgctgca aggacaaccg    60
gctgggtcc ttgcgcgccg cggctcaggg aggagcaccg actgcgccgc accctgagag   120
atggttggtg ccatgtggaa ggtgattgtt tcgctggtcc tgttgatgcc tggcccctgt   180
gatgggctgt ttcgctccct atacagaagt gtttccatgc cacctaaggg agactcagga   240
cagccattat ttctcacccc ttacattgaa gctgggaaga tccaaaaagg aagagaattg   300
agtttggtcg gccctttccc aggactgaac atgaagagtt atgccggctt cctcaccgtg   360
aataagactt acaacagcaa cctcttcttc tggttcttcc cagctcagat acagccagaa   420
gatgccccag tagttctctg gctacagggt gggccgggag gttcatccat gtttggactc   480
tttgtggaac atgggcctta tgttgtcaca agtaacatga ccttgcgtga cagagacttc   540
ccctggacca caacgctctc catgcttaca attgacaatc cagtgggcac aggcttcagt   600
tttactgatg atacccacgg atatgcagtc aatgaggacg atgtagcacg ggatttatac   660
agtgcactaa ttcagttttt ccagatattt cctgaatata aaaataatga ctttatgtc    720
actggggagt cttatgcagg gaaatatgtg ccagccattg cacacctcat ccattccctc   780
aaccctgtga gagaggtgaa gatcaacctg aacggaattg ctattggaga tggatattct   840
gatcccgaat caattatagg gggctatgca gaattcctgt accaaattgg cttgttggat   900
gagaagcaaa aaaagtactt ccagaagcag tgccatgaat gcatagaaca catcaggaag   960
cagaactggt ttgaggccct tgaaaatactg gataaactac tagatggcga cttaacaagt  1020
gatccttctt acttccagaa tgttacagga tgtagtaatt actataactt tttgcggtgc  1080
acggaacctg aggatcagct ttactatgtg aaattttttgt cactcccaga ggtgagacaa  1140
gccatccacg tgggaatca gacttttaat gatggaacta tagttgaaaa gtacttgcga   1200
gaagatacag tacagtcagt taagcctatgg ttaactgaaa tacttgaata ttataaggtt  1260
ctgatctaca atggccaact ggacatcatc gtgcagctg ccctgacaga gcgctccttg   1320
atgggcatgg actgcaaagg atcccaggaa tacaagaagg cagaaaaaa agttggaag   1380
atctttaaat ctgacagtga agtggctggt tacatccggc aagtgggtga cttccatcag  1440
gtaattattc gaggtggagg acatatttta ccctatgacc agcctctgag agcttttgac  1500
atgattaatc gattcattta tggaaaagga tgggatcctt atgttggata aactaccttc  1560
ctaaaagaga acatcagagg ttttcattgc tgaaaagaaa atcgtaaaaa cagaaaatgt  1620
cataggaata aaaaaattat cttttcatat ctgcaagatt ttttttcatca ataaaaatta  1680
tccttg                                                              1686

SEQ ID NO: 52              moltype = AA   length = 476
FEATURE                    Location/Qualifiers
source                     1..476
                           mol_type = protein
                           organism = Homo sapiens
SEQUENCE: 52
MVGAMWKVIV SLVLLMPGPC DGLFRSLYRS VSMPPKGDSG QPLFLTPYIE AGKIQKGREL    60
SLVGPFPGLN MKSYAGFLTV NKTYNSNLFF WFFPAQIQPE DAPVVLWLQG GPGGSSMFGL   120
FVEHGPYVVT SNMTLRDRDF PWTTTLSMLY IDNPVGTGFS FTDDTHGYAV NEDDVARDLY   180
SALIQFFQIF PEYKNNDFYV TGESYAGKYV PAIAHLIHSL NPVREVKINL NGIAIGDGYS   240
DPESIIGGYA EFLYQIGLLD EKQKKYFQKQ CHECIEHIRK QNWFEAFEIL DKLLDGDLTS   300
DPSYFQNVTG CSNYYNFLRC TEPEDQLYYV KFLSLPEVRQ AIHVGNQTFN DGTIVEKYLR   360
EDTVQSVKPW LTEIMNNYKV LIYNGQLDII VAAALTERSL MGMDWKGSQE YKKAEKKVWK   420
IFKSDSEVAG YIRQAGDFHQ VIIRGGHIL PYDQPLRAFD MINRFIYGKG WDPYVG        476

SEQ ID NO: 53              moltype = AA   length = 406
FEATURE                    Location/Qualifiers
source                     1..406
                           mol_type = protein
                           organism = Homo sapiens
SEQUENCE: 53
MKSYAGFLTV NKTYNSNLFF WFFPAQIQPE DAPVVLWLQG GPGGSSMFGL FVEHGPYVVT    60
SNMTLRDRDF PWTTTLSMLY IDNPVGTGFS FTDDTHGYAV NEDDVARDLY SALIQFFQIF   120
PEYKNNDFYV TGESYAGKYV PAIAHLIHSL NPVREVKINL NGIAIGDGYS DPESIIGGYA   180
EFLYQIGLLD EKQKKYFQKQ CHECIEHIRK QNWFEAFEIL DKLLDGDLTS DPSYFQNVTG   240
CSNYYNFLRC TEPEDQLYYV KFLSLPEVRQ AIHVGNQTFN DGTIVEKYLR EDTVQSVKPW   300
LTEIMNNYKV LIYNGQLDII VAAALTERSL MGMDWKGSQE YKKAEKKVWK IFKSDSEVAG   360
YIRQAGDFHQ VIIRGGHIL PYDQPLRAFD MINRFIYGKG WDPYVG                   406

SEQ ID NO: 54              moltype = AA   length = 490
FEATURE                    Location/Qualifiers
source                     1..490
                           mol_type = protein
                           organism = Homo sapiens
SEQUENCE: 54
MVGAMWKVIV SLVLLMPGPC DGLFRSLYRS VSMPPKGDSG QPLFLTPYIE AGKIQKGREL    60
SLVGPFPGLN MKSYAGFLTV NKTYNSNLFF WFFPAQIQPE DAPVVLWLQG GPGGSSMFGL   120
FVEHGPYVVT SNMTLRDRDF PWTTTLSMLY IDNPVGTGFS FTDDTHGYAV NEDDVARDLY   180
SALIQFFQIF PEYKNNDFYV TGEHPFVIGH FNICPSQSYA GKYVPAIAHL IHSLNPVREV   240
KINLNGIAIG DGYSDPESII GGYAEFLYQI GLLDEKQKKY FQKQCHECIE HIRKQNWFEA   300
FEILDKLLDG DLTSDPSYFQ NVTGCSNYYN FLRCTEPEDQ LYYVKFLSLP EVRQAIHVGN   360
QTFNDGTIVE KYLREDTVQS VKPWLTEIMN NYKVLIYNGQ LDIIVAAALT ERSLMGMDWK   420
GSQEYKKAEK KVWKIFKSDS EVAGYIRQAG DFHQVIIRGG GHILPYDQPL RAFDMINRFI   480
YGKGWDPYVG                                                          490

SEQ ID NO: 55              moltype = AA   length = 298
FEATURE                    Location/Qualifiers
source                     1..298
```

-continued

```
                           mol_type = protein
                           organism = Homo sapiens
SEQUENCE: 55
MGCFAPYTEV FPCHLRETQD SHYFSPLTLK LGRSKKIQPE DAPVVLWLQG GPGGSSMFGL    60
FVEHGPYVVT SNMTLRDRDF PWTTTLSMLY IDNPVGTGFS FTDDTHGYAV NEDDVARDLY   120
SALIQFFQIF PEYKNNDFYV TGEEPEDQLY YVKFLSLPEV RQAIHVGNQT FNDGTIVEKY   180
LREDTVQSVK PWLTEIMNNY KVLIYNGQLD IIVAAALTER SLMGMDWKGS QEYKKAEKKV   240
WKIFKSDSEV AGYIRQAGDF HQVIIRGGGH ILPYDQPLRA FDMINRFIYG KGWDPYVG     298

SEQ ID NO: 56              moltype = AA   length = 233
FEATURE                    Location/Qualifiers
source                     1..233
                           mol_type = protein
                           organism = Homo sapiens
SEQUENCE: 56
MFGLFVEHGP YVVTSNMTLR DRDFPWTTTL SMLYIDNPVG TGFSFTDDTH GYAVNEDDVA    60
RDLYSALIQF FQIFPEYKNN DFYVTGESYA GKYVPAIAHL IHSLNPVREV KINLNGIAIG   120
DGYSDPESII GGYAEFLYQI GLLDEKQKKY FQKQCHECIE HIRKQNWFEA FEILDKLLDG   180
DLTSDPSYFQ NVTGCSNYYN FLRCTEPEDQ LYYVKFLSLP EVRQAIPRGE SDF          233

SEQ ID NO: 57              moltype = DNA   length = 23
FEATURE                    Location/Qualifiers
source                     1..23
                           mol_type = other DNA
                           organism = synthetic construct
misc_feature               1..23
                           note = Synthetic sequence; gRNA Recognition Sequence
SEQUENCE: 57
gtaaagcatg gagagcgttg tgg                                             23

SEQ ID NO: 58              moltype = DNA   length = 23
FEATURE                    Location/Qualifiers
source                     1..23
                           mol_type = other DNA
                           organism = synthetic construct
misc_feature               1..23
                           note = Synthetic sequence; gRNA Recognition Sequence
SEQUENCE: 58
ctcattgact gcatatccgt ggg                                             23

SEQ ID NO: 59              moltype = DNA   length = 23
FEATURE                    Location/Qualifiers
source                     1..23
                           mol_type = other DNA
                           organism = synthetic construct
misc_feature               1..23
                           note = Synthetic sequence; gRNA Recognition Sequence
SEQUENCE: 59
ctgtagccag agaactactg ggg                                             23

SEQ ID NO: 60              moltype = DNA   length = 23
FEATURE                    Location/Qualifiers
source                     1..23
                           mol_type = other DNA
                           organism = synthetic construct
misc_feature               1..23
                           note = Synthetic sequence; gRNA Recognition Sequence
SEQUENCE: 60
ccacggatat gcagtcaatg agg                                             23

SEQ ID NO: 61              moltype = DNA   length = 23
FEATURE                    Location/Qualifiers
source                     1..23
                           mol_type = other DNA
                           organism = synthetic construct
misc_feature               1..23
                           note = Synthetic sequence; gRNA Recognition Sequence
SEQUENCE: 61
tcaatgagga cgatgtagca cgg                                             23

SEQ ID NO: 62              moltype = DNA   length = 23
FEATURE                    Location/Qualifiers
source                     1..23
                           mol_type = other DNA
                           organism = synthetic construct
misc_feature               1..23
                           note = Synthetic sequence; gRNA Recognition Sequence
SEQUENCE: 62
tcacccctta cattgaagct ggg                                             23
```

```
SEQ ID NO: 63            moltype = DNA  length = 23
FEATURE                  Location/Qualifiers
source                   1..23
                         mol_type = other DNA
                         organism = synthetic construct
misc_feature             1..23
                         note = Synthetic sequence; gRNA Recognition Sequence
SEQUENCE: 63
gcatagcccc ctataatctg agg                                                  23

SEQ ID NO: 64            moltype = DNA  length = 23
FEATURE                  Location/Qualifiers
source                   1..23
                         mol_type = other DNA
                         organism = synthetic construct
misc_feature             1..23
                         note = Synthetic sequence; gRNA Recognition Sequence
SEQUENCE: 64
agtgtttcca tgccacctaa ggg                                                  23

SEQ ID NO: 65            moltype = DNA  length = 23
FEATURE                  Location/Qualifiers
source                   1..23
                         mol_type = other DNA
                         organism = synthetic construct
misc_feature             1..23
                         note = Synthetic sequence; gRNA Recognition Sequence
SEQUENCE: 65
cttcccagct tcaatgtaag ggg                                                  23

SEQ ID NO: 66            moltype = DNA  length = 23
FEATURE                  Location/Qualifiers
source                   1..23
                         mol_type = other DNA
                         organism = synthetic construct
misc_feature             1..23
                         note = Synthetic sequence; gRNA Recognition Sequence
SEQUENCE: 66
ttggactctt tgtggaacat ggg                                                  23

SEQ ID NO: 67            moltype = DNA  length = 23
FEATURE                  Location/Qualifiers
source                   1..23
                         mol_type = other DNA
                         organism = synthetic construct
misc_feature             1..23
                         note = Synthetic sequence; gRNA Recognition Sequence
SEQUENCE: 67
atgccaccta agggagactc agg                                                  23

SEQ ID NO: 68            moltype = DNA  length = 23
FEATURE                  Location/Qualifiers
source                   1..23
                         mol_type = other DNA
                         organism = synthetic construct
misc_feature             1..23
                         note = Synthetic sequence; gRNA Recognition Sequence
SEQUENCE: 68
gtccttctca gtcttatgca ggg                                                  23

SEQ ID NO: 69            moltype = DNA  length = 23
FEATURE                  Location/Qualifiers
source                   1..23
                         mol_type = other DNA
                         organism = synthetic construct
misc_feature             1..23
                         note = Synthetic sequence; gRNA Recognition Sequence
SEQUENCE: 69
ccaacaagcc aatttggtac agg                                                  23

SEQ ID NO: 70            moltype = DNA  length = 23
FEATURE                  Location/Qualifiers
source                   1..23
                         mol_type = other DNA
                         organism = synthetic construct
misc_feature             1..23
                         note = Synthetic sequence; gRNA Recognition Sequence
```

```
SEQUENCE: 70
gaggtgaaga tcaacctgaa cgg                                          23

SEQ ID NO: 71          moltype = DNA  length = 23
FEATURE                Location/Qualifiers
source                 1..23
                       mol_type = other DNA
                       organism = synthetic construct
misc_feature           1..23
                       note = Synthetic sequence; gRNA Recognition Sequence
SEQUENCE: 71
ttccacaaag agtccaaaca tgg                                          23

SEQ ID NO: 72          moltype = DNA  length = 23
FEATURE                Location/Qualifiers
source                 1..23
                       mol_type = other DNA
                       organism = synthetic construct
misc_feature           1..23
                       note = Synthetic sequence; gRNA Recognition Sequence
SEQUENCE: 72
tgtaagtctt attcacggtg agg                                          23

SEQ ID NO: 73          moltype = DNA  length = 23
FEATURE                Location/Qualifiers
source                 1..23
                       mol_type = other DNA
                       organism = synthetic construct
misc_feature           1..23
                       note = Synthetic sequence; gRNA Recognition Sequence
SEQUENCE: 73
tgtcctgagt ctcccttagg tgg                                          23

SEQ ID NO: 74          moltype = DNA  length = 23
FEATURE                Location/Qualifiers
source                 1..23
                       mol_type = other DNA
                       organism = synthetic construct
misc_feature           1..23
                       note = Synthetic sequence; gRNA Recognition Sequence
SEQUENCE: 74
caatgaggac gatgtagcac ggg                                          23

SEQ ID NO: 75          moltype = DNA  length = 23
FEATURE                Location/Qualifiers
source                 1..23
                       mol_type = other DNA
                       organism = synthetic construct
misc_feature           1..23
                       note = Synthetic sequence; gRNA Recognition Sequence
SEQUENCE: 75
atactggata aactactaga tgg                                          23

SEQ ID NO: 76          moltype = DNA  length = 23
FEATURE                Location/Qualifiers
misc_feature           1..23
                       note = Synthetic sequence; gRNA Recognition Sequence
source                 1..23
                       mol_type = other DNA
                       organism = synthetic construct
SEQUENCE: 76
tgcattcatg gcactgcttc tgg                                          23
```